US008206971B2

(12) United States Patent
Scholl et al.

(10) Patent No.: US 8,206,971 B2
(45) Date of Patent: Jun. 26, 2012

(54) MODIFIED BACTERIOCINS AND METHODS FOR THEIR USE

(75) Inventors: Dean M. Scholl, South San Francisco, CA (US); Steven R. Williams, San Francisco, CA (US)

(73) Assignee: AvidBiotics Corporation, South San Francisco, CA (US)

( * ) Notice: Subject to any disclaimer, the term of this patent is extended or adjusted under 35 U.S.C. 154(b) by 164 days.

(21) Appl. No.: 12/701,431

(22) Filed: Feb. 5, 2010

(65) Prior Publication Data

US 2010/0261258 A1 Oct. 14, 2010

Related U.S. Application Data

(60) Division of application No. 11/929,867, filed on Oct. 30, 2007, now Pat. No. 7,700,729, which is a continuation-in-part of application No. 11/748,432, filed on May 14, 2007, now Pat. No. 7,732,586.

(60) Provisional application No. 60/747,299, filed on May 15, 2006.

(51) Int. Cl.
C12N 1/20 (2006.01)
(52) U.S. Cl. .................................................. 435/252.3
(58) Field of Classification Search .......................... None
See application file for complete search history.

(56) References Cited

U.S. PATENT DOCUMENTS

| | | | |
|---|---|---|---|
| 4,142,939 A | 3/1979 | Morse et al. |
| 4,861,754 A | 8/1989 | Farkas-Himsley |
| 5,223,409 A | 6/1993 | Ladner et al. |
| 5,260,212 A | 11/1993 | Marugg et al. |
| 5,571,698 A | 11/1996 | Ladner et al. |
| 6,355,411 B1 | 3/2002 | Ausubel et al. |
| 6,818,418 B1 | 11/2004 | Lipovsek et al. |
| 7,655,775 B2 | 2/2010 | Stiles et al. |
| 7,662,592 B2 | 2/2010 | Stern et al. |
| 2003/0175207 A1 | 9/2003 | Olstein et al. |
| 2004/0156831 A1 | 8/2004 | Ramachandran et al. |
| 2006/0121450 A1 | 6/2006 | Miller et al. |
| 2006/0229244 A1 | 10/2006 | Dorit et al. |

FOREIGN PATENT DOCUMENTS

| | | |
|---|---|---|
| WO | WO99/16873 A1 | 4/1999 |
| WO | WO99/27129 A1 | 6/1999 |
| WO | WO00/60070 A1 | 10/2000 |
| WO | WO01/01786 A | 1/2001 |
| WO | WO2005/046579 A2 | 5/2005 |

OTHER PUBLICATIONS

Matsui, et al., "Regulation of Pyocin Genes in *Pseudomonas aeruginosa* by Positive (prtN) and Negative (prtR) reuglatory Genes", Journal of Bacteriology, 175(5):1257-1263 (1993).
Calamita, G., et al.,"The *Escherichia coli* aquaporin-A water channel", Molecular Microbiology 37(2):254-262 (2000).
Chappell, J. D., et al.,"The crystal structure of reovirus attachment protein reveals evolutionary relationship to adenovirus fiber," The EMBO Journal 21(1-2):1-11 (2002).
Cheng, K.H., et al.,"incidence of contact lens-associated microbial keratitis and is related morbidity", Lancet 354:181-185 (1999).
Choi, K.-H., et al.,"A Tn-7 based broad-range baterial cloning and expression system", Nature Methods 2(6):443-448 (2005).
Choi, H.-K., et al.,"An imporved method for rapid generation of unmarked *Pseudomonas aeruginosa* deletion mutants." BMC Microbiol. 5:30 (2005).
Chuanchuen, R., et al.,"Benchtop and microcentrifuge preparation for *Pseudomonas aeruginosa* competent cells," BioTechniques 33:760-763 (2002).
Coetzee, H.E., et al.,"Bacteriophage-tail-like particles associated with intra-species killing of *Proteus vulgaris*", J. Gen. Virol. 2:29-36 (1968).
Cole, N., et al.,"Different strains of *Pseudomonas aeruginosa* isolated from ocular infections or inflammation display distince corneal pathologies in an animal mode", Curr. Eye Res. 17:730-735 (1998).
Cooper, R.L., et al.,"Infective keratitis in soft contact lens wearers", Br. J. Ophthalmol 61:250-254 (1977).
Cotter, P.A., et al.,"A mutation in the *Bordetella bronchiseptica* bvgS gene results in reduced virulence and increased resistance to starvation, and identifies a new class of Bvg-regulated antigens", Mol. Microbiol. 24(4):671-685 (1997).
Cowell, B.A., et al.,"Use of an animal model in studies of bacterial corneal infection," Inst. Lab Animal Re. J. 40(2):43-50 (1999).
Curtis, M.D., et al.,"Investigation of the specificity of the interaction between colicin E9 and its immunity protein by site-directed mutagenesis", Molecular Micrbobiology 5(11):2727-2733 (1991).
Davis, M.M., et al.,"T-cell antigen receptor genes and T-cell recognition", Nature 334:395-403 (1988).
Daw, et al.,"Bacteriocins: Nature, Function, Structure", Micron 27(6):467-479 (1996).
Deho, G., et al., "Alternative promoters in the development of bacteriophage plasmid P4," J. Virol. 62(5):1697-1704 (1988).
Desplats, C., et al.,"The diversity and evolution of the T4-type bacteriophages", Res Microbiol, 154(4):259-267 (2003). Drickamer, K., et al.,"C-type lectin-like domains", Current Opinion in Structural Biology 9:585-590 (1999).
Drickamer, K., et al.,"Two distinct classes of carbohydrate-recognition dominas in animal lectins", The Journal of Biological Chemistry 263(20):9557-9560 (1988).
Dykes, G.A., et al.,"Selection and fitness in bacteriocin-producing bacteria", Proc. R. Soc. Lond. B, 264:683-687 (1997).
Dyke, J., et al.,"Growth inhibition and pyocin receptor properties of endotoxin from *Psuedomonas aeruginose*." Proc Soc Exp Biol Med, 145:1405-1408 (1974).

(Continued)

Primary Examiner — Suzanne M Noakes
(74) Attorney, Agent, or Firm — Sughrue Mion, PLLC

(57) ABSTRACT

Modified forms of naturally occurring bacteriocins, such as the R-type pyocins of *Pseudomonas aeruginosa*, are disclosed as are methods for producing them in GRAS organisms. The bacteriocins are modified at the ends of their tail fibers in a region responsible for binding specificity and affinity to their cognate binding partners, or receptors, such as those on the surface of bacteria. Methods for the use of the modified bacteriocins, such as to bind receptors, including virulence or fitness factors, on the surfaces of bacteria, are also described.

7 Claims, 26 Drawing Sheets

OTHER PUBLICATIONS

Emsley, P., et al.,"Crystallographic characterization of pertactin, a membrane-associated protein from *Bordetella perussis*", J. Mol. Biol., 235:772-773 (1994).

Farmer, III, J.J., et al.,"Epidemiologic fingerprinting of *Pseudomonas aeruginosa* by the production of and sensitivity to pyocin and bacteriophage", Applied Microbiol. 18(5):760-765, Nov. 1969.

Filiatrault, M.J., et al.,"Construction and characterization of *Haemophilus ducreyi* lipooligosaccharide (LOS) mutants defective in expression of Heptosyltransferase II and beta1, 4-Glucosyltransferase: Identification of LOS Glycoforms containing lactosamine repeats", Infection and immunity 68(6):3352-3361 (2000).

Filiatrault, M.J., et al.,"Genetic analysis of a pyocin-resistant lipooligosaccharide (LOS) mutant of *Haemophilus ducreyi*: restoration of full-length LOS restroes pyocin sensitivity", Journal of Baceteriology 183(19):5756-5761 (2001).

Fish, D.N., et al.,"Development of resistance during antimicrobial therapy: A review of antibiotic clases and patient characteristics in 173 studies," Pharmacotherapy, 15(3):279-291 (1995).

Fleiszig, S.M.J., et al.,"The pathogenesis of bacterial keratitis: studies with *Pseudomonas aeruginosa*", Clin. exp. optom. 85(5):271-278 (2002).

Gerke, J.R., et al.,"Experimental *Pseudomonas aeruginosa* infection of the mouse cornea", Infect. immun. 3(2):209-216 (1971).

Gillor, O., et al.,"genetically engineered bacteriocins and their potential as the next generation of antimicrobials", Current Pharmaceutical Design 11:1067-1075 (2005).

Goodman, A.L., et al.,"A signaling network reciprocally regulates genes associated with acute infection and chronic persistence in *Pseudomonas aeruginosa*", Developmental Cell, 7:745-754 (2004).

Govan, J.R.W., et al.,"Microbial pathogenesis in cystic fibrosis:Mucoid *Pseudomonas aeruginosa* and *Burkholderia cepacia*", MicrobiologicalReviews 60:539-574 (1996).

Haas, H., et al.,"Protective effect ofg pyocin against lethal *Pseudomonas aeruginosa* infections in mice", The Journal of Infectious Diseases, 129(4):470-472 (1974).

Haggard-Ljungquist, E., et al.,"DNA sequences of the tail fiber genes of bacteriophage P2: evidence for horizontal tranfer of tail fiber genes among unrelated bacteriophages", J. Baceteriol. 174(5):1462-1477 (1992).

Hayashi, T., et al.,"Cytotoxin-converting phages CTZ and PS21, are R pyocin-related phages", FEMS Microbiol. Lett. 122:239-244 (1994).

Hazlett, L.D., et al.,"Experimental eye infection caused by *Pseudomonas aeruginosa*," Ophthalmic Res. 8:311-318 (1976).

He, J., et al.,"the broad host range pathogen *Pseudomonas aeruginosa* strain PA14 carries two pathogenicity islands harboring plant and animal virulence genes", PNAS, 101(8):2530-2535 (2004).

Held, H., et al.,"Comprehensive mutational analysis of the M13 major coat protein", J. Mol. biol. 340:587-597 (2004).

Hensley, S.B., et al.,"As industry profits elsewhere, U.S. lacks vaccine, antibiotics", The wall Street Journal (Nov. 8, 2005) p. A1.

Hester, G., et al.,"structure of mannose-specific snowdrop (*Galanthus nivalis*) lectin is representative of new plant lectin family", Nat. Struct. Biol. 2:471-479 (1995).

Higerd, T.B., et al.,"morphological studies on relaxed and contracted forms of purified pyocin particles", Journal of Bacteriology 98(3):1378-1389 (1969).

Hirabayashi, J., et al.,"Effect of amino acid substitution by site-directed mutagenesis on the carbohydrate recognition and stability of human 14-kDa beta-galactoside-biding lectin", The Journal of biological chemistry 266(35):23648-23653 (1991).

Ho, T.D., et al.,"Enteroherorrhagic *Escherichia cli* O157:H7 gal mutants are sensitive to bacteriophage P1 and defective in intestinal colonization." Infect. Immuno. 75:1661-6 (2007) EPub Dec. 11, 2006.

Hoang, T.T., et al.,"A broad-host-range Fip=FRT recombination for site-specific excision of chromosomally-located DNA sequences: application for isloation of unmarked *Pseudomonas aeruginosa* mutants" Gene 212(1):77-86 (1998).

Hobden, J,A., et al.,"iontophoretic application of tobramyscin to uninfected and *Pseudomonas aeruginosa*-infected rabbit corneas," Antimicrob agents chemother 32:978-981 (1988).

Holder, I, A., et al.,"*P. aeruginosa* burn infections: pathogenesis and treatment,. In M campa, M Bendinelli , and H Friedman (ed.) *Pseudomonas aureginosa* as an oppurtunistic pathogen." Plenum Press, New york, N.Y pp. 275-295(1993).

Holm, L., et al.,"Protein structure comparison by alignment of distance matrices", J. Mol. Biol, 233:123-138 (1993).

Iijima, A., et al.,Mode of action of pyocin R1, J. Biochem. 83:395-402(1978).

Ishii, S., et al.,"The fine structure of a pyocin" J. Biochem 13:428-431 (1965).

Ito, S., et al.,"Isolation and characterization of pyocins from several strains of *Pseudomonas aeruginosa*", J. Gen. Appl. Microbiol. 16:205-214 (1970).

Jabrane, A., et al.,"Characterization of serracin P, a phage-tail-like bacteriocin, and its activity against *Erwinia amylovora*, the fire blight pathogen", Appl. Environ. Microbiol. 68(11):5704-5710 (2002).

Jacobs, et al.,"Comphrehensive transposon mutant library of *Psudomonas aeruginosa*", PNAS 100(24):14339-14344 (2003).

Jakes, K.S., et al.,"A hybrid toxin from bacteriophage f1 attachment protein and colicin E3 has altered cell receptor specificity," Journal of bacteriology 170(9):4231-4238 (1998).

Jakoby, G.A., et al.,"Resistance plasmids of *Pseudomonas*," The Bacteria, 10:265-294 (1986).

Jarvis, W.R., et al.,"Predominant pathogens in hospital infections," J. Antimicrob. Chemother., 29(a supp):19-24 (1992).

Kageyama, M., et al.,"On the purification and some properties of a pyocin, a bacteriocin produced by *Pseudomonas aeruginosa*", Life Sciences 9:471-476 (1962).

Kageyama, M., et al.,"Studies of a pyocin I physical and chemical properties", J. Biochem. 55(1):49-53 (1964).

Kageyama, M., et al.,"studies of a pyocin III. Biological properties of the pyocin", J. Biochem 55(1):59-64 (1964).

Kageyama, M., et al.,"Bacteriocins and bacteriophages in *Pseudomonas aeruginosa*", Microbial drug resistance 291-305 (1975).

Kageyama, M., et al.,"Characterization of a bacteriophage related to R-type pyocins", J. Virol. 32(2):951-957 (1979).

Kagayama, M., et al.,"Construction and characterization of pyocin-colicin chimeric proteins", Journal of Bacteriology 178(1):103-110 (1996).

Kahn, M.L., et al.,"Bacteriophage P2 and P4", Methods Enzymol. 204:264-280 (1991).

Kingsbury, D., et al.,"Bacteriocin production by strains of *Neisseria meningitides*", Journal of Bcteriology 91(5):1696-1699 (1966).

Kogelberg, H., et al.,"new structural insights into lectin-type proteins of the miinume system", Current opinion in structural biology 11:635-643 (2001).

Kumazaki, T., et al.,"Isolation and characterization of Pyocin R1 fibers", J. Biochemistry 91:825-835 (1982).

Kumazaki, T., et al.,"Comparative study on fibers isolated from four R-type pyocins, phage-tail like bacteriocins of *Pseudomonas aeruginosa*", J. Biochem, 92(5):1559-1566 (1982).

Lasky, L.,"Selectin-carbohydrate interactions and the initiation of the inflammatory response", Annu. Rev. Biochem 64:113-139 (1995).

Lee, E.J., et al.,"Role of *Pseudomonas aeruginosa* ExsA in penetration through corneal epithelium in a novel in vivo model", Investiative ophthalmology & Visual Science 44(12):5220-5227 (2003).

Levin, B.R., et al.,"Population and evolutionary dynamics of phage therapy", Nature Reviews—Microbiology 2:166-173 (2004).

Liu, M., et al.,"Reverse transcriptase-mediated tropism switching in *Bordetella bacteriophage*", Science 295:2091-2094 (2002).

Liu, M., et al.,"Genomic and genetic analysis of bordetella bacteriophages encoding reverse transcriptase-mediated tropism-switcing cassetes", J. Bacteriology 186:476-481 (2004).

Luo, Y., et al.,"Crystal structure of enteropathogenic *Escherichia coli* intimin-receptor complex", Nature 405:1073-1077 (2000).

Mah-Sadorra, JH., et al.,"trends in contact lens-related corneal ulcers," Cornea 24:51-58 (2005).

McMahon, et al.,"The C-type lectin fold as an evolutionary solution for massive sequence variation", Nature Struct. &Molecular Biol. 12:886-892 (2005).

McNamara, N.A., et al.,"Soft lens extended wear affects epithelial barrier function", Ophthalmology 105:2330-2335 (1998).

Meadow, P.M., et al.,"Receptor site for R-type pyocins and bacteriophage E79 in the core part of the lipoplysaccharide of *Pseudomonas aeruginosa* PAC1", J. Gen. Microbiol. 108:339-343 (1978).

Merrikin, D.J., et al.,"Use of Pyocin 78-C2 in the treatment of *Pseudomonas aeruginosa* infection in mice", Applied microbiology 23(1):164-165 (1972).

Michel-Braind,Y., et al.,"The pyocins of *Psuedomonas aeruginose*" Biochimie 84(5-6):499-510 (2002).

"Microbial threats to health: emergence, detection and response", Institute of medicine, Washington, D.C. pp. 1-8(Mar. 2003).

Mitchell, et al.,"Structural basis for oligosaccharide-mediated adhesion of *Psedomonas aeruginosa* in the lungs of cystic fibrosis patients", Natrual structural biology 9(12):918-921 (2002).

Mooi, F.R., et al.,"Polymorphism in the *Bordetella pertussis* virulence factors P.69/pertactin and pertussis toxin in the Netherlands:temporal treands and evidence for vaccine-driven evolution", Infect. Immun. 66(2):670-675 (1998).

Morse, S.A., et al.,"Pyocin inhibition of *Neisseria gonorrhoeae*:mechanism of action", Antimicrob Agents Chemother 18(3):416-423 (1980).

Morse, S.A., et al.,"Inhibition of *Neisseria gonorrhoeae* by a bacteriocin from *Pseudomonas aeruginosa*", Antimicrob Agents Chemother 10(2):354-362 (1976).

Mosig, G., et al.,"T4 and related phages: structure and development" The Bacteriophages.Calender, R., 2:225-267, 2006.

NCBI Sequence Viewer, pp. 1-2 at http://www.ncbi.nim.nih.gov/entrez/viewer.fcgi?db=protein&val=40950108, Visited on Apr. 13, 2007.

Nakayama, K., et al.,"The complete nucleotide sequence of thetaCTX, a cytotoxin-converting phage of *Pseudomonas aeruginosa*: implications for phage evolution and horizontal gene tranfers via bacteriophages", Mol. Microbiol. 31(2)399-419 (1999).

Nakayama, K., et al.,"The R-type pyocin of *Pseudomonas aeruginosa* is related to P2 phage, and the F-type is related to the lambda phage", Molecular Microbiology 38(2):213-231 (2000).

Nallapareddy, S.R., et al.,"*Enterococcus faecalis* adhesion, Ace, Mediates attachment to extracellular matrix protein collagen type IV and Laminin as well as collagen Type I." Infect. Immun. 68(9):5218-5224 (2000).

Nguyen, H., et al.,"DNA inversion in the tail fiber gene alters the host range specificity of carotovoricin Er, a phage-tail-like bacteriocin f phytopathogenic *Erwinia carotovora* subsp. carotovora Er" Journal of Bacteriology 183(21):6274-6281 (2001).

Papagianni, M., et al.,"Ribosomally synthesized peptides with antimicrobial properties:biosynthesis, structure, function and applications", biotechnology advances 21:465-499 (2003).

Papanikolopoulou, K., et al.,"Formation of highly stable chimeric trimers by fusion of an adenovirus fiber shafter fragment with the foldon domain of bacteriophage T4 fibritin", Journal of Biological Chemistry 279(10):8991-8998 (2004).

Preston, M.I., et al.,"Rapid and sensitive method for evaluating *Pseudomonas aeruginosa* virulence factors during corneal infetions in mice" Infection and Immunity 63:3497-3501 (1995).

Qu, Y., et al.,"In vivo bypass of chaperone by extended coiled-coil motif in T4 tail fiber", J. Bacteriol 186(24):8363-8369 (2004).

Qui, X-Q., et al.,"A novel engineered peptide, a narrow spectrum antibiotics, is effective against vancomycin-resistant *Enterococcus faecalis*" Antimicrobial agents and chemotherapy 49(3):1184-1189 (2005).

Ramphal, R., et al.,"Adherence of *Pseudomonas aeruginosa* to the injured cornea: a step in the pathogenesis of corneal infections," Ann. Ophthalmol. 12:421-425 (1981).

Rich, et al.,"Ace is a collagen binding MSCRAMM from *Enterococcus faecalis*"m J. Biol. Chem. 274(38):26939-26945 (1999).

Riley, M.A., et al.,"Positive selection for colicin diversity in bacteria", Mol. Biol. Evol. 10(5):1048-1059 (1993).

Riley, M.A. et al.,"Bacteriocins: evolution, ecology, and application", Annu. Rev. Microbiol. 56:117-37 (2002).

Rolands, P.S., et al.,"Microbiology of acuteotitis externa." Laryngoscope 112:1166-1177 (2002).

Rudner, et al.,"A family of membrane-embedded metalloproeases involved in regulated proteolysis of membran-associated transcription factors", PNAS, 96(26):14765-14770 (1999).

Sano, Y., et al.,"Genetic determinant of pyocin AP41 as an insert in the *Pseudomonas aeruginosa* chromosome", Journal of bacteriology 158(2):562-570 (1984).

Schweizer, H.P., et al.,"Vectors to express foreign genes and techniques to moniter gene expression in pseudomonads," current opinion in biotechnology 12"439-445 (2001).

Schweizer, H.P., et al.,"Improved methods for gene analysis and expression in *Pseudomonas* ssp." Molecular Biology of Pseudomonads 19:229-237 (1996).

Sharon, N., et al.,"History of lectins: from hemagglutinins to biological recognition molecules" Glycobiology 14(11):53R-62R (2004).

Shimizu,Y,, et al.,"Specific cleavage at fibers of a bacteriophage-tail-like bacteriocin, pyocin R1 by successive treatment with organomercurial compounds and trypsin", J. Virology 44(2):692-695 (1982).

Shinomiya, T., et al.,"Bactericidal activity of the tail of *Pseudomonas aeruginosa* bacteriophage PS17", J. of Virology 32:958-67 (1979).

Shinomiya, T., et la.,"Studies on biosynthesis and morphogenesis of R-type pyocins of *Pseudomonas aeruginosa*", J Biochem 72:39-48 (1972).

Shinomiya, T., et al "Genetic determinant of pyocin R2 in *Pseudomonas aeruginosa* PAO I. location of the pyocin R2 gene cluster between the trpCD and trpE genes", Mol. Gen. Genet 189:375-381 (1983a).

Shinomiya, T. "Pheontypic Mixing of Pyocin R2 and Bacteriophage PS17 in *Pseudomonas aeruginosa* POA", Journal of Virology 49(2):310-314 (1984).

Shinomiya, T., et al.,"Genetic comparison of bacteriophage PS17 in *Pseudomonas aeruginosa* POA", Journal of Bacteriology 49(2):310-341 (1984).

Shinomiya, T., et al.,"Genetic comparison of bacteriophage PS17 in *Pseudomonas aeruginosa* R-type pyocin", Journal of Bacteriology 171(5):2287-2292 (1989).

Shore, D., et al.,"Determination of capsid size by satellite bacteriophage P4." Proc. Natl. Acad. Sci. USA 75:400-404 (1977).

Sinclair, M.I., et al.,"A chromosomally located transposon in *Pseudomonas aeruginosa*" J. acteriol 151(2):569-579 (1982).

Sreedhar et al.,"*Enterococcus faecalis* adhesin, ACE, mediates attachment to extracellular matrix proteins collagen type IV and Laminin as well as collegen Type I." Infect. Immun. 68(9):5218-5224 (2000).

Strauch, E., et al.,"Characterization of enterocoliticin, a phage tail-like bacteriocin, and its effect on pathogenic *Yersinia enterocolotica* strains", applied and environmental microbiology 67(12):564-5642 (2001).

Sunshine, M.G., et al.,"P2 phage amber mutants: characterization by use of a polarity supressor."Virology 46:691-702 (1971).

Takeya, K., et al.,"Rod-shaped pyocin 28," J. Gen. Virol. 4:145-149 (1969).

Talbot, G.H., et al.,"Bad Bugs Need drugs: an update on the development pipeline from the antimicrobiol availility taskforece of the infectous diseases society of america", Clin Infect Dis 42:657-668 (2006).

Tambers, S., et al.,"Role of the novel OprD family of Porins in nutrient uptake in *Pseudomonas aeruginosa*", J. of Bacteriology 18(1):45-54 (2006).

Taylor, M., et al.,"Structure-funtion analysis of C-type animal lectins" Methods in Enzymology 363:3-16(2003).

Tetart, F., et al.,"Genomone plasticity in the distal tail fiber locus of the T-even bacteriophage: recombination between conserved motifs swaps adhesion specificity," J. Mol. Biol. 282:543-556 (1998).

Thompson, N.E., et al.,"Genetic transofrmation in *Staphylococcus aureus*: demonstration of a cometence-conferring factor of bacteriophage origin in bacteriophage 80alpha lysates" J. Bacteriol. 148:294-300 (1981).

Torma, J., et al.,"Crystal structure of a lectin-like natural killer cell receptor bound to its MHC class I ligand", Nature 402:623-631 (1999).

Twining, S.S, et al.,"Effect of vitamin A deficiency on the early response to experimental *Pseudomonas keratitis*" Inves Ophthalmol. Vis. Sci 37(4):511-522 (1996).

Uhl, M.A., et la.,"Integration of multiple domains in a two-compnent sensor protein: the *Bordetell pertussis* BvgAS phosphorelay", EMBO J. 15(5):1028-1036 (1996).

Uratani, Y., et al.,"Pyocin R1 inhibits active transport in *Pseudomonas aeruginosa* and depoloarizes membrane potential", Journal of Bacteriology 157 (2):632-636 (1984).

Van Horn, D.L., et al.,"Pathogenesis of experimental *Pseudomonas keratitis* in the guinea pig: bacterioloic, clinical and microscopic observations", Invest Ophthalmol Vis Sci 17(11):1076-1086 (1978).

Van Raaij, M.J., et al.,"A thriple beta-spiral in the adenovirus fiber shaft reveals a new structural motif for a fibrous protein", Nature 401:935-938 (1999).

Van Raaij, M.J., et al.,"Crystal structure of a heat and protease-stable part of the bacteriophage T4 short tail fibre", J. Mol. Biol. 314:11137-1146 (2001).

Van Der Wal, F.J., et al.,"Optimization of baceriocin release protein (BRP)-mediated protein relase by *Escherichia coli*: random mutageneis of the pCloDF10-derived BRP gene to uncouple lethality and quasi-lysis from protein release", Applied and Environmental microbiolgy 64(2):392-398 (1998).

Waddell, T.E., et al.,"Construction of mini-Tn10 luxABcam/Ptac-ATS and its use for developing a bacteriophage that transduces bioluminescence to *Escherichia coli* O157:H7." FEMS microbio. Lett. 182(2):285-289 (2000).

Weigele, P.R., et al.,"Homotrimeric Beta-stranded viral adhesin and tail proteins", J. of Bacteriology 185(14):4022-4030 (2003).

Wies, W., et al.,"Structure of the calcium-dependent lectin domain from a rat mannose-binding protein determined by MAD phasing", Science 254:1608-1615 (1991).

Weis, W., et al.,"Structure of a C-type mannnose-binding protein complexed with an oligosaccharide", Nature 260:127-134 (1992).

Wenzel, R.P., "The antibiotic pipeline-challenges, costs and values" New Engl. J. Med. 351:523-526 (2004).

West, S.H.E., et al.,"Construction of imporved *Escherichia-Pseudomonas* shuttle vectors derived from pUC18/19 and sequence of the region required for their replication in *Pseudomonas aeruginosa*", Gene 128:81-86 (1994).

Williams, et al.,"Retargeting T-type pyocins to generate novel bactericidal protein complexes," App. Eng. Micro. 74(12):3868-3876 (2008).

Wong, et al.,"Insertion mutagenesis and membrane topology model of the *Pseudomonas aeruginosa* outer membrane protein OprM" J. Bacteriol. 182(9):2402-2410 (2000).

Yoichi, M., et al.,"Alteration of tail fiber protein gp38 enables T2 phage to infect *Escherichia coli* O157:H7", Journal of Biotechnology 115:101-107 (2005).

Young, et al.,"Phage lysis", Phages: their role in bacterial pathogenesis and biotechnology 92-127(2006).

Zierdt, C.H., et al.,"Dissociation in *Pseudomonas aeruginosa*", J. Bacteriol. 87(5):1003-1010 (1964).

Ziermann, R., et al.,"Characterization of the cos site of bacteriophages P2 and P4" Gene 96:9-15 (1990).

Zink, R., et al.,"Characterization of cryptic prophages (monocins) in *Listeria* and sequence analysis of a hollin.endolysin gene", Microbiology 141:2577-2584 (1995).

Zolfaghar, I., et al.,"Mutation of retS encoding a putative hybrid two-component regulatory protein in *Pseudomonas aeruginosa*, attenuates multiple virulence mechanisms" Microbes Infect. 7:1305-1316 (2005).

Doulatov, S., et al.,"Tropism switching in borfdetella bacteriophage defines a family of diversity-generating retroelements", Nature 431:476-481 (2004).

Hashemolhosseine, S., et al.,"Determinants of receptor specifically of coliphages of the T4 family. A chaperone alters the host range", J.Mol. Biol. 241(4):524-533 (1994).

Lee, F.K.N, et al.,"The R-type pyocin of *Pseudomonas aeruginosa* C is a bacteriophage tail-like particle that contains single stranded DNA", Infection and Immunity 67(2):717-725 (1999).

Ackermann, H.W.,"Bacteriophage Observations and evolution," Res. Microbiol. 154:245-251 (2003).

Aiache, J,M., et al., "The formulation of drug for ocular administration", J. Biomater Appl. 11:329-348 (1997).

Akerley, B.J., et al.,"Ectopic expression of flagellar regulon alters development of the *Bordetella*-host interaction", Cell 80:611-620 (1995).

Anantharaman, et al.,"Application of comparative genomics in the identification and analysis of novel families of membrane-associated receptors in bacteria", BMC Genomics 4:34 (2003).

Anisimov, A.P., et al.,"Treatment of plague:promising alernatives to antibodies", Journal of Medical Microbiology 55:1461-1475 (2006).

Archibald, L. et al.,"Antimicrobial resistance in isloates from inpatients and outpatients in the United States: Increasing importance of the Intensive care unit," Clin. Infectious Dis. 24(2):211-215 (1997).

Bad Bugs, No Drugs: As Antibiotics Discovery Stagnates . . . A Public Health Crisis Brews, Infectious Diseases Society of America pp. 1-35 (Jul. 2004).

Batchelor, M., et al.,"Structural basis for recognition of the translocated intimin receptor (Tir) by intimin from enteropathogenic *Escherichia coli*", EMBO J. 19(11):2454-2464 (2000).

Bertani, L., et al.,"The P2-like phages and their parasite, P4." In R. Calender (ed.) THe Baceriophages 2:73-143 (1998).

Beste, G., et al.,"Small antibody-like proteins with prescribed ligand specificities derived from the lipocalin fold", Proc. Natl. Acad. Sci USA 96:1898-1903 (1999).

Birmingham, V.A., et al.,"Genetic transformation in *Staphlyococcus aureus*: Isolation and characterization of a competence-conferring factor from bacteriophage 80a lysates", Journal of Bacteriology, 148:301-307(1981).

Blackwell, C.C., et al.,"Sensitivity of thermophilic *Campylobacters* to R-type pyocins of *Pseudomonas aeruginosa*", J. Med. Microbiology, 15:247-251 (1982).

Blackwell, C.C., et al.,"Typing of non-serogroupable *Neisseris meningitidis* by means of sensitivity to R-type pyocins of *Pseudomonas aeruginose*," J. Infect. 3(4):370-8 (1981).

Bonev, B.B., et al.,"Targeting extracellular pyrophosphates underpins the high selectivity of nisin", The FASEB Journal 18:1862-1869 (2004).

Bowen, B.R., et al.,"Characterization of a human homologue of the murine peripheral lymph node homing receptor", The Journal of Cell Biology, 109:421-427 (1989).

Bradley, "Ultrastructure of bacteriophages and bacteriocins", Bacteriol. Revs, 31(4):230-314 (1967).

Brazas, M.D., et al.,"Ciprofloxacin induction of a susceptibility determinant in *Pseudomonas aeruginoas*", Antimicrobial Agents and Chemotherapy 49(8):3222-3227 (2005).

Burda, M.R., et al.,"Folding of coliphage T4 short tail fiber in virto. Analysing the role of a bacteriophage-encoded chaperone", Eur. J. Biochem. 265(2):771-778 (1999).

Burns, R.P.,"*Pseudomonas aeruginosa* keratitis: mixed infections of the eye," Am. J. Opthalmol. 67:257-262 (1969).

Barbirz, S., et al., "Crystal structure of Escherichia coli phage HK620 tailspike: podoviral tailspike endoglycosidase modules are evolutionarily related", Molecular Microbiology, 69(2), 303-316 (2008).

Emsley, P., et al. "Structure of *Bordetella pertussis* virulence factor P.69 pertactin", Nature (1996) 381:90-92.

Shinomiya, T., "Genetic determinant of pyocin R2 in *Pseudomonas aeruginosa* PAO. II. Physical characterization of pyocin R2 genes using R-prime plasmids constructed from R68.45" Mol Gen Genet. 1983;189(3):382-9.

Villafane, R., et al., "Conservation of the N-terminus of some phage tail proteins", Arch Virol 150:2609-2621 (2005).

R-type pyocin
A)
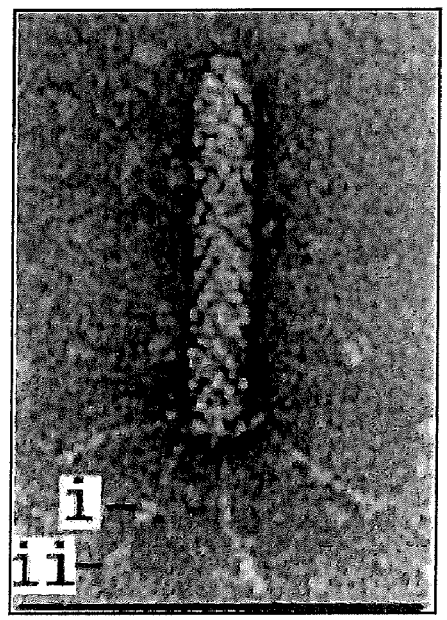
B)
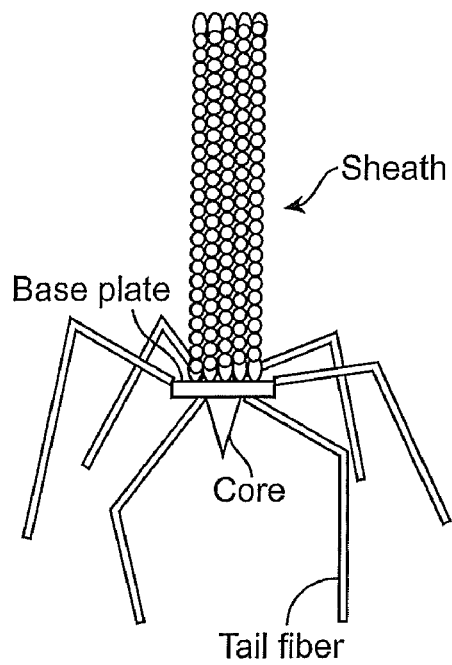
FIG. 1

Complementing the R2 pyocin structure with an R2-P2 tail fiber fusion
A)
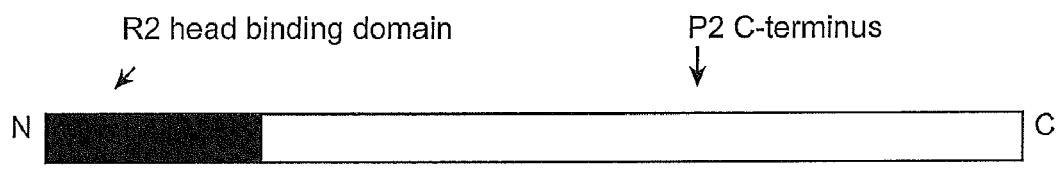
B)
Wild type R2       R2 complemented with R2-P2 tail fiber fusion.
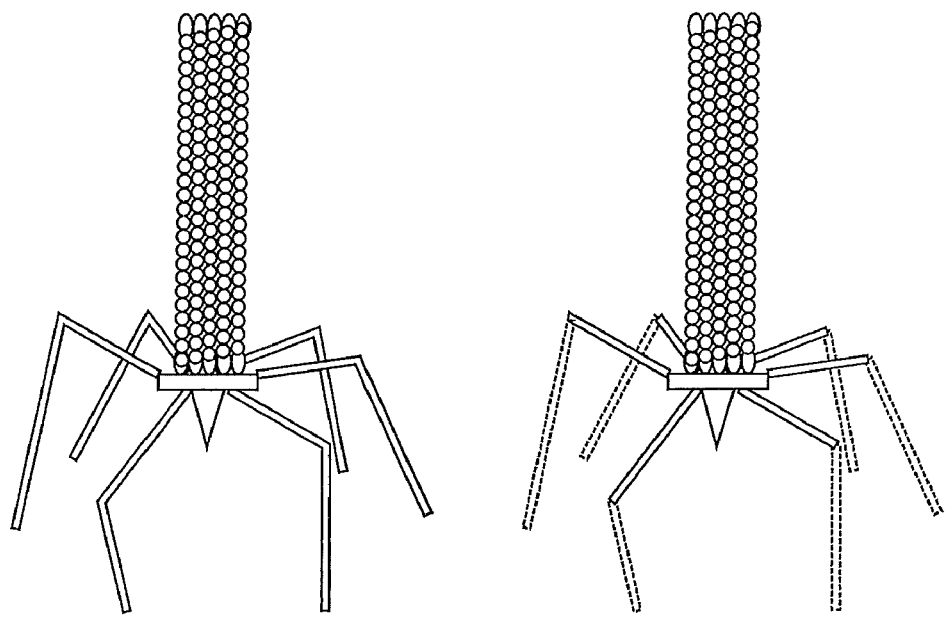
FIG. 3

Trans complementation of the PA01Δprf15 R2 pyocin structure with various R-type pyocin tail fibers, tail fiber fusions and chaperones

| Tail Fiber (Prf15) | Bactericidal Activity prf15 expressed alone | Bactericidal Activity prf15 and cognate chaperone | % sequence identity of PRF15 to R2 PRF15 | % sequence identity of aa 1-429 | % sequence identity of aa 430-end | % sequence identity of Prf16 to R2 Prf16 |
|---|---|---|---|---|---|---|
| R1 | + | +++ | 82 | 99 | 52 | 32 |
| R2 | ++ | +++ | 100 | 100 | 100 | 100 |
| R3 | ++ | +++ | 99 | 99 | 98 | 98 |
| R4 | ++ | +++ | 98 | 99 | 99 | 99 |
| R5 | - | +++ | 83 | 97 | 58 | 35 |
| R2-P2 | - | +++(P2) | 14 | na | na | 6 |
| R2-L413c | - | +++(413) | 19 | na | na | 6 |

FIG. 8

Construction of *Yersinia pestis* specific pyocin tail fiber.

FIG. 10

Figure 11.
A.
R2-P2 tail fiber fusion
| R2 BPAR | P2 RBD |
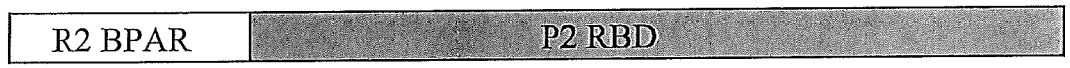
R2-V10 tail fiber fusion
| R2 BPAR | phiV10 RBD |
B.
EDL933
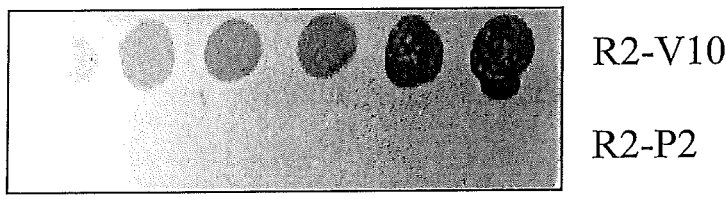
R2-V10
R2-P2
TEA026
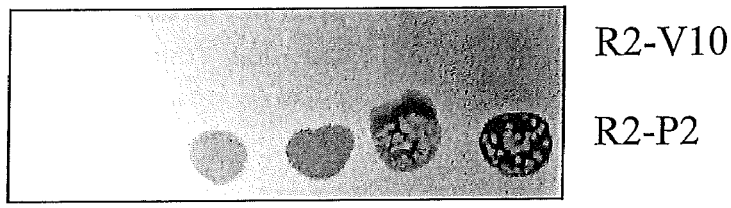
R2-V10
R2-P2
[Pyocin]

FIGURE 13A
SEQUENCE LISTINGS

SEQ ID NO:1 >R1 prf15
MTTNTPKYGGLLTDIGAAALAAASAAGKKWQPTHMLIGDAGGAPGDTPDPLPSAAQKSLINQRHRAQLN
RLFVSDKNANTLVAEVVLPVEVGGFWIREIGLQDADGKFVAVSNCPPSYKAAMESGSARTQTIRVNIAL
SGLENVQLLIDNGIIYATQDWVKEKVAADFKGRKILAGNGLVGGGDLSADRSIGLAPSGVTAGSYRSVT
VNANGVVTQGSNPTTLAGYAIGDAYTKADTDGKLAQKANKATTLAGYGITDALRVDGNAVSSSRLAAPR
SLAASGDASWSVTFDGSANVSAPLSLSATGVAAGSYPKVTVDTKGRVTAGMALAATDIPGLDASKLVSG
VLAEQRLPVFARGLATAVSNSSDPNTATVPLMLTNHANGPVAGRYFYIQSMFYPDQNGNASQIATSYNA
TSEMYVRVSYAANPSIREWLPWQRCDIGGSFTKTTDGSIGNGVNINSFVNSGWWLQSTSEWAAGGANYP
VGLAGLLIVYRAHADHIYQTYVTLNGSTYSRCCYAGSWRPWRQNWDDGNFDPASYLPKAGFTWAALPGK
PATFPPSGHNHDTSQITSGILPLARGGLGANTAAGARNNIGAGVPATASRALNGWWKDNDTGLIVQWMQ
VNVGDHPGGIIDRTLTFPIAFPSACLHVVPTVKEVGRPATSASTVTVADVSVSNTGCVIVSSEYYGLAQ
NYGIRVMAIGY SEQ ID NO:2 >R1 prf16
MIFFHAATGGFYSKEIHGSRMPLEDEMHPLEDAEYQALLRAQSEGKRIVTDHTGRPICVDPPAPAKDIL
VQRERIWRDRQLQLTDGPLARHRDEQDLGKTTTLSQEQLRELTLYRAVLRDWPIAAEFPDLNARPEPPA
WLQSLITP SEQ ID NO:3 >R2 prf15
MTTNTPKYGGLLTDIGAAALATASAAGKKWQPTHMLIGDAGGAPGDTPDPLPSAAQKSLINQRHRAQLN
RLFVSDKNANTLVAEVVLPVEVGGFWIREIGLQDADGKFVAVSNCPPSYKAAMESGSARTQTIRVNIAL
SGLENVQLLIDNGIIYATQDWVKEKVAADFKGRKILAGNGLLGGGDLSADRSIGLAPSGVTAGSYRSVT
VNANGVVTQGSNPTTLAGYAIGDAYTKADTDGKLAQKANKATTLAGYGITDALRVDGNAVSSSRLAAPR
SLAASGDASWSVTFDGSANVSAPLSLSATGVAAGSYPKVTVDTKGRVTAGMALAATDIPGLDASKLVSG
VLAEQRLPVFARGLATAVSNSSDPNTATVPLMLTNHANGPVAGRYFYIQSMFYPDQNGNASQIATSYNA
TSEMYVRVSYAANPSIREWLPWQRCDIGGSFTKEADGELPGGVNLDSMVTSGWWSQSFTAQAASGANYP
IVRAGLLHVYAASSNFIYQTYQAYDGESFYFRCRHSNTWFPWRRMWHGGDFNPSDYLLKSGFYWNALPG
KPATFPPSAHNHDVGQLTSGILPLARGGVGSNTAAGARSTIGAGVPATASLGASGWWRDNDTGLIRQWG
QVTCPADADASITFPIPFPTLCLGGYANQTSAFHPGTDASTGFRGATTTTAVIRNGYFAQAVLSWEAFG
R SEQ ID NO:4 >R2 prf16
MKGEYYFSPSQVAFYPASLREVYEYAGCWPVDGEWVSAELHEQLMNEQAAGRAISSDVNGNPVAIERPP
LSRQQRSTHERRWRDSQLLATDGLVVRHRDQLETGKETTLLPVQYHELMSYRASLRDWPEEPLFPDSGG
RPSVPDWLRRYVTP SEQ ID NO:5 >R3 prf15
MTTNTPKYGGLLTDIGAAALAAASAAGKKWQPTHMLIGDAGGAPGDTLDPLPSAAQKSLINQRHRAQLN
RLFVSDKNANTLVAEVVLPVEVGGFWIREIGLQDADGKFVAVSNCPPSYKAAMESGSARTQTIRVNIAL
SGLENVQLLIDNGIIYATQDWVKEKVAADFKGRKILAGNGLLGGGDLSADRSIGLAPSGVTAGSYRSVT
VNANGVVTQGSNPTTLAGYAIGDAYTKADTDGKLAQKANKATTLAGYGITDALRVDGNAVSSSRLAAPR
SLAASGDASWSVTFDGSANVSAPLSLSATGVAAGSYPKVTVDTKGRVXAGMALAATDIPGLDASKLVSG
VLAEQRLPVFARGLATAVSNSSDPNTATVPLMLTNHANGPVAGRYFYIQSMFYPDQNGNASQIATSYNA
TSEMYVRVSYAANPSIREWLPWQRCDIGGSFTKEADGELPGGVNLDSMVTSGWWSQSFTAQAASGANYP
IARAGLLHVYAASSNFIYQTYQAYDGESFYFRCRYSNTWLPWRRMWHGGDFNPSDYLLKSGFYWNALPG
KPATFPPSAHNHDVGQLTSGILPLARGGVGSNTAAGARSTIGAGVPATASLGASGWWRDNDTGLIRQWG
QVTCPADADASITFPIPFPTLCLGGYANQTSAFQPGTDASTGFRGATTTTAVIRNGYFAQAVLSWEAFG
R

FIGURE 13B

SEQ ID NO:6 >R3 prf16
MKGEYYFSPSQVAFYPASLREVYEHAGCWPVDGEWVSAELHEQLMNEQAAGRAISSDVNG
NPVAIERPPLSRQQRSTHERRWRDSQLLATDGLVVRHRDQLETGKETTLLPVQYHELMSY
RASLRDWPEEPLFPDSGGRPSVPDWLRRYVTP SEQ ID NO:7 >R4 prf15
MTTNTPKYGGLLTDIGAAALAAASAAGKKWQPTHMLIGDAGGAPGDTPDPLPSAAQKSLI
NQRHRAQLNRLFVSDKNANTLVAEVVLPVEVGGFWIREIGLQDADGKFVAVSNCPPSYKA
AMESGSARTQTIRVNIALSGLENVQLLIDNGIIYATQDWVKEKVAADFKGRKILAGNGLV
GGGDLSADRSIGLAPSGVTAGSYRSVTVNANGVVTQGSNPTTLAGYAIGDAYTKADTDGK
LAQKANKATTLAGYGITDALRVDGNAVSSSRLAAPRSLAASGDASWSVTFDGSANVSAPL
SLSATGVAAGSYPKVTVDTKGRVTAGMALAATDIPGLDASKLVSGVLAEQRLPVFARGLA
TAVSNSSDPNTATVPLMLTNHANGPVAGRYFYIQSMFYPDQNGNASQIATSYNATSEMYV
RVSYAANPSIREWLPWQRCDIGGSFTKEADGELPGGVNLDSMVTSGWWSQSFTAQAATGA
NYPIVRAGLLHVYAASSNFIYQTYQAYDGESFYFRCRHSNTWFPWRRMWHGGDFNPSDYL
LKSGFYWNALPGKPATFPPSAHNHDVGQLTSGILPLARGGVGSNTAAGARSTIGAGVPAT
ASLGASGWWRDNDTGLIRQWGQVTCPADADASITFPIPFPTLCLGGYANQTSAFHPGTDA
STGFRGATTTTAVIRNGYFAQAVLSWEAFGR SEQ ID NO:8 >R4 prf16
MKGEYYFSPSQVAFYPXSLREVYEYAGCWPVDGEWVSAELHEQLMNEQAAGRAISSDVNG
NPVAIERPPLSRQQRSAHERRWRDSQLLATDGLVVRHRDQLETGKETTLLPVQYHELMSY
RASLRDWPEEPLFPDSGGRPSVPDWLRRYVTP SEQ ID NO:9 >R5 prf15
MTTNTPKYGGLLTDIGAAALAAASAAGKKWQPTHMLIGDAGGAPGATPDPIPAATQTKLI
NQRYRAQLNRLFVSDKNINTLVAEVVLPVEVGGFWIREIGLQDADGKFVAVSNCPPSYKA
AMESGSARTQTIRVNIALSGLENVQLLIDNGIIYATQDWVKEKVAADFKGRKILAGNGLV
GGGDLSADRSIGLAPSGVTAGSYRSVTVNANGVVTQGSNPSTLAGYAIGDAYTKADTDGK
LAQKANKATTLAGYGITDALRVDGNAVSSSRLAAPRSLAASGDASWSVTFDGSANVSAPL
SLSATGVAAGSYPKVTVDTKGRVTAGMALAATDIPGLDASKLVSGVLAEQRLPVFARGLA
TAVSTTSDPNTATVPLMLTNHANGPVAGRYFYIQSMFYPDQNGNASQIATSYNATSEMYV
RVSYAANPSARDWLPWKRCDIGGSFSKEADGALGGAVNLNSLITSGWWYQTANAQAESGA
NYPVPRAGLLQVHNAGTNFIYQTYQVYDGEGFYFRCRYTNTWYPWRRVWHGADFNPNDYL
LKSGFTWAALPGKPATFPPTGHNHDAAQITSGILPLARGGLGSNTAAGARNNIGAGVPAT
ANRSLNGWWKDNDTGLIVQWMTVSVGDHPGGIVNRSLTFPIAFPTTCLHVVPSVKELGRP
ATSASTVTLADVSVSTTGCVIVATEYHGAVQNYAIRLVAIGC SEQ ID NO:10 >R5 prf16
MIFFHAATGGFYSKDVHGDRMPIDARMYPLEEAEYLALLVAQSEGKQIVADAAGRPFCID
PPAPAEEVLAHRERIWRDRQLTLTDGPIARHRDELDLGKITTLNQAQLLELTLYRASLRD
WPASAAFPDLGARPEPPLWLEPLITP SEQ ID NO:11 > OprM
MKRSFLSLAVAAVVLSGCSLIPDYQRPEAPVAAAYPQGQAYGQNTGAAAVPAADIGWREF
FRDPQLQQLIGVALENNRDLRVAALNVEAFRAQYRIQRADLFPRIGVDGSGTRQRLPGDL
STTGSPAISSQYGVTLGTTAWELDLFGRLRSLRDQALEQYLATEQAQRSAQTTLVASVAT
AYLTLKADQAQLQLTKDTLGTYQKSFDLTQRSYDVGVASALDLRQAQTAVEGARATLAQY
TRLVAQDQNALVLLLGSGIPANLPQGLGLDQTLLTEVPAGLPSDLLQRRPDILEAEHQLM
AANASIGAARAAFFPSISLTANAGTMSRQLSGLFDAGSGSWLFQPSINLPIFTAGSLRAS
LDYAKIQKDINVAQYEKAIQTAFQEVADGLAARGTFTEQLQAQRDLVKASDEYYQLADKR
YRTGVDNYLTLLDAQRSLFTAQQQLITDRLNQLTSEVNLYKALGGGWNQQTVTQQQTAKK
EDPQA

FIGURE 13C

SEQ ID NO:12 > OprJ
MRKPAFGVSALLIALTLGACSMAPTYERPAAPVADSWSGAAAQRQGAAIDTLDWKSFIVD
AELRRLVDMALDNNRSLRQTLLDIEAARAQYRIQRADRVPGLNAAATGNRQRQPADLSAG
NRSEVASSYQVGLALPEYELDLFGRVKSLTDAALQQYLASEEAARAARIALVAEVSQAYL
SYDGALRRLALTRQTLVSREYSFALIDQRRAAGAATALDYQEALGLVEQARAEQERNLRQ
KQQAFNALVLLLGSDDAAQAIPRSPGQRPKLLQDIAPGTPSELIERRPDILAAEHRLRAR
NADIGAARAAFFPRISLTGSFGTSSAEMSGLFDGGSRSWSFLPTLTLPIFDGGRNRANLS
LAEARKDSAVAAYEGTIQTAFREVADALAASDTLRREEKALRALANSSNEALKLAKARYE
SGVDNHLRYLDAQRSSFLNEIAFIDGSTQRQIALVDLFRALGGGWDEGRSLVVHRGGRS

SEQ ID NO:13 > OprN
MIHAQSIRSGLASALGLFSLLALSACTVGPDYRTPDTAAAKIDATASKPYDRSRFESLWW
KQFDDPTLNQLVEQSLSGNRDLRVAFARLRAARALRDDVANDRFPVVTSRASADIGKGQQ
PGVTEDRVNSERYDLGLDSAWELDLFGRIRRQLESSDALSEAAEADLQQLQVSLIAELVD
AYGQLRGAQLREKIALSNLENQKESRQLTEQLRDAGVGAELDVLRADARLAATAASVPQL
QAEAERARHRIATLLGQRPEELTVDLSPRDLPAITKALPIGDPGELLRRRPNIRAAERRV
AASTADVGVATADLFPAGQPQRLPRLHRRAGSQIGSSAARAWSVGPSISWAAFDLGSVRA
RLRGAKADADAALASYEQQVLLALEESANAFSDYGKRQERLVSLVRQSEASRAAAQQAAI
RYREGTTDFLVLLDAEREQLSAEDAQAQAEVELYRGIVAIYRSLGGGWQPSA

SEQ ID NO:14 > AprF
MRRLMTWLFGAFLLLLREDAFALGLLDGYHLALENDPQFQAAIQEHEAGRQYRALGRAAL
LPRLVYSYNRGRSWSDVTQTTTRGDFKEDRDYDSYVSTLSLQQPLFDYEAFSRYRKGVAQ
ALLSDERFRSQSQELLVRVLEAYTGALLAQDQIELARAQKRSYREQFQLNQRQFERGNGT
RTDTLETQARFNLAQAQEIEARDSQDAALRELERLVGAPLEIADLAPLGERFQVRPLSPA
SYTAWRDLALAENPELASLRHAVDVARYEVEQNRADFLPRLGLYASTGKSKSGSENTYNQ
RYETDSVGIQLSVPLFSGGETLAATRQATHRMEKSHYDLDDKVRETLNQVRKMYNQSSSS
AAKIRAYEMTVDSARTLVMATRKSIAAGVRVNLDLLNAEQALYSAMNELSKAKYDYLTAW
ARLRFYAGVLDEADLELVAANFVSGETPARRRDCATTDCPAPLHTLSKTDTEENRSALN

SEQ ID NO:15 > OpmM
MNRLRACLLSSALLSASSAQALGLLDAYQLAVRHDPTFQAALHERRAGSENRAIGRAGLL
PSLRYDYNKARNDSTVSQGDARVERDYRSYASTLSLEQPLFDYEAYARYRQGEAQALFAD
EQFRGRSQELAVRLFAAYSETLFAREQVVLAEAQRRALETQLAFNQRAFEEGEGTRTDLL
ETRARLSLTRAEEIAASDRAAAARRTLEAMLGQALEDRELAAPIERFPALRLQPATFEGW
RQVALQRSAELGAQRHALEAAAYEVERNRAGHLPRLSLYASSSKTHSASESTYEQKYDTD
SVGLRLSLPLFEGGRVSAATRQAGDKYAQAQAELDAQVASVINDLHSQFDLTASSLAKVR
AYEMAVAAAREQVTATRRSVAGGERVNRDVLDAEQQFYGARRDLAEARYAYLNAWLRLRQ
LAGVLEDRDLAVLAAYFGAGEGRAQVTAAIR

SEQ ID NO:16 > OpmA
MKGTPLLLIASLALGACSLGPDFTRPDRPAPGEWSLQAAAGNPSHLAAAPLAAQWWTLFD
DAQLNALLQRVQRANLDLRSAAARLQQSRAIRRSLGGDALPSVDASGNYQRQRTTSAGLF
DPSGKAGKGNYNHALAGFDASWELDFWGRVRRELEAADATVEASENELRDVQVSVLAEAA
RDYIQLRGEQNRAAIIRDNLETARRSLELTRTRLANGVATDLEVAQALAQVASMEARLPE
VEKNQAHLVNALGYLVGASPGSLLAELGPARAIPRPPGSVPVGLPSELAQRRPDIRRAEA
RLHAATASIGVAKADFYPRITLNGNFGFESLQLSSLGDWDHRQFAIGPAFSLPIFEGGRL
RGRLELREAQQQEAAIDYQRTVLRAWQEVDDAMHDYAANQRRQERLGEAVAQNRRALQSA
REQYRAGAVDFLSVLDSQRQLLDNQEQQVASDEAVSLTLVNLYKALGGGWSPTSDPASG

SEQ ID NO:17 > OpmD
MKRSYPNLSRLALALAVGTGLAACSVGPDYQRPQSPPPRVASEHLGEFSGERREAPWWSF
FDDPQLVRLVDQALARNHDIREARANLRSARALFDDRWLDQLPQVTSQAGYSRSIEQQLD
YDGEPRRRLAESYRAGFDAQWEIDLFGRLGRLSDAALARAEAADADLRLVRLSIAADTAR
AYFEIQGYQRRLDVARAQVRSWRDTLELTRSSLQLGSGLPEDVENAQANLLRSEAAIPPL
TTALESARYRLDVLRGEAPGSGAPILDGGAAAPLAKNLPLGDVDRLILQRPDVVSAERQL
AASTEDVGAATAELYPRLDLGGFIGFFALRSGDLGSASRAFELAPSVSWPAFRLGNVRAR
LRAVEAQSDAALARYQRSLLLAQEDVGNALNQLAEHQRRLVALFQSATHGANALEIANER
YRAGAGSYLAVLENQRALYQIREELAQAETASFVNVIALYKALGWGSGDLAPGAGQLAAG
ETAGANR

FIGURE 13D

SEQ ID NO:18 > OpmE
MKPYLRSSLSALILLGGCAAVGPDYAPPSASAPASFGAMPAGIDGSGVEIEWWRGFDEPA
LESLIQRALAANLDIALAGARLDEAKALLRENREEFLPRGGPAFDYQARRRGEVETPAGQ
QRDIETYRGALDASWEIDLFGRVRRSVEAAEAQAGSREALLRNVQASVAATVAMSWFQLQ
GIEAELAVVHDIAGNQRDSLEMVERLVSAGSAHEFDRLRAEALLHNVEAAVPDLERRRAA
TRNALAVLLAEAPQAFSPPVARASGERLTLRTLGVGDPAGLLARRADIAAAERNLAAATA
RIGVETAGLYPQVEVRGSIGLVAGNLDALDESGTSFNVLNPVIRWALLDRGRVWARIAAS
EARAQEALILYDRTVLRALQETDDAFNGYGAAADRLRLRLLEATANREAARLARERFVQG
DGEYLDVLEAERSDYLSRRALSIARTEQRLAVVGIYKALGGGWEACAGARRCGVATDDTS
PGVARQRDSRS

SEQ ID NO:19 >PS17 gene H
MSTNQYGGFLTDKGAAKQVEAASGGLRRNITHMLIGDAGGAPGQTPDPVPSPLQTKLVRQ
RYRVKLNRLVAADNSPSVLIAEAILPQDVGGWWMRELGLEDSDGDMIAVANCAPSYKPLV
NEGSGRTQTVRLHIAFSHAETVDLLIDPNVVTATVADLQNALLEVRATNDATGQMTRGTD
GKLALPLSLSLTGIAAGTYRSLTVDAKGRATSGSNPTTLGGYGITDALAKSDAVDVPAPN
KLLRLNAASQLPASITGNAATATKLAVPRMLSFTGDATGGASFDGSANAAVALTLANSGV
TAGTYAKVTVNGKGLVTGGAQLTAADIPALDAGKVVSGVLPIARGGTGNAIGQAATAVKL
ASPRTLAIAGDATGSAAFDGSANASISVTLANTGVAVGTYTKVRVNAKGLVTSAASLTAD
DVPWLDASKVTSGMFADARLPWYAQGLCTSAPNTTDPNTTNIPLILTNHENGPIPGTFFY
IQTMMYNQRNGNAAQIAVRYAANAEMYVRYMYDVGNKRGVWSAWKRCDVGGSFAKEADGE
LGGGVNLDTMIASGWWHQPFSANAKNGTNYPVGEAGLLTVHAPTSTMIYQTYRGYAAGGL
YWRCRYNGTWSAWYRAWDSGNFNPANYVARSEYSWASLPGKPATFPPSGHNHDATQITSG
ILPLARGGLGANNAVTARSNIGAGTIATASLGSSGWWRDNDTGYIRQWGRVTVPGDGSAA
ITFPIAFPSVCLGGFAGQTANFHPGTDASTSFYNQSTTGATLENGYQFQAVLLWEAFGR SEQ ID NO:20 >PS17 gene G
MSASDYVFSPSARVFYPVALREVYETGEGWPADAVPVSNERYLHLLAGQEAGMRIAANAS
GQPVLVDPPPLTEAERRTKARAWRDAQLAQTDGMVARHRDERDLGNDTTLQPEQFVEVMN
YRAALRNWPDDPAFPDPASRPEPPAWLAEEGTN SEQ ID NO:21 >VHML 34
MAGLKLQFTEAGLAELISAKEQGIKGAISHLAFGDMAYTPNKSQTRLQREQERVEIADYQ
DGGLSLRMAAVFSGEKEYAIREIGVFLSTGTLLGVYSQSGKTIGYRTPSVKVMQWLTLNI
TALPSDSVTVVVGTENLNLILDAEFMESAASFMRLGAATIRQALWNLQLSEKIRALES SEQ ID NO:22 >VHML 35
MGTITEQIESLKTASAEXTAAXQALAQEVSGKMAAIDKKTNDSIAKVKSTYDQKANGLTI
IATDGYRKAVEHNSGGRNTVIYDAQGNPNIMCVIPRFNIEDLGLTELDLGTGVHPAFVTN
GAPRGEILVGKYLASSAAGGSAVIGGPQPRTSVNYDTAKQLCTQKGDNWHLMSIHEWAAI
ALWSLANGTVPRGNTNYGRSHEAKWETARRADNGLPGDTSGTGRTDTGKGPATWNHDHTE
FGVCDLVGNVWEWIDQMKLDDGQILTTLDNNPGVAEANWHRHPAYFDSTSDNQSGAGNNG
SPVLSNSVTKRNGPADDDSHDYPYMHNPHFAAITKSAGYXPNELLRRLLIESATATTVGG
GLWCRNYGDRFPLRGGYWNNGSSAGLGALYLSYARSNSNSSIGFRPAFFV SEQ ID NO:23 >VHML 38
MFSYIFQGRTHTDTTRSYMNSLGMTQEQVDSVLQQKDFEEAQNLVKRQEAYRLESDPLFM
EWQYDNTPESEQAWRDKVAEIKARYPLPSES SEQ ID NO:24 >MTD
MSTAVQFRGGTTAQHATFTGAAREITVDTDKNTVVVHDGATAGGFPLARHDLVKTAFIKA
DKSAVAFTRTGNATASIKAGTIVEVNGKLVQFTADTAITMPALTAGTDYAIYVCDDGTVR
ADSNFSAPTGYTSTTARKVGGFHYAPGSNAAAQAGGNTTAQINEYSLWDIKFRPAALDPR
GMTLVAGAFWADIYLLGVNHLTDGTSKYNVTIADGSASPKKSTKFGGDGSAAYSDGAWYN
FAEVMTHHGKRLPNYNEFQALAFGTTEATSSGGTDVPTTGVNGTGATSAWNIFTSKWGVV
QASGCLWTWGNEFGGVNGASEYTANTGGRGSVYAQPAAALFGGAWNGTSLSGSRAALWYS
GPSFSFAFFGARGVCDHLILE

FIGURE 13E

SEQ ID NO:25 >P2 gene H
MSIKFRTVITTAGAAKLAAATAPGRRKVGITTMAVGDGGGKLPVPDAGQTGLIHEVWRHALNKISQDKR
NSNYIIAELVIPPEVGGFWMRELGLYDDAGTLIAVANMAESYKPALAEGSGRWQTCRMVIIVSSVASVE
LTIDTTTVMATQDYVDDKIAEHEQSRRHPDASLTAKGFTQLSSATNSTSETLAATPKAVKAAYDLANGK
YTAQDATTARKGLVQLSSATNSTSETLAATPKAVKTVMDETNKKAPLNSPALTGTPTTPTARQGTNNTQ
IANTAFVMAAIAALVDSSPDALNTLNELAAALGNDPNFATTMTNALAGKQPKDATLTALAGLATAADRF
PYFTGNDVASLATLTKVGRDILAKSTVAAVIEYLGLQETVNRAGNAVQKNGDTLSGGLTFENDSILAWI
RNTDWAKIGFKNDADGDTDSYMWFETGDNGNEYFKWRSRQSTTTKDLMTLKWDALNILVNAVINGCFGV
GTTNALGGSSIVLGDNDTGFKQNGDGILDVYANSQRVFRFQNGVAIAFKNIQAGDSKKFSLSSSNTSTK
NITFNLWGASTRPVVAELGDEAGWHFYSQRNTDNSVIFAVNGQMQPSNWGNFDSRYVKDVRLGTRVVQL
MARGGRYEKAGHTITGLRIIGEVDGDDEAIFRPIQKYINGTWYNVAQV SEQ ID NO:26 >P2 gene G
MQHLKNIKSGNPKTKEQYQLTKNFDVIWLWSEDGKNWYEEVKNFQPDTIKIVYDENNIIVAITRDASTL
NPEGFSVVEVPDITSNRRADDSGKWMFKDGAVVKRIYTADEQQQQAESQKAALLSEAENVIQPLERAVR
LNMATDEERARLESWERYSVLVSRVDPANPEWPEMPQ SEQ ID NO:27 >R2-P2 1-164:158-669
MTTNTPKYGGLLTDIGAAALATASAAGKKWQPTHMLIGDAGGAPGDTPDPLPSAAQKSLINQRHRAQLN
RLFVSDKNANTLVAEVVLPVEVGGFWIREIGLQDADGKFVAVSNCPPSYKAAMESGSARTQTIRVNIAL
SGLENVQLLIDNGIIYATQDWVKEKLAEHEQSRRHPDASLTAKGFTQLSSATNSTSETLAATPKAVKAA
YDLANGKYTAQDATTARKGLVQLSSATNSTSETLAATPKAVKTVMDETNKKAPLNSPALTGTPTTPTAR
QGTNNTQIANTAFVMAAIAALVDSSPDALNTLNELAAALGNDPNFATTMTNALAGKQPKDATLTALAGL
ATAADRFPYFTGNDVASLATLTKVGRDILAKSTVAAVIEYLGLQETVNRAGNAVQKNGDTLSGGLTFEN
DSILAWIRNTDWAKIGFKNDADGDTDSYMWFETGDNGNEYFKWRSRQSTTTKDLMTLKWDALNILVNAV
INGCFGVGTTNALGGSSIVLGDNDTGFKQNGDGILDVYANSQRVFRFQNGVAIAFKNIQAGDSKKFSLS
SSNTSTKNITFNLWGASTRPVVAELGDEAGWHFYSQRNTDNSVIFAVNGQMQPSNWGNFDSRYVKDVRL
GTRVVQLMARGGRYEKAGHTITGLRIIGEVDGDDEAIFRPIQKYINGTWYNVAQV SEQ ID NO:28 >L-413c gene H
MSTKFKTVITTAGAAKLAAATVPGGKKVNLSAMAVGDGNGKLPVPDAGQTKLVHEVWRHALNKVSVDNK
NKNYIVAELVVPPEVGGFWMRELGLYDDAGTLIAVSNMAESYKPELAEGSGRAQTCRMVIILSNVASVE
LSIDASTVMATQDYVDDKIAEHEQSRRHPDATLTEKGFTQLSSATNSTSEKLAATPKAVKAANDNANSR
LAKNQNGADIQDKSAFLDNIGVTSLTFMKHNGMIPTTDNLDSYGPEEKYLGTWSCPSQSTAKPESGYPE
DKGNGVLEVFNAGRFHCTQRYTTRTGNIYIRMLDAEWNPASPTWSAWRVITSGTRPLSTSIDLNSLGGA
EHLGIWRNSSTSIASFERHFPEDGSFGQGILEVFEGGLYGRMQRYTTRSGTMYIRGLTASWDAENPQWE
DWIAVGYQSTGWTYSGDLDDLLKPGIYSVTKQATNAPVTDSKDLAVGSIVEVKKRCDIESYIQTYTTVS
ATDAYKNRTFQRTRASGEADWGEWAEVYNSKSLLTKLGVGGVTDRLSSLDWQTYDFVPGSMITVRLSDM
TNIPDGMEWGVIDTNLINITVGPSEGGGVARSMQVWRSTSNKTNYRFFTVRLYGNPGERSFNIRRLPII
DEAQTWEAKQTFSAGLSGELSGNAATATKLKTARKINNVSFDGTSDINLTPKNIGAFASGKTGDTVAND
KAVGWNWSSGAYNATTGGASTLILHFNIGEGSCPAAQFRVNYKNGGIFYRSARDGYGFEADWSEFYTTT
RKPTAGDVGALSLSGGQLNGALGIGTSSDLGGNSIVLGDNDTGFKQNGDGNLDVYANSVHVMRFVSGSI
QSNKTINITGRVNPSDYGNFDSRYVRDVRLGTRVVQTMQKGVMYEKSGHVITGLGIVGEVDGDDPAVFR
PIQKYINGTWYNVAQV SEQ ID NO:29 > L-413c gene G
MQHLKNIKSGNPKTKEQYQLTKNFDVIWLWSEDGKNWYEEVSNFQEDTIKIVYDENNIIVGITRDASTF
NPEGFSVVEVPDITANRRADDSGKWMFKDGAVIKRIYTADEQQQQAESQKAALLSEAESVIQPLERAVR
LNMATDEERSRLEAWERYSVLVSRVDPANPEWPEMPQ

FIGURE 13F

SEQ ID NO:30 >R2-L-413c 1-164:158-913
MTTNTPKYGGLLTDIGAAALATASAAGKKWQPTHMLIGDAGGAPGDTPDPLPSAAQKSLINQRHRAQLN
RLFVSDKNANTLVAEVVLPVEVGGFWIREIGLQDADGKFVAVSNCPPSYKAAMESGSARTQTIRVNIAL
SGLENVQLLIDNGIIYATQDWVKEKVAEHEQSRRHPDATLTEKGFTQLSSATNSTSEKLAATPKAVKAA
NDNANSRLAKNQNGADIQDKSAFLDNIGVTSLTFMKHNGMIPTTDNLDSYGPEEKYLGTWSCPSQSTAK
PESGYPEDKGNGVLEVFNAGRFHCTQRYTTRTGNIYIRMLDAEWNPASPTWSAWRVITSGTRPLSTSID
LNSLGGAEHLGIWRNSSTSIASFERHFPEDGSFGQGILEVFEGGLYGRMQRYTTRSGTMYIRGLTASWD
AENPQWEDWIAVGYQSTGWTYSGDLDDLLKPGIYSVTKQATNAPVTDSKDLAVGSIVEVKKRCDIESYI
QTYTTVSATDAYKNRTFQRTRASGEADWGEWAEVYNSKSLLTKLGVGGVTDRLSSLDWQTYDFVPGSMI
TVRLSDMTNIPDGMEWGVIDTNLINITVGPSEGGGVARSMQVWRSTSNKTNYRFFTVRLYGNPGERSFN
IRRLPIIDEAQTWEAKQTFSAGLSGELSGNAATATKLKTARKINNVSFDGTSDINLTPKNIGAFASGKT
GDTVANDKAVGWNWSSGAYNATTGGASTLILHFNIGEGSCPAAQFRVNYKNGGIFYRSARDGYGFEADW
SEFYTTTRKPTAGDVGALSLSGGQLNGALGIGTSSDLGGNSIVLGDNDTGFKQNGDGNLDVYANSVHVM
RFVSGSIQSNKTINITGRVNPSDYGNFDSRYVRDVRLGTRVVQTMQKGVMYEKSGHVITGLGIVGEVDG
DDPAVFRPIQKYINGTWYNVAQV

SEQ ID NO:31 >T4 tail fiber (gp37)
MATLKQIQFKRSKIAGTRPAASVLAEGELAINLKDRTIFTKDDSGNIIDLGFAKGGQVDGNVTINGLLR
LNGDYVQTGGMTVNGPIGSTDGVTGKIFRSTQGSFYARATNDTSNAHLWFENADGTERGVIYARPQTTT
DGEIRLRVRQGTGSTANSEFYFRSINGGEFQANRILASDSLVTKRIAVDTVIHDAKAFGQYDSHSLVNY
VYPGTGETNGVNYLRKVRAKSGGTIYHEIVTAQTGLADEVSWWSGDTPVFKLYGIRDDGRMIIRNSLAL
GTFTTNFPSSDYGNVGVMGDKYLVLGDTVTGLSYKKTGVFDLVGGGYSVASITPDSFRSTRKGIFGRSE
DQGATWIMPGTNAALLSVQTQADNNNAGDGQTHIGYNAGGKMNHYFRGTGQMNINTQQGMEINPGILKL
VTGSNNVQFYADGTISSIQPIKLDNEIFLTKSNNTAGLKFGAPSQVDGTRTIQWNGGTREGQNKNYVII
KAWGNSFNATGDRSRETVFQVSDSQGYYFYAHRKAPTGDETIGRIEAQFAGDVYAKGIIANGNFRVVGS
SALAGNVTMSNGLFVQGGSSITGQVKIGGTANALRIWNAEYGAIFRRSESNFYIIPTNQNEGESGDIHS
SLRPVRIGLNDGMVGLGRDSFIVDQNNALTTINSNSRINANFRMQLGQSAYIDAECTDAVRPAGAGSFA
SQNNEDVRAPFYMNIDRTDASAYVPILKQRYVQGNGCYSLGTLINNGNFRVHYHGGGDNGSTGPQTADF
GWEFIKNGDFISPRDLIAGKVRFDRTGNITGGSGNFANLNSTIESLKTDIMSSYPIGAPIPWPSDSVPA
GFALMEGQTFDKSAYPKLAVAYPSGVIPDMRGQTIKGKPSGRAVLSAEADGVKAHSHSASASSTDLGTK
TTSSFDYGTKGTNSTGGHTHSGSGSTSTNGEHSHYIEAWNGTGVGGNKMSSYAISYRAGGSNTNAAGNH
SHTFSFGTSSAGDHSHSVGIGAHTHTVAIGSHGHTITVNSTGNTENTVKNIAFNYIVRLA SEQ ID NO:32 >T4 chaperone (gp38)
MKIYHYYFDTKEFYKEENYKPVKGLGLPAHSTIKKPLEPKEGYAVVFDERTQDWIYEEDHRGKRAWTFN
KEEIFISDIGSPVGITFDEPGEFDIWTDDGWKEDETYKRVLIRNRKIEELYKEFQVLNNMIEASVANKK
EKFYYKNLKRFFALLEKHEHLGGEFPSWPEKEQKPWYKRLFKHYV

FIGURE 13G

SEQ ID NO:33 >AB17 tail fiber
MATLKQIQFKRSKTAGARPAASVLAEGELAINLKDRVLFTKDDQGNIIDLGFAKGGSIDG
NVIHTGNYNQTGDYTLNGVFTQTGNFNLTGIARVTRDIIAAGQIMTEGGELITKSSGTAH
VRFFDNNSRERGIIYAPANDGLTTQVLNIRVQDYAAGSESTYAFSGSGLFTSPEVSAWKS
ISSPQILTNKVITNNKSTGDYDIYSMADNVPLSESTTAINHLRVMRNAVGSGIFHEVKDN
DGITWYSGDGLDAYLWSFTWSGGIKSSHSISIGLTPGNKDYSILGPSSIALGDNDTGFKW
HQDGYYFSVNNGTKTFLFNPSETTSLRKFVAGYSTNGTDLTTPPTENYALATVVTYHDNN
AFGDGQTLLGYYQGGNYHHYFRGKGTTNINTHGGLLVTPGNIDVIGGSVNIDGRNNSSTL
MFRGNTTGYSSVDNMDIKVWGNTFVDPSGGIRKNIMEISDATSWMSYIQRLTTGEVEMNV
NGSFESSGVTAGDRGVHTTGEISSGAVNALRIWNADYGAIFRRSEGSLHIIPTAYGEGKN
GDIGPLRPFSLALDTGKVTIPDLQSSYNTFAANGYIKFVGHGAGAGGYDIQYAQAAPIFQ
EIDDDAVSKYYPIVKQKFLNGKAVWSLGTEINSGTFVIHHLKEDGSQGHTSRFNQDGTVN
FPDNVSVGGGEATIARNGNIWSDIWKTFTSAGDTTNIRDAIATRVSKEGDTMTGTLWINK
DAAGIVLNPPLTSDSSFIRSDTAGANNWYIGKGGADNGLGFYSYVTQGGVYITNNGEISL
SPQGQGTFNFNRDRLHINGTQWAAHQGGGWGNQWNQEAPVFVDFGNVGNDSYYPIIKGKS
GITNEGYISGVDFGMRRITNTWAQGIIRVGNQENGYDPQAVYEFHHNGTFYAPSLLKSSR
VSAGGGDPAWGGPCIVLGDNDTGLLWENDGIFNAYANGQGVFSFRPGLAQTFGDVNFHCN
AGMYVRDNIDVNDVYIRSDIRCKSEIKLIKNAQEKSKLLGGYTYLLKNSVTDEVKPSAGL
IAQEVQEVLPELVSEDKETGLLRLNYNGIIGLNTAAINEHTDEIKELKSEITELKALIKS
LIK SEQ ID NO:34 >AB17 tail fiber assembly
MAVVGIPGWIGTSAVAETGQRWMTAASRELRLGNPSWMSQFAGRSREIIHTLGADHNFNG
QWFRDRCFEAGSAPIVFNITGNLVSYSKDVPLFFMYGDTPNEYVTLNIHGGVHMWGRGGN
GTVNGNPGTNGGDVIQNDIGGRLRIWNYGVIASGGGGGGAVSLXNSWAPNATAGGGGGRP
FGIGGGGVNWPGGNASYDAPGGAGYTSQFGGGNGGDAGGRGGDGWGNHLSRSGGGAPGRA
VFGSSPSWGATGTIYGSWI SEQ ID NO:35 > OpmQ
MKNLSLISACLLLGACGSTPAPLDSGLAAPSQWRYLAAGRSDASDIRQWWKAFGAPELDS
LLQRALLNSQDLGAAVARVRQAQASAVIAGAPLLPELNATLGASRQKLLRDSGYSGTDAT
SDNDAVDSFSAGLSASYEVDFWGGRQAAYRSALESLKASEYDRATVELTLLSGVANSYLQ
VLALREQQRIARLNLDNAEHVLRLVETRHAAGSATALEVAQQSSLVASQRKQLPLLEQQA
HEALITLATLIGEPVQALQVAERPFDSLRWPETGAGLPSELLSRRPDIANAEAQLAAAQA
DVQVARAALFPKLTLSASLSSGANRAADTFRNPYYNLGANLLAPIFNHGRLRAERDRSLA
RQEELLETYRKAILTAFADTERSLNSIDGLDRQLHWQQQELEQAQRAFDLSDSRYQAGAE
TLLTVLETQRTLYAAQDAAVQLRLARLQASVGLYKALGGGWQSDRQGLARKD SEQ ID NO:36 > OpmB
MKHTPSLLALALVAALGGCAIGPDYQRPDLAVPAEFKEAEGWRRAEPRDVFQRGAWWELY
GDQTLNDLQMHLERSNQTLAQSVAQFRQAEALVRGARAAFFPSITGNVGKTRSGQGGGDS
TVLLPGGSTVSSGGSGAISTSYSTNLSVSWEVDLWGKLRRQLEANQASLHASAADLAAVR
LSQQSQLAQNYLQLRVMDEQIRLLNDTVTAYERSLKVAENKYRAGIVTRADVAQARTQLK
STQAQAIDLKYQRAQLEHAIAVLVGLPPAQFNLPPVASVPKLPDLPAVVPSQLLERRPDI
ASAERKVISANAQIGVAKAAYFPDLTLSAAGGYRSGSLSNWISTPNRFWSIGPQFAMTLF
DGGLIGSQVDQAEATYDQTVATYRQTVLDGFREVEDYLVQLSVLDEESGVQREALESARE
ALRLAENQYKAGTVDYTDVVTNQATALSNERTVLTLLGSRLTASVQLIAAMGGGWDSADI
ERTDERLGRVEEGLPPSP SEQ ID NO:37 OpmJ
MPLASHLRCVALALGISTALGCANRNQPAPRAESLDPGLSRVAGTRGDALPAQWWTLYQD
PGLNHLVAAALRHNRDLAAADAHARALLGHLRGAQGERWPRTEVGYGYQYGRDGDDQTLA
EATDEDLHSQWKHTVRLDLSYQLDLWGEVRARIAAAKADAEAAQAARDLLRVSVASQTTL
AYVRACALARRAEVQRRSVGLLDASLALSERQLAAGLSSELQRRRLLALRERTRAALPML
EARRRAALYELALLSGRSPRQLDAPAATCAGIPQLRRALPTGDGWSLLARRPDVRAAERR
LAAADARRALAEAELYPRISFAVGAETSAATLAGLGSGALAYAAGPLLSWRFPNRESAR
GRLDSAAAERDAALARFDGAVLGALREVERALALYAGERQRRADLQRALDEQRHAYRLAR
SNYRAGALDALELLDSQRSLVADRARLVDAEMRVAERQVELFRALGGGWQAASSPSHQEN
GQ

FIGURE 13H

```
SEQ ID NO:38 > OpmG
MPFPLLHPWPQRLALASAILLAAGCVTSEGLEPNARLQPAGALQAGRSLDGVALSPAAWP
RQDWWTGLGDRQLDQLIGEALQGTPDLQIAEARARQAAATAQAQDAARQPTLDAKASYSG
IRAPTSVAPAPLGGRYSAIKYLSLGFNYDFDLWGGERAAWEAALGQANAARIDSQAARIG
LSASIARAYSDLAHAFTVRDLAEEELKRSQRMTELSQKRMSAGLDSKVQLQQTQTQLATA
RQQLSAAEQDIASARIALAVLLGKGPDRGLELQRPQPLNPASLSLPSVLPAELLGRRADI
VAARWRVEAARRNIDSAKTEFYPNLNLGAMAGLAALHTSDVLQAPSRFFQVAPAISLPIF
DGGRRRANLAERDADYDLAVGQYNKTLVQALGEVSDDLGKLRSLEQQVIDQRQARDIARS
NFDLAMRRYGEGVGSYLDALSVQQQLLVAERQLASLESQQIDLSVQLVQALGGGFQPDSR
SAALATAKAPAE

SEQ ID NO:39 > OpmI
VPRALRKELTLVGSFVGFLVVFSAISGCVSTGDIAPEAATLDANALATDHAIQAAAREAG
WPQAQWWKVYADPQLDAWIEKALDGNPGLAVAHARVRQAKSMAGLVESIESPQIEGKGSL
VRHRWPDDYFYGPGDLARTTSWNNSTEIGLNYKLDLWGRDRSDSERAVDLAHMAAAEARQ
AQLELEGNIVRAYVQLSLQYAEMDIAKAMLQQQRDILALAQRRLRGGIGTHFEVSQAEVP
LPETERRIEVIDEEIQLTRNLLAALAGKGPGEGRTIRRPSLNLAAQPSLPSALPAELLGR
RPDVVARRWQVAALAKGVDVARADFYPNVDLMASVGFSAVGGGMLEFFRSAKYTYSAGPA
VTLPIFDGGRLRSQLGEAAAGYDAAVEQYNQTLVDALKNISDQLIRLHSVDIQKDFAAQS
VASAQKTYDIATLAYQRGLTDYLNVLNAQTRLFQQQLVQEQVQAARLAAHASLLTALGGG
VGAGADTPAQRKLAPENVPVRAVSSR

SEQ ID NO:40 > OpmH
MLRRLSLAAAVAAATGVAWAAQPTPLPTKTDLISVYKEAVDNNADLAAAQADYLARKEVV
PQARAGLLPQLGAGARVGDTRIAFDERPATVKRNSQVVQATLSQPLFRADRWFQWQAAKE
TSDQARLEFSATQQDLILRSAETYFTVLRAQDNLATSKAEEAAFKRQLDQANERFDVGLS
DKTDVLEAQASYDTARANRLIAEQRVDDAFQALVTLTNRDYSAIEGMRHTLPVVPPAPND
AKAWVDTAVQQNLRLLASNYAVNAAEETLRQRKAGHLPTLDAVAQYQKGDNDALGFANSA
ANPLVHYGKYVDERSIGLELNIPIYSGGLTSSQVRESYQRLNQSEQSREGQRRQVVQDTR
NLHRAVNTDVEQVQARRQAIISNQSSLEATEIGYQVGTRNIVDVLNAQRQLYAAVRDYNN
SRYDYILDTLRLKQAAGTLSPADLEALSAYLKQDYDPDKDFLPPDLAKAAAEQLQSKPRQ
QY

SEQ ID NO:41 > OpmK
MRALAGLLCGLLGLVPGAAAYEPDVFGTTGQVAGQAVYDLGGSGLPCRGGPPPTELSLEE
AIERILCHDPQTRLAWANAKAQAQVGIGKSAYLPRLDGRLDASRGYSDMDYRDAPYLSG
DGHRHRRGASLQLSWVLFDFGRRSAALRNAQQLLLAANASQDATLQNTFALAAQAYYDAL
AAQRSLAASRQVAELAAQNLEAADAKYRAGAAALSDRLQAQTALSQASLAQVRDEGALSN
ALGVIALRMGLAPDTPLRLSGELEAQPDTGFVKAIDEMLAEARREHPALLAAQARLKAAA
ASVEESRAAGRPSLALSANLARSHSDQAMAFNGDTRERDRSIGLQLNIPLFEGFERTYQV
RNALARREASEAELADTEQQVSLEVWNNYQSLSVETRSLARTRELVEQSRQSLEVVQGRY
RSGVGSMIELLNALTAYASAEDQHIRALGNWQTSRLRLAASLGRLGFWSLR

SEQ ID NO:42 > OpmN
MPILRPLASAGKRACWLLMGLCLGLPALANEAPVSFNGTSISLEQALERALRSNPELAAV
GRETEIASGARQQAGLIPNPDLSWSVEDTRQGNRQTSVSIAQPLELGGKRGARVEVAKRG
SEIAWTQLEVRRAELRAQVRGAYYAALTAQERVRLAKTSLDLARRALQAADRRVKAGSIS
SVERVRAQVLADNAQLDLSQAELEQQRTYVQLSSTWDEPQPGFARVGGALDAVPASITRG
ALLRHLDESPTLRLAAQEVARGEAQVDLEKRQRIPNLTVSIGSKYDQTARDGRGERVNLI
GLSMPLPLFDRNQGNIYAAQSRADQARDLQRATLLRLRSEAVQAYDQLRTSEQELALVRR
DLLPGAQSALDSMTRGFEMGKFNFLDVLDAQRTLVGVRAQYVRALDAAAQARVSMERLLG
EDIGHLGQ
```

FIGURE 13I

SEQ ID NO:43 > OpmF
MNRWGLGVLWLVTALPVAASVNPALSPDVPSMAREQGRSVLLSEQVIDLSLSDAVYLGLR
NNRGIRSAYLQRIAQKFDLRVAADAFNPKLVVRGDYRANRATEDRTRTSNVSPTATLLGE
YGTRFSLAWVKQFRTADEAGRYRSDGLDLTVVQPLLRDAGWDVTTAPLRLARLSEDANRL
QLKASVSQTISQVIGAYRELLRAQEQARIAREALARTQELLEVNRAMIRAGRMAEFEIVQ
TEADVASQELNVEESTNQVDSARLALLQLLALDLSTQIRASDALAATPIEVDRQQAIRTA
LQQQPEYLQRLIGSRQADLNLVLAKNQRLWDVSLVGGASQIRDRYSEGGGDNSRSWDSYA
GVQVEIPIGDLSRRQAEVRAQVDVENQKILIEDARQTLEQNVIDAVRDLGTRWRQYQIAQ
RATALSRRKLEIEREKLRVGRSSNFQVLSFETDLRNVENTQLNALISFLNAQTQLDLIVG
MTLDSWEISLNDH

SEQ ID NO:44 > OpmL
MRGRRQYARKGRRHGKGAIWLLSLGLPMFASAMPLDQAVRAGLAIHPEVRSAMAEADRAG
TEVEMAKGGYYPSVTMSGGPQEFDFGEIVYDLTASQMLYDWGRVTSKVDSASATQRKLSE
AVLVARDDAALDIVETYLDVLASERRVEAVREHIQRLDGIREMTQARGGDGYADRSELDR
ANLELSRAQEQLSLEKGNLQDARNQYAILVGQEPADLVEPEPMSLQRYLAASDMARVIRE
SPLQRKALEDANVAEAEVREAKASLLPQLNLEASALRREIGGHPESDSVVSLRFRMDTFQ
GLSNFRRPTAAQQRLESAKWSADAMQRDIRRQLQNLFDNGDTLRWREQSLTQQVTESEQV
GELYREQFEVGRRDVIDLLNVQRERFEAERQLINLRIERKRIEYRAAAQVGLLGPLLENR
LNHGS

SEQ ID NO:45 >phiCTX gene H
MTSPKYGGLLTDIGAAALIAASEAGKKWQPTHMLIGDAGGAPGETADPIPSAAQTKLIRQ
RYRAQLNRLFVSEQSANVLAELVLPMAIGGFWIREIGLEDADGKFVAVANCPPSFKASV
ESGSARTQTIRVQIILSGMEHVELIIDDGIVYATQDWVTAKVAADFKGRKVLAGNGLVGG
GDLSADRTIALPASGVGAGTYRAVTVNANGIVTAGSNPTTLGGYGITDALHASEAVTTPT
ANKLLRLNAAGLLPASITGNAATASRLAAPITLSASGDATWSARFDGATNVNGVLTLANS
GVTAGTYAKVTVNAKGLVTGATGLVASDIPALDAGKITSGILPAARGGTGNGIGQAATAV
KLVAPRTIYLGGDVSGSTTFDGSANAGITVTLANGVNAGSYPKVTVNAKGLVTGGGGLTA
ADIPALDASKIATGRLDLERLPLVSQGLATAVHTSVDPNSVVIPLVLTNHANGPVAGRYY
YIQTMFYPTVEGNATQIATGYAGVADMYVRYAYASPATTDSSKREWSAWVRCDLGGAFAH
APDGELGGYVNLDSMIASGWWHQPFTANAKNGANYPVGEAGLLTVHAPTASMIYQTYRGY
AAGGLYWRCRYNGTWSAWYRAWDSGNFNPANYVAKSEYSWASLPGKPSNFPPSVHVHSAA
SRGVSGWYKNNDTGVIFQWVNLSIGDHPGGVIDRVVTFPIAFPNACLHVVPTVRENGRPA
IPASTVTVAEKARTATNCTIVSSEYIGNVQNFGINVFAIGY

SEQ ID NO:46 > AV085
GCTTCAATGTGCAGCGTTTGC

SEQ ID NO:47 > AV088
GCCACACCGGTAGCGGAAAGGCCACCGTATTTCGGAGTAT

SEQ ID NO:48 > AV087
ATACTCCGAAATACGGTGGCCTTTCCGCTACCGGTGTGGC

SEQ ID NO:49 > AV086
TCCTTGAATTCCGCTTGCTGCCGAAGTTCTT

SEQ ID NO:50 > AV110
TTTATTAGCGGAAGAGCCGACTGCACGGTGCACCAATG

SEQ ID NO:51 > AV114
CCCTCGAATTCATGAATACTGTTTCCTGTGTGAAATTG

SEQ ID NO:52 > AV118
CTTCCTTTCATGACGACCAATACTCCGAA

SEQ ID NO:53 > AV116
ACCACGAATTCTTCATCGTCCAAATGCCTC

FIGURE 13J

SEQ ID NO:54 > AV107
CACCATCTAGACAATACGAGAGCGACAAGTC

SEQ ID NO:55 > AV091
TCCTCAAGCTTACGTTGGTTACCGTAACGCCGTG

SEQ ID NO:56 > AV127
TTCTTTAAGCTTTTCCTTCACCCAGTCCTG

SEQ ID NO:57 > AV124
CCTCCTGAATTCTTATTGCGGCATTTCCG

SEQ ID NO:58 > AV126
TCCTTCGAATTCTTACACCTGCGCAACGT

SEQ ID NO:59 > AV125
CCTCCTGAATTCTTATTGCGGCATTTCCG

SEQ ID NO: 60
phiV10 tail protein (putative O157 depolymerase)
Bacteriophage phiV10
Accession AAZ95917.1
>phiV10 tail protein
MTVSTEVNHNEYTGNGVTTSFPYTFRVFKESDLVVQVVDLNDNITVLTLDTDYTVTGAGG
YEGGNVILATALANGYQISISRELSVTQETDLRNQGKFFAEVHEDAFDKTMLIQQVRSW
FSLALRKPSFVANYYDAMDNYIRNLRDPVRPQDAATKKYVDGVAETNLSRTLRTPEPIPA
LPGIEQRKNKIVAMDDTGNPIMVLPESGSATDVMIQLAANDGFKFIGQCPDILTLRTIEP
EKNGQRITLRQHTIGTGLGGGVFRAVLDGTGYTDDDGVVIKTAGGSVWLRVNADKVNPFM
FGATGVADDTAALQKMLECGRAAELGTNVWKASNLELNNKSCSLSGSGLHVSRIEQISGA
TGALLTITQDCSLIYLSDCGLYGDGITAGTSGVTMETGNPGGAPSYPFNTAPDVRRDLYI
SNVHITGFDELGFDYPETNFSVSTHGLFIRNIKKTGAKIGTTDFTWTNLQIDTCGQECLV
LDGAGNCRIIGAKLIWAGSENETPYSGLRISNSQNVNMTGVELQDCAYDGLYIKNSTVAI
SGLNTNRNSASSNLSYHNMVFENSIVTVDGYVCRNYAATSLYDLNSQAGNVRCIGSDSTV
LINGIYESEVNSERLMGDNNLIQPYSGDLIINGLKNYYTYTGSVKNNIPTFDGVVTTATY
VSAPSILGQGNMLKLTQSNKDKLLFSDKVSRHGCTIGLVLIPSFTGATTMTAFTLGSGYS
PSGNSAVMQFIVNSSGVQTIAILLSGDGITQTLTSDLTTEQALASGGVYHFAMGFAPGRL
WWSIIDINTGRRIRRAYRQPDLHAAFNSIFNSGTSSITAFSGPLAGDIACEGAGSHVYVG
GFSSESDYAASRMYGLFTPVDLKQYSFRTLNGNI

FIGURE 13K

Genbank ABQ88383

SEQ. ID. NO.:61
>CUS3 endosilidase tail spike
MTDITANVIVSMPSQLFTMARSFKAVANGKIYIGKIDTDPVNTENQIQVYVENEDGSHVP
VSQPIIINAAGYPVYNGQIAKFVTVQGHSMAVYDAYGAQQFYFPNVLKYDPDQLRQQLED
TDGANKYPKLQIARWRDSYDVRGWGAIGDVHDDTSALSELLSVATGGEKIDGRGLTFKV
STLPDVSRFKNARFLFERIPGQPLFYVSEDFIQGELFKITDTPWYNAWTQDKTFVYDNVI
YAPFMAGDRHGVNNLHVAWVRSGDDGKTWTTPEWLTDLHENYPTVNYHCMSMGVVRNRLF
AVIETRTVSGNKLQVAELWDRPMSRSLRVYGGITKAANQQVAYIRITDHGLFAGDFVNFS
NSGVTGVTGNMTVTTVIDKNTFTVTTQNTQDVDQNNEGRYWSFGTSFHSSPWRKTSLGTI
PSFVDGSTPVTEIHSFATISDNSFAVGYHNGDIGPRELGILYFSDAFGSPGSFVRRRIPA
EYEANASEPCVKYYDGILYLTTRGTLSTQPGSSLHRSSDLGTSWNSLRFPNNVHHSNLPF
AKVGDELIIFGSERAFGEWEGGEPDNRYAGNYPRTFMTRVNVNEWSLDNVEWVNVTDQIY
QGGIVNSAVGVGSVCIKDNWLYYIFGGEDFLNPWSIGDNNRKYPYVHDGHPADLYCFRVK
IKQEEFVSRDFVYGATPNRTLPTFMSTSGVRTVPVPVDFTDDVAVQSLTVHAGTSGQVRA
EVKLEGNYAIIAKKVPSDDVTAQRLIVSGGETTSSADGAMITLHGSRSSTPRRAVYNALE
HLFENGDVKPYLDNVNALGGPGNRFSIVYLGSNPVVTSDGTLKTEPVSPDETLLDAWGDV
RYIAYKWLNAVAIKGEEGARIHHGVIAQQLRDVLISHGLMEEESTTCRYAFLCYDDYPAV
YDDVITGQREMPLTDNDGSIIVDEDDNPVMVMEDIIERVEITPAGSRWGVRPDLLFYIEA
AWQRREIERIKARLDLIEGKH Genbank AF335538 (complete genome of HK620)

SEQ. ID. NO.:62
>HK620 tail spike
MTDSINANVVVSMPSQLFTMARSFKAVANGKIYIGKIDTDPVNPENRIQVYVENEDGSHV
PVSQPIIINAAGYPVYNGQIAKFVTVQGHSMAVYDAYGAQQFYFPNVLKYDPDQFRAIIE
SPEGAGHVGYQYRRNTGSTMRMVSDVLDERVSLWDFHCDPSGNVIQPGPNVDSRQYLQAA
IDYVSSNGGGTITIPAGYTWYLGSYGVGGIAGHSGIIQLRSNVNLNIEGRIHLSPFFDLK
PFQVFVGFDNGDPASSGNLENCHIYGHGVVDFGGYEFGASSQLRNGVAFGRSYNCSVTGI
TFQNGDVTWAITLGWNGYGSNCYVRKCRFINLVNSSVNADHSTVYVNCPYSGVESCYFSM
SSSFARNIACSVELHQHDTFYRGSTVNGYCRGAYVVMHAAEAAGAGSYAYNMQVENNIAV
IYGQFVILGSDVTATVSGHLNDVIVSGNIVSIGERAAFSAPFGAFIDIGPDNSGASNVQD
IQRVLVTGNSFYAPANITDSAAITLRANLNGCTFIANNFDCRYMVYNAPGTTSPVVQNLV
WDKSNVIGGTHANQRAGQNLFDMQFASVVNSTIEVQLSCEDLSMFSCILFPASCQLSYSK
ITVDSAWTKSMSNTAVFEGNQQAGANVYVSYPATVNLTSYNTQGAVPFFSTDTNYAWVTS
AYSLSINENLDFSPPATYTNKANGQLVGVGYNEIGGVRSVSVRLMLQRQV Genbank NP_958190

SEQ. ID. NO.:63
>Sf6 tail spike
MTDIITNVVIGMPSQLFTMARSFKAVANGKIYIGKIDTDPVNPENQIQVYVENEDGSHVP
VSQPIVINAAGYPVYNGQIAKFVTEQGHSMAVYDAYGSQQFYFQNVLKYDPDQFGPDLIE
QLAQSGKYSQDNTKGDAMIGVKQPLPKAVLRTQHDKNKEAISILDFGVIDDGVTDNYQAI
QNAIDAVASLPSGGELFIPASNQAVGYIVGSTLLIPGGVNIRGVGKASQLRAKSGLTGSV
LRLSYDSDTIGRYLRNIRVTGNNTCNGIDTNITAEDSVIRQVYGWVFDNVMVNEVETAYL
MQGLWHSKFIACQAGTCRVGLHFLGQCVSVSVSSCHFSRGNYSADESFGIRIQPQTYAWS
SEAVRSEAIILDSETMCIGFKNAVYVHDCLDLHMEQLDLDYCGSTGVVIENVNGGFSFSN
SWIAADADGTEQFTGIYFRTPTSTQSHKIVSGVHINTANKNTAANNQSIAIEQSAIFVFV
SGCTLTGDEWAVNIVDINECVSFDKCIFNKPLRYLRSGGVSVTDCYLAGITEVQKPEGRY
NTYRGCSGVPSVNGIINVPVAVGATSGSAAIPNPGNLTYRVSLFGDPASSGDKVSVSGV
TINVTRPSPVGVALPSMVEYLAI

FIGURE 13L

Genbank NP_720339

SEQ. ID. NO.:64
phage ST64T tail spike
MTDITANVVVSNPRPIFTESRSFKAVANGKIYIGQIDTDPVNPANQIPVYIENEDGSHVQ
IAQPLIINAAGKIVYNGQLVKIVTVQGHSMAIYDANGSQVDYIANVLKYDPDQYSIEADK
KFKYSVKLSDYPTLQDAASAAVDGLLIDVDYHFYNGEKVDFGGKVLTIECKAKFIGDGNL
IFTKLGKGSRIAGVFMESTTTPWVIKPWTDDNQWLTDAAAVVATLKQSKTDGYQPTVSDY
VKFPGIETLLPPNAKGQNITSTLEIRECIGVEVHRASGLMAGFLFRGCHFCKMVDANNPS
GGKDGIITFENLSGDWGKGNYVIGGRTSYGSVSSAQFLRNNGGFERDGGVIGFTSYRAGE
SGVKTWQGTVGSTTSRNYNLQFRDSVVIYPVWDGFDLGADTDMNPELDRPGDYPITQYPL
HQLPLNHLIDNLLVRGALGVGFGMDGKGMYVSNITVEDCAGSGAYLLTHESVFTNIAIID
TNTKDFQANQIYISGACRVNGLRLIGIRSTDGQGLTIDAPNSTVSGITGMVDPSRINVAN
LAEEGLGNIRANSFGYDSAAIKLRIHKLSKTLDSGALYSHINVGPGSGSAWTQLTAISGN
TPDAVSLKVNHKDCRGAEIPFVPDIASDDFIKDSSCFLPYWENNSTSLKALVKKPNGELV
RLTLATL SEQ. ID. NO.:65
>epsilon15 tail spike
MTVSTEVDHNDYTGNGVTTSFPYTFRIFKKSDLVVQVVDLNENITELILDTDYTVTGAGG
YTCGDVVLSSPLANGYQISISRELPVTQETDLRNQGKFFAEVHENAFDKLTMLIQQVRSW
LSLALRKPSFVANYYDALGNYIRNLRDPSRPQDAATKNYVDNLSEGNNSYADNLFSRTLR
VPEKINTLPSSLDRANKIPAFDSNGNAIVIIPQSGSASDVLIELAKPSGSGLVGFSHSNN
YNPGMVGEKLQNVVYPTDAPFYAPTDGTSDATTALQSAITHCEGKNAVLCINKSFSVSDS
LSISSPLCVFAMNEQCGIVSSAPAGHAAVIFNGDNICWNGGFIRGLNQPSSSTIRQDGVL
LNGNDCVLDNVSINGFFAKGLHTSNADGSGVGIRDYGTRNTISKCRVEYNKFGISLEGKD
GWVLGNYVSNHYRMSSEAKPWDDTSNYWDGIVGGGEWLGVATGYLIDGNEFEDNGQSGIY
AGGNGGIFAKNRITNNHIHGNWNRGIDFGVVQRLANSDVYENIITDNIVHNNRAANIWLA
GVRDSIINNNNSWFTDDYRSMFAGNFDACVCLTLADGGEKAAPTGNQVNGNRCKTLESDD
QISGFTLNITDTARGNQVRDNVLSPIGEAYIPNPELYAVNNIDIPTEFAFTPQLIGGSGV
TLGNSSGKLTANGNVFSLSLSISAQSVSSPSGSLTIGYIPGLSGTSVRHHNVRTEFYNNL
NTTMQRAQPYVNIGDSADQLRVYRLADGLSKDDLLEYFMSNSDLRMVGDIEIEPYNFSRS
VTVVGHSFCTSDVMSTELNRLLGTDIYNFARGGASDVEVAMSQEAITRQYAPVGGSIPAS
GSVALTPTEVGIFWNGATGKCIFGGIDGTFSTTLVNAGTGETQLVFTRDSAGSAVSVSTT
ATFAMRPYTRFNTNTIPAGRKHSLHRDDIYIVWGGRNSTDYTRYVSELHTMVANMHTQRF
VICPEFPYDTETTGTTGATNLAALNNNLKADFPDNYCQISGVDLLQNFKSKYNPAYAGDV
TDIANGITPRSLREDNLHPSETLQPNGLYIGAKVNADFIAQFIKSKGWGG SEQ ID NO: 66
Accession AAA6437
>galacturonase
MRGLFLLALGAIPALVSGQLSGSVGPLTSASTKGATKTCNILSYGAVADNSTDVGPAITS
AWAACKSGGLVYIPSGNYALNTWVTLTGGSATAIQLDGIIYRTGTASGNMIAVTDTTDFE
LFSSTSKGAVQGFGYVYHAEGTYGARILRLTDVTHFSVHDIILVDAPAFHFTMDTCSDGE
VYNMAIRGGNEGGLDGIDVWGSNIWVHDVEVTNKDECVTVKSPANNILVESIYCNWSGGC
AMGSLGADTDVTDIVYRNVYTWSSNQMYMIKSNGGSGTVSNVLLENFIGHGNAYSLDIDG
YWSSMTAVAGDGVQLNNITVKNWKGTEANGATRPPIRVVCSDTAPCTDLTLEDIAIWTES
GSSELYLCRSAYGSGYCLKDSSSHTSYTTTSTVTAAPSGYSATTMAADLATAFGLTASIP
IPTIPTSFYPGLTPYSALAG

FIGURE 13M

SEQ ID NO: 67
R2-V10 Fusion
>R2 1-164:V10 204-875
MATNTPKYGGLLTDIGAAALATASAAGKKWQPTHMLIGDAGGAPGDTPDPLPSAAQKSLI
NQRHRAQLNRLFVSDKNANTLVAEVVLPVEVGGFWIREIGLQDADGKFVAVSNCPPSYKA
AMESGSARTQTIRVNIALSGLENVQLLIDNGIIYATQDWVKEKVLPESGSATDVMIQLAA
NDGFKFIGQCPDILTLRTIEPEKNGQRITLRQHTIGTGLGGGVFRAVLDGTGYTDDDGVV
IKTAGGSVWLRVNADKVNPFMFGATGVADDTAALQKMLECGRAAELGTNVWKASNLELNN
KSCSLSGSGLHVSRIEQISGATGALLTITQDCSLIYLSDCGLYGDGITAGTSGVTMETGN
PGGAPSYPFNTAPDVRRDLYISNVHITGFDELGFDYPETNFSVSTHGLFIRNIKKTGAKI
GTTDFTWTNLQIDTCGQECLVLDGAGNCRIIGAKLIWAGSENETPYSGLRISNSQNVNMT
GVELQDCAYDGLYIKNSTVAISGLNTNRNSASSNLSYHNMVFENSIVTVDGYVCRNYAAT
SLYDLNSQAGNVRCIGSDSTVLINGIYESEVNSERLMGDNNLIQPYSGDLIINGLKNYYT
YTGSVKNNIPTFDGVVTTATYVSAPSILGQGNMLKLTQSNKDKLLFSDKVSRHGCTIGLV
LIPSFTGATTMTAFTLGSGYSPSGNSAVMQFIVNSSGVQTIAILLSGDGITQTLTSDLTT
EQALASGGVYHFAMGFAPGRLWWSIIDINTGRRIRRAYRQPDLHAAFNSIFNSGTSSITA
FSGPLAGDIACEGAGSHVYVGGFSSESDYAASRMYGLFTPVDLDKQYSFRTLNGNI SEQ ID NO: 68
R2-V10 Fusion
>R2 1-164:V10 217-875
MATNTPKYGGLLTDIGAAALATASAAGKKWQPTHMLIGDAGGAPGDTPDPLPSAAQKSLI
NQRHRAQLNRLFVSDKNANTLVAEVVLPVEVGGFWIREIGLQDADGKFVAVSNCPPSYKA
AMESGSARTQTIRVNIALSGLENVQLLIDNGIIYATQDWVKEKVLAANDGFKFIGQCPDI
LTLRTIEPEKNGQRITLRQHTIGTGLGGGVFRAVLDGTGYTDDDGVVIKTAGGSVWLRVN
ADKVNPFMFGATGVADDTAALQKMLECGRAAELGTNVWKASNLELNNKSCSLSGSGLHVS
RIEQISGATGALLTITQDCSLIYLSDCGLYGDGITAGTSGVTMETGNPGGAPSYPFNTAP
DVRRDLYISNVHITGFDELGFDYPETNFSVSTHGLFIRNIKKTGAKIGTTDFTWTNLQID
TCGQECLVLDGAGNCRIIGAKLIWAGSENETPYSGLRISNSQNVNMTGVELQDCAYDGLY
IKNSTVAISGLNTNRNSASSNLSYHNMVFENSIVTVDGYVCRNYAATSLYDLNSQAGNVR
CIGSDSTVLINGIYESEVNSERLMGDNNLIQPYSGDLIINGLKNYYTYTGSVKNNIPTFD
GVVTTATYVSAPSILGQGNMLKLTQSNKDKLLFSDKVSRHGCTIGLVLIPSFTGATTMTA
FTLGSGYSPSGNSAVMQFIVNSSGVQTIAILLSGDGITQTLTSDLTTEQALASGGVYHFA
MGFAPGRLWWSIIDINTGRRIRRAYRQPDLHAAFNSIFNSGTSSITAFSGPLAGDIACEG
AGSHVYVGGFSSESDYAASRMYGLFTPVDLDKQYSFRTLNGNI SEQ ID NO: 69
R2-V10 Fusion
>R2 1-161:V10 211-875
MATNTPKYGGLLTDIGAAALATASAAGKKWQPTHMLIGDAGGAPGDTPDPLPSAAQKSLI
NQRHRAQLNRLFVSDKNANTLVAEVVLPVEVGGFWIREIGLQDADGKFVAVSNCPPSYKA
AMESGSARTQTIRVNIALSGLENVQLLIDNGIIYATQDWVKTDVMIQLAANDGFKFIGQC
PDILTLRTIEPEKNGQRITLRQHTIGTGLGGGVFRAVLDGTGYTDDDGVVIKTAGGSVWL
RVNADKVNPFMFGATGVADDTAALQKMLECGRAAELGTNVWKASNLELNNKSCSLSGSGL
HVSRIEQISGATGALLTITQDCSLIYLSDCGLYGDGITAGTSGVTMETGNPGGAPSYPFN
TAPDVRRDLYISNVHITGFDELGFDYPETNFSVSTHGLFIRNIKKTGAKIGTTDFTWTNL
QIDTCGQECLVLDGAGNCRIIGAKLIWAGSENETPYSGLRISNSQNVNMTGVELQDCAYD
GLYIKNSTVAISGLNTNRNSASSNLSYHNMVFENSIVTVDGYVCRNYAATSLYDLNSQAG
NVRCIGSDSTVLINGIYESEVNSERLMGDNNLIQPYSGDLIINGLKNYYTYTGSVKNNIP
TFDGVVTTATYVSAPSILGQGNMLKLTQSNKDKLLFSDKVSRHGCTIGLVLIPSFTGATT
MTAFTLGSGYSPSGNSAVMQFIVNSSGVQTIAILLSGDGITQTLTSDLTTEQALASGGVY
HFAMGFAPGRLWWSIIDINTGRRIRRAYRQPDLHAAFNSIFNSGTSSITAFSGPLAGDIA
CEGAGSHVYVGGFSSESDYAASRMYGLFTPVDLDKQYSFRTLNGNI

FIGURE 13N

SEQ ID NO: 70
P22 tail spike (endorhamnosidase)
Bacteriophage p22
Accession AAF75060
>P22 tail spike
MTDITANVVVSNPRPIFTESRSFKAVANGKIYIGQIDTDPVNPANQIPVYIENEDGSHVQ
ITQPLIINAAGKIVYNGQLVKIVTVQGHSMAIYDANGSQVDYIANVLKYDPDQYSIEADK
KFKYSVKLSDYPTLQDAASAAVDGLLIDRDYNFYGGETVDFGGKVLTIECKAKFIGDGNL
IFTKLGKGSRIAGVFMESTTTPWVIKPWTDDNQWLTDAAAVVATLKQSKTDGYQPTVSDY
VKFPGIETLLPPNAKGQNITSTLEIRECIGVEVHRASGLMAGFLFRGCHFCKMVDANNPS
GGKDGIITFENLSGDWGKGNYVIGGRTSYGSVSSAQFLRNNGGFERDGGVIGFTSYRAGE
SGVKTWQGTVGSTTSRNYNLQFRDSVVIYPVWDGFDLGADTDMNPELDRPGDYPITQYPL
HQLPLNHLIDNLLVRGALGVGFGMDGKGMYVSNITVEDCAGSGAYLLTHESVFTNIAIID
TNTKDFQANQIYISGACRVNGLRLIGIRSTDGQGLTIDAPNSTVSGITGMVDPSRINVAN
LAEEGLGNIRANSFGYDSAAIKLRIHKLSKTLDSGALYSHINGGAGSGSAYTQLTAISGS
TPDAVSLKVNHKDCRGAEIPFVPDIASDDFIKDSSCFLPYWENNSTSLKALVKKPNGELV
RLTLATL SEQ.ID. NO.: 71
>1-2340 PS17 putative tail fiber CDS (analogous to prf15)
>2337-2798 putative chaperone CDS (analogous to prf16)
ATGAGCACCAATCAATACGGGGGCTTCCTCACCGACAAGGGGGCCGCCAAGCAGGTCGAGGCTGCATCCGGCGGC
TTGCGACGGAACATCACCCACATGCTGATCGGTGACGCGGGCGGTGCGCCCGGCCAGACGCCGGACCCGGTACCC
AGCCCCTTGCAAACCAAGCTCGTTCGGCAGCGCTATCGGGTCAAGTTGAACCGCCTGGTAGCCGCTGACAACAGT
CCCAGCGTGTTGATCGCCGAGGCGATCTTGCCGCAGGACGTGGGCGGTTGGTGGATGCGTGAGCTGGGACTGGAG
GACTCCGATGGCGACATGATCGCTGTTGCCAACTGCGCGCCGAGTTACAAGCCGCTGGTGAACGAGGGGTCGGGA
CGGACGCAAACGGTGCGCCTGCATATCGCGTTCAGTCATGCGGAAACGGTCGATCTGCTGATCGACCCGAACGTG
GTCACCGCGACGGTGGCGGATCTGCAAAATGCGCTGCTGGAAGTGCGCGCGACCAACGACGCGACCGGACAGATG
ACGCGAGGCACAGACGGAAAGCTGGCCCTGCCTCTCGCTGAGCCTGACAGGCATTGCCGCCGGCACCTATCGC
AGCCTCACGGTCGACGCGAAGGGGCGCGCTACCAGCGGCAGCAACCCTACCACCCTGGGCGGGTACGGCATTACC
GACGCGCTGGCCAAGAGCGATGCTGTCGACGTGCCCGCGCCGAATAAGCTGCTGCGGCTCAACGCTGCCAGCCAG
TTGCCGGCATCGATTACCGGCAACGCGGCGACTGCCACCAAGCTTGCCGTTCCGCGCATGCTGTCGTTTACAGGG
GACGCCACGGGGGGCGCATCGTTCGACGGGAGTGCCAACGCGGCTGTAGCGCTGACCCTGGCGAATTCGGGGGTT
ACTGCTGGTACCTATGCCAAGGTCACGGTGAACGGCAAGGGTTTGGTCACCGGCGGGGCGCAGCTCACTGCGGCA
GATATCCCGGCGCTGGATGCTGGCAAAGTTGTTTCGGGTGTCCTGCCCATAGCTCGTGGCGGCACCGGCAACGCC
ATCGGCCAGGCTGCAACTGCGGTCAAACTGGCATCCCCTCGCACACTGGCAATCGCTGGGGATGCCACCGGCAGC
GCTGCATTCGACGGCAGCGCAAACGCCAGCATTTCGGTTACGCTGGCCAATACCGGTGTCGCCGTCGGCACCTAC
ACGAAGGTCAGAGTGAACGCTAAAGGACTTGTCACCAGTGCCGCATCGTTGACGGCTGACGATGTTCCTTGGCTG
GACGCGTCAAAAGTGACGTCGGCGCATGTTCGCCGATGCCCGCCTGCCCTGGTACGCACAAGGGCTATGCACCAGC
GCACCCAACACGACGGACCCGAACACCACGAACATCCCGTCATCCTCACGAATCACGAGAACGGTCCGATTCCG
GGGACTTTTTTTCTATATCCAGACGATGATGTACAACCAGCGCAACGGCAATGCCGCCCAGATTGCAGTGCGCTAC
GCGGCGAATGCCGAAATGTATGTGCGCTACATGTACGACGTCGGGAACAAGCGCGGGTCTGGTCGGCCTGGAAA
CGCTGCGATGTGGGCGGCTCATTTGCTAAAGAGGCGGATGGCGAACTGGGGGGTGGGGTCAACCTAGACACCATG
ATTGCCTCTGGGTGGTGGCATCAACCGTTCAGCGCGAACGCCAAGAACGGCACGAACTATCCCGTGGGAGAGGCC
GGTTTGCTGACCGTCCACGCACCCACTTCCACGATGATTTATCAGACTTACCGTGGCTACGCCGCCGGCGGTCTG
TACTGGCGCTGCCGCTACAACGGCACCTGGTCAGCATGGTATCGCGCATGGGACTCCGGCAACTTCAACCCTGCC
AACTACGTGGCCAGGTCGGAATACTCCTGGGCGTCCTTACCAGGGAAGCCCGCAACATTCCCTCCTTCCGGGCAC
AACCATGACGCCACCCAAATTACATCGGGCATTTTGCCGCTGGCCCGTGGCGGCCTTGGCGCCAACAACGCCGTA
ACGGCACGAAGCAACATCGGCGCGGGACTATCGCGACCGCATCGCTGGGAAGCAGCGGCTGGTGGCGGGATAAC
GATACGGGGTACATCCGGCAGTGGGGCCGGGTGACTGTGCCTGGTGATGGCTCCGCGGCGATCACCTTCCCCATC
GCGTTCCCCAGTGTCTGCTTGGGTGGATTCGCTGGCCAAACTGCGAATTTCCACCCAGGAACCGACGCGAGCACA
TCGTTCTATAACCAGTCGACGACAGGTGCAACTTTGGAAAACGGGTATCAATTCCAGGCGGTTTTGCTTTGGGAG
GCATTCGGTCGATGAGCGCTAGCGACTATGTTTTCTCGCCGTCCGCGCGGGTGTTCTATCCCGTGGCGTTGCGGG
AGGTGTACGAGACCGGGGAGGGCTGGCCGGCCGATGCGGTGCCTGTCAGCAATGAACGCTATCTGCACCTGCTTG
CCGGGCAGGAGGCCGGGATGCGGATCGCTGCTAACGCCTCCGGCAGCCGGTTCTTGTCGATCCGCCACCCCTCA
CCGAGGCGGAGCGGCGGACGAAGGCTCGGGCCTGGCGTGACGCTCAGCTTGCACAGACCGATGGCATGGTGGCTC
GGCATCGTGACGAGCGCGACCTGGGGAATGACACCACTCTCCAACCTGAGCAGTTCGTAGAGGTTATGAACTATC
GCGCGGCCCTGCGCAATTGGCCGGACGACCCGGCATTCCCCGACCCCGCCTCCAGGCCGGAGCCGCCTGCCTGGC
TGGCCGAAGAAGGCACCAACTAA

MODIFIED BACTERIOCINS AND METHODS FOR THEIR USE

RELATED APPLICATIONS

This application is a divisional of Ser. No. 11/929,867 filed Oct. 30, 2007 and claims benefit to U.S. application Ser. No. 11/748,432, filed May 14, 2007, which claims benefit to U.S. Provisional Application 60/747,299, filed May 15, 2006, which are incorporated by reference as if fully set forth.

FIELD OF THE DISCLOSURE

This disclosure relates to modified forms of naturally occurring high molecular weight (hmw) bacteriocins, such as the R-type pyocins of *Pseudomonas aeruginosa*. The bacteriocins are modified at the ends of their tail fibers in a region responsible for binding specificity and affinity to their cognate binding partners, or receptors, such as those on the surface of bacteria. Methods for the use of the modified bacteriocins, such as to bind receptors, including virulence or fitness factors, on the surfaces of bacteria, are also described. This disclosure also relates to R-type pyocins wherein the tail fibers are modified to include globular proteins, which proteins can bind and degrade cell surface structures, such as polysaccharides. Unnatural systems for production of R-type pyocins by bacterial cells generally regarded as safe ("GRAS") by regulatory authorities are described as are R-type pyocins produced by such GRAS bacteria.

BACKGROUND OF THE DISCLOSURE

Currently far more global attention is focused on threats from viral pathogens than from bacterial diseases. However, omnipresent antibiotic-resistant bacteria continue to wreak havoc on patient care and cost containment in hospitals and other medical care facilities. At the same time, there is a retreat from antibiotic development in favor of drugs for chronic diseases and life style improvements. In the last twenty years only two new classes of antibiotics (oxazolidinones and lipopeptides) have been introduced into the U.S. market (Wenzel, 2004).

In the United States alone, there are over 2 million cases of hospital acquired bacterial infections every year. Of these, approximately 90,000 people will die. The most alarming statistic is that over 70% of these bacterial culprits are resistant to at least one antibacterial drug (Bad Bugs, No Drugs, 2004). This number continues to increase at an alarming rate. The annual cost to the U.S. economy of these antibiotic-resistant nosocomial infections exceeds $5 billion. The reality of this threatening global situation will force a new approach to the development and use of antibacterial agents (Talbot et al., 2006). Where extensive use (and abuse) of antibiotics in human and animal medicine flourished, so has the emergence of antibiotic-resistant bacterial pathogens to the point that many antibiotics that were once "wonder drugs" are now clinically ineffective (Microbial Threats to Health, 2003).

As one example, *Pseudomonas aeruginosa* is a ubiquitous pathogen for plants and animals that is exhibiting a rapidly rising incidence of resistance to multiple antibiotic drugs (Microbial. Threats to Health, 2003; Bad Bugs, No Drugs, 2004). *P. aeruginosa* is an aerobic, motile, gram-negative, rod. *P. aeruginosa* normally inhabits soil, water, and vegetation. Although it seldom causes disease in healthy people, it is an opportunistic pathogen which accounts for about 10% of all nosocomial infections (National Nosocomial Infection Survey report-Data Summary from October 1986-April 1996). *P. aeruginosa* is the most common pathogen affecting Cystic Fibrosis (CF) patients with 61% of the specimens culturing positive (Govan, J. R. W. and V. Deretic, 1996, Microbiol. Reviews, 60(3):530-574) as well as one of the two most common pathogens observed in intensive care units (Jarvis, W. R. et al., 1992, J. Antimicrob. Chemother., 29(a supp.):19-24).

Mortality from some *P. aeruginosa* infections can be as high as 50%. Presently, *P. aeruginosa* infection can still be effectively controlled by antibiotics, particularly by using a combination of drugs. However, resistance to several of the common antibiotics has been shown and is particularly problematic in intensive care units (Archibald, L. et al., 1997, Clin. Infectious Dis., 24(2):211-215; Fish, D. N., et al., 1995, Pharmacotherapy, 15(3):279-291). Additionally, *P. aeruginosa* has already demonstrated mechanisms for acquiring plasmids containing multiple antibiotic resistance genes (Jakoby, G. A. (1986), The bacteria, Vol. X, The biology of *Pseudomonas*, pp. 265-294, J. R. Sokach (ed.) Academic Press, London) and at present there are no approved vaccines for *Pseudomonas* infection.

Like many other bacterial species, strain variability in *P. aeruginosa* is quite significant. Variability has been shown to occur by a number of different mechanisms, these include, but are not limited to, the integration of prophages into a bacterial genome (Zierdt, C. H. and P. J. Schmidt, 1964, J. Bacteriol. 87:1003-1010), the addition of the cytotoxin gene from bacteriophages (Hayashi, T., et al., 1994, FEMS Microbiol. Lett. 122:239-244) and via transposons (Sinclair, M. I. and B. W. Holloway, 1982, J. Bacteriol. 151:569-579). Through this type of diversity, new pathogenic mechanisms have been incorporated into *P. aeruginosa*. These and other transitions such as the conversion to the mucoid phenotype, commonly seen in CF, clearly illustrate the need for continued vigilance.

These concerns point to the need for diagnostic tools and therapeutics aimed at proper identification of drug-resistant strains and eradication of virulence.

Many bacteria produce bacteriocins, which are bactericidal substances. Bacteriocins are composed of polypeptides and vary in molecular weight. While bacteriocins have been used for their antibacterial properties, some have more limited bactericidal spectra than many clinically used antibiotics. For example some bacteriocins have been reported as recognizing, and so acting on members of the same or closely related species by binding receptor sites on sensitive, or susceptible, organisms.

As a broad classification, bacteriocins have been divided into three types. The first are small molecules which are thermal stable. Examples of this first type include Colicin V (where colicins are specific to coliform bacteria). The second type, S-type pyocins produced by *P. aeruginosa*, are higher molecular weight protein molecules. The third type includes bacteriocins that genetically and morphologically resemble the tail portions of bacteriophages. Examples of this latter type include the F-type and the R-type pyocins of *P. aeruginosa* as well as enterocoliticin of *Yersinia*. These pyocins have been reported as being derived from ancestral bacteriophages. The F-pyocins have structural similarities to the lambda phage family, and the latter two R-type pyocins are related to the P2 phage family.

R-type pyocins are similar to the non-flexible and contractile tail portions of bacteriophages of the myoviridae family and are encoded in a single cluster of genes in the *Pseudomonas* genome (Shinomiya et al., 1983). See FIG. 1. After binding specifically to a target bacterium these pyocins form a pore in the bacterial cell, compromising the integrity of its cytoplasmic membrane and causing membrane depolarization. F-type pyocins are also similar to a bacteriophage tail, but they have a flexible and non-contractile rod-like structure. Pyocins are produced by the majority of *P. aeruginosa* strains, and some strains synthesize more than one pyocin.

R-type pyocins are complex high molecular weight bacteriocins produced by some *Pseudomonas aeruginosa* strains, and have bactericidal activity against certain other *P. aeruginosa* strains (for a review see Michel-Briand and Baysse, 2002). Five R-type pyocins have been identified to date and, based on their target spectra (see below), are termed R1 through R5. Strain PAO1 produces R2 pyocin, which is encoded in a gene cluster consisting of 16 open reading frames (ORFs), 12 of which show significant sequence similarity to ORFs of bacteriophages P2, PS17, ΦCTX, and other P2-like phages (Nakayama et al., 2000). Pyocin production is induced by DNA damage (Matsui et al., 1993) and is regulated by RecA, which degrades PrtR, the repressor of PrtN, a positive transcription regulator of the cluster. Induction of pyocin genes results in synthesis of approximately 200 pyocin particles per bacterial cell followed by lysis of the cell by mechanisms similar to those of bacteriophage lysis. Pyocins rapidly and specifically kill target cells by first binding to the lipopolysaccharide (LPS) via their tail fibers, followed by sheath contraction and core penetration through the bacterial outer membrane, cell wall and cytoplasmic membrane. This penetration compromises the integrity of the cytoplasmic membrane and depolarization of the membrane potential (Uratani and Hoshino, 1984). In many respects pyocins can be viewed as defective prophages adapted by the host to produce protease- and acid-resistant, noninfectious antibacterial particles consisting only of the adapted tail apparatus, that is, without capsids or DNA. The replication of the pyocin genes requires the replication of the bacterial genome in which they are embedded.

The five different pyocin receptor specificities are related linearly to one another with two branches. (Ito et al, 1970; Meadow and Wells, 1978; Kageyama, 1975). R5 pyocin has the broadest spectrum and includes the specificities of the other four. The receptors for the other four R-types form two branches, or families of specificities, that diverge from R5. One branch includes the receptors for R3, R4, and R2, in that order where the receptor specificity for R3 pyocin is the most distal from the cell surface. The second branch contains the R1 receptor, which seems to have a specificity determinant unrelated to those for R2, R3, and R4. The two branches seem to be attached to the receptor for R5 since all *P. aeruginosa* strains that are sensitive to any of R1-R4 pyocins are sensitive also to R5, while some strains are sensitive only to R5 pyocin. Some *P. aeruginosa* strains are resistant to all 5 naturally occurring R-type pyocins.

*P. aeruginosa* pyocins specifically kill mainly strains of *P. aeruginosa* but have also been shown to kill some strains of *Hemophilius, Neisseria* and *Campylobacter* species (Filiatrault et al., 2001; Morse et al, 1976; Morse et al, 1980; Blackwell et al., 1981, 1982).

The specificity of R-type pyocins is conferred by the tail fiber encoded by the gene: prf15. PRF15 protein is very closely related to the tail fibers of phages of the Myoviridae family, particularly P2-like phages (Nakayama et al., 2000). These tail fibers are homotrimers arranged symmetrically on a base plate structure with six copies per particle, as shown in FIG. 1. The N-terminal region of the tail fiber binds to the baseplate, and the C-terminal portion, probably near the tip, binds to the bacterial receptor and thereby confers killing specificity. A cognate chaperone, PRF16 protein, encoded by prf16 gene (in the case of R-type pyocins) is located immediately downstream of prf15, and is needed for proper folding of the tail fiber and/or assembly of the tail fibers on the pyocin structure. R-type pyocin particles have been described as immunochemically and genetically similar to the tails of certain *P. aeruginosa* bacteriophages (Kageyama 1975, Kageyama et al. 1979, Shinomiya et al. 1989, and Shinomiya et al. 1983b). It has been proposed that R-type pyocins and *Pseudomonas* bacteriophages, such as PS-17 and ΦCTX, are related through a common ancestral lysogenic bacteriophage from which genes encoding head proteins and replication functions were lost and the residual phage genes adapted for their function as components of the defensive R-type pyocins (Shinomiya et al. 1989).

Similar R-type high molecular weight bacteriocins have been described in other bacteria including *Yersinia enterocolitica* (Strauch et al., 2001), *Listeria monocytogenes* (Zink et al, 1995), *Staphylococcus aureus* (Birmingham & Pattee, 1981) and *Erwinia amylovora* (Jabrane et al., 2002). Classification and nomenclature of bacteriocins have undergone changes over time, particularly given expanding evidence of their origin, chemistry and activities. Typically, the naming of bacteriocins is based on the producing species. For example, *E. coli* produces bacteriocins termed colicins; *Pseudomonas aeruginosa* produces pyocins; *Listeria monocytogenes* produces monocins; *Yersinia enterociliticus* produces enterocoliticins; and so forth. Historically, the classification began with the identification of about 20 colicins which were classified as A-V. In most cases, each bacteriocin appears to be specific in action to the same, or to taxonomically related, species of organisms. Pyocin-producing strains typically are resistant to their own pyocin. A general assay for the concentration of bacteriocin is described in U.S. Pat. No. 4,142,939.

Certain pathogenic *E. coli* strains, such as *E. coli* O157:H7, are food-borne pathogens. Outbreaks of illnesses from *E. coli* O157:H7-contaminated meats, raw vegetables, dairy products, juices, and the like, have caused considerable morbidity and mortality. Agents and methods are needed to effectively and safely sterilize or sanitize food products that could be contaminated with these pathogenic bacteria.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE DISCLOSURE

This disclosure relates to engineered fauns of the class of bacteriocins that resemble, but are distinct from, bacteriophage tails. These bacteriocins include R-type pyocins, tail-like bacteriocins, R-type bacteriocins, or other high molecular weight (hmw) bacteriocins related to the tail structures of bacteriophages. For ease of reference, the term "hmw bacteriocin" will be used herein to refer to the bacteriocins of the disclosure, including, but not limited to, R-type bacteriocins, R-type pyocins, monocins, enterocoliticins, meningocins and competence factor of *Staphylococcus aureus* (Thompson and Pattee, 1981).

Natural hmw bacteriocins are typically thermolabile, trypsin resistant, and can be induced by agents, which activate the SOS system. For example, they also have been identified in many enterobacteria, *Pseudomonas* species, *Rhizobium lupin, Listeria monocytogenes, Bacillus* species, *Yersinia* species, *Erwinia* species, and *Flavobacterium* species.

An engineered hmw bacteriocin is composed of multiple copies of a number of different polypeptide subunits and possesses one or more, usually six, tail fibers made up of tail fiber proteins. Each tail fiber contains a receptor binding domain (RBD) which binds to, or interacts with, a receptor to form a binding pair. The RBD is the portion of a tail fiber that comprises the bacteria binding property that makes it the first member of the binding pair. An RBD as disclosed herein comprises modification of a protein in the tail fiber to form a modified tail fiber. The modified tail fiber with the other polypeptide subunits forms an engineered (or modified) hmw bacteriocin. The receptor to which the RBD binds is the second member of the binding pair, and may be the same as, or different from, the receptor for a bacteriocin without the modified tail fiber. In some embodiments of the disclosure, the second member of a binding pair is a virulence or fitness factor of a pathogenic bacterium. In other embodiments, the second member is a component of the outermost layer(s) of a bacterial cell, such as a cell membrane or, in the case of gram-positive bacteria, cell wall component.

In comparison to an hmw bacteriocin lacking the modified tail fiber, an engineered hmw bacteriocin may differ in the number, manner, and binding strength of its interactions with a receptor. Thus an engineered hmw bacteriocin may have different or additional binding properties (e.g. binding specificities, affinities, and/or avidities) in comparison to a bacteriocin without the modification. An engineered hmw bacteriocin is not a naturally occurring molecule but may be a modified version of a naturally occurring molecule. Alternatively, an engineered hmw bacteriocin may be a modified version of another non-naturally occurring bacteriocin. In most embodiments, an engineered hmw bacteriocin remains a lethal agent for bacterial cells expressing a receptor bound by the bacteriocin.

In a first aspect, the disclosure includes an hmw bacteriocin comprising a tail fiber protein with a modified RBD. Non-limiting examples of hmw bacteriocins include R-type pyocins. In some embodiments, the modified RBD comprises a change in the amino acid sequence of the domain relative to a naturally occurring bacteriocin. Non-limiting examples of a change in amino acid sequence include substitution, insertion (addition), or deletion of one or more amino acids. Of course combinations of one or more substitutions, insertions (additions), and deletions may also be used.

In other embodiments, the tail fiber comprises a heterologous, or non-bacteriocin, sequence in one or more of the three tail fiber protein monomers that make up a single trimeric tail fiber. And while the tail fibers in a native, or naturally occurring, bacteriocin may be homotrimeric to form an RBD, the tail fiber of an engineered hmw bacteriocin is either heterotrimeric, where one or two of the protein monomers is different from the other(s), or homotrimeric where all three protein monomers are identically non-native (non-naturally occurring). The presence of heterologous (or non-native) sequence, in one or more protein monomers allows the trimer to form a tail fiber with a modified RBD.

The heterologous sequence is thus in a part of the monomer(s) such that at least the RBD of the tail fiber is altered in an assembled trimer. The altered RBD changes the binding characteristics and properties of the tail fiber and thereby the binding activity of a hmw bacteriocin containing the tail fiber. In some embodiments, the heterologous RBD is derived from another bacteriocin or a tail protein from a bacteriophage or prophage. In many cases, the heterologous RBD is a polypeptide including at least part of the C-terminal portion of a tail fiber protein of a bacteriocin, a bacteriophage tail fiber protein, or a presumptive tail fiber protein, the sequence of which has been derived from a gene of a viable or even defective lysogenic bacteriophage found within the genome of a bacterium.

The heterologous RBD can be derived from a bacteriophage that encodes a tail protein or a tail spike-like protein, which protein is globular and preferably, polysaccharide specific. Tail spikes are tail components, usually homotrimeric in structure, such as those found in bacteriophages P22 and epsilon 15. They perform similarly to tail fiber proteins and can be engineered. Therefore, for the purposes of this disclosure, tail spikes or portions thereof are considered RBDs. These proteins can bind and degrade cell surface polysaccharide structures. The same motif of the tail spike protein structure that binds the enzyme substrate can provide the RBD function, since the substrate for the enzyme may also serve as the receptor on the surface of the target bacteria. For example, phiV10 is a bacteriophage belonging to the podoviridae group, and can infect *E. coli* O157:H7 strains. (Waddell & Poppe 2000; Genbank NC_007804). The phiV10 tail spike (SEQ ID NO: 60) specifically recognizes, binds to, and degrades the O157 antigen on the surface of pathogenic *E. coli* O157:H7. Other globular proteins with polymer binding and degrading activities, such as but not limited to, SEQ. ID NO.: 61, 62, 63, 64, and 65 can serve as RBD structures in engineered hmw bacteriocins.

The tail spike of the CUS3 prophage of K1 strain of *E. coli* RS218, SEQ. ID. NO.:61 is an endosialidase very similar to that of the tail proteins of phages K1E, and K1F that recognize and degrade the capsule of K1 strains of *E. coli*. The CUS3 tail spike has a head binding domain similar to the P22 tail spike protein and a C-terminus related to the other phage endosialidases. Fusing this tail spike or a portion thereof to the R2 tail fiber base plate attachment region (BPAR) will create a pyocin that can kill K1 strains of *E. coli*.

The tail spike of bacteriophage HK620, SEQ. ID. NO.:62, is the tail spike of HK620, a P22-like phage. It is specific for the O-antigen of *E. coli* H. Fusing this tail spike or a portion thereof to the R2 tail fiber BPAR will create a pyocin that can kill H strains of *E. coli*.

The tail spike of phage Sf6, SEQ. ID. NO.:63, is also P22-like and recognizes and degrades the *Shigella flexneri* O-antigen. Fusing this tail spike or a portion thereof to the R2 tail fiber BPAR will create a pyocin that can kill *Shigella flexneri* strains.

The tail spike of phage ST64T, SEQ. ID. NO.:64, is P22-like, and recognizes the O-antigen of *Salmonella typhimurium* DT64. Fusing this tail spike or a portion thereof to the R2 tail fiber BPAR will create a pyocin that can kill *Salmonella typhimurium* strains such as DT64.

Phage epsilon15 tail spike, SEQ. ID. NO.:65, is similar to the phiV10 tail spike and specific for group E1 *Salmonella enterica*. Fusing this tail spike or a portion thereof to the R2 tail fiber BPAR will create a pyocin that can kill group E1 *Salmonella enterica* strains.

Tail spike proteins and portions thereof may fold properly without the facilitation by a specific chaperone. Thus, the generation of fusions between an R-type pyocin tail fiber and a heterologous tail spike protein as an RBD may not require an RBD-specific chaperone as usually does the fusion between an R-type pyocin tail fiber and a heterologous tail fiber protein from another R-type pyocin or a myoviridae such as P2, L-413c, AB17 or PS17.

The heterologous RBD is fused to a polypeptide containing a BPAR of a hmw bacteriocin or a myoviridae phage tail fiber protein. The BPAR containing polypeptide may contain all or part of the N-terminal portion of an hmw bacteriocin tail fiber, where the N-terminal portion can consist of any part of the tail fiber except the very C-terminus.

In other embodiments, the heterologous RBD is derived from the major tropism determinant (MTD) of *Bordetella* bacteriophage. Non-limiting examples include a heterologous RBD comprising a modified or diversified tropism determinant, optionally with all or part of the RBD of a tail fiber of a bacteriophage. In some embodiments, the bacteriophage tail fiber is that of the *Vibrio harveyi* myovirus-like (VHML) bacteriophage or its diversified derivatives or those of another prophage or bacteriophage that comprises a Diversity Generating Retroelement (DGR) structure.

The disclosure further includes a portion of an engineered hmw bacteriocin where the portion retains the bacteriocin's activity of binding a receptor on a bacterial cell surface and then promoting the penetration of the cell membrane. Thus the portion may be any that retains the binding (recognition) and membrane penetration activities of an engineered hmw bacteriocin. In some embodiments, the portion comprises one or more bacteriocin polypeptides that are truncated.

In a related aspect, the disclosure includes modified tail fibers that may be part of an hmw bacteriocin of the disclosure. The trimeric tail fiber may comprise one or more tail fiber proteins with a modified RBD or a heterologous RBD. In some embodiments, the modified monomeric tail fiber protein is derived from an R-type bacteriocin while in other embodiments, the tail fiber protein is derived from a bacteriophage tail fiber or a bacteriophage tail spike protein.

The disclosure also includes native, isolated, or recombinant nucleic acid sequences encoding a modified tail fiber protein, as well as vectors and/or (host) cells containing the coding sequences. The vectors and/or host cells may be used to express the coding sequences to produce native, isolated, or modified tail fiber proteins which form tail fibers and are incorporated into an engineered hmw bacteriocin of the disclosure. A sequence encoding a modified tail fiber protein may also be introduced into a bacterial cell which produces, or is capable of producing, an hmw bacteriocin in the presence of the modified tail fiber protein.

In some instances the bacterium for production will be those designated as "generally recognized as safe," or "GRAS," under the U.S. Federal Food, Drug, and Cosmetic Act, such as for food additives or food ingredients. Typically any substance that is intentionally added to food is a food additive that is subject to review and approval by the U.S. Food and Drug Administration (FDA) unless the substance is generally recognized by experts as having been adequately shown to be safe under the conditions of its intended use. A GRAS substance can be utilized without pre-approval.

Expression of the modified tail fiber protein results in the production of a modified hmw bacteriocin by the cell. If natural bacteriocin tail fiber protein sequence(s) or the nucleic acid(s) encoding such protein is/are inactivated or removed, then only modified hmw bacteriocins will be produced. If natural bacteriocin tail fiber protein sequence(s) or the nucleic acid(s) encoding such protein are retained, then modified hmw bacteriocins will be produced along with the natural bacteriocin tail fibers, and the modified pyocins generated may be mixtures of both modified pyocins and natural pyocins. In addition, the pyocins generated from such production host bacteria may contain bivalent (multivalent) pyocins, that is, contain single pyocin particles with a mixture of two types of tail fibers, each with its specific binding properties. Such multivalent pyocins have multiple, that is, two or more, binding and killing specificities within the same pyocin particle or molecule. The transfected bacteria may be propagated to produce hmw bacteriocins that prevent or inhibit the growth of other bacteria that express a receptor bound by the modified hmw bacteriocin or by one of the hmw bacteriocins from the mixture of natural plus modified hmw bacteriocins.

In some embodiments, the receptor is a virulence or fitness factor of a virulent or pathogenic bacterial strain such that exposure to the modified hmw bacteriocin prevents or inhibits growth of the virulent or pathogenic strain. Non-limiting examples of virulence factors targeted by an engineered hmw bacteriocin include those encoded by the sequences disclosed in U.S. Pat. No. 6,355,411 and published patent application WO 99/27129 (Ausubel et al.).

The exposure is optionally via contact, or co-culturing, with transfected bacteria expressing the hmw bacteriocin. The disclosure includes allowing propagation of the transfected bacteria in vivo, on or within an animal or plant subject. The in vivo application of the transfected bacteria provides a state of protection against bacteria expressing a surface receptor targeted by the engineered hmw bacteriocin. The state of protection is analogous to a state of immunity, where the transfected bacteria essentially augment or supplement the animal or plant organism's immune or other defense system.

In other embodiments, the nucleic acid sequence coding an RBD of a modified monomeric tail fiber protein is part of a genetic system which permits the identification, physical isolation and/or selection of the coding sequence. As non-limiting examples, the genetic system may comprise the coding sequence in a phage, lysogenic phage, transducing particle, cosmid, or phage genome allowing its identification, isolation, and/or selection. In some embodiments, the sequence is fused with a portion of a fiber gene and expressed to produce a modified tail fiber trimer that will cause the modified hmw bacteriocin to bind to the surface of and kill the host organism harboring the lysogenic phage from which the RBD coding sequence was identified or isolated. Detection of a phenotype in the modified tail fiber trimer permits the sequence to be selected and/or screened, identified, and isolated. In some embodiments, the phenotype may be a desired, and possibly rare, receptor-binding property.

The disclosure includes a library of phages, transducing particles, cosmids, or phage genomes, containing a plurality of DNA and/or RNA sequences, each encoding a modified tail fiber protein. This coupling of binding phenotype to encoding genotype of the RBD allows the expression of a plurality of modified RBDs such that the sequences encoding them are represented within the library. In some embodiments, the members of a library each contain a sequence encoding one modified tail fiber protein such that homotrimeric tail fibers are expressed and available for screening or selection to determine the respective binding phenotype of a library member. In other embodiments, the members of a library include those with more than one sequence encoding a modified tail fiber protein such that heterotrimeric tail fibers disclosed herein may be expressed and screened or selected for their binding phenotypes. The binding phenotype of a member of the library is thus coupled to the respective coding sequence(s). Once the genotype encoding the desired or advantageous RBD has been so identified, it can be used to create the tail fiber for a modified hmw bacteriocin. By deploying the cognate chaperone function of a tail fiber, such as that of VHML, that naturally diversifies its RBD, one can be assured of proper folding of a tail fiber containing a diversified RBD derived from VHML.

Vectors, host cells, phages, transducing particles, cosmids, phage genomes, and libraries as disclosed herein may be considered compositions comprising a tail fiber protein encoding nucleic acid molecule.

Compositions of the disclosure also comprise fusion proteins resulting from the fusion of the RBD protein to the BPAR protein. For example, all or part of the phiV10 tail spike is fused to the BPAR of the R-type pyocin tail fiber PRF15. In some instances, these fusion proteins can be provided in the context of other proteins, or phage or cellular components. Alternatively, they may be isolated or separated. The fusion proteins can be part of a library and available for screening or selection, and/or may be associated with a carrier or excipient for administration. They can be prepared via recombinant methods or synthesized chemically.

Additional compositions of the disclosure comprise an engineered hmw bacteriocin or an anti-bacterial portion thereof. The compositions are anti-bacterial by virtue of the hmw bacteriocin, and may comprise a carrier or excipient. Of course the carrier or excipient is one that is suitable for use in combination with a multisubunit complex protein like an hmw bacteriocin. In some embodiments, the carrier or excipient is pharmaceutically acceptable such that the composition may be used clinically or agriculturally. In other embodiments, the carrier or excipient is suitable for topical, pulmonary, gastrointestinal, or systemic administration, such as to a human or a non-human animal. In additional embodiments, the carrier or excipient is suitable for administration to a surface or to a non-animal organism such as a plant or fresh produce from a plant as non-limiting examples.

A composition as disclosed herein may comprise more than one fusion protein or engineered hmw bacteriocin or comprise one or more additional agents, including but not limited to, a naturally occurring hmw bacteriocin desired for use with the engineered hmw bacteriocin. Non-limiting examples of an additional agent include an enzyme, an antibiotic, an anti-fungal agent, a bactericide, an analgesic, and an anti-inflammatory agent.

In a further aspect, the disclosure provides methods of using an hmw bacteriocin related product described herein. Embodiments of the disclosure include methods of inhibiting bacterial cell growth or inducing bacterial cell death. Such methods comprise contacting a susceptible bacterial cell or cells with an effective amount of an engineered hmw bacteriocin, or with an anti-bacterial portion thereof, such as a fusion protein. Alternatively a composition containing the hmw bacteriocin, or anti-bacterial portion thereof, may be used. In some cases, an effective amount may be equivalent to as few as one, on average, hmw bacteriocin per bacterial cell. Higher amounts also may be used.

In other embodiments, a method of compromising the integrity of the cytoplasmic membrane of a bacterium is provided. The compromise may result in the loss of membrane potential and/or loss of some cellular contents. Such methods comprise contacting the membrane with a fusion protein, or an engineered hmw bacteriocin, or anti-bacterial portion thereof. In many cases, the membrane will be that of virulent or pathogenic bacteria.

In some embodiments, the methods of the disclosure may comprise in vivo application (or administration) of a fusion protein or an engineered hmw bacteriocin, or an anti-bacterial portion thereof, within a subject. Alternatively, the methods may comprise in vitro or ex vivo contacting.

In a yet additional aspect, the disclosure provides a method of forming non-virulent bacteria from virulent progenitor bacteria. The method comprises contacting virulent bacteria with an engineered hmw bacteriocin, or an anti-bacterial portion thereof, which binds a virulence or fitness factor of the virulent bacteria. The contacting may be under conditions wherein not all of the bacteria are killed, or wholly inhibited in cell growth, by the used amount of hmw bacteriocin, or anti-bacterial portion thereof. The contacting provides a selective pressure that allows the targeted bacterium to survive the engineered hmw bacteriocin or anti-bacterial portion thereof and to propagate only if it has become a non-virulent mutant or modified bacteria progeny that is not susceptible (and so resistant) to the engineered hmw bacteriocin or anti-bacterial portion thereof. In some embodiments, the resistance is due to the lack of expression of the virulence or fitness factor or receptor for the engineered hmw bacteriocin, or anti-bacterial portion thereof, thereby avoiding attack by the engineered hmw bacteriocin. In another embodiment the resistance may be due to an alteration in the virulence or fitness factor such that it no longer serves as an effective receptor for the RBD of the modified pyocin and in the altered form also compromises its virulence or fitness function. The acquisition of resistance by the surviving progeny, and the resultant change in virulence or fitness of a formerly virulent bacterium, can be determined in vivo or in vitro to demonstrate its compromised pathogenicity.

In a related aspect, the disclosure provides a method of maintaining a population of non-virulent bacteria by contact with an engineered hmw bacteriocin, or an anti-bacterial portion thereof, which binds to and mediates its bactericidal effect via a virulence or fitness factor of the virulent bacteria. The presence of the hmw bacteriocin prevents growth (or generation or propagation) of virulent bacteria and so maintains the population as non-virulent. In some embodiments, the contacting may be by use of a bacterial cell, as described herein, which expresses the engineered hmw bacteriocin or anti-bacterial portion thereof.

The details of one or more embodiments of the disclosure are set forth in the accompanying drawings and the description below. Other features, objects, and advantages of the disclosure will be apparent from the drawings and detailed description, and from the claims.

BRIEF DESCRIPTION OF THE DRAWINGS

FIG. 1 provides the electron micrograph of an R-type pyocin particle revealing 4 of the 6 tail fibers in Panel A, and a schematic of the major components of an R-type pyocin particle in Panel B.

FIG. 2 provides spot serial (5×) dilution assays of wild type pyocins (R2), pyocin particles produced from the tail fiber deletion strain (PA01Δprf15), and pyocins complemented with the R2-P2 tail fiber fusion. Target bacteria are *P. aeruginosa* 13s and *E. coli* C1a. Wild type R2 pyocin particles can kill *Pseudomonas* but not *E. coli*. The tail fiber deletion strain produces no active pyocin particles, but when complemented in trans with the R2-P2 tail fiber fusion, it now can kill *E. coli* C1a.

FIG. 3 is complementing the R2 pyocin structure with an R2-P2 tail fiber fusion. The C-terminal (RBD) portion of the P2 tail fiber gene was fused to the N-terminal (BPAR) portion of the R2 tail fiber, as shown in part A.

Part B of FIG. 3 shows a schematic of the wild type R2 pyocin (left). The R2 pyocin is complemented with the R2 (BPAR)-P2 (RBD) fusion construct to produce particles (right) that have the chimeric tail fibers incorporated into the structure. The R2-P2 particles have an altered killing spectrum and now target certain *E. coli* strains.

Figure 4:
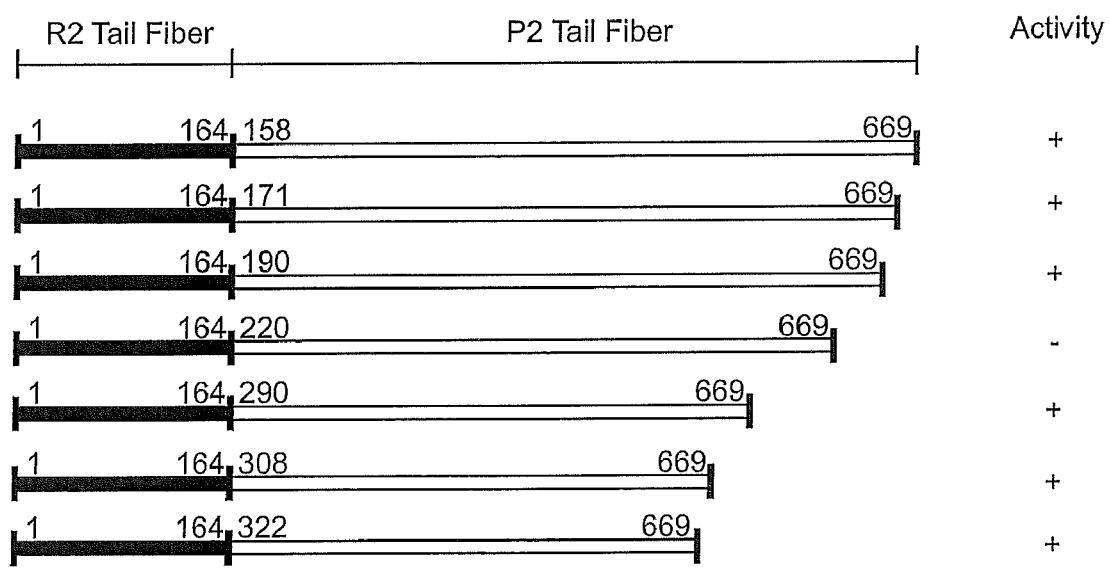

FIG. 4 provides a multiple R2-P2 fusions and their bactericidal activities. The N-terminus, 1-164 amino acids, of R2 (Base-Plate Binding Region, "BPAR") was fused to various C-terminal portions of P2 (RBD). The numbers represent the amino acid reside numbers of the respective proteins. The bactericidal activity of the modified pyocins (against *E. coli* C) containing each of the constructed tail fibers are indicated as present (+) or absent (−).

Figure 5:
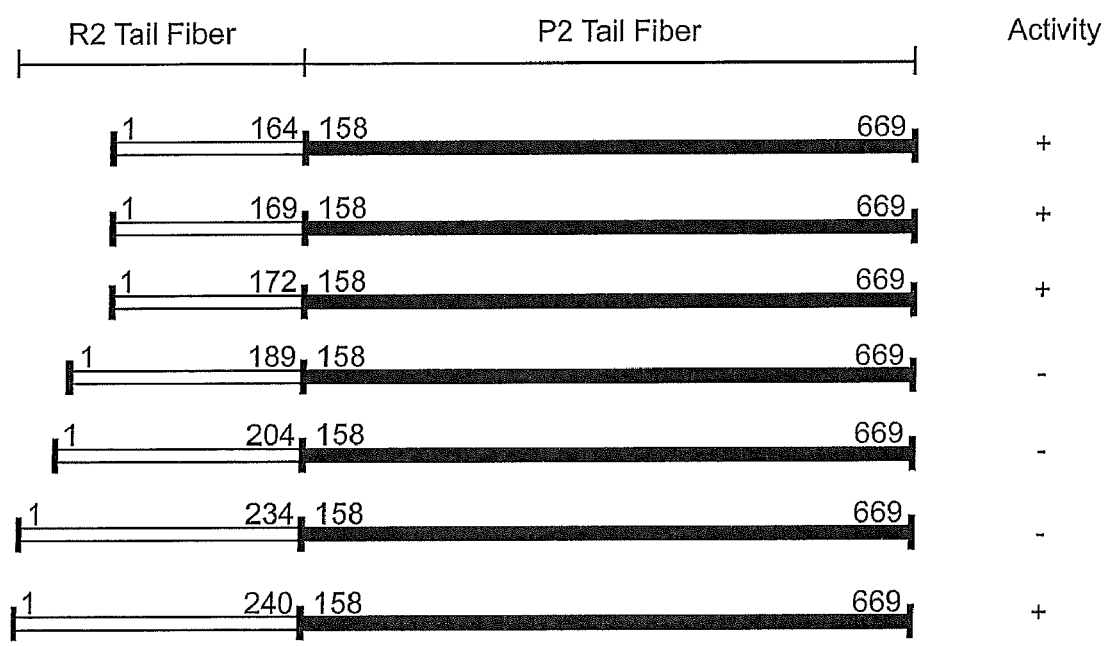

FIG. 5 shows various portions of the N-terminus of the R2 tail fiber (BPAR) fused to the C-terminal 158-669 portion (RBD) of the P2 tail fiber. The numbers represent the amino acid reside numbers of the respective proteins. The bactericidal activity of the modified pyocins (against *E. coli* C) containing each of the constructed tail fibers are indicated as present (+) or absent (−).

Figure 6:
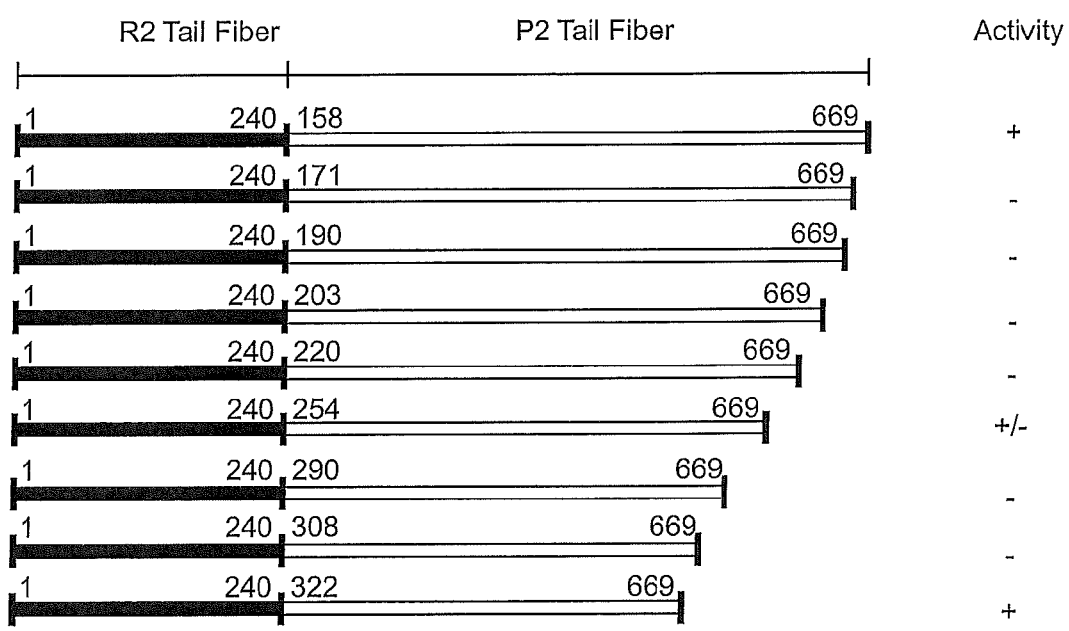

FIG. 6 shows multiple R2-P2 fusions and their bactericidal activities. N-terminus, 1-240 amino acids, of R2 (BPAR) was fused to various C-terminal portions of P2 (RBD). The numbers represent the amino acid reside numbers of the respective proteins. The bactericidal activity of the modified pyocins (against *E. coli* C) containing each of the constructed tail fibers are indicated as present (+) or absent (−).

Figure 7:
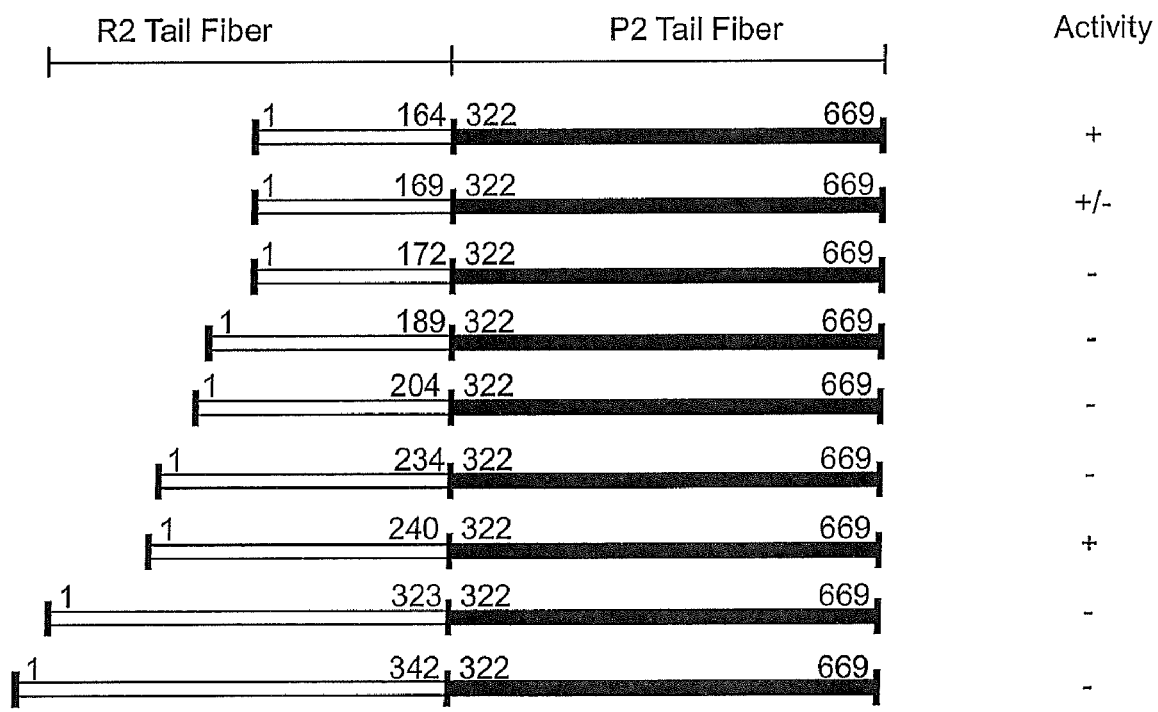

FIG. 7 provides various portions of the N-terminus of the R2 tail fiber (BPAR) fused to the C-terminal 322-669 portion (RBD) of the P2 tail fiber. The numbers represent the amino acid reside numbers of the respective proteins. The bactericidal activity of the modified pyocins (against *E. coli* C) containing each of the constructed tail fibers are indicated as present (+) or absent (−).

FIG. 8 shows the trans complementation of the PA01Δprf15 R2 pyocin structure with various R-type pyocin tail fibers, tail fiber fusions and chaperones. Activities of the R1 through R5 complemented pyocins were assessed by spotting onto indicator strain *Pseudomonas aeruginosa* 13s, which is sensitive to all pyocin types. The R2-P2 complemented pyocins were tested for activity using *E. coli* C as the indicator, and the R2-L-413c complemented pyocin was tested on *Yersinia pestis* strain KIM.

The R2, R3, and R4 PRF15 tail fibers could be complemented by the endogenous PRF16 of the PA01Δprf15 R2 pyocin. R1 and R5 PRF15 tail fibers, which differ at the C-terminus compared to R2, required, for maximal activity, their own cognate PRF16 (which itself differs from the R2 counterpart). Both the R2-P2 and R2-L-413c fusions, which contain the C-terminus (RBD) of the phage P2 and L-413c tail fibers, respectively, require their cognate tail fiber assembly chaperones encoded by gene G of the phage.

Figure 9:
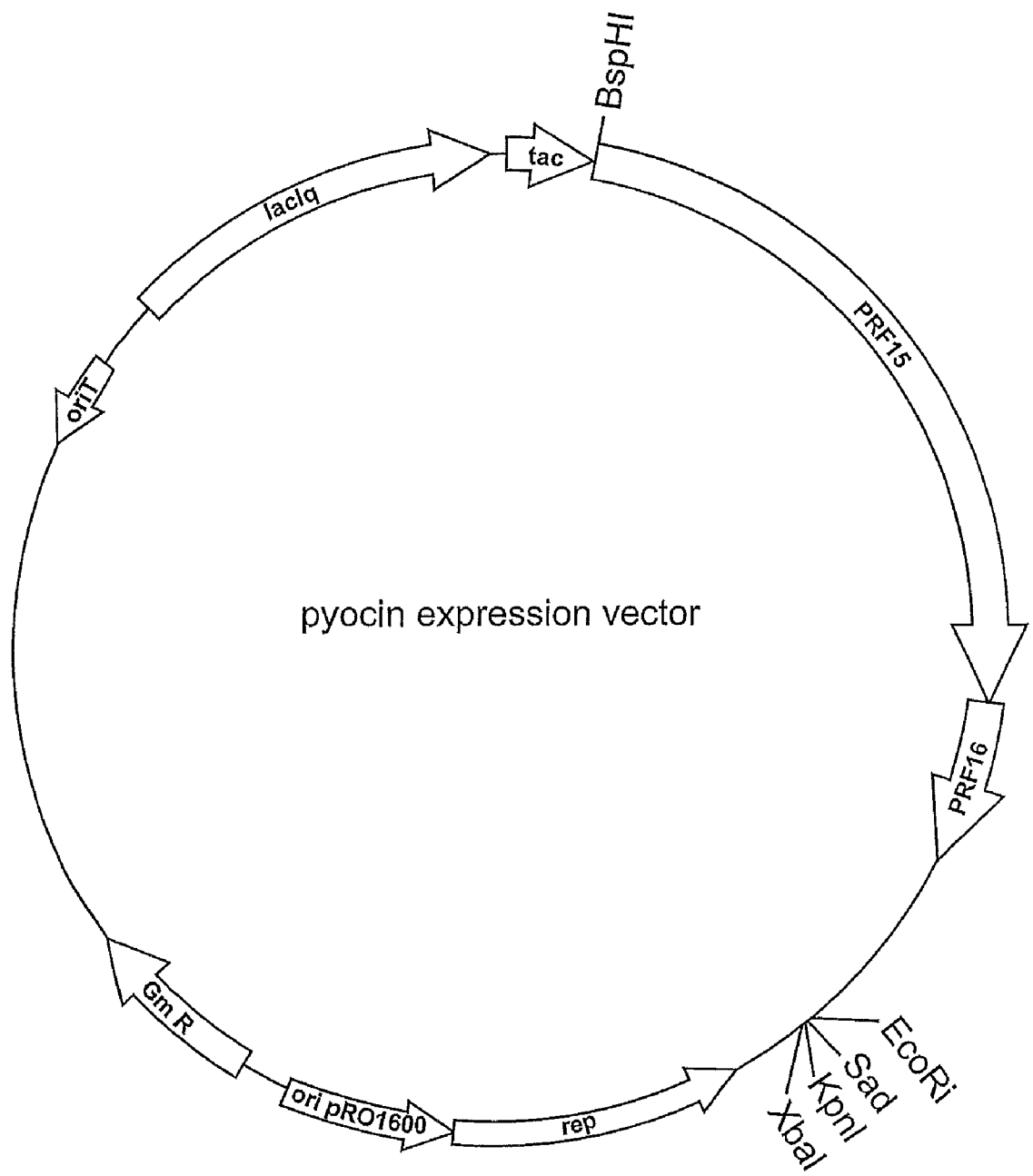

FIG. 9 shows the pyocin tail fiber and chaperone expression vector pUCP30T. The genes, prf15 and prf16, are expressed using a *Pseudomonas/E. coli* shuttle vector (Schweitzer) with replication origins (ori pRO1600, rep, and oriT) for both species. Cloning sites are shown by the indicated restriction enzyme sites of cleavage. The plasmid confers gentamicin resistance (Gm R) and is maintained by adding gentamicin to the culture media. Transcription of both genes is driven by the tac promoter which is negatively regulated by lacI$^Q$. When transformed into *Pseudomonas aeruginosa* strain PA01Δprf15, the genes, e.g. prf15 and prf16, incorporated into the plasmid are expressed in trans after being induced with IPTG simultaneously with the mitomycin C induction of those pyocin genes remaining in the PAO1 Δprf15 host production bacteria.

FIG. 10 provides the construction of *Yersinia pestis* specific pyocin tail fiber. Similar to the strategy that was used to construct R2-P2, the C-terminal (RBD) encoding portion of the L-413c tail fiber gene was fused to an N-terminal portion (BPAR) of the R2 tail fiber. When expressed in trans to complement the R2 tail fiber deletion strain PA01Δprf15, modified pyocin particles are produced containing the chimeric R2-L-413c tail fibers that can efficiently kill *Y. pestis* but not *Pseudomonas*.

FIG. 11A shows representative tail fiber fusions of the bacteriophages P2 and phiV10 tail fiber receptor binding domains (RBD) to the R2 pyocin tail fiber base plate attachment region (BPAR).

FIG. 11B provides bactericidal activities of pyocins that have incorporated either the R2-P2 tail fiber fusion or the R2-V10 tail fiber fusion into their structures. Pyocins were produced by expressing the tail fiber fusions in trans in PAO1Δprf15 while simultaneously inducing the pyocin genes. Pyocin activity was assessed by the spot method on lawns of *E. coli* EDL933 and TEA026. EDL933 is a wild type strain that produces the O157 antigen. TEA026 is a mutant of EDL933 defective in O-antigen production (Ho and Waldor, 2007). EDL933 is sensitive to R2-V10 but not R2-P2. TEA026 is sensitive to pyocin R2-P2 but not R2-V10. This indicates that the O157-antigen is the receptor for the V10 RBD and that the P2 RBD recognizes the lipopolysaccharide.

Figure 12:
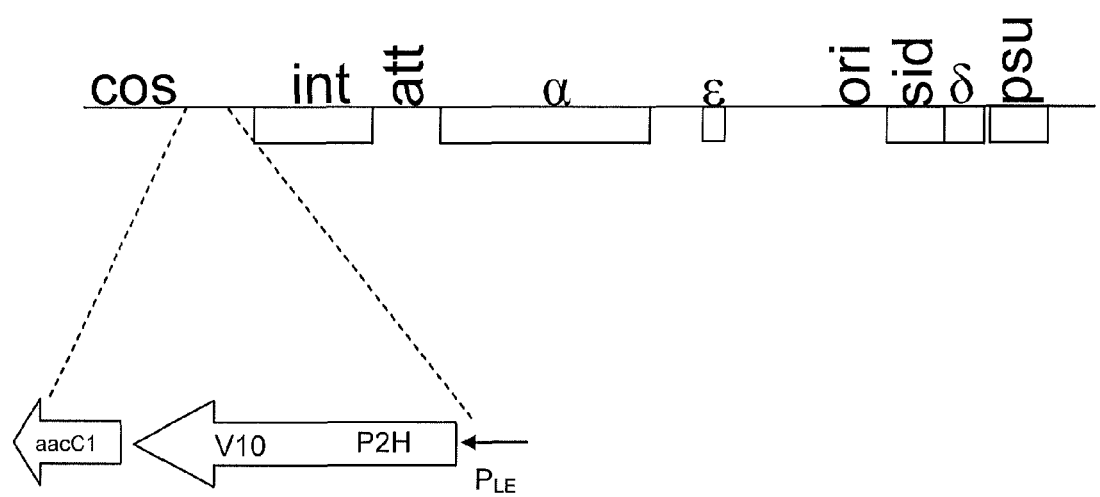

FIG. 12 is a cartoon of the P4 plasmid, pDG218, containing the genes for gentamicin resistance (aacC1) and a fusion tail fiber such as P2 H-V10 inserted in the non-essential region of the P4 satellite phage and driven by the left early promoter, $P_{LE}$. The other indicated genes and functions are from P4sid$_1$ (Shore et al., 1977).

FIG. 13 provides the amino acid sequences or nucleic acid sequences for SEQ ID NOS:1-71, provided on pages 13A-13N.

DEFINITIONS

As used herein, an hmw bacteriocin includes an R-type pyocin, tail-like bacteriocin, R-type bacteriocin, and R-type pyocins, monocins, enterocoliticins, meningocins, or other high molecular weight (hmw) bacteriocins. An hmw bacteriocin includes modified versions of R-type pyocins, enterocoliticins, monocins, and meningocins (see Kingsbury "Bacteriocin production by strains of *Neisseria meningitidis*." J. Bacteriol. 91(5):1696-9, 1966). A modified or engineered hmw bacteriocin may be a modified R-type pyocin selected from the R1, R2, R3, R4, or R5 pyocin of *P. aeruginosa*. The modified or engineered bacteriocins may include the tail spikes of a bacteriophage, such as phiV10.

A bacteriocin of the disclosure may be thermolabile, mild acid resistant, trypsin resistant, sedimentable by centrifugation at about 65,000×g, and resolvable by electron microscope (see Jabrane et al. Appl. Environ. Microbiol. 68:5704-5710, 2002; Daw et al. Micron 27:467-479, 1996; Bradley Bacteriol. Revs. 31:230-314, 1967; and Kageyama et al. Life Sciences 9:471-476, 1962. In many cases, an engineered hmw bacteriocin disclosed herein has one or more, in any combination, of these properties. An additional property common to bacteriocins and engineered hmw bacteriocins disclosed herein is that they do not contain nucleic acid and thus are replication deficient such that they cannot reproduce themselves after or during the killing of a target bacterium as can many bacteriophages.

R-type pyocins, and other hmw bacteriocins disclosed herein, are complex molecules comprising multiple protein, or polypeptide, subunits and resemble the tail structures of bacteriophages of the myoviridae family. In naturally occurring R-type pyocins, the subunit structures are encoded by the bacterial genome such as that of *P. aeruginosa* and form pyocins to serve as natural defenses against other bacteria (Kageyama, 1975). A sensitive, target bacterium can be killed by a single R-type pyocin molecule (Kageyama, 1964; Shinomiya & Shiga, 1979; Morse et al., 1980; Strauch et al., 2001).

A "target bacterium" or "target bacteria" refer to a bacterium or bacteria that are bound by an engineered hmw bacteriocin of the disclosure and/or whose growth, survival, or replication is inhibited thereby. The term "growth inhibition" or variations thereof refers to the slowing or stopping of the rate of a bacteria cell's division or cessation of bacterial cell division, or to death of the bacteria.

As used herein, a "nucleic acid" typically refers to deoxyribonucleotide or ribonucleotides polymers (pure or mixed) in single- or double-stranded form. The term may encompass nucleic acids containing nucleotide analogs or modified backbone residues or linkages, which are synthetic, naturally occurring, and non-naturally occurring, which have similar binding, structural, or functional properties as the reference nucleic acid, and which are metabolized in a manner similar to the reference nucleotides. Non-limiting examples of such analogs include, without limitation, phosphorothioates, phosphoramidates, methyl phosphonates, chiral-methyl phosphonates, 2-0-methyl ribonucleotides, and peptide-nucleic acids (PNAs). The term nucleic acid may, in some contexts, be used interchangeably with gene, cDNA, mRNA, oligonucleotide, and polynucleotide.

A particular nucleic acid sequence also encompasses conservatively modified variants thereof (such as degenerate codon substitutions) and complementary sequences, as well as the sequence explicitly indicated. Specifically, degenerate codon substitutions may be achieved by generating sequences in which the third ("wobble") position of one or more selected (or all) codons is substituted with mixed-base and/or deoxyinosine residues. Thus a nucleic acid sequence encoding a protein sequence disclosed herein also encompasses modified variants thereof as described herein.

The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission.

Virulence factors are those molecules that contribute to the pathogenicity of an organism but not its general viability. Upon the loss of a virulence factor the organism is less pathogenic but not necessarily less viable. Virulence factors may have any one of numerous functions, for example, regulating gene expression, providing adhesion or mobility, pumping out antibiotic agents, or forming protective coatings including biofilms.

Fitness factors are those molecules that contribute to the organism's general viability, growth rate or competitiveness in its environment. Upon the loss of a fitness factor, the organism is less viable or competitive and because of this compromise, indirectly less pathogenic. Fitness factors may also possess any one of numerous functions, for example, acquiring nutrients, ions or water, forming components or protectants of cell membranes or cell walls, replicating, repairing or mutagenizing nucleic acids, providing defense from or offense towards environmental or competitive insults.

Some virulence and fitness factors are present on the surface of the bacterium and thereby accessible to an hmw bacteriocin disclosed herein. By binding to some surface virulence or fitness factors, an hmw bacteriocin can mediate killing by puncturing the cell membranes, compromising the integrity of the cytoplasmic membrane and/or dissipating the membrane potential of the cell. Those surface accessible molecules most likely to support hmw bacteriocin binding and killing are proteins, polysaccharides, and lipopolysaccharides of the outer membrane. Accordingly, potential targets for engineered hmw bacteriocins are virulence factors and fitness factors that are proteins, polysaccharides and lipopolysaccharides of the outer membrane. Some non-limiting examples of virulence factor targets for engineered pyocins include intramembrane cleaving protease (iCLIP) metalloproteases; IL and IIL galactose- and fucose-binding lectins; microbial surface components recognizing adhesive matrix molecule (MSCRAMM) proteins; and adhesin, such as ACE.

The ultimate success of targeting a specific virulence factor depends on its topography on the bacterial surface, its density on the surface, perhaps its two-dimensional mobility within the outer membrane, and its prevalence in clinical or field isolates of the pathogen. For example, OprM is a porin-like outer membrane protein involved in multiple efflux pumps, e.g. the MexAB system, and prevalent in many gram-negative bacteria (Wong and Hancock, 2000). TolC, similar to OprM, is a required accessory protein for many efflux pumps of gram-negative pathogens (Koronakis et al., 2004; Piddock, 2006). In addition, several members of the YcrC family of secretins are outer membrane proteins necessary for the translocation of pathogenic effector proteins by the type three secretion system ("T3SS"), on which many gram-negative pathogens such as *P. aeruginosa* and *Yersinia pestis* are dependent for intoxicating their mammalian host (Galan and Collmer. 1999; Koster et al., 1997; Cornelis, 2006). In addition, the YscW family members are lipoproteins also anchored in the outer membrane to assist the insertion of the secretins into the membrane (Burghout et al., 2004).

Additional non-limiting examples of virulence and fitness factors include an aquaporin, such as the *E. coli* aquaporin-Z water channel (see Calamita, 2000); RetS (see Goodman et al., 2004; and Zolfaghar et al., 2005); members of the 7TMR-DISM family (see Anantharaman et al., 2003); OprM (see Wong et al., 2000; and SEQ ID NO:11); bacterial proteins such as OprJ (SEQ ID NO:12), OprN (SEQ ID NO:13), AprF (SEQ ID NO:14), OpmM (SEQ ID NO:15), OpmA (SEQ ID NO:16), OpmD (SEQ ID NO:17), OpmE (SEQ ID NO:18), OpmQ (SE ID NO:35), OpmB (SEQ ID NO:36), OpmJ (SEQ ID NO:37), OpmG (SEQ ID NO:38), OpmI (SEQ ID NO:39), OpmH (SEQ ID NO:40), OpmK (SEQ ID NO:41), OpmN (SEQ ID NO:42), OpmF (SEQ ID NO:43), or OpmL (SEQ ID NO:44); OprD family of porins (see Tamber et al., 2006); ACE, or the *E. faecalis* OG1RF encoded ACE gene (see Sreedhar et al., 2000; and Rich, et al., 1999); PA-IL and PA-IIL galactose- and fucose-binding lectins (see Mitchell et al., 2002); plant and animal virulence genes described by He et al., 2004; extracellular pyrophosphate moieties (see Bonev et al., 2004); metalloproteases (see Rudner et al., 1999); and transposon encoded surface molecules (see Jacobs et al., 2003).

Other non-limiting examples of virulence factors targeted by a disclosed engineered hmw bacteriocin include those encoded by the open reading frames (ORFs) disclosed in U.S. Pat. No. 6,355,411 and WO 99/27129. In some embodiments, a factor targeted by a bacteriocin disclosed herein is one encoded by the following ORFs from the U.S. patent:

| ORF number | Encoding |
| --- | --- |
| 5 | Unknown |
| 9 | Unknown |
| 21 | Possibly receptor |
| 23 | Possibly ABC transporter |
| 33 | Unknown |
| 41 | Possibly mucin like |
| 43 | Unknown |

-continued

| ORF number | Encoding |
|---|---|
| 51 | Unknown |
| 53 | Possibly mucin like |
| 85 | Unknown |
| 89 | Possibly lipoprotein receptor |
| 91 | Unknown |
| 95 | Possibly proteophosphoglycan, cell surface |
| 107 | Possibly ABC |
| 110 | Possibly membrane glycosyltransferase |
| 113 | Possibly multidrug resistance protein MexA |
| 132 | Possibly muc d |
| 134 | Possibly 6-UDP mannose dehydrogenase |
| 149 | Possibly MDR transporter potential target |
| 150 | Possibly multidrug resistance protein MexA |
| 203 | Possibly ABC transporter ATPase component |
| 204 | Possibly ATPase component of ABC transport |
| 205 | Possibly ATPase component of ABC transport |
| 206 | Possibly ATPase component of ABC transport |
| 207 | Possibly ATPase component of ABC transport |
| 208 | Possibly ATPase component of ABC transport |
| 209 | Possibly ABC |
| 213 | Possibly NhaP-type Na+/H+ and K+/H+ antiporters |
| 215 | Unknown |
| 227 | Possibly receptor |
| 239 | Possibly deoxycytidine triphosphate deaminase |
| 241 | Possibly UTPase |
| 249 | Unknown |
| 255 | Unknown |
| 261 | Possibly 6-phosphoglyconate dehydrogenase |
| 263 | Possibly ABC transporter |
| 273 | Unknown |
| 277 | Possibly PE-PGRS family member |
| 289 | Possibly 6-phosphogluconate dehydrogenase |
| 291 | Possibly Glycosyl transferase |
| 297 | Possibly ligA |
| 301 | Possibly glycosyltransferase |
| 309 | Possibly cation/multidrug efflux pump |
| 323 | Unknown |
| 327 | Unknown |
| 331 | Possibly sensor with putative PilR kinase |
| 333 | Possibly Tonb protein transport |
| 341 | Possibly Pil R |
| 349 | Possibly Pil A or R |
| 363 | Possibly orfz |
| 365 | Possibly ABC transporter |
| 375 | Possibly mucin |
| 377 | Possibly fimT pilus |
| 381 | Possibly H1 immobilization antigen |
| 383 | Possibly fimU |
| 387 | Possibly PilV pilus |
| 393 | Possibly pilW et |
| 401 | Possibly pil X |
| 403 | Possibly antigen cd3 |
| 411 | Unknown |
| 413 | Unknown |
| 419 | Possibly pil E |
| 421 | Possibly pyl y2 |
| 427 | Possibly PE-PGRS outer membrane antigen |
| 437 | Possibly ABC ligA |

DETAILED DESCRIPTION OF MODES OF PRACTICING THE DISCLOSURE

General

Hmw bacteriocins have the ability to quickly kill bacteria. A few early reports of in vivo studies have shown that they can be effective in mice for this application (Haas et al., 1974; Merrikin and Terry, 1972). This invention provides that when administered preferably either intraperitonealy or intravenously, wild type R2 pyocin can rescue mice from acute, lethal peritonitis caused by antibiotic-resistant *Pseudomonas aeruginosa* and that R2 pyocins can act at very low doses, such as $10^9$ pyocins or less than 1 µg total protein in a single dose (data not shown).

For hmw bacteriocins to be clinically useful as antibacterial agents, however; the problem of their narrow bactericidal spectra must be addressed. While this can be viewed as an advantage in that it is possible to specifically target a particular species or strain without affecting the normal flora and thereby causing minimal collateral damage, the types of species/strains that are sensitive to known bacteriocins are limited. For example, R-type pyocins currently are known to be produced by some *Pseudomonas aeruginosa* strains, and have activity against a narrow range of other *Pseudomonas* strains and a few other gram negative species. R-type bacteriocins from other species have been reported (such as *Erwinia*, see Jabrane 2002, and *Yersinia enterocolitica*, see Strauch) but the occurrence appears to be limited. Myoviridae phages, on the other hand, are quite widespread and common and are found throughout both the gram negative and gram positive bacterial classes.

This disclosure demonstrates that it is possible to change the spectrum of a hmw bacteriocin. A major spectrum determinant among both pyocins and their related phages lies in the tail fiber, which binds to the bacterial surface specifically, interacting through its C-terminal portion (RBD) with a component of the LPS or other cell surface structure. The LPS can be highly variable between different species and strains of bacteria, and bacteriophage tail fibers are themselves highly variable, particularly in this C-terminal region that interacts with the cell surface (Tetart, Desplats). This variability apparently reflects phages' constant adaptations to changing host surfaces. It has been observed that different phage types that infect the same host (*E. coli* phages P2, Mu, and P1) have sequence similarity in the C-terminal portion of the tail fiber (Haggard-Ljungquist E, Halling C, Calendar R.), indicating that horizontal transfer in these genetic regions likely plays a role in host specificity. For example, R2 pyocin has a very high degree of sequence similarity to *Pseudomonas* phage phiCTX, a phage that is also very closely related to *E. coli* phage P2. Comparing the tail fiber sequences of the R2 pyocin and P2, more sequence similarity is seen at the N-terminus (BPAR) than with the C-terminus (RBD), suggesting that the C-terminus plays the role in host specificity.

As disclosed herein, it is possible to alter the target spectrum of a pyocin or other hmw bacteriocin by engineering the C-terminal portion of the tail fiber gene. It is notable that this spectrum change can occur across species and genus barriers, demonstrating that natural R-type pyocins and other natural hmw bacteriocins can be modified as disclosed herein and developed into antimicrobials with broader spectra.

Modified HMW Bacteriocins

The disclosure provides engineered hmw bacteriocins with altered binding specificities and/or affinities. In some embodiments, an hmw bacteriocin of the disclosure specifically binds to exposed surface molecules that act as virulence factors or fitness factors of pathogenic bacteria. The term "specifically (or selectively) binds" refers to a binding reaction that is determinative of the presence of the bound ligand, often in a heterogeneous population of proteins and other biological matter. As a result, the engineered hmw bacteriocin once bound specifically can generically kill the pathogenic bacteria. Furthermore, in order to become resistant to the engineered hmw bacteriocin, the targeted pathogenic bacteria must lose its recognition or binding site for the hmw bacteriocin. Stated differently, if the modified hmw bacteriocin specifically and exclusively uses the virulence or fitness factor as its receptor, the bacteria would be forced to compromise or even completely lose its virulence or fitness in order to escape killing by the engineered hmw bacteriocin.

A modified hmw bacteriocin of the disclosure resembles a bacteriophage tail but comprises a binding capability, or receptor binding domain (RBD), that has been changed relative to an unmodified, naturally occurring, or native bacteriocin. The RBD may be changed in amino acid sequence by use of recombinant DNA techniques as described herein. The term "recombinant", typically used with reference to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. So a recombinant cell expresses genes that are not found within the native (non-recombinant) form of the cell or expresses native genes that are abnormally expressed, under expressed, or not expressed at all.

In many embodiments, the RBD may be modified to be that of a tail fiber or tail spike from another bacteriocin or a bacteriophage. As one non-limiting example disclosed herein, the RBD of R2 pyocin is modified by fusing the C-terminal portion of the tail fiber protein (RBD) of a phage (that infects a different host) to the N-terminal portion (BPAR) of the R2 tail fiber protein. By fusing the C-terminus of the P2 tail fiber to the R2 PRF15 and co-expressing the P2 cognate chaperone, the target bacteria spectrum of the R2 was changed to kill *E. coli* C. See FIG. 2.

In additional embodiments, hmw bacteriocins are engineered otherwise. The disclosure includes an hmw bacteriocin designed or selected to recognize, or target, a surface molecule of a bacterium (such as a pathogenic bacterium). The surface molecule may be considered a receptor on a bacterium recognized, or bound, by the hmw bacteriocin.

The disclosure is based on the properties of an hmw bacteriocin tail fiber to bind to, or interact with, a receptor to form a binding pair. The binding or interaction occurs through the RBD of the tail fiber, which is the first member of the binding pair, with the receptor being the second member of the pair. In many embodiments, the receptor is a bacterial cell surface molecule or portion thereof. In other embodiments, the receptor is a molecule with properties of a virulence or fitness factor of a pathogenic bacterium.

A modified or engineered hmw bacteriocin disclosed herein comprises a tail fiber having both a base plate attachment region (BPAR) and a modified, or heterologous, RBD. As described herein, the tail fiber is a trimeric structure of three tail fiber protein subunits, each of which also comprises a first domain corresponding to, and forming, the BPAR in a tail fiber and a second domain corresponding to, and forming, a modified or heterologous RBD in a tail fiber.

Typically, "heterologous" when used with reference to portions of a protein or nucleic acid sequence indicates that the sequence comprises two or more subsequences that are not usually found in the same relationship to each other in nature. For instance, a heterologous protein indicates that the protein comprises two or more subsequences that are not found in the same relationship to each other in nature. "Heterologous" also means that the amino acid or nucleic acid sequence is not normally found in conjunction with the other sequences or is not normally contained in the selected plasmid, vector, or host. In other words, it is not native to the system for which it is now utilized. For example, proteins produced by an organism that is not the wild type source of those proteins.

So in many embodiments, the disclosure includes an hmw bacteriocin tail fiber protein comprising a BPAR of the protein and a modified, or heterologous, RBD. The BPAR is typically at the N-terminal region of a tail fiber protein, while the RBD is typically at the C-terminal region. Other than the modified, or heterologous, RBD, the tail fiber protein may be that of any naturally occurring hmw bacteriocin, with a pyocin, monocin, enterocoliticin, or meningocin being non-limiting examples. In some embodiments, the tail fiber protein of R1-pyocin, R2-pyocin, R3-pyocin, R4-pyocin, and R5-pyocin, as represented by SEQ ID NO:1, 3, 5, 7, 9, respectively, may be used as described herein. In additional embodiments, the tail fiber protein may be that or those of the ΦCTX phage SEQ ID NO:45, or that of phage PS17 SEQ ID NO:19 or that of the VRML bacteriophage SEQ ID NO:21 and 22.

Embodiments of the disclosure include combinations of an hmw bacteriocin tail fiber protein BPAR and a RBD from a bacteriophage tail fiber protein, as shown in FIG. 3. In some cases, a combination may include the N-terminal amino acids from position 1 to about position 164 or position 240 of a bacteriocin tail fiber protein. This polypeptide fragment may be fused to a region of a bacteriophage tail fiber protein including its C-terminal portion containing an RBD. The region may be a polypeptide fragment lacking the N-terminal region from position 1 to about position 150, about position 170, about position 190, about position 290, about position 300, or about position 320.

Using the R2 pyocin and the P2 phage tail fiber protein as non-limiting examples, the BPAR containing fragment may include the N-terminal amino acids from position 1 to position 164 or 240. See FIGS. 4-7. The RBD containing fragment may include the C-terminal, and from about 347 to about 755 amino acids in length of the P2 or related phage tail fiber proteins. The fusion may be readily prepared by recombinant DNA techniques with nucleic acid sequences encoding the R2 tail fiber protein, such as prf15, and the P2 phage gene H encoding its tail fiber protein. When the RBD is derived from the tail fiber of another hmw bacteriocin or myoviridae, the cognate chaperone of the RBD needs to be co-expressed with the fusion tail fiber genes in order to ensure the assembly of the modified tail fibers into a functioning pyocin structure. See FIG. 8.

Another non-limiting example is the use of the R2 pyocin and the phiV10 phage. The BPAR containing fragment may include the N-terminal amino acids from position 1 to position 161 or 164 of the PRF15 protein. The RBD containing fragment may include the c-terminal amino acids from position 204, 211, or 217 to position 875 of the V10 tail spike protein. See FIG. 11A, and SEQ ID NOs: 67, 68, 69.

In other embodiments, a modified RBD comprises a change in the amino acid sequence of the RBD relative to a naturally occurring RBD or relative to the BPAR present in the tail fiber protein. Non-limiting examples of a change in amino acid sequence include substitution, insertion (or addition), or deletion of one or more amino acids.

In embodiments comprising the substitution of RBD amino acid residues, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 22%, about 24%, about 26%, about 28%, about 30%, about 35%, about 40%, about 45%, or about 50%, or more, of the C-terminal in a tail fiber protein are substituted. In some embodiments, the substitutions are within about 245, about 260, about 275, or about 290, or more, residues from the C-terminal.

The positions for substitution maybe any one or more, in any combination, within that region. Exemplary positions include, but are not limited to, 448, 449, 452, 453, 454, 455, 459, 460, 462, 463, 464, 469, 472, 473, 474, 475, 478, 480, 484, 485, 486, 491, 494, 496, 497, 498, 499, 505, 506, 507, 508, 510, 512, 514, 517, 518, 519, 520, 521, 523, 527, 528, 530, 531, 533, 535, 537, 538, 541, 543, 546, 548, 561, 603, 604, 605, 606, 610, 618, 621, 624, 626, 627, 628, 629, 631, 632, 633, 638, 641, 642, 645, 646, 647, 648, 649, 650, 651, 652, 653, 654, 655, 657, 659, 663, 664, 665, 666, 667, 668, 669, 670, 671, 672, 673, 674, 675, 676, 677, 678, 679, 680, 681, 682, 683, 684, 685, 686, 687, 688, 689, and 691, as well as any combination thereof, in SEQ ID NO:1, 3, 5, 7, or 9. In some embodiments, the substitution is conservative as described herein. In other embodiments, the substitution is with a non-conservative substitution.

In further embodiments, insertions and deletions of amino acid residues within the same region at the C-terminal of a tail fiber protein may be made.

Other sources of RBDs include, but are not limited to, T-4 and other T-even or pseudoT-even phages, phages T-3 and T-7, T-7 super-group of phages, phage Mu, phage P22, phage L-413c, podophages, lambdoid phages and even polysaccharide binding or specific protein binding enzymes or ligands, the binding properties of which can serve RBD functions as did the tail spike protein of phiV10.

RBD from Diversification

In further embodiments, a tail fiber protein comprises a substitution with, or insertion of, an RBD derived from an organism that diversifies the structure by deploying a Diversity Generating Retroelement (DGR), as described in published Patent Application US 2006-0121450, published Jun. 8, 2006 (incorporated herein by reference as if fully set forth). The major tropism determinant (MTD) of *Bordetella* bacteriophage BPP-1 is one such structure. The sequence of MTD is represented by SEQ ID NO:24 as disclosed herein. In other embodiments, the substitution is with part of the MTD sequence, such as, but not limited to, the region from residue 49 to 381, from residue 171 to 381, or from residues 306 to 381, of SEQ ID NO:24. The insertion of the MTD sequence, or any fragment thereof (such as those listed above), to the end of a tail fiber protein, such as after position 691 of SEQ ID NO:3, is within the embodiments disclosed herein. The substitution of the MTD sequence, or any fragment thereof (such as those listed above), may be for any non-BPAR region of a tail fiber protein. Non-limiting examples include the region of SEQ ID NO:1, 3, 5, 7, or 9 beginning at about position 643, 625, 562, 448, 428, 231, and 163 through to the C-terminus of the sequence (see FIGS. 4-7 for exemplifications of these substitutions).

As described herein, the tropism determinant sequence in a tail fiber may be diversified to produce a plurality of modified or heterologous RBDs. The nucleic acid sequence encoding the tropism determinant comprises a variable region (VR) which may be operatively linked, in cis or in trans, to a template region (TR) such that the TR is a template sequence that directs site-specific mutagenesis of the VR. The operative linkage of the VR and TR regions also includes an operative linkage to sequences encoding a reverse transcriptase (RT) activity, which may be present in trans relative to the VR. Sites of variability in the VR of the tropism determinant correspond to adenine residues in the generally homologous template region, TR, which itself is invariant and essential for sequence alterations in the VR. So while an initial molecule may contain a TR that is identical to the VR, the adenine residues present in the TR will result in the mutagenesis or diversification of the corresponding positions in the VR sequence. So if the TR sequence is a perfect direct repeat of the sequence in the VR, diversification of the VR region results in one or more adenine residues in the VR, also found in the TR, being mutated to another nucleotide, that is cytosine, thymine or guanine, without change in the TR sequence. This system may be used to alter the VR region, and thus the RBD, of a modified tail fiber protein as described herein.

Upon diversification, the tail fiber protein may be varied such that the resultant RBD has at least 80%, at least 85%, at least 90%, or at least 95% homology to the major tropism determinant (MTD) of *Bordetella* bacteriophage BPP-1, as represented by SEQ ID NO:24. As described herein, the tail fiber protein and tropism determinant combination may be a substitution, or an insertion, of a tropism determinant sequence or portion thereof into the tail fiber protein sequence. Thus the resultant tail fiber protein may be viewed as comprising a substitution or insertion with a binding domain with at least 80%, at least 85%, at least 90%, or at least 95% homology as recited above.

A nucleic acid molecule encoding a tail fiber and a tropism determinant combination may be used for diversification and sequence variation. Thus nucleic acid combinations of sequences encoding all or part of a tail fiber protein, and all or part of a tropism determinant, are within the disclosed embodiments. Other embodiments include nucleic acid molecules encoding any tail fiber protein with a modified or heterologous RBD as disclosed herein. In some embodiments, the encoded modified or heterologous RBD comprises a change in the amino acid sequence of the RBD relative to a naturally occurring RBD or relative to the BPAR present in the tail fiber protein as described above.

In additional embodiments, a tail fiber protein encoding nucleic acid molecule may be made available for diversification to faun a modified tail fiber protein disclosed herein. The nucleic acid molecule, under control of a suitable promoter, is operatively placed 5' to an atd-TR-brt region. The TR sequence may be referred to as TR' and prepared based upon the VR sequence as discussed below. The resulting nucleic acid construct may carry a deletion of the transcription terminator structure upstream of the atd.

A region of the nucleic acid molecule encoding the C-terminal end of the tail fiber protein as described above, is selected to be the VR and then operatively linked to a TR' sequence containing adenine residues at positions, that when varied, direct amino acid changes in the sequence encoded by the VR. Such adenine residues may be deliberately designed to be the first or second position of codons within the VR. The TR' sequence can initially be identical to the selected VR followed by site directed mutagenesis or de novo nucleic acid synthesis to prepare a TR' sequence that contains adenine residues only at the corresponding positions to direct mutagenesis and diversification in the encoded tail fiber protein.

Preparation and Use of HMW Bacteriocins

The nucleic acid molecules described herein may be used to express and prepare tail fiber proteins, including modified or engineered proteins, by any means known to the skilled person. In some embodiments, the expression is via the use of a vector containing the nucleic acid molecule operably linked to a heterologous promoter that can direct the expression of the encoded tail fiber protein. The promoter can be controlled by an exogenous molecule that acts as an inducer or co-repressor to express or not express the tail fiber proteins.

In many embodiments, the expression may occur with expression of an accessory gene, such as a tail fiber "chaperone" encoding sequence reported for various bacteriophages. The presence of a cognate chaperone for the RBD portion when derived from a tail fiber of a hmw bacteriocin or myoviridae facilitates assembly of an hmw bacteriocin of the disclosure without necessarily becoming a part of the bacteriocin, as shown in FIG. 8. One non-limiting example of a chaperone is encoded by R2 prf16 (SEQ ID NO:4), and it corresponds to (or is the cognate chaperone for) the R2 pyocin tail fiber protein encoded by prf15 (SEQ ID NO:3). Other examples include gene G in the P2 (SEQ ID NO:26), gene G on L-413c (SEQ ID NO:29), the cognate chaperone, SEQ ID NO: 20, for the PS17 tail fiber, and the Orf 38 (SEQ ID NO:23) in VHML bacteriophages, each of which is the cognate chaperone to the respective tail fiber gene in each of these myoviridae phages. These genes are homologues to the phage T4 gp38 (SEQ ID NO:32), which is known to be responsible for proper folding of the T4 tail fiber (SEQ ID NO:31) into trimers (Burda, Qu, Hashemolhosseni).

The use of a cognate chaperone is advantageous because a non-cognate chaperone may be insufficient to correctly fold a given tail fiber protein and/or assemble it into an hmw bacteriocin, as shown in FIG. 8. As a non-limiting example, the R2 prf16 gene product has been observed to be insufficient to complement the folding of a modified tail fiber compromising an R2BPAR fused to a P2 RBD portion of a tail fiber. Without being bound by theory, and offered to improve the understanding of the present disclosure, it is believed that a chaperone may act specifically on the C-terminal portion of its cognate tail fiber protein and that the tail fibers and their chaperones have co-evolved. However, Qu et al. isolated a T4 gp37 tail fiber mutant that suppresses the requirement for gp38, its cognate chaperone. This mutant had in gp37a duplication of a coiled-coil motif, which may itself play a role in folding. Therefore, it is further believed that a tail fiber protein may be designed to contain such a change so that it folds properly without the need to co-express a cognate chaperone.

Therefore, embodiments of the disclosure include a bacterial cell transfected with a nucleic acid molecule encoding a modified or engineered tail fiber protein, optionally co-expressed with a chaperone, as described herein. Expression of the nucleic acid molecule, optionally with an accessory (chaperone) protein, results in the production of modified or engineered tail fibers of the disclosure. The disclosure also includes expression of more than one modified or engineered tail fiber protein through the use of more than one nucleic acid molecule to result in mixed homotrimeric tail fibers or even heterotrimeric tail fibers. Additionally, sequences encoding the tail fiber protein and chaperone may be contained within a single nucleic acid molecule, such as a plasmid or other vector, or by separate molecules. Where a single nucleic acid molecule is used, the sequences optionally may be under the control of the same regulatory sequence(s). Alternatively, the coding sequences may be under separate regulatory control.

In some embodiments, the bacterial cell is also capable of expressing the additional subunits to form an hmw bacteriocin comprising a modified or engineered tail fiber. In one group of embodiments, the endogenous tail fiber protein coding sequence of the bacterial cell is inactivated or deleted. Optionally, the other subunits may be encoded by sequences on a nucleic acid molecule, such as a plasmid or other vector, separate from that which contains a sequence encoding a tail fiber protein and/or chaperone. Thus the tail fiber protein and/or chaperone may be provided one or more nucleic acid molecules in trans relative to the other subunits.

The nucleic acids, vectors, and bacterial cells may be used in a method of producing a modified or engineered hmw bacteriocin as disclosed herein. Such a method may comprise culturing bacterial cells containing nucleic acid molecules as described above under conditions resulting in the expression and production of the tail fiber and hmw bacteriocin. In some embodiments of the disclosure the conditions are in vivo within an animal.

In one group of embodiments, a method of preparing an hmw bacteriocin comprises expressing the bacteriocin subunits, including the modified or engineered tail fiber protein, in a host bacterium, and harvesting the hmw bacteriocin from the bacterial culture. The host bacterium is a complementary host production bacterium that encodes and expresses the other subunits necessary for the production of the bacteriocin. The term "host bacterium" or "host bacteria" refers to a bacterium or bacteria used to produce an hmw bacteriocin disclosed herein. Host bacteria or bacterium may also be referred to as "host production bacterium", "host production bacteria", "production bacterium" or "production bacteria". The "harvesting of an hmw bacteriocin from a bacterial culture" generally comprises removing the bacteriocin from the host bacterial culture.

In an alternative group of embodiments, a method of preparing an hmw bacteriocin with a modified tail fiber as described herein is provided. The method may comprise preparing a nucleic acid molecule encoding a modified tail fiber protein by any means disclosed herein and expressing the nucleic acid molecule in a cell under conditions wherein an hmw bacteriocin is produced.

Embodiments of the disclosure include an hmw bacteriocin comprising a tail fiber protein as described herein. In one group of embodiments, the bacteriocin comprises a tail fiber protein comprised in part of the amino acid sequence represented by SEQ ID NO:1, 3, 5, 7, 9. In other embodiments, the bacteriocin is a modified or engineered pyocin, monocin, enterocoliticin, or meningocin comprising a tail fiber with a heterologous modified RBD. In many embodiments, the heterologous modified RBD binds a bacterial virulence or fitness factor.

In further embodiments, engineered hmw bacteriocins with multivalent tail fibers are disclosed. MTD of Bordetella bronchiseptica bacteriophage BPP-1 has been found by X-ray crystallographic analysis to be a highly intertwined pyramidal homotrimer with the three sets of twelve non-contiguous variable amino acid residues forming three rather flat receptor-binding sites at the tetrahedron's base and located in a convergently evolved C-type lectin ("CTL") domain. Comparison of the structures of five MTD variants at 1.5 Å resolution showed that the main chain conformation of variable residues is structurally invariant, with inserts in the CTL and trimeric assembly both contributing to formation of a static scaffold for combinatorial display of variable residues, thereby minimizing the incidence of protein misfolding (McMahon et al., 2005). Thus a single tail fiber may be generated to contain three properly folded mixed monomers, since the structures of the variant tropism determinant fibers are identical except for the non-interacting, solvent-exposed twelve amino acid residues.

The structure of the dominant MTD-P1 variant bound to its receptor, the Bordetella virulence factor pertactin, also has been solved by crystallography and characterized. One of the monomers of MTD binds to one structural domain on pertactin; a second identical monomer of the same MTD binds a different, non-symmetrical structural domain of the same (monomeric) pertactin molecule; a third MTD monomer remains unbound.

The above variant MTD structures and the binding interaction between MTD and its target, pertactin, may be applied to the design and selection of multivalent tail fibers. For example, it is evident that an MTD monomer can exhibit affinities for two different structural domains and yet in multimeric format possess sufficient avidity to effect functional phage binding and infection. Furthermore, not all monomers of a fiber need be bound to a receptor to provide adequate avidity for phage binding and infection. These data and conclusions along with the knowledge that for at least T4 bacteriophages, also a member of the myoviridae family, only three (homotrimeric) tail fibers need be bound to receptors to trigger tail sheath contraction and core penetration of bacterial membranes, indicates several means of generating a multivalent hmw bacteriocin.

Such engineered multivalent hmw bacteriocins have broader host ranges and are capable of binding to more than a single virulence or fitness factor even on the same bacterial organism, thereby making it more difficult for targeted bacteria to develop resistance by mutational loss of expression of all targeted, relevant receptors. An R-type bacteriocin can be engineered to possess two independent sets of three identical tail fibers. The fibers of one set comprised of the same three non-identical monomers, and the fibers of the other set comprised of three different non-identical monomers. Each monomer can possess binding affinities for two different epitopes (e.g. two different receptors), just as does the tropism determinant. Thereby any bacterium expressing any one or more of the 12 different targeted receptor molecules (2 "epitopes"/monomer times 3 monomers/tail fiber times 2 sets of different tail fibers/R-type bacteriocin equals 12 targeted receptors) would bind the engineered multivalent hmw bacteriocin and trigger its penetration of the membrane. Such engineered hmw bacteriocins have an unnaturally broad host range and, in addition, make it highly unlikely that a bacterium expressing more than a single targeted receptor could become resistant to the engineered hmw bacteriocins.

In other aspects, methods for the use of an hmw bacteriocin of the disclosure are provided. In some embodiments, a method of compromising the integrity of the cytoplasmic membrane of a bacterium is disclosed. The method may comprise contacting a target bacterium with a fusion peptide or an hmw bacteriocin, or portion thereof, as disclosed herein. Alternatively, the contact may be with an hmw bacteriocin containing composition disclosed herein.

In one group of embodiments, the contacting occurs in vivo within a subject. Thus a method of compromising the membrane integrity of a bacterium in a subject is disclosed. The method may comprise administering a fusion peptide or an hmw bacteriocin or a portion thereof as described herein to the subject. In another group of embodiments, the contacting occurs ex vivo or in vitro.

The methods can be used as a stand-alone therapy or as an adjunctive therapy, such as for the treatment of bacterial populations. Numerous antimicrobial agents (including antibiotics and chemotherapeutic agents) are known which would be useful in combination with these methods to treating bacteria-based conditions.

In yet additional embodiments, a method of forming non-virulent or unfit bacteria progeny from virulent progenitor bacteria is provided. The method may comprise contacting virulent bacteria with an hmw bacteriocin which binds a virulence or fitness factor of said virulent progenitor bacteria as disclosed herein. The method then may continue by allowing selection of non-virulent bacteria progeny that no longer express the virulence or fitness factor.

In an alternative embodiment, a method of maintaining a population of non-virulent bacteria is provided. The method may comprise contacting the population with an hmw bacteriocin which binds a virulence or fitness factor of virulent bacteria. The method then continues and prevents propagation of virulent bacteria. Without being bound by theory, and offered to improve the understanding of the disclosure, an emergence of bacterial resistance to an engineered hmw bacteriocin will be accompanied by a compromised virulence or fitness of the pathogenic bacteria.

The methods of the disclosure also may be applied in an environment where bacterial growth is not desired or is considered to be harmful. Non-limiting examples include the sterilizing of environments, including medical settings and operating room facilities; as well as food or food preparation surfaces or areas, including where raw meat or fish are handled or discarded. The methods may also be used to sterilize heat sensitive objects, medical devices, and tissue implants, including transplant organs.

In particular, food or food products are affected by pathogenic or undersirable bacteria, such as certain strains of *E. coli*. However, in some instances, only certain species or groups of bacteria are pathogenic, so specific bacteriocin can be designed to target these groups or species. For example, one may choose to kill or mitigate an *E. coli* strain, such as O157:H7, but leave other natural, non-harmful *E. coli* unaffected. Therefore, selective or whole, santization or sterilization of bacteria is possible depending upon the use of one or more bacteriocins.

In another embodiment, methods of diagnostic screening or selection are provided. A sample of a suspected or known bacteria can be screened against one or more engineered bacteriocins to identify their potential therapeutic effects against the bacteria.

Furthermore, the engineered bacteriocins can be utilized to selectively or generally detect the presence of the pathogenic bacteria. In some instances, the bacteriocins would be labeled with a detectable marker, such that in the presence of the targeted bacteria, the label would be detected or identified.

Target Bacteria

The engineered hmw bacteriocins of the disclosure may be modified to target a receptor on a variety of bacterial species and strains, including pathogenic bacteria, such as nosocomial or pyogenic bacteria, as non-limiting examples. In addition to targeting the virulence factors of select bacteria as described herein, bacteria that are already susceptible to bacteriophages are one non-limiting group of bacteria that may be inhibited by an hmw bacteriocin, such as an engineered pyocin, of the disclosure. These bacteria include the gram negative bacteria that are susceptible, as well as not susceptible, to naturally occurring pyocins. Additional non-limiting examples include gram negative bacteria as a group as well as gram positive bacteria. There are reports of hmw bacteriocin-like entities in gram positive bacteria that target other gram positive bacteria (Thompson & Pattee, 1981; Birmingham & Pattee, 1981; Zink et al., 1995). In some embodiments, the target bacterium is identified or diagnosed. Non-limiting examples of such bacteria include those of the genus *Escherichia, Staphylococcus, Clostridium, Acinetobacter, Pseudomonas,* or *Streptococcus*.

As a non-limiting example of targeting a virulence factor, the disclosure includes the use of a phage tail fiber protein RBD like that of the tail spike protein from the podoviridae phage phiV10 that infects *E. coli* O157:H7 but does not infect a mutant strain TEA026 derived therefrom that has lost the O157 antigen (Ho and Waldor, 2007). The binding of this phage requires the presence of the O157 antigen, a virulence factor, involved in gut colonization by the pathogenic *E. coli* O157:H7 organism (Ho and Waldor, 2007). Therefore, an hmw bacteriocin of the disclosure may contain a modified tail fiber protein containing the globular RBD from the tail spike protein (SEQ ID NO:60) of the above described phage phiV10 such that the modified hmw bacteriocin targets a virulence factor, the O157 antigen, of *E. coli* O157:H7. The globular tail spike protein does not have a cognate chaperone as it apparently folds without such, and thus a chaperone is not required for the assembly of its fusion with the BPAR of R2Prf15.

An "infection" refers to growth of bacteria, such as in a subject or tissue or non-bacterial cell, wherein the bacteria actually or potentially could cause disease or a symptom in the subject, tissue or non-bacterial cell. Treatment of an infection may include prophylactic treatment of substances or materials. Non-limiting examples include donated organs, tissues, and cells; medical equipment, like a respirator or dialysis machine; or wounds, such as those during or after surgery. Other uses include the removal of target bacteria which may cause problems upon further growth. In additional embodiments, an hmw bacteriocin is used to treat food, plants or harvested parts of plants with bacterial infections or contaminations, or to treat environmental occurrences of the target bacteria, such as in a hospital or commercial setting.

The disclosure provides for the treatment, by administration or contact with an hmw bacteriocin disclosed herein to target the bacteria, of such infections in tissues and subjects as follows. The infections include the common infections of the cornea ("keratitis" and corneal ulcers), at least two-thirds of which are caused by *P. aeruginosa*. Approximately 30% of these pathogens are reported to be resistant to multiple antibiotics (Mah-Sadorra et al., 2005). Bacterial infection of the cornea is considered a relatively uncommon, but serious condition, requiring urgent medical attention, because of the potential for reduced vision or even vision loss in the affected eye(s). Other common infections which may be treated, and are caused by antibiotic-resistant *P. aeruginosa*, include ear infections, e.g. "swimmer's ear" (Roland & Stroman, 2002), those secondary to severe burns and wounds (Holder, 1993), and cystic fibrosis. Cystic fibrosis is consistently aggravated by chronic, antibiotic-resistant infections caused by *P. aeruginosa* and its close relative, *Burkholderia cepacia* (Govan & Deretic, 1996), and these pathogens in cystic fibrosis may be treated by use of an engineered hmw bacteriocin. Because bacteriocins like pyocins will tolerate freeze-drying (Higerd et al., 1969), the disclosure includes a freeze-dried formulation of a bacteriocin for administration to enhance the likelihood of successful delivery to the upper and/or lower airway of the respiratory tract.

As described herein, the treatment of a subject is typically of "a subject in need of treatment". The determination, or diagnosis, of the need for treatment may be made by a skilled person, such as a clinician, by use of art recognized means. In some embodiments, the subject is an animal or plant with a bacterial infection that is potentially life-threatening or that impairs health or shortens the lifespan of the organism.

In additional embodiments, a method to kill or inhibit the growth of bacteria in a biofilm is provided. Such a method may comprise contacting a biofilm with an hmw bacteriocin disclosed herein which targets bacteria in the biofilm.

As described herein, an anti-bacterial hmw bacteriocin is used to inhibit growth, survival, or replication of a particular bacterium. The bacterium may be a pathogenic or environmentally deleterious strain, or may be treated in a prophylactic manner. A pathogenic microorganism generally causes disease, sometimes only in particular circumstances.

The bacteria may also be that of a nosocomial (hospital derived) infection, environmental bacteria, and pyogenic (pus forming) bacteria. The methods and compositions of the disclosure can be used to inhibit growth of nosocomial bacteria, including bacteria that populate a typical hospital environment, or bacteria that are present on human skin or nose or in the human gastrointestinal tract, or bacteria that infect and form pus in wounds. Nosocomial infections are infections which become evident during a hospital stay or are related to a procedure performed in a hospital. These procedure-related infections often become evident after patients are discharged from the hospital. The most common nosocomial bacterial infections are urinary tract infections, surgical-site infections, pneumonia, *C. difficile* associated diarrhea and pseudomembrane colitis, and serious systemic infections in which bacteria can be grown from blood.

The methods and compositions of the disclosure may be used to inhibit growth of gram negative or gram positive bacteria. Non-limiting examples of gram positive bacteria include *Staphylococcus* (pyogenic), *Enterococcus* (opportunistic), *Streptococcus, Enterococcus, Bacillus, Micrococcus, Mycobacterium, Corynebacterium*, and *Clostridium*. Non-limiting examples of gram negative bacteria include *Pseudomonas* (pyogenic), *E. coli* (opportunistic), *Salmonella* (opportunistic), *Campylobacter* (opportunistic), *Proteus* (pyogenic), *Klebsiella* (opportunistic), *Enterobacter* (pyogenic), *Citrobacter* (pyogenic), gram negative non-fermenter rods (such as *Acinetobacter*), and *Shigella*. The pyogenic cocci are spherical bacteria that cause various suppurative (pus-producing) infections in animals. Included are the gram-positive cocci *Staphylococcus aureus, Streptococcus pyogenes*, and *Streptococcus pneumoniae*, and the gram-negative cocci, *Neisseria gonorrhoeae*, and *N. meningitidis*.

In additional embodiments, the disclosed methods and compositions of the disclosure are used to inhibit growth, particularly of antibiotic resistant bacteria. Non-limiting examples include numerous bacterial pathogens that have become multi-drug resistant (MDR).

Engineering Pyocins

Francois Jacob discovered and first described pyocins as high molecular weight bacteriocins (Jacob, 1954). Similar bacteriocin-like entities have been described in multiple other gram negative bacteria (Coetzee et al., 1968) as well as in *Listeria moncytogenes* (Zink et al. 1995) and *Staphylococcus aureus* (Thompson and Pattee, 1981), both of which are gram positive organisms. While pyocins morphologically resemble the tails of contractile (myoviridae) bacteriophages, they are not simple defective phages; there are meaningful differences. For example, differences exist in physical and chemical stability between pyocins and phage tails (Kageyama & Egami, 1962; Nakayama et al., 2000). While the host ranges of pyocins are relatively narrow and usually restricted to strains of the same species, there are exceptions (Morse et al, 1976; Blackwell et al., 1982). On the other hand, myoviridae bacteriophages can exhibit broad host ranges, and their host ranges, like those of R-type pyocins, are determined by the binding specificities of the tips of their tail fibers (Tetart et al., 2001).

For numerous phage tail fibers, the distal (3'-terminal) third of the gene varies in mutants or variants with altered phage host ranges, or "tropisms" (Ackermann, 2003). As a non-limiting example, the major tropism determinant (MTD), the receptor binding protein of *Bordetella* bacteriophage BPP-1, varies greatly in sequence (Liu et al., 2004; Doulatov et al. 2004). Variation in tropism determinants depends on a phage-encoded retroelement (Diversity Generating Retroelement, or DGR) that belongs to a family of DGRs implicated in generating sequence variation in various phage and bacterial genomes. The *Bordetella* DGR can produce more than $10^{13}$ different sequence variants of MTD, rivaling the $10^{14}$-$10^{16}$ possible sequences of antibodies. Tropism determinant variants are produced by a unique adenine-specific mutagenesis process involving DGR-encoded reverse transcriptase (bRT) and a stable template region (TR). Variability in MTD is focused to 12 adenine-encoded amino acids that are scattered across its C-terminal variable region (VR) (Doulatov et al. 2004). The 3-dimensional crystal structures of numerous *Bordetella* MTD variants have been solved and confirm, as described below, that the tip of the structure determines the binding specificity and thereby the major tropism (host range) of the phage (McMahon et al., 2005). Thus, as further described below, the tropism determinant and its related DGR system may be used in the practice of the disclosure.

Many *Pseudomonas* species possess the genes for the R-type pyocins (Takeya et al., 1969; Kageyama, 1975). The R-type pyocin locus consists of about 16 complementation groups including about 10 structural genes plus regulatory and chaperone genes (Shinomiya et al. 1983a; Shinomiya et al., 1983b). Morphologically and genetically the R-type pyocins resemble the tails of myoviridae bacteriophages but have no head structure and thus no nucleic acid content (Kageyama, 1964; Ishii et al., 1965; Shimizu et al., 1982). They are thought to have evolved from the phage tail structure of a P2-related ancestor, but they are not simple defective phages, having been further adapted for their role as defensive bactericidal agents (Nakayama et al, 2000). Similar to bacteriophages, however, pyocins do bind to specific molecular "receptors" on target bacteria and penetrate their membranes with a "core" or needle-like structure (Uratani & Hoshino, 1984). As an immediate consequence of the core penetration of the membranes, the bacterium is killed by compromise of the integrity of its cytoplasmic membrane and dissipation of its membrane potential, a bactericidal event that can result from an attack by a single pyocin (Iijima, 1978; Uratani & Hoshino, 1984; Strauch et al., 2001).

The RBD, or Receptor Binding Determinant of R-pyocin binding, of a typical R-type pyocin binds to a bacterial surface molecule. In the case of an R2 pyocin isolate, the RBD resides in the carboxy-terminal portion of its tail fiber. The tail fiber is a homotrimer of the product of the prf15 gene (Nakayama et al., 2000). Modification of the RBD in the prf15 gene and recombination of the modified prf15 gene into a system that produces R-type pyocins allows production of an engineered pyocin with modified binding specificity.

The major tropism determinant (MTD) of *Bordetella* bacteriophage possesses several unique and useful properties as a binding domain. The functional form of MTD in *Bordetella* bacteriophage is a homotrimer that binds the virulence factor protein, pertactin, in *Bordetella*. Thus, the MTD gene may be fused to the distal end of the prf15 gene to take advantage of the MTD properties. So as described herein, an aspect of the disclosure includes construction of a fusion protein between the *P. aeruginosa* R-type pyocin tail fiber protein (PRF15) and the major tropism determinant (MTD) of *Bordetella* phage, BPP-1. A PRF15-MTD fusion may be used to complement in trans a *P. aeruginosa* PA01Δprf15 to bind and kill pertactin-expressing *Bordetella bronchiseptica* or pertactin-expressing *E. coli*.

Additionally, the P2 or P4 bacteriophage may be used as a surrogate to harbor the prf15-MTD or other tail fiber fusion genes such that the genotype is coupled to the binding phenotype of the tail fiber. This permits efficient transduction, selection, and isolation of the tail fiber gene encoding the desired RBD.

Modes of Administration

An engineered hmw bacteriocin of the disclosure may be administered by any suitable means. Non-limiting examples include topical or localized administration as well as pulmonary (inhalation), gastrointestinal, by catheter or drip tube, or systemic administration to a subject. Representative, and non-limiting, examples of systemic administration include intraperitoneal and intravenous administration. The protective effects of intraperitoneally and intravenously administered pyocins have been demonstrated in mice infected systemically with lethal doses *P. aeruginosa* strains sensitive in vitro to the administered pyocins (Merrikin & Terry, 1972; Haas et al., 1974). In some embodiments, contact between an hmw bacteriocin disclosed herein and a target bacterial population results in a decrease in the population of at least 10, at least 100, at least 1000, or at least 10,000, or more, fold decrease relative to the absence of the bacteriocin. In other embodiments, the contact may result in a decrease in detectability of the bacteria by at least 5, at least 10, at least 20, at least 30, at least 40, or at least 50, or more, fold relative to the absence of the bacteriocin.

An engineered hmw bacteriocin of the disclosure may be administered to any subject afflicted with, diagnosed as afflicted with, or suspected of being afflicted with, an infection or contamination by bacteria susceptible to the hmw bacteriocin. Non-limiting examples of such a subject include animal (mammalian, reptilian, amphibian, avian, and fish) species as well as insects, plants and fungi. Representative, and non-limiting, examples of mammalian species include humans; non-human primates; agriculturally relevant species such as cattle, pigs, goats, and sheep; rodents, such as mice and rats; mammals for companionship, display, or show, such as dogs, cats, guinea pigs, rabbits, and horses; and mammals for work, such as dogs and horses. Representative, and non-limiting, examples of avian species include chickens, ducks, geese, and birds for companionship or show, such as parrots and parakeets. An animal subject treated with an engineered bacteriocin of the disclosure may also be a quadruped, a biped, an aquatic animal, a vertebrate, or an invertebrate, including insects.

In some embodiments, the subject to be treated is a human child or other young animal which has yet to reach maturity. Thus the disclosure includes the treatment of pediatric conditions comprising infection with bacteria or other microorganism susceptible to an hmw bacteriocin of the disclosure.

The disclosure also provides for the treatment or prevention of an opportunistic infection, such as that resulting from an undesirable growth of bacteria that are present in the microbial flora of a human subject or a non-human animal. An opportunistic infection may be the result of an immunosuppressed condition in a subject or the result of antibiotic treatment that alter the commensal flora of the genitourinary (GU) or gastrointestinal (GI) tract. Thus the disclosure also provides for the treatment or prophylaxis of immunosuppressed subjects and subjects exposed to other pharmaceutical agents. An hmw bacteriocin with its anti-bacterial activity may be used in combination with another anti-bacterial or anti-microbial agent, such as an antibiotic or anti-fungal agent as non-limiting examples. An "anti-microbial agent" is an agent or compound that can be used to inhibit the growth of, or to kill, single celled organisms. Anti-microbial agents include antibiotics, chemotherapeutic agents, antibodies (with or without complement), chemical inhibitors of DNA, RNA, protein, lipid, or cell wall synthesis or functions.

In some embodiments, an hmw bacteriocin or fusion protein is formulated with a "pharmaceutically acceptable" excipient or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. In many embodiments, the carrier or excipient is suitable for topical or systemic administration. Non-limiting pharmaceutically suitable carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Additional formulations and pharmaceutical compositions disclosed herein comprise an isolated hmw bacteriocin specific for a bacterial host; a mixture of two, three, five, ten, or twenty or more bacteriocins that target the same bacterial hosts; and a mixture of two, three, five, ten, or twenty or more bacteriocins that target different bacterial hosts or different strains of the same bacterial host.

Optionally, a composition comprising an hmw bacteriocin of the disclosure may also be lyophilized using means well known in the art. Subsequent reconstitution and use may be practiced as known in the field.

Also provided are formulations comprising microencapsulated hmw bacteriocin. In some embodiments, these may provide sustained release kinetics or allow oral ingestion to pass through the stomach and into the small or large intestine. In general, the pharmaceutical compositions can be prepared in various forms, such as granules, tablets, pills, suppositories, capsules (e.g. adapted for oral delivery), microbeads, microspheres, liposomes, suspensions, salves, pastes, lotions, and the like. Pharmaceutical grade organic or inorganic carriers and/or diluents suitable for oral and topical use can be used to make up compositions comprising the therapeutically-active compounds. Stabilizing agents, wetting and emulsifying agents, salts for varying the osmotic pressure, or buffers for securing an adequate pH value may be included.

An hmw bacteriocin is typically used in an amount or concentration that is "safe and effective", which refers to a quantity that is sufficient to produce a desired therapeutic response without undue adverse side effects like those described above. An hmw bacteriocin may also be used in an amount or concentration that is "therapeutically effective", which refers to an amount effective to yield a desired therapeutic response, such as, but not limited to, an amount effective to slow the rate of bacterial cell division, or to cause cessation of bacterial cell division, or to cause death or decrease rate of population growth of the bacteria. The safe and effective amount or therapeutically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

Additionally, and in anticipation of a possible emergence of bacterial resistance to an engineered hmw bacteriocin, there can be a concomitant compromise of the organisms' virulence or fitness where the bacteriocin targets the virulence or fitness factor of the targeted bacteria. Because a major, but non-limiting, mechanism by which a bacterium may become resistant to an hmw bacteriocin is the loss of its receptor for the bacteriocin, the targeting of a virulence or fitness factor as disclosed herein provides many advantages over traditional antibiotics and bacteriophages. The resistance to traditional antibiotics and bacteriophages can result from many different mechanisms other than loss of the receptor or target molecule of the antibacterial agent. As non-limiting examples, an hmw bacteriocin of the disclosure would not be subject to a bacterial efflux pump to remove the bacteriocin from the cellular environment and would not be subject to a bacterial nucleic acid deactivation mechanism.

Having now generally described the inventive subject matter, the same will be more readily understood through reference to the following examples which are provided by way of illustration, and are not intended to be limiting of the disclosure, unless specified.

EXAMPLES

The following examples are offered to illustrate, but not to limit the claimed subject matter.

Example 1

Modified hmw Bacteriocins Containing a Fusion Protein a) Complementation System

To facilitate the preparation of a modified hmw bacteriocin as described herein, construction of a system to complement tail fibers in trans was established. Using the R2 pyocin as a representative model, creation of a deletion of the R2 prf15 coding sequence in the *P. aeruginosa* PAO1 genome was used to create a platform in which a complementing tail fiber protein, such as a modified prf15 gene product, was expressed in trans.

Generally, the deletion was made by the method of Hoang et al. to create *P. aeruginosa* strain PAO1Δprf15. The prf16 coding region, SEQ ID NO:4, for the R2 chaperone overlaps the end of the R2 prf15 gene by 8 nucleotides and the ribosome binding site lies within the prf15 coding region, SEQ ID NO:3. The PRF16 protein, which is not necessarily incorporated into the pyocin structure, has been reported to be required for assembly of the trimeric tail fiber and thus for maximum bactericidal activity (FIG. 8 and Nakayama et al., 2000). Therefore, both the transcription start site for prf16 and its ribosome binding site were left intact such that the chaperone would be produced upon induction of the modified pyocin construct encoding a "tail-less," defective pyocin.

Briefly, an in-frame deletion of codons 11-301 of prf15 was made in PAO1 as follows. A 1.1 kb KpnI-AgeI fragment upstream of the desired deletion was amplified by PCR from PA01 genomic DNA using primers AV085 (5'-GCTTCAAT-GTGCAGCGTTTGC) (SEQ ID NO:46), and AV088 (5'-GC-CACACCGGTAGCGGAAAGGCCACCGTATTTCGGAG-TAT) (SEQ ID NO:47), and a 2.2 kb AgeI-EcoRI fragment was amplified using primers AV087 (5'-ATACTC-CGAAATACGGTGGCCTTTCCGCTACCGGTGTGGC) (SEQ ID NO:48) and AV086 (5'-TCCTTGAATTCCGCT-TGCTGCCGAAGTTCTT) (SEQ ID NO:49). The resulting restriction fragments were cloned into the KpnI and EcoRI sites of pEX18Gm (Hoang et al) to make pEXGm-Δprf15. The finished construct was transformed into strain PAO1 by electroporation (Chuanchuen et al). Integrants were selected with 100 µg/ml gentamicin, and segregants were then selected in media containing 5 µg/ml sucrose and lacking NaCl and gentamicin. Deletion candidates were confirmed by PCR analysis, pyocin induction, and sequencing of a PCR-amplified fragment.

Strain PAO1Δprf15 grows similarly to its parent strain, PAO1, and the pyocin encoding genes remain inducible through the SOS response, leading to lysis of the cell. While there appears to be some production of pyocin gene products, stable "tail-less" pyocin particles were not produced from PAO1Δprf15.

R2 pyocin prf15 was expressed in trans by first cloning the coding sequence into the broad host range *Pseudomonas/E. coli* shuttle vector, pUCP30T. See FIG. 9. In some initial constructs, transcription was driven constitutively or under lacI control from the tac promoter. But in other constructs, transcription was modified to be regulated with an endogenous prf15 promoter such that expression would be regulated through the SOS response. This permitted the expression of the modified prf15 gene to be induced synchronously with the expression of the other pyocin genes residing in the PAO1Δprf15 genome.

Briefly, the broad host-range vector pUCP30T (Schweizer, H. P et al) was modified by filling in the unique BspHI site to form pUCP30TABsp. A tac promoter was amplified by PCR from an MTD expression vector (a gift from Jeffery F. Miller, UCLA) using primers AV110 (5'-TTTATTAGCGGAA-GAGCCGACTGCACGGTGCACCAATG) (SEQ ID NO:50) and AV114 (5'-CCCTCGAATTCATGAATACT-GTTTCCTGTGTGAAATTG) (SEQ ID NO:51), then cloned into pUCP30TABsp to create pUCP-tac.

The R2 PRF15 coding region was amplified from a subclone using primers AV118 (5'-CTTCCTTTCATGACGAC-CAATACTCCGAA) (SEQ ID NO:52) and AV116 (5'-AC-CACGAATTCTTCATCGTCCAAATGCCTC) (SEQ ID NO:53), while R2 prf15 and prf16 were amplified using primers AV118 and AV086 (5'-TCCTTGAATTCCGCTTGCT-GCCGAAGTTCTT) (SEQ ID NO:49). The amplified fragments of prf15 and prf15/16 were cloned into pUCPtac digested with BspHI and EcoRI to yield pUCP-tac-prf15 and PUCP-tac-prf15/16.

For expression using the endogenous prf15 promoter, prf15 and prf16 were amplified together with the 1088 bp sequence upstream of prf15 from a subclone using primers AV107 (5'-CACCATCTAGACAATACGAGAGCGA-CAAGTC) (SEQ ID NO:54) and AV091 (5'-TCCT-CAAGCTTACGTTGGTTACCGTAACGCCGTG) (SEQ ID NO:55) and cloned into pUCP30T digested with XbaI and HindIII to create pUCP-R2p-prf15/16.

Bacteria in log phase suspension growth and containing the expression plasmids were treated with 3 μg mitomycin C/ml to induce pyocin production. Stable pyocins were produced upon induction with yields similar to that of wild type PAO1. The pyocins had the same bactericidal spectrum and level of activity as R2 pyocin produced from PAO1. Thus, production of a stable pyocin complex required the expression of a tail fiber protein in addition to expression of the other pyocin encoding genes, and expression of the tail fiber gene in trans was sufficient.

When prf15 was expressed constitutively from the tac promoter, cell growth was markedly slower than when it was regulated by lacI or the endogenous promoter. Although it appears that production of PRF15 alone in the cell is detrimental, yields of pyocins generated from both promoters are comparable.

A plasmid construct was prepared from which R2 prf16 was co-expressed with R2 prf15 to insure proper temporal expression prf16 for folding of PRF15 expressed in trans.

b) Recombinant hmw Bacteriocins

Figure 2:
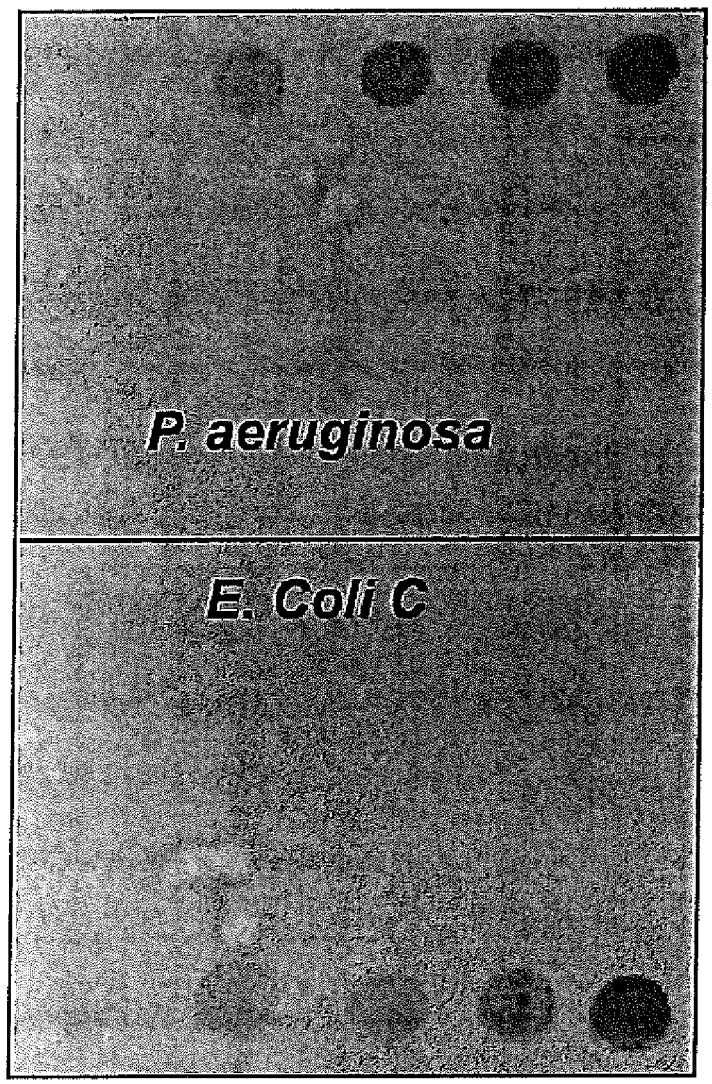

As described herein, five different R-type pyocins, based on spectra and termed R1-5, have been recognized. Because gene sequences encoding the tail fiber proteins were known only for R1 (SEQ ID NO:1) and R2 (SEQ ID NO:3), PCR was used to isolate and sequence the R3 (SEQ ID NO:5), R4 (SEQ ID NO:7), and R5 (SEQ ID NO:9) pyocin tail fiber genes along with their cognate chaperone encoding sequences present in their producer strains, SEQ ID NO:6, 8, and 10, respectively. The chaperone genes of pyocins R1 and R2 were also cloned and sequenced, SEQ ID NO:2 and 4, respectively. To confirm the hypothesis that the tail fiber dictates spectra, the sequences encoding R1, R3, R4, and R5 pyocin tail fiber proteins were obtained and expressed in trans in PAO1Δprf15 such that they would be incorporated into the R2 pyocin structure. Each of the resulting recombinant strains was then induced to produce pyocins and the spectrum of each was determined by spot assays, as shown in FIGS. 2 and 8.

c) Fusion Proteins as Functional Tail Fibers on Pyocins: R2-P2

A fusion of the R2 tail fiber prf15 gene and bacteriophage P2 gene H sequences was created, expressed and used to produce additional modified hmw bacteriocins of the disclosure. Bacteriophage P2, which infects many *E. coli* strains, has a tail fiber encoding gene H, (SEQ ID NO:25) that has significant sequence similarity to R2 prf15 (SEQ ID NO:3), particularly at the N-terminus-encoding portion. The portion of gene H encoding the C-terminal 551 amino acid residues of the P2 tail fiber protein, which is the putative region conferring target specificity (RBD), was fused to the portion of prf15 encoding the 164 amino acid N-terminal baseplate-binding (BPAR) portion of R2 PRF15 to encode a modified tail fiber protein (SEQ ID NO:27).

Bacteriophage P2 also encodes a putative tail fiber chaperone, encoded by gene G (SEQ ID NO:26), similar to that encoded by R2 pyocin prf16 (SEQ ID NO:4), and the chaperones of many of the other myoviridae phages. Because it is likely that the gene G encoded chaperone is important for folding the C-terminal portion of the P2 tail fiber protein in the fusion, constructs were made to co-express P2 gene G.

The portion of R2 prf15 encoding amino acids 1-164 was amplified from a subclone using primers AV118 and AV127 (5'-TTCTTTAAGCTTTTCCTTCACCCAGTCCTG) (SEQ ID NO:56) and was digested with BspHI and HindIII. The portion of P2 gene H encoding amino acids from position 158-669 was amplified from a P2 phage stock (Richard Calendar) using primers AV124 (5'-CCTCCTGAATTCTTAT-TGCGGCATTTCCG) (SEQ ID NO:57) and AV126 (5'-TC-CTTCGAATTCTTACACCTGCGCAACGT) (SEQ ID NO:58). P2 gene H 158-669 plus gene G was amplified using primers AV124 and AV125 (5'-CCTCCTGAATTCTTAT-TGCGGCATTTCCG) (SEQ ID NO: 59). Each of the PCR products from P2 were digested with HindIII and EcoRI. pUCP-tac-R2-P2H was created by cloning the prf15 fragment encoding the 1-164 amino acid fragment together with the P2 gene H fragment encoding the 158-669 amino acid fragment into pUCP-tac digested with BspHI and EcoRI. pUCP-tac-R2-P2HG was generated by cloning the prf15 fragment encoding the 1-164 amino acid fragment together with the P2 gene H fragment encoding the 158-669 amino acid fragment plus gene G into pUCP-tac digested with BspHI and EcoRI.

Briefly, PA01Δprf15 was transformed with the prf15-P2 gene H fusion constructs and pyocin production was induced with mitomycin C. Pyocin particles were purified and tested for activity by spot tests and by the bacterial survival assay (see FIG. 2). The purified pyocin particles containing the R2-P2 fusion tail fiber had bactericidal activity against *E. coli* strain C1a but were incapable of killing *P. aeruginosa* strain 13s. Furthermore, the expression of P2 gene G was needed to produce active pyocin. This supports the hypothesis that the chaperone is required for proper folding of the C-terminal portion of the tail fiber, as shown in FIG. 8.

The abilities of a range of different R2-P2 tail fiber protein fusions to form functional pyocins that kill *E. coli* C1a were explored by a series of different R2-P2 fusions. Representative examples of these fusions are shown in FIGS. 4-7, along with the indication of their resulting bactericidal activities against *E. coli* C1a.

d) Additional Fusion Proteins as Functional Tail Fibers on Pyocins: R2-L-413c

An additional modified hmw bacteriocin has been produced to target *Y. pestis*. L-413c is a yersiniophage that infects most strains of *Y. pestis* (Richard Calendar, personal communication). Most of the L-413c genome is highly similar to P2 with the notable exception of its tail fiber gene H, SEQ ID NO:28, which has diverged considerably from that of P2. Without being bound by theory, and offered to improve the understanding of the disclosure, variation in the tail fiber gene H, and thus the encoded protein, is the feature that most likely accounts for its differing host range.

The N-terminus of L-413c gene H (SEQ ID NO:28), however, shares considerably sequence similarity to its P2 counterpart (SEQ ID NO:25), likely due to its function of baseplate binding. A fusion was constructed to create a fusion tail fiber with the N-terminal 1-164 amino acids from R2 PRF15 fused to the C terminal (positions 158-913) portion of the L-413c tail fiber to create a modified tail fiber, as shown in FIG. 10 (SEQ ID NO:30). The fusion was expressed in PAO1Δprf15 along with the L-413c tail fiber cognate chaperone, gene G (SEQ ID NO:29), as described above. After induction, the produced pyocin particles killed *Y. pestis* KIM as well as *E. coli* C and thus had a killing spectrum analogous to the host range of yersiniophage L-413c. The modified pyocins did not kill any of the tested *Pseudomonas* strains.

e) Additional Fusion Proteins as Tail Fibers on Pyocins: R2-VHML

A further modified hmw pyocin particle has been made with a novel fusion tail fiber created between the *P. aeruginosa* R2 pyocin tail fiber BPAR (encoded by prf15) and one of the two tail fiber genes (SEQ ID NO:21 AND 22) of *Vibrio harveyi* Myovirus-Like (VHML) bacteriophage. We fused the diversifiable portion of the tail fiber (Oakey and Owens, 2000; Oakey et al., 2002; Doulatov et al. 2004) to the R2 pyocin tail fiber. The orf35 gene [SEQ ID NO:22] and that of its presumed cognate chaperone, orf38 [SEQ ID NO:23], were synthesized based on new DNA sequence data obtained from Dr. Oakey's VHML phage provided to the Australian National Genome Center in Brisbane. A series of fusions was generated between R2 prf15 and the orf35 gene, and the fusions were co-expressed with orf38 in PAO1Δprf15. For example, the fusion between BPAR R2 1-164 and VHML Orf35 26-410 formed robust R-type pyocin particles that could be purified and revealed the R-type pyocin proteins including fusion tail fibers of the expected size when analyzed by SDS PAGE.

Data generated in our laboratory has shown that with one exception, the only chimeric R-type pyocin tail fiber structures forming R-type pyocin particles that can be purified and reveal appropriate proteins on SDS PAGE were those that exhibit bactericidal activity on the expected target bacteria. The one exception has been this one chimeric R2 prf15-VHML orf35 fusion. This chimeric R-type pyocin preparation was not bactericidal for any of the *Vibrio* species tested, but the strain of *V. harveyi* from which the lysogenic VHML bacteriophage was isolated for DNA sequencing cannot be imported to the U.S. because of its pathogenicity to crustacean and oysters. We conclude that we have generated an "orphan" chimeric R2 prf15-VHML orf35 pyocin and that the resulting modified hmw bacteriocin with the VHML-derived RBD can be subjected to diversification by the natural DGR of VHML.

f) Additional Fusion Proteins as Functional Tail Fibers on Pyocins: R2-V10

Bacteriophage phiV10 belongs to the podoviridae group and can infect most common *E. coli* O157:H7 strains (Waddell and Poppe, 2000; Genbank NC_007804). Phage phiV10 does not encode a tail fiber like that of phage P2 or R-type pyocins but instead encodes a tail spike-like protein similar to that of bacteriophages P22 and epsilon15. These tail spikes are globular proteins that typically are polysaccharide-specific and degrade the surface polysaccharide structures to which they bind. It is likely that the phiV10 tail spike specifically recognizes, binds to and degrades the O157 antigen on the surface of the pathogenic *E. coli* O157:H7.

We deployed as RBD various C-terminal portions, such as aa 204-875, 211-875, and 217-875, of the phiV10 tail spike protein (SEQ ID NO.:60) by genetically fusing them individually to N-terminal BPAR encoding portions, such as aa 1-161 and 1-164, of the R2 pyocin tail fiber. When three of these recombinant fusion genes (R2Prf15 1-164:V10 tail spike 204-875[SEQ ID NO.: 67]; R2Prf15 1-164:V10 tail spike 217-875 [SEQ ID NO.: 68]; and R2Prf15 1-161:V10 tail spike 211-875 [SEQ ID NO.: 69]) were expressed individually in the appropriate *Pseudomonas* strain (PAO1Δprf15), those pyocin particles produced and released had incorporated into their structure functional R2-V10 tail fusions. These chimeric pyocin particles had bactericidal activity against all eight *E. coli* O157:H7 strains in our laboratory but did not kill any other *E. coli* strains, including mutants of EDL933 that have a defective O157 antigen. Furthermore, the chimeric R2-V10 pyocin digested the O157 antigen as evidenced by SDS PAGE of LPS extracted from *E. coli* EDL933. We have therefore created a recombinant R-type pyocin that specifically recognized and digested the O157 antigen, a known virulence factor of *E. coli* O157:H7, and killed specifically *E. coli* O157:H7 strains.

To determine whether mutants resistant to R2-V10 pyocin that might emerge from *E. coli* O157:H7 treated with R2-V10 pyocin would loose their O157 virulence factor, we selected, with and without prior chemical mutagenesis, EDL933 *E. coli* mutants resistant to R2-V10 pyocins. The LPS structures of seven independent mutants were analyzed by SDS PAGE to determine whether they had altered O-antigen structures. Each of the seven had different qualitatively or profoundly quantitatively altered O157 antigens demonstrating that resistance to R2-V10 did result in loss of the virulence factor, O157, from the *E. coli* O157:H7 pathogen.

When modeling the phiV10 tail spike protein with the Quickfire software (Imperial College, London), which utilizes a suite of protein structure analysis programs, we found that it predicted in the C-terminal 422 amino acids [SEQ ID NO: 60] structural homology with a galacturonase [SEQ ID NO: 66]. This explained the ability of portions of the V10 tail spike when fused to the N-terminal portion of pyocin Prf15 [such as SEQ ID NO:67, 68, 69] to enable the recombinant R-type pyocin to kill *E. coli* O157 by binding to the O157 antigen, which contained alpha-D-Gal2NAc, but not to kill the TEA026 mutant known to lack alpha-D-Gal2NAc in its O-antigen or the other 7 classes of EDL933 mutants described above. Quickfire also showed that the phiV10 tail spike has structural homology to the endorhamnosidase of phage P22 tail spike [SEQ ID NO: 70], a phage tail protein known to bind and degrade the *Salmonella* O-antigen. Thus, the fusion of protein with such a catalytic function to the N-terminal BPAR of the tail fiber of an R-type pyocin conveyed to the recombinant R-type pyocin the ability to utilize the enzyme's substrate binding property to target and kill bacteria expressing the enzyme's substrate on its surface.

Thus, R-type pyocins have been engineered to have different specificities using tail proteins from phages with tail structures naturally dissimilar to R-type pyocins, thus creating unnatural R-type pyocins.

g) Additional Fusion Proteins as Functional Tail Fibers on Pyocins: R2-PS17

*Pseudomonas aeruginosa* phage PS17 was obtained from the Félix d'Hérelle Reference Center for Bacterial Viruses, Universtie Laval, Canada. PS17 plaques were produced by infection of *Pseudomonas aeruginosa* strain PML14. PML14 cells lysogenic for phage PS17 were isolated by streaking cells from a plaque onto fresh tryptic soy agar plates. Lysogeny was verified by colony PCR amplification with primers AV168 and AV167, which were designed from Genbank sequence BPSFIFII. An overnight culture of the lysogenic cells was diluted 1:100 in 200 ml tryptic soy broth and shaken (225 rpm) at 37° C. until the optical density at 600 nm was approximately 0.2. Mitomycin C was added to a final concentration of µg/ml, and the culture was shaken a further 5 hours, at which time lysis was apparent. Deoxyribonuclease (Invitrogen, 1 unit/40 ml) was added, and the lysate was incubated at 37° C. for 30 minutes to reduce viscosity. The debris was then removed by centrifugation at 12,000 rpm for 30 minutes in a Beckman JA-25.50 rotor. The lysate was titered on strain PML14 and determined to be approximately $8 \times 10^9$ pfu/ml. Phage DNA was isolated from 40 ml of the cleared lysate using a Qiagen Lambda miniprep kit, following the manufacturer's instructions and using 3 columns from the kit. The DNA was resuspended in a total of 40 µl.

Based on the restriction map in Shinomiya and Ina (1989), we cloned and sequenced a ~4.2 kb BglII fragment. A 1 µl sample of PS17 phage DNA was digested with BglII then electrophoresed in an agarose gel. The appropriate fragment was excised from the gel, purified, and ligated together with pUC19 vector DNA digested with BamHI. Competent *E. coli* cells were transformed with the ligation products and transformants were selected on LB agar plates containing 100 µg/ml carbenicillin. Plasmid minipreps were prepared and used for DNA sequence analysis. Two overlapping open reading frames (SEQ. ID. NO.: 71) were found with significant homology to various tail fiber genes and chaperones. In plasmid pUC19-PS-B3, there were approximately 53 bp between the termination codon of the presumed chaperone open reading frame and the SacI restriction enzyme recognition site derived from the vector polylinker.

pUCP30T was digested with BspHI, the ends were made blunt by treatment with the Klenow fragment of DNA polymerase I in the presence of dNTPs, and the vector was religated to form pSW107, which lacked a BspHI site.

A $lac^q$ gene and a rrnBT2 terminator sequence were amplified by a two-step PCR using a suitable plasmid vector containing $lacI^q$, such as pMAL-c2E, as template and primers AV140 and AV027 in the first step and primers AV141 and AV27 in the second step. The PCR product was digested with SapI and ligated together with SapI-digested pSW107 to form plasmid pDG19.

A tac promoter was amplified by PCR using a suitable plasmid vector pGEX-2T as template and primers AV169 and AV114. The PCR product was digested with SapI and EcoRI and ligated together with SapI- and EcoRI-digested pDG19 to form plasmid pDG35.

The presumed tail fiber and chaperone open reading frames were amplified by PCR from plasmid pUC19-PS-B3 using primers AV238 and AV047. The PCR product was digested with BspHI and SacI and ligated together with BspHI- and SacI-digested pDG35 to form pDG65.

A DNA fragment containing R2 prf15 and prf16 was amplified by PCR from PAO1 genomic DNA using the primers PRF13-F and AV086. The PCR product was cloned using a "Zero Blunt TOPO PCR Cloning Kit for Sequencing" from Invitrogen. The resulting clone was designated pTOPO-R2.

A fragment of the R2 prf15 open reading frame representing codons 1-223 was amplified by PCR using pTOPO-R2 as template and primers AV118 and AV287. A fragment of PS17 presumed tail fiber open reading frame representing the C-terminal portion from codon 220 through the termination codon

```
Primer sequences (listed 5' to 3'):
AV168     TCACGGTAACGAATGTGGACG                                  (SEQ ID NO: 72)

LAV1671   TTTCAGCCAGTTGGTCGACAC                                  (SEQ ID NO: 73)

AV140     CCTGACGGATGGCCTTTTCTATTATCACTGCCCGCTTTCCAGTCG          (SEQ ID NO: 74)

AV141     TTTCTTTGCTCTTCCGCTAGAAGGCCATCCTGACGGATGGCCTTTTCT       (SEQ ID NO: 75)

AV027     TTTCTGCTCTTCAAGCCGACACCATCGAATGGTGCA                   (SEQ ID NO: 76)

AV169     TTTATTAGCGGAAGAGCCACGCGTGACTGCACGGTGCACCAATG           (SEQ ID NO: 77)

AV114     CCCTCGAATTCATGAATACTGTTTCCTGTGTGAAATTG                 (SEQ ID NO: 78)

AV238     AACCCACGAAGACCTCATGAGCACCAATCAATACG                    (SEQ ID NO: 79)

AV047     CGCCAGGGTTTTCCCAGTCACGAC                               (SEQ ID NO: 80)

PRF13-F   TATCGAGAACTGCTGCTGCGGG                                 (SEQ ID NO: 81)

AV086     TCCTTGAATTCCGCTTGCTGCCGAAGTTCTT                        (SEQ ID NO: 82)

AV118     CTTCCTTTCATGACGACCAATACTCCGAA                          (SEQ ID NO: 83)

AV287     TCGGTAATGCCGTACCCGCCCAGGGTGGTCGGATTGCTGC                (SEQ ID NO: 84)

AV286     GCAGCAATCCGACCACCCTGGGCGGGTACGGCATTACCGA                (SEQ ID NO: 85)

AV293     AAACCAAGAGCTCTTAGTTGGTGCCTTCTTCGGC                     (SEQ ID NO: 86)
``` after codon 779 plus the presumed chaperone open reading frame was amplified by PCR using pUC19-PS-B3 as template and primers AV286 and AV293. The resulting PCR products contained 20 bp overlapping sequences. The two fragments were assembled by overlap PCR using primers AV118 and AV293. The resulting fragment was digested with BspHI and SacI and ligated together with BspHI- and SacI-digested pDG35 to form plasmid pSW122.

PS17 plaques normally have a turbid "bulls-eye" appearance on a lawn of sensitive cells. PS17 phages were plated on strain PML14, and a few rare plaques with a clear appearance were picked. The clear-plaque phage were purified by replating and picking isolated plaques with a clear appearance. An isolate designated PS17-c5 was chosen for further use.

P. aeruginosa strain PA01 was deleted of nucleotides 10-2067 of its prf15 coding sequence (SEQ. ID. NO.: 3) by a method analogous to that described to create PAO1Δprf15 in Example 1 to create PAO1-mΔprf15. A 50 ml culture of PAO1-mΔprf15 in tryptic soy broth was shaken at 37° C. until the optical density at 600 nm was approximately 0.2. One plaque of PS17-c5 was transferred from a plate to the liquid culture. After an additional 3 hours shaking at 37° C. the optical density at 600 nm dropped, and lysis was apparent. The culture was then left to shake overnight (16 hours). Following the overnight incubation, the culture had become turbid again. A sample of the culture was inoculated onto a tryptic soy agar plate and incubated overnight. Colonies were checked for PS17 lysogeny by colony PCR with primers AV168 and AV167 and appeared negative. A clonal isolate designated PAO1-mΔprf15-c5$^R$ was chosen for further use as a host production bacterium for R2-PS17 modified pyocins. Cells were made electrocompetent by a method similar to that described by Choi and Schweizer (2005) and transformed with pDG65 and pSW122. Transformants were selected and maintained with 100 μg/ml gentamicin.

For expression of R2-PS17 pyocins, overnight cultures of PAO1-mΔprf15-c5$^R$ in tryptic soy broth supplemented with 100 μg/ml gentamicin were diluted 1:100 into G medium (Shinomiya, 1972) containing 50 μg/ml gentamicin. The cultures were incubated at 37° C. with shaking (225 rpm) until the optical density at 600 nm was approximately 0.2. Mitomycin C was then added to a final concentration of 3 μg/ml, and the cultures were shaken at 37° C. 3-4 hours. Optionally, deoxyribonuclease was added at 1 unit per 40 ml, and the lysate was incubated at 37° C. for 15-30 minutes to decrease viscosity. Debris was removed by centrifugation at 12,000 rpm in a Beckman JA-25.50 rotor for 30 minutes at 4° C. The supernatant was transferred to a fresh centrifuge tube, and pyocins were pelleted at 22,000 rpm (approximately 58,500× g) for 1 hour at 4° C. The pellets were resuspended at 3% of the original volume in 10 mM Tris-HCl pH 7.5, 50 mM NaCl and stored at 4° C.

The bactericidal activity of the recombinant "R2-PS17" pyocin preparations were demonstrated by spotting dilutions on PS17-sensitive *Pseudomonas aeruginosa* strains such as PML14.

h) Additional Fusion Proteins as Functional Tail Fibers on Pyocins: R2-MTD

The major tropism determinant (MTD) of the *Bordetella* bacteriophage BPP-1 has a C-type lectin (CTL) domain, which serves as a binding determinant for many different types of molecules and in many different biological contexts (Drickamer, 1999; McMahon et al., 2005). In BPP-1, MTD is incorporated as a homotrimeric globular domain located at the end of the phage tail, where it can bind to the surface protein pertactin, a virulence factor expressed on the outer surface of *Bordetella bronchiseptica* and *Bordetella pertussis* (Liu et al., 2004). In this context, MTD is also the target of phage-mediated homing mutagenesis, which can result in the bacteriophage acquiring a novel binding determinant for infecting its ever changing host.

Recent structural studies on the MTD domain and several of its diversified variants, have shown how the trimeric fiber tip forms a rigid scaffold that can contain more than 10 trillion variant binding ligands (McMahon et al. 2005). Fusing the MTD domain onto the pyocin tail fiber protein and then diversifying the MTD domain using the DGR system described by Miller and colleagues (Liu et al., 2004; Doulatov et al., 2004), creates a very large library of variants, from which to select and obtain the genes encoding pyocin tails with altered binding specificity.

Example 2

Assays of Fusion Proteins a) Pyocin Purification and Assays

PAO1 or appropriate derivatives were grown shaking at 200 rpm at 37° C. in G medium supplemented with 50 μg/ml gentamicin when needed to maintain plasmids. When the cultures reached OD600 of about 0.250, mitomycin C was added to a final concentration of 3 μg/ml. Cultures were incubated for an addition 2.5 hours until lysis occurred. Five units (1 unit/μl) of DNase1 (Invitrogen) was added to 200 ml of culture, and the culture was allowed to incubate an additional 30 mins. Debris was removed by centrifugation at 12,000 rpm in a Beckman JLA-16.250 rotor for 1 hour. Saturated ammonium sulfate was slowly added, at a rate of 1 ml/min, to the supernatant stirring on ice, to a final added volume of 65 ml per 100 ml of the supernatant of the lysate. This was stored at 4° C. overnight. The ammonium sulfate precipitate was collected by centrifugation at 12,000 rpm in a Beckman JA-25.50 rotor for 1 hour, 4° C., and the pellet was resuspended in 10 ml of TN50 buffer (10 mM tris, 50 mM NaCl, pH 7.5). Pyocin particles in the resuspended solution were then sedimented at 22,000 rpm (58,500×g) in a Beckman JA-25.50 rotor for 1 hour, 4° C., and resuspended in 3-5 ml of TN50 buffer. Pyocin preps were judged to be >90% pure by SDS polyacrylamide gel electrophoretic analysis.

Quantitative pyocin assays were performed by counting bacterial survival in a slightly modified method as described by Kagayama et al., 1964. Pyocin samples were incubated with target bacteria (approximately 1×10$^9$ CFU/ml) for 40 minutes at 37° C. The samples were then diluted and plated to count survivors. The number of pyocin particles is related to the fraction of bacterial survivors in a Poisson distribution, m=−1nS, where m=the average number of lethal events/cell and S is the fraction of survivors. The total number of active pyocin particles/ml=m×cells/ml. Strain13s was the *Pseudomonas aeruginosa* used in these assays and is a clinical isolate resistant to many anitibiotics, but sensitive to all 5 R-type pyocins. The *E. coli* target was C1a, kindly provided by Richard Calendar.

Semi-quantitative assays were also performed by a spot method where pyocin samples were serially diluted in TN50 buffer and spotted on lawns of target bacteria. After overnight incubation at 37° C., pyocin activity could be observed by a clear zone of killing on the lawn. FIG. 2 shows representative results from this assay format.

Example 3

Recombinant Bacteriophages to Screen Engineered Tail Fibers

The P4 bacteriophage was used as a surrogate to harbor a tail fiber fusion gene such that the genotype was coupled to the binding phenotype of the tail fiber. This has allowed efficient selection, transduction and isolation of the gene for the desired tail fiber.

Bacteriophage P2 is a temperate coliphage which can infect other enteric species, and can replicate in, but not infect, *P. aeruginosa* (Bertani & Six, 1988; Kahn et al., 1991). R-type pyocins are closely related genetically and structurally to P2, and the P2 tail fiber protein, encoded by gene H, shows homology to PRF15 at the N-terminal portion, where base plate attachment occurs (Haggard-Ljungquist et al., 1992; Nakayama et al., 2000). Deploying the P2 or P4 bacteriophage as a surrogate phage, in which plasmid-encoded tail fibers were incorporated in the phage particle in place of the P2 phage-encoded fibers, permitted the display and selection of fusion fibers in a context that closely resembled its intended functional context in the pyocin.

The tail fiber genotype was physically coupled to the binding phenotype in a transducing phage particle for genetic selection, similar to phage display technology. When a P2 phage with an amber mutation in its fiber protein gene H (made in an amber suppressor+*E. coli*) infected *E. coli* harboring a P4-based plasmid with a cos packaging site, which normally acts as a signal for packaging bacteriophage genomic DNA (Ziermann & Calendar, 1991; Kahn et al., 1991), it packaged the cos-containing P4 plasmid in the heads of newly synthesized P2/P4 phage particles. The P4-based plasmid, FIG. 12, encoded and expressed the tail fusion gene. The fusion tail fibers expressed from the P4 plasmid in the P2 infected *E. coli* were incorporated into the P2/P4 particles in place of the defective (amber truncated) gene H product (P2 tail fiber protein). Upon lysis of the infected bacteria by the expression of the P2 holin and lysozyme, the released P2/P4-based transducing particles carried the cos-containing P4 plasmid encoding the tail fiber fusion gene rather than the P2 genome and had attached the recombinant fusion tail fibers rather than the amber truncated P2 tail fibers.

Specifically, plasmid pSW166 was constructed by replacing the region corresponding to bases 226-2594 of bacteriophage P4sid$_1$ (Shore et al. 1977) with the 763 bp fragment consisting of the promoter and coding region of aacC1 (gentamicin acetyltransferase 3-1) from plasmid pUCP30T (Schweizer, 2001; NCBI accession U33752) flanked by restriction sites introduced by PCR amplification (MfeI and KpnI next to the promoter and EcoRI next to the termination codon), cloned in the same orientation as the P4 int gene.

Plasmid pDG211 was constructed by inserting between the MfeI and KpnI sites a 274 bp fragment derived by PCR amplification and consisting of a P4 $P_{LE}$ promoter (Dehó et al., 1988) corresponding to bases 8585-8835 (complementary strand) such that the promoter was in the same polarity as aacC1 and NheI and NcoI sites were created between the KpnI site and the $P_{LE}$ promoter.

DNA fragments derived by PCR amplification encoding amino acids 1-157 of the P2 gene H tail fiber gene and amino acids 218-875 of the phiV10 tail spike gene were inserted between the NcoI and KpnI sites of pDG211 to create pDG218, FIG. 12.

A 1 ml culture of *E. coli* C1a harboring plasmid pDG218 was grown to OD600 of 1.0, supplemented with 1 mM CaCl$_2$ and infected with P2amH72vir20 (Sunshine et al., 1971) at a multiplicity of infection of approximately 2. After a 10 minute pre-adsorption, the cells were shaken at 225 rpm at 37° C. for 50 minutes. The bacteria and debris were removed by centrifugation in a microcentrifuge for 1 minute, and the lysate supernatant was saved.

Cultures (200 µl) of each *E. coli* TEA026 and *E. coli* EDL933 (Ho and Waldor, 2007) target cells were supplemented with 2.5 mM CaCl$_2$ and 2.5 mM MgCl$_2$. Supernatant (50 µl) from the lysate (previous step) was added and preadsorbed for 10 minutes. The cells were then diluted with 700 µl broth and shaken at 225 rpm at 37° C. for 1 hour. Aliquots (10 µl) of each cell suspension was plated on LB agar plates containing 15 µg gentamicin/ml. The plates were then incubated overnight at 37° C. While an estimated 1000 colonies grew on the EDL933 plate, none grew on the TEA026 plate.

A control P4-based, negative control plasmid, pDG212, which was constructed to contain the complete, unfused P2 gene H tail fiber gene rather than the P2-V10 fusion gene as in pDG218, was similarly packaged from *E. coli* C1a after infection with P2amH72vir20. When 10 µl of the control lysate was incubated with *E. coli* C1a on gentamicin-containing plates, 10,000 colonies grew but none appeared when the same control lysate was incubated with EDL933 on gentamicin containing plates. Thus, the false positive frequency for generating gentamicin-resistant colonies of EDL933 from transfection with P4 particles that do not harbor the O157-specific binding property is less than $10^{-4}$.

Transducing phage particles with the ability to bind cells and trigger the bacteriophage injection mechanism confered gentamicin resistance to successfully targeted bacteria, from which the selected fiber fusion gene was isolated from the plasmid after replication of the bacteria under gentamicin selection. The functional V10-based RBD gene isolated by PCR was fused to the BPAR (aa 1-164) of R2 prf15, expressed in trans in PA01Δprf15 and recombinant pyocins isolated and assayed for bactericidal activity on *E. coli* TEA026 and *E. coli* EDL933. As described for the P2/P4 particle, the RBD from V10 tail spike protein when fused to BPAR from R2 pyocin PRF15, conveyed specificity to the resulting modified pyocin such that it was bactericidal for EDL933 but not for the mutant TEA026, lacking the O157 antigen. The tail fiber gene on the P4 plasmid is easily further manipulated to create many fusion junctions and to diversify the RBD in order to redesign and optimize the function of the modified tail fiber RBD.

A related P4 virion particle was made to carry recombinant tail fibers generated by fusing an BPAR portion of P2 gene H encoding aa 1-158 to the portion of the tail fiber gene of *Pseudomonas* phage, PS17, encoding an RBD of aa 164-779. The gene H-PS17 tail fiber fusion gene was co-expressed with the latter's cognate chaperone from a P4-based plasmid, pDG224, similar to pDG218. Once harvested from the lysate of a P2amH72vir20 infected *E. coli* C1a harboring pDG224, the P4 particles conveyed by transformation gentamicin resistance to *P. aeruginosa* strain PML14 but not to *P. aeruginosa* strain PA14. PS17 phage also infected the former but not the latter *P. aeruginosa* strain. Thus, the P4-based surrogate system has provided selection methods to couple recombinant genotype to recombinant tail fiber binding phenotype even across genera of bacteria.

This approach also overcomes many of the difficulties imposed by C-terminal display of a trimeric protein when using conventional phage display systems (Held & Sidhu, 2004). Bacteriophage P2 has tail fibers that genetically and morphologically resemble those of pyocins (Nakayama et al., 2000). Tail fibers attach to the base plates of P2 and pyocins via their N-termini, and there is significant sequence similarity of the N-termini of P2 and R2 pyocin tail fibers (Nakayama et al, 2000; Haggard-Ljungquist et al., 1992). Furthermore, the tail fiber gene of the P2-related phage, PS17, can complement the R2 pyocin tail fiber gene, prf15 (Shinomiya, 1984; Shinomiya & Ina, 1989).

Alternatively, portions of the tail fiber gene orf35 of VHML phage of *Vibrio harveyii* (which like BPP-1 also contains a functioning DGR) is fused to the N-terminal domain of P2 gene H. This recombinant construction will then allow the P4-based selection of RBDs of particular interest, as described above, after the DGR-driven diversification of the VHML VR embedded in the orf35 RBD.

Example 4

Methods to Recover the Desired Tail Fiber Gene

A P2 or P4 bacteriophage carrying an engineered tail fiber gene acted as a surrogate to couple pyocin tail fiber genotype to binding phenotype. By selecting or screening for specific binding phenotypes from the diversified or mutagenized libraries of the tail fiber genes harbored in such surrogate bacteriophages, one can isolate the tail fiber genes that encode a desired binding specificity. The selection may be carried out by single or multiple enrichment cycles of adsorbing the surrogate bacteriophages or transducing particles onto solid-phase target molecules, either by first removing undesired binders and then isolating, from among the remaining surrogates, those that bind to the intended target molecules, or visa versa. Alternatively, the selection may occur by applying either binding step alone. Ultimately, the surrogate exhibiting the desired binding phenotype can be subject to DNA extraction and isolation of the harbored tail fiber gene by cloning restriction enzyme fragments or by PCR reactions using oligonucleotide primers that bind specific DNA sequences peripheral to the diversified portion of the tail fiber gene.

Even though the surrogate phages or transducing P4 particles will not form plaques on the target-expressing bacteria, the infected or transduced bacteria will still acquire antibiotic resistance, such as P4 plasmid-encoded gentamicin resistance, along with the harbored plasmid or phasmid and therefore can be selectively grown and subsequently extracted to isolate the multi-copy plasmid and its desired tail fiber gene.

These techniques permitted the identification and isolation of surrogate bacteriophages or transducing particles exhibiting the desired, specific binding phenotypes from which we extracted and isolated the desired, specific, unnatural hmw bacteriocin tail fiber genes. Furthermore, the binding of surrogates to mammalian molecules, cells or tissues can be deployed to deplete from the libraries any genes encoding tail fibers that might cause adverse events if incorporated into therapeutic hmw bacteriocins.

There is an available library of insertional mutant *Pseudomonas aeruginosa* bacterial strains differing from highly pathogenic parental PA14 *Pseudomonas aeruginosa* only by the lack of expression of a series of specific virulence factors, one missing from each non-redundant, isogenic mutant (see the website at ausubellab.mgh.harvard.edu/cgi-bin/pa14/home.cgi). These isogenic mutant strains provide tools for ensuring the specificity of the surrogate bacteriophages for the targeted virulence factors and not for other prevalent surface molecules. For example, the population of surrogate P4 bacteriophages can be incubated with a high density culture of a *Pseudomonas aeruginosa* mutant missing a particular targeted virulence factor in order to adsorb and deplete from a population of surrogate bacteriophages or transducing particles, those that bind to surface molecules present on both the isogenic mutant and the virulent parental strain. The depleted population will be enriched in surrogates binding to the desired virulence factor. Once surrogate bacteriophages that do bind to and infect the bacteria expressing the particular virulence or fitness factor are isolated, each can be screened directly for its inability to infect the isogenic mutant strain lacking the targeted factor. The selected plasmid can be repackaged in surrogate transducing particles and recycled any number of times through the adsorption-depletion and infection process to further enrich and eventually purify the pUC-based plasmid encoding the desired tail fibers for targeting the virulence or fitness factor.

A tail fiber gene, recombinant or natural, encoded in a recombinant P4 genome can be subject to mutagenesis, particularly in the portion of the RBD domain that confers specificity, by any one of several methods familiar to one ordinarily skilled in the art. The mutagenized P4 genomic plasmid is transformed at low multiplicity into *E. coli* C, and the gentamicin-resistant transformants are subsequently infected by phage P2 amber H (P2amH72vir20). As described above, a library of P4 virion particles will be packaged and produced and will have tail fibers with mutant RBD portions, the gene for which will be encoded specifically within the packaged recombinant P4 genome. Some of these mutations will encode binding capabilities specific for a given target receptor on a target bacteria. The P4 genome harboring the mutant RBD with the desired, and even rare, binding specificity can be selected by infecting the target bacterial strain with the virion library and isolating gentamicin-resistant bacterial colonies. The resistant bacteria will harbor P4 genomes that encode a mutant RBD portion that has acquired specificity for the target bacterial strain.

An example of selecting a rare desired binding phenotype and thereby genotype from a large population of undesired P4 particles was demonstrated by mixing different proportions of lysates of P4 particles from *E. coli* C1a harboring pDG212 (P2 tail fiber) and *E. coli* C1a harboring pDG218 (P2-V10 recombinant tail fiber). When the mixtures contained 0%, 1%, 99%, or 100% of the P4 particles with the P2-V10 tail fibers or the converse number of P4 particles with P2 tail fibers, the appropriate numbers of EDL933 or *E. coli* C1a transformed colonies grew on gentamicin containing agar plates. That is the P4 particles harvested from *E. coli* harboring pDG218 could only transfect and convey gentamicin-resistance to EDL933 bacteria; while those harvested from *E. coli* harboring pDG212 could only transfect and convey gentamicin-resistance to *E. coli* C1a bacteria. The frequency of false positive growth, that is formation of gentamicin-resistant colonies of *E. coli* EDL933 after attempted transformation with P4 from pDG212-harboring *E. coli*, was less than $10^{-5}$. The converse was also observed, that is formation of gentamicin-resistant colonies of *E. coli* C1a after attempted transformation with P4 from pDG218-harboring *E. coli*, was less than $10^{-5}$.

The DNA encoding mutant RBDs with desired binding phenotype can be isolated by the PCR method using primers within the gene H sequence 5' to the RBD and sequences 3' to the RBD but immediately outside the RBD coding region. The selected RBD DNA sequence will be fused with the BPAR portion of an R-type pyocin prf15 gene, such as that portion encoding aa 1-164, and expressed in trans in bacteria such as PA01Δprf15 or a production strain as described below to make recombinant R-type pyocins with a novel, desired binding and bactericidal specificity.

Example 5

Methods for Producing Engineered Hmw Bacteriocins

The modified tail fiber gene is recombined either (i) into a plasmid under a regulated promoter for expression in production bacteria also harboring, for example on a bacterial artificial chromosome (BAC), the R-pyocin gene cluster (including the endolysin genes) from which the resident prtR, prtN, prf15 and holin (prf9 or PA0614) genes have been deleted or otherwise disabled, or (ii) into the pyocin cluster containing BAC vector itself, using a plasmid-mediated allelic exchange reaction.

a) Expression of R-Type Pyocins in *E. coli*

The R2 pyocin gene cluster was cloned in four different variations using five different cloned fragments derived from PCR products.

Fragment 1 was amplified by PCR from PA01 genomic DNA using primers AV461 and PRF13R, then digested with restriction enzymes EcoRI and HindIII. The resulting fragment represented bases 4267-7856 of Genbank sequence AB030825. Primer AV461 added an EcoRI site. This fragment lacked genes prt-R and prt-N.

Fragment 2 was amplified by PCR from PA01 genomic DNA using primers AV529 and PRF13R, then digested with restriction enzymes EcoRI and HindIII. The resulting fragment represented bases 2975-7856 of Genbank sequence AB030825. Primer AV529 added an EcoRI site. This fragment contained genes prt-R and prt-N.

Fragment 3 was amplified from PA01 genomic DNA using primers AV333 and AV334, then digested with HindIII and NheI. The resulting fragment represented bases 7856-14280 of Genbank sequence AB030825. This fragment contains a full-length prf/5 gene.

Fragment 4 was amplified from PA01-rΔprf15 genomic DNA using primers AV333 and AV334, then digested with HindIII and NheI. The resulting fragment represented bases 7856-9155 and 10028-14280 of Genbank sequence AB030825. This fragment contained a prf15 gene with an 873 bp internal deletion.

Fragment 5 was amplified from PA01 genomic DNA using primers AV407 and AV404, then digested with NheI and PacI. The resulting fragment represented bases 14,280-19,860 of Genbank sequence AB030825. Primer AV404 added a PacI site.

A fragment of pBR322 (comprising nucleotides 2334-4353 of Genbank sequence SYNPBR322) including the origin of replication and the β-lactamase gene was amplified using primers AV337 and AV338. The resulting fragment was digested with NotI, and a multiple cloning site was created by ligating the NotI-digested vector with kinased and annealed oligos AV339 and AV340. The resulting plasmid was designated pDG121.

The plasmid pDG173 contained fragments 1, 3 and 5, inserted respectively between the EcoRI and PacI sites of pDG121.

The plasmid pDG174 contained fragments 2, 3 and 5, inserted respectively between the EcoRI and PacI sites of pDG121.

The plasmid pDG175 contained fragments 1, 4 and 5, inserted respectively between the EcoRI and PacI sites of pDG121.

The plasmid pDG176 contained fragments 2, 3 and 5, inserted respectively between the EcoRI and PacI sites of pDG121.

Chemically competent cells of *E. coli* strain BL21 (non-λDE3 lysogen; Novagen Cat. No. 69449-3) were transformed with plasmids pDG173, pDG174, pDG175 or pDG176. The retention of the plasmids was selected and maintained with 50 µg/ml carbenicillin.

For expression of pyocins, overnight cultures of strain BL21 in LB broth supplemented with 50 µg/ml carbenicillin were diluted 1:100 into G medium (Shinomiya, 1972) containing 25 µg/ml carbenicillin. The cultures were incubated at 37° C. with shaking (225 rpm) until the optical density at 600 nm was approximately 0.2. Mitomycin C was then added to a final concentration of 33.3 ng/ml, and the cultures were shaken at 37° C. overnight (15-22 hours). The cultures still appeared turbid. Cells and debris were removed by centrifugation at 12,000 rpm (approximately 17,400×g) in a Beckman JA-25.50 rotor for 30 minutes at 4° C. The supernatant was transferred to a fresh centrifuge tube, and pyocins were pelleted at 22,000 rpm (approximately 58,500×g) for 1 hour at 4° C. The pellets were resuspended at 3% of the original volume in 10 mM Tris-HCl pH 7.5, 50 mM NaCl and stored at 4° C. The bactericidal activity of each preparation was assayed on strain 13s of *P. aeruginosa*. 10 µl of each sample was electrophoresed on a 4-20% polyacrylamide tris-glycine SDS gel (SDS-PAGE) alongside molecular weight standards. The preparations from the *E. coli* transformants containing pDG173 and pDG174 exhibited potent bactericidal activities and clear R-type pyocin protein subunits on SDS-PAGE analyses. The preparations from the *E. coli* transformants containing pDG175 and pDG176 did not exhibit bactericidal activity and did not demonstrate substantive R-type pyocin protein subunits on SDS-PAGE analyses, all as predicted.

```
PCR primer sequences:
PRF13-R    GCACCGTTACCCGATCCGCGA                          (SEQ ID NO: 87)

av333      TCGAGACGATTTACCAAGAGCTG                        (SEQ ID NO: 88)

av334      TTCCACGACCAGTCCGGAAAATG                        (SEQ ID NO: 89)

av337      TTTATTTGCGGCCGCGACGAAAGGGCCTCGTGATAC           (SEQ ID NO: 90)

av338      TTTATTTGCGGCCGCAAATACCGCATCAGGCGCTCTTC         (SEQ ID NO: 91)

av339      GGCCGCTTATTAACAAGCTTCACACACGCTAGCCCACCACGC     (SEQ ID NO: 92)

av340      GGCCGCGTGGTGGGCTAGCGTGTGTGAAGCTTGTTAATAAGC     (SEQ ID NO: 93)

av404      CCCCCCCTTAATTAACTTGAGTCAGGATGGACATG            (SEQ ID NO: 94)

av407      AAGGCATTCGAGACCGTCAAG                          (SEQ ID NO: 95)

av461      TTTCCTTGAATTCGCTCGGCAATCTACAGACCGATG           (SEQ ID NO: 96)

AV529      TTTCCCTGAATTCATTACTTGCCCACGCAGAAGGCGCTTTC      (SEQ ID NO: 97)
``` b) Expression of R-Type Pyocins in *Pseudomonas fluorescens*

Kinased and annealed oligos AV530 and AV531 were ligated into EcoRI- and HindIII-digested broad-host range plasmid vector pUCP30T (Genbank XXU33752). The resulting plasmid was designated pDG171.

```
Primer sequences:
AV530  AGCTgcggccgcGAATTCacgcgtAAGCTTactagtGCTAGCTTAATTAA  (SEQ ID NO: 98)

AV531  aattTTAATTAAGCTAGCactagtAAGCTTacgcgtGAATTCgcggccgc  (SEQ ID NO: 99)
```

The ~15.6 kb EcoRI-PacI fragment from pDG173 was ligated into EcoRI- and PacI-digested pDG171 to create pDG193.

The ~16.9 kb EcoRI-PacI fragment from pDG174 was ligated into EcoRI- and PacI-digested pDG171 to create pDG194.

The ~14.7 kb EcoRI-PacI fragment from pDG175 was ligated into EcoRI- and PacI-digested pDG171 to create pDG195.

The ~16.0 kb EcoRI-PacI fragment from pDG176 was ligated into EcoRI- and PacI-digested pDG171 to create pDG196.

*Pseudomonas fluorescens* (ATCC Cat. No. 13525) were made electrocompetent by a method similar to that described by Choi and Schweizer (2005), and transformed with pDG193, pDG194, pDG195 or pDG196. Transformants were selected and maintained with 100 µg/ml gentamicin.

For expression of pyocins, overnight cultures in tryptic soy broth supplemented with 100 µg/ml gentamicin were diluted 1:100 into G medium (Shinomiya, 1972) containing 50 µg/ml gentamicin. The cultures were incubated at 37° C. with shaking (225 rpm) until the optical density at 600 nm was approximately 0.2. Mitomycin C was then added to a final concentration of 3 µg/ml, and the cultures were shaken at 37° C. 3-4 hours. Debris was removed by centrifugation at 12,000 rpm (approximately 17,400×g) in a Beckman JA-25.50 rotor for 30 minutes at 4° C. The supernatant was transferred to a fresh centrifuge tube, and pyocins were pelleted at 22,000 rpm (approximately 58,500×g) for 1 hour at 4° C. The pellets were resuspended at 3% of the original volume in 50 mM NaCl, 10 mM Tris-HCl, pH 7.5 and stored at 4° C. The bactericidal activity of each preparation was assayed on strain 13s of *P. aeruginosa*. 10 µl of each sample was electrophoresed on a 4-20% polyacrylamide tris-glycine SDS gel (SDS-PAGE) alongside molecular weight standards. The preparations from the *E. coli* transformants containing pDG193 and pDG194 exhibited potent bactericidal activities and clear R-type pyocin protein subunits on SDS-PAGE analyses. The preparations from the *E. coli* transformants containing pDG195 and pDG196 did not exhibit bactericidal activity and did not demonstrate substantive R-type pyocin protein subunits on. SDS-PAGE analyses, all as predicted.

Upon induction of the pyocin genes and the engineered tail fiber gene, such as by inducing prtN directly via an engineered regulatable promoter such as lac or tac, the host cells synthesize pyocins until their nutrients are depleted and they cease growing (Young, Ry, 2006). The producing bacteria do not lyse in the absence of chloroform because the holin gene inactivation prevents cytoplasmic endolysin access to the bacterial cell wall, as is necessary for cell lysis. The exhausted cells are harvested by centrifugation or filtration and then frozen until one desires to harvest the soluble pyocins that have filled the cellular cytoplasm. Upon thawing, the inner cellular membrane ruptures, releasing endolysin to lyse the bacteria and thereby release the harvest of modified pyocins. The disruption of the bacterial membranes can be accelerated or completed if necessary by the addition of small quantities of chloroform to the aqueous solvent in which the bacterial paste is thawed.

REFERENCES

Ackermann H W. 2003. Bacteriophage observations and evolution. Res Microbiol. 154:245-251

Aiache J M, S Meski, E Beyssac, G Serpin. 1997. The formulation of drug for ocular administration. J Biomater Appl. 11:329-48

Anantharaman et al. "Application of comparative genomics in the identification and analysis of novel families of membrane-associated receptors in bacteria." BMC Genomics, 4:34, 2003

Bad Bugs, No Drugs: As Antibiotic Discovery Stagnates A Public Health Crisis Brews, July 2004. Infectious Diseases Society of America Beisel K W, L D Hazlett, R S Berk. 1983. Dominant susceptibility effect on the murine corneal response to *Pseudomonas aeruginosa*. Proc Soc Exp Biol Med. 172:488-491

Bertani L E, and E W Six. 1988. The P2-like phages and their parasite, P4. In R. Calendar (ed.), The Bacteriophages, vol. 2. Plenum Publishing Corp., New York. pp 73-143

Birmingham V A, P A Pattee. 1981. Genetic Transformation in *Staphylococcus aureus*: Isolation and Characterization of a Competence-Conferring Factor from Bacteriophage 80α Lysates. Journal of Bacteriology 148:301-307

Blackwell C C, and Law J A. 1981. Typing of non-serogroupable *Neisseria meningitidis* by means of sensitivity to R-type pyocins of *Pseudomonas aeruginosa*. J Infect. 3(4): 370-8.

Blackwell C C, F P Winstanley, W A Telfer-Brunton. 1982. Sensitivity of thermophilic campylobacters to R-type pyocins of *Pseudomonas aeruginosa*. J. Med Microbiology. 15:247-51

Bonev et al. "Targeting extracellular pyrophosphates underpins the high selectivity of nisin." The FASEB Journal. 18:1862-1869, 2004

Burda M R, Miller S. Folding of coliphage T4 short tail fiber in vitro. Analysing the role of a bacteriophage-encoded chaperone. Eur J. Biochem. 1999 October; 265(2):771-8.

Burns R P. 1969. *Pseudomonas aeruginosa* keratitis: mixed infections of the eye. Am J Opthalmol. 67:257-262

Calamita, "The *Escherichia coli* aquaporin-Z water channel." Molecular Microbiology 37(2):254-262, 2000

Chappell J D, A E Prota, T S Dermody, T Stehle. 2002. The crystal structure of reovirus attachment protein σ1 reveals evolutionary relationship to adenovirus fiber. The EMBO Journal 21:1-11

Cheng K H, S L Leung, H W Hoekman. 1999. Incidence of contact lens-associated microbial keratitis and its related morbidity. Lancet. 354:181-185

Choi, K.-H. and Schweizer, H.P., BMC Microbiol. 5, 30 (2005).

Choi H K, J B Gaynor, K G White, C Lopez, C M Bosio, R R Karkhoff-Schweizer, H P Schweizer. 2005. A T-7 based broad-range bacterial cloning and expression vector. Nature Methods. 2:443-448

Chuanchuen, R, Narasaki, C. T. and Schweizer, H. P., Benchtop and micro centrifuge preparation of *Pseudomonas aeruginosa* competent cells, BioTechniques 33:760-763 (October 2002).

Coetzee H L, H C De Klerk, J N Coetzee, J A Smit. 1968. Bacteriophage-tail-like particles associated with intra-species killing of *Proteus vulgaris*. J Gen Virol. 2:29-36.

Cole N, M D P Willcox, S M J Fleiszig. 1998. Different Strains Of *Pseudomonas Aeruginosa* Isolated From Ocular Infections Or Inflammation Display Distinct Corneal Pathologies In An Animal Model. Curr Eye Res. 17:730-735

Cooper R L, I J Constable. 1977. Infective keratitis in soft contact lens wearers. Br J Opthalmol. 61:250-254

Cowell B A, C Wu, S M J Fleiszig. 1999, Use of an Animal Model in Studies of Bacterial Corneal Infection. Inst Lab Animal Res J. 40:43-50

Dehó, G., Zangrossi, S., Ghisotti, D. & Sironi, G. (1988) *J. Virol.* 62(5), 1697-1704.

Desplats C, Krisch H M. The diversity and evolution of the T4-type bacteriophages. Res Microbiol. 2003 May; 154 (4):259-67.

Doulatov S, A Hodes, L Dai, N Mandhana, M Liu, R Deora, RW Simons, S Zimmerly, J F Miller. 2004. Tropism switching in *Bordetella* bacteriophage defines a family of diversity-generating retroelements. Nature. 431:476-481

Drickamer K. 1999. C-type lectin-like domains. Current Opinion in Structural Biology. 9:585-590 Farmer J J, L G Herman. 1969.

Dyke J, Berk R S. Growth inhibition and pyocin receptor properties of endotoxin from *Pseudomonas aeruginosa*. Proc Soc Exp Biol Med. 1974; 145:1405-1408.

Epidemiologic Fingerprinting of *Pseudomonas aeruginosa* by the Production of and Sensitivity to Pyocin and Bacteriophage. Applied Microbiol. 18:760-765

Filiatrault M J, Munson R S Jr, and Campagnari A A. 2001. Genetic analysis of a pyocin-resistant lipooligosaccharide (LOS) mutant of *Haemophilus ducreyi*: restoration of full-length LOS restores pyocin sensitivity. *J Bacteriol.* 183 (19):5756-61.

Fleiszig S M J, D J Evans. 2002. The pathogenesis of bacterial keratitis: studies with *Pseudomonas aeruginosa*. Clin Exp Optom. 85.5:271-278

Gerke J R, M V Magliocco. 1971. Experimental *Pseudomonas aeruginosa* infection of the mouse cornea. Infect Immun. 3:209-216

Gillor, O, L M Nigro, A. Riley. 2005. Genetically engineered bacteriocins and their potential as the next generation of antimicrobials. Curr. Pharm. Des. 11:1067-1075

Goodman et al. "A Signaling Network Reciprocally Regulates Genes Associated with Acute Infection and Chronic Persistence in *Pseudomonas aeruginosa*." Developmental Cell 7:745-754, 2004

Govan, J R W & V Deretic. 1996. Microbial Pathogenesis in Cystic Fibrosis: Mucoid *Pseudomonas aeruginosa* and *Burkholderia cepacia*, Microbiological Reviews. 60:539-574

Haas H, Sacks T, Saltz N. Protective effect of pyocin against lethal *Pseudomonas aeruginosa* infections in mice. J Infect Dis. 1974 April; 129(4):470-2.

Haggard-Ljungquist E, Halling C, Calendar R. NA sequences of the tail fiber genes of bacteriophage P2: evidence for horizontal transfer of tail fiber genes among unrelated bacteriophages. J. Bacteriol. 1992 March; 174(5):1462-77.

Hashemolhosseini S, Montag D, Kramer L, Henning U. Determinants of receptor specificity of coliphages of the T4 family. A chaperone alters the host range. J Mol. Biol. 1994 Aug. 26; 241(4):524-33.

Hazlett L D, D Rosen, R S Berk. 1976. Experimental eye infections caused by *Pseudomonas aeruginosa*. Ophthalmic Res. 8:311-318

He et al. "The broad host range pathogen *Pseudomonas aeruginosa* strain PA14 carries two pathogenicity islands harboring plant and animal virulence genes." PNAS 101: 2530-2535, 2004

Held H, S S Sidhu. 2004. Comprehensive Mutational Analysis of the M13 Major Coat Protein, J Mol. Biol. 340:587-97

Hensley S, B Wysocki. As Industry Profits Elsewhere, U.S. Lacks Vaccines, Antibiotics, The Wall Street Journal Nov. 8, 2005: p A1

Higerd T B, C A Baechler, R S Berk. 1969. Morphological Studies On Relaxed and Contracted Forms of Purified Pyocin Particles. J. Bacteriology. 98:1378-89

Ho T. D., Waldor M. K 2007. Enterohemorrhagic *Escherichia coli* O157:H7 gal mutants are sensitive to bacteriophage P1 and defective in intestinal colonization. Infect. Immune. 75:1661-6. Epub 2006 Dec. 11

Hoang, T. T., Karkhoff-Schweizer, R. R., Kutchma, A. J. and Schweizer, H. P., A broad-host-range Flp-FRT recombination system for site-specific excision of chromosomally-located DNA sequences: application for isolation of unmarked *Pseudomonas aeruginosa* mutants Gene 212 (1), 77-86 (1998)

Hobden J A, D S Rootman, R J O'Callaghan, J M Hill. 1988. Iontophoretic application of tobramycin to uninfected and *Pseudomonas aeruginosa*-infected rabbit corneas. Antimicrob Agents Chemother. 32:978-981

Holder I A. 1993. *Pseudomonas aeruginosa* Burn Infections: Pathogenesis and Treatment. In M Campa, M Bendinelli, and H Friedman (ed.) *Pseudomonas aeruginosa* as an Opportunistic Pathogen. Plenum Press, New York, N.Y. pp. 275-295

Iijima M. 1978. Mode of Action of Pyocin R1. J. Biochem (Tokyo) 83:395-402

Ishii S, Y Nishi, and F Egami. 1965. The fine structure of a pyocin. J. Mol. Biol. 13:428-431

Ito, S., Kagayama, M. and F. Egami. Isolation and characterization of pyocins from several strains of *Pseudomonas aeruginosa*. J. Gen. Appl. Microbiol. 16 205-214 (1970).

Jabrane A, Sabri A, Compere P, Jacques P, Vandenberghe I, Van Beeumen J, Thonart P Characterization of serracin P, a phage-tail-like bacteriocin, and its activity against *Erwinia amylovora*, the fire blight pathogen. Appl Environ Microbiol. 2002 November; 68(11):5704-10.

Jacob F. 1954. Biosynthése induite et mode d'action d'une pyocin, antibiotique de *Pseudomonas* pyocyanea. Annals Inst. Pasteur. 86:149-60

Jacobs et al. "Comprehensive transposon mutant library of *Pseudomonas aeruginosa*." PNAS 100(24):14339-14344, 2003

Kageyama M, F Egami. 1962. On the purification and some properties of a pyocin, a bacteriocin produced by *Pseudomonas aeruginosa*. Life Sciences 9: 471-6

Kageyama M, K Ikeda, and F Egami. 1964. Studies of a pyocin. III. Biological properties of the pyocin. J. Biochem. 55:59-64.

Kageyama M, Shimomiya T, Aihara Y, Kobayashi M. 1979. Characterization of a bacteriophage related to R-type pyocins. J. Virol. 32:951-957.

Kageyama M. 1964. Studies of a pyocin I. Physical and chemical properties. J. Biochem. 55:49-53

Kageyama, M. Bacteriocins and bacteriophages in *Pseudomonas aeruginosa*, in: Microbial Drug Resistance, University Park Press, Baltimore. pp 291-305 1975.

Kahn M L, R G Ziermann, D W Deho, M Ow, G Sunshine, R Calendar. 1991. Bacteriophage P2 and P4. Methods Enzymol. 204:264-280

Kumazaki T, Y Shimizu, S I Ishii. 1982. Isolation and Characterization of Pyocin R1 Fibers. J. Biochemistry. 91:825-35

Lee E J, D J Evans and S M J Fleiszig. 2003. Role of *Pseudomonas aeruginosa* ExsA in Penetration through Corneal Epithelium in a Novel in vivo Model. Investigative Opthalmology & Visual Science. 44:5220-5227

Lee F K, Dudas K C, Hanson J A, Nelson M B, LoVerde P T, Apicella M A. 1999 The R-type pyocin of *Pseudomonas aeruginosa* C is a bacteriophage tail-like particle that contains single-stranded DNA. Infect Immun. 67(2):717-25.

Liu M, M Gingery, S R. Doulatov, Y Liu, A Hodes, S Baker, P Davis, M Simmonds, C Churcher, K Mungall, M A Quail, A Preston, E T Harvill, D J Maskell, F A Eiserling, J Parkhill, and J F Miller. 2004. Genomic and Genetic Analysis of Bordetella Bacteriophages Encoding Reverse Transcriptase-Mediated Tropism-Switching Cassettes. J. Bacteriology. 186 476-481

Mah-Sadorra J H, S G Yavuz, D M Najjar, P R Laibson, C J Rapuano, E J Cohen. 2005. Trends in contact lens-related corneal ulcers. Cornea. 24:51-58

Matsui H, Sano Y, Ishihara H, Shinomiya T. Regulation of pyocin genes in *Pseudomonas aeruginosa* by positive (prtN) and negative (prtR) regulatory genes. J. Bacteriol. 1993 March; 175(5):1257-63.

McMahon S A, J L Miller, J A Lawton, D E Kerkow, A Hodes, M A Marti-Renom, S Doulatov, E Narayanan, A Sall, J F Miller, P Ghosh. 2005. The C-type Lectin Fold as an Evolutionary Solution for Massive Sequence Variation. Nature Struct. & Molecular Biol. 12:886-892

McNamara N A, K A Polse, S A Fukunaga, J S Maebori, R M Suzuki. 1998. Soft lens extended wear affects epithelial barrier function. Opthalmology. 105:2330-2335

Meadow, P. M., and Wells P. L. Receptor sites for R-type pyocins and bacteriophage E79 in the core part of the lipopolysaccharide of *Pseudomonas aeruginosa* PAC1. J. Gen. Microbiol. 108:339-343. 1978

Merrikin D J, Terry C S. Use of pyocin 78-C2 in the treatment of *Pseudomonas aeruginosa* infection in mice. Appl Microbiol. 1972 January; 23(1):164-5.

Michel-Briand, Y., and Baysse, C. The pyocins of *Pseudomonas aeruginosa*. Biochimie. 2002 May-June; 84(5-6):499-510.

Microbial Threats To Health: Emergence, Detection, And Response, March 2003 Institute of Medicine, Washington, D.C.

Mitchell et al. "Structural basis for oligosaccharide-mediated adhesion of *Pseudomonas aeruginosa* in the lungs of cystic fibrosis patients." Nature Structural Biology 9:918-921, 2002

Morse S A, Jones B V, and Lysko P G. 1980. Pyocin inhibition of *Neisseria gonorrhoeae*: mechanism of action. Antimicrob Agents Chemother. 18(3):416-23.

Morse S A, Vaughan P, Johnson D, and Iglewski B H. 1976. Inhibition of *Neisseria gonorrhoeae* by a bacteriocin from *Pseudomonas aeruginosa*. Antimicrob Agents Chemother. 10(2):354-62.

Mosig G and F Eiserling. 2006. T4 and Related Phages: Structure and Development, in The Bacteriophages. Calendar, R. ed. Second edition, Oxford University Press, NY, N.Y. pp 225-267

Nakayama K, Kanaya S, Ohnishi M, Terawaki Y, Hayashi T. The complete nucleotide sequence of phi CTX, a cytotoxin-converting phage of *Pseudomonas aeruginosa*: implications for phage evolution and horizontal gene transfer via bacteriophages. Mol. Microbiol. 1999 January; 31(2):399-419.

Nakayama K, Takashima K, Ishihara H, Shinomiya T, Kageyama M, Kanaya S, Ohnishi M, Murata T, Mori H, Hayashi T. The R-type pyocin of *Pseudomonas aeruginosa* is related to P2 phage, and the F-type is related to lambda phage. Mol. Microbiol. 2000 October; 38(2):213-31.

Papanikolopoulou K, V Forge, P Goeltz, and A Mitraki. 2004. Formation of Highly Stable Chimeric Trimers by Fusion of an Adenovirus Fiber Shaft Fragment with the Foldon Domain of Bacteriophage T4 Fibritin. Journal of Biological Chemistry. 279: 8991-8998

Preston M I, S M L Fleiszig, T S Zaidi, J B Goldberg, V D Shortridge, M I Vasil, G B Pier. 1995. Rapid and Sensitive Method for Evaluating *Pseudomonas aeruginosa* Virulence Factors during Corneal Infections in Mice. Infection and Immunity 63:3497-3501

Qu Y, Hyman P, Harrah T, Goldberg E. In vivo bypass of chaperone by extended coiled-coil motif in T4 tail fiber. J. Bacteriol. 2004 December; 186(24):8363-9.

Ramphal R, M T McNiece, F M Polack. 1981. Adherence of *Pseudomonas aeruginosa* to the injured cornea: a step in the pathogenesis of corneal infections. Ann. Opthalmol. 13:421-425

Rich, et al. "ACE is a collagen binding MSCRAMM from *Enterococcus faecalis*." J. Biol. Chem. 274:26939-26945, 1999

Riley M A, J E Wertz. 2002. Bacteriocins: evolution, ecology, and application. Annu. Rev. Microbiol. 56:117-137

Roland P S, D W Stroman. 2002. Microbiology of Acute Otitis Externa. Laryngoscope. 112:1166-1177

Rudner et al. "A family of membrane-embedded metalloproteases involved in regulated proteolysis of membrane-associated transcription factors." PNAS 96(26):14765-14770,1999

Schweizer H P. 2001. Vectors to express foreign genes and techniques to monitor gene expression in Pseudomonads. Current Opinion in Biotechnology. 12:439-445

Schweizer, H. P., Klassen, T. and Hoang, T., Improved methods for gene analysis and expression in *Pseudomonas*, Unpublished Shimizu Y, T Kamazaki, S I Ishii. 1982. Specific Cleavage at Fibers of a Bacteriophage-Tail-Like Bacteriocin, Pyocin R1 by Successive Treatment with Organomercurial Compounds and Trypsin. J Virology 44:692-695

Shinomiya, T, *J. Biochem.*, 72, 39-48 (1972).

Shinomiya T & S Ina. 1989. Genetic Comparison of Bacteriophage PS17 and *Pseudomonas aeruginosa* R-Type Pyocin. J. Bacteriology 171:2287-2292

Shinomiya T, S Shiga, A Kikuchi, M Kageyama. 1983b. Genetic determinant of pyocin R2 in *Pseudomonas aeruginosa* PAO. II. Physical characterization of pyocin R2 genes using R-prime plasmids constructed from R68.45. Mol Gen Genet. 189:382-389

Shinomiya T, S Shiga, M Kageyama. 1983a. Genetic determinant of pyocin R2 in *Pseudomonas aeruginosa* PAO. I. Localization of the pyocin R2 gene cluster between the trpCD and trpE genes. Mol Gen Genet. 189:375-38

Shinomiya T, S Shiga. 1979. Bactericidal Activity of the Tail of *Pseudomonas aeruginosa* Bacteriophage PS17. J of Virology 32:958-967

Shinomiya T. 1984. Phenotypic Mixing of Pyocin R2 and Bacteriophage PS17 in *Pseudomonas aeruginosa* PAO. J. Virology. 49:310-314

Shore, D., Dehó, G., Tsipis, J & Goldstein, R. (1977) *Proc Natl. Acad. Sci. USA* 75, 400-404.

Sreedhar et al. "*Enterococcus faecalis* Adhesin, ACE, Mediates Attachment to Extracellular Matrix Proteins Collagen Type IV and Laminin as well as Collagen Type I." Infect. Immun. 68(9):5218-5224, 2000

Strauch E, Kaspar H, Schaudinn C, Dersch P, Madela K, Gewinner C, Hertwig S, Wecke J, Appel B. Characterization of enterocoliticin, a phage tail-like bacteriocin, and its effect on pathogenic *Yersinia enterocolitica* strains. Appl Environ Microbiol. 2001 December; 67(12):5634-42.

Sunshine, M., G., Thorn, M., Gibbs, W., Calendar, R. & Kelly, B. (1971) *Virology* 46, 691-702.

Takeya K, Y Minamishima, Y Ohnishi, K Amako. 1969. Rod-shaped pyocin 28, J. Gen. Virol. 4:145-149

Talbot G H, J Bradley, J E Edwards, D Gilbert, M Scheld, J G Bartlett. 2006. Bad Bugs Need Drugs: An Update on the Development Pipeline from the Antimicrobial Availability. Clin Infect. Dis. 42:657-668

Tamber et al. J. Bact. 188(1):45-54, 2006

Tetart F, C Desplats, M Kutateladze, C Monod, H-W Ackermann, H M Kirsch. 2001. Phylogeny of the Major Head and tail genes of the Wide-Ranging T4-Type Bacteriophages. J Bacteriology 183:358-366

Tetart F, Desplats C, Krisch H M. Genome plasticity in the distal tail fiber locus of the T-even bacteriophage: recombination between conserved motifs swaps adhesin specificity. J Mol. Biol. 1998 Sep. 25; 282(3):543-56.

Thompson N E, P A Pattee. 1981. Genetic transformation in *Staphylococcus aureus*: demonstration of a competence-conferring factor of bacteriophage origin in bacteriophage 80a lysates. J. Bacteriol. 148:294-300

Twining S S, X Zhou, D P Shulte, P M Wilson, B Fish, J Moulder. 1996. Effect of vitamin A deficiency on the early response to experimental *Pseudomonas* keratitis. Invest Opthalmol V is Sci. 37:511-522

Uratani, Y., and Hoshino, T. Pyocin R1 inhibits active transport in *Pseudomonas aeruginosa* and depolarizes membrane potential. J. Bacteriol. 1984 February; 157(2):632-6.

van Horn D L, S D Davis, R A Hyndiuk, T V P Alpren. 1978. Pathogenesis of experimental *Pseudomonas* keratitis in the guinea pig: bacteriologic, clinical, and microscopic observations. Invest Opthalmol V is Sci. 17:1076-1086 van Raaij M J, A Mitraki, G Lavigne, S Cusack. 1999. A triple β-spiral in the adenovirus fibre shaft reveals a new structural motif for a fibrous protein. Nature. 401:935-38.

van Raaij M J, G Schoehn, M R Burda, S Miller. 2001. Crystal Structure of a Heat and Protease-stable Part of the Bacteriophage T4 Short Tail Fibre. J. Mol. Biol. 314:1137-1146

Waddell T E, Poppe C, 2000. Construction of mini-Tn10luxABcam/Ptac-ATS and its use for developing a bacteriophage that transduces bioluminescence to *Escherichia coli* O157:H7. FEMS Microbio. Lett. 182(2):285-289.

Weigele P R, E Scanlon, and J King. 2003. Homotrimeric, β-Stranded Viral Adhesins and Tail Proteins. J of Bacteriology. 185:4022-4030

Wenzel R P. 2004. The Antibiotic Pipeline—Challenges, Costs, and Values New Engl J. Med. 351:523-526

West S H E, H P Schweizer, A K Sample, L J Runyen-Janecky. 1994. Construction of Improved *Escherichia*-Pseudomonas Shuttle Vectors Derived from pUC18/19 and Sequence of the Region Required for Their Replication in *Pseudomonas aeruginosa* Gene 128:81-86

Wong et al. "Insertion Mutagenesis and Membrane Topology Model of the *Pseudomonas aeruginosa* Outer Membrane Protein OprM." J. Bacteriol. 182(9):2402-2410, 2000

Young, Ry, "Phage Lysis" in Phages, Waldor, Friedman and Adhya, eds. ASM Press, Washington, D.C., p 95, 2006

Ziermann R, R Calendar. 1991. Characterization of the cos site of bacteriophages P2 and P4. Gene. 96:9-15

Zink R, M J Loessner and S Scherer. 1995. Characterization of cryptic prophages (monocins) in *Listeria* and sequence analysis of a holin/endolysin gene. Microbiology. 141:2577-2584

Zolfaghar et al. "Mutation of retS, encoding a putative hybrid two-component regulatory protein in *Pseudomonas aeruginosa*, attenuates multiple virulence mechanisms." Microbes Infect. Jul. 15, 2005 Epub ahead of print All references cited herein are hereby incorporated by reference in their entireties, whether previously specifically incorporated or not. As used herein, the terms "a", "an", and "any" are each intended to include both the singular and plural forms.

Having now fully described the disclosed subject matter, it will be appreciated by those skilled in the art that the same can be performed within a wide range of equivalent parameters, concentrations, and conditions without departing from the spirit and scope of the disclosure and without undue experimentation. While this disclosure has been described in connection with specific embodiments thereof, it will be understood that it is capable of further modifications. This application is intended to cover any variations, uses, or adaptations of the subject matter following, in general, the principles of the disclosure and including such departures from the disclosure as come within known or customary practice within the art to which the subject matter pertains and as may be applied to the essential features hereinbefore set forth.

What is claimed is:

1. An isolated bacterium comprising nucleic acid encoding proteins of an R-type high molecular weight (hmw) bacteriocin from another microorganism, wherein the bacterium expresses the proteins comprising the R-type hmw bacteriocin having bactericidal activity.

2. The bacterium of claim 1 which is classified as a GRAS (generally recognized as safe) bacterium.

3. The bacterium of claim 1 which is *E. coli* or *Pseudomonas fluorescens*.

4. The bacterium of claim 1 in which the expression of the bacteriocin proteins is under the control of a promoter heterologous to the bacteriocin.

5. The bacterium of claim 4 whereby an exogenous molecule acts as an inducer or co-repressor of the promoter to express or not express the R-type hmw bacteriocin proteins.

6. The bacterium of claim 1 wherein the nucleic acid encoding the R-type hmw bacteriocin proteins has an inactivated holin gene.

7. The bacterium of claim 6, wherein the holin gene has been inactivated by deletion.

* * * * *

SEQUENCE LISTING

<160> NUMBER OF SEQ ID NOS: 99

<210> SEQ ID NO 1
<211> LENGTH: 701
<212> TYPE: PRT
<213> ORGANISM: Pseudomonas aeruginosa

<400> SEQUENCE: 1

Met Thr Thr Asn Thr Pro Lys Tyr Gly Gly Leu Leu Thr Asp Ile Gly
1               5                   10                  15

Ala Ala Ala Leu Ala Ala Ala Ser Ala Ala Gly Lys Lys Trp Gln Pro

```
                     20                  25                  30
Thr His Met Leu Ile Gly Asp Ala Gly Gly Ala Pro Gly Asp Thr Pro
                 35                  40                  45
Asp Pro Leu Pro Ser Ala Ala Gln Lys Ser Leu Ile Asn Gln Arg His
 50                  55                  60
Arg Ala Gln Leu Asn Arg Leu Phe Val Ser Asp Lys Asn Ala Asn Thr
 65                  70                  75                  80
Leu Val Ala Glu Val Val Leu Pro Val Glu Val Gly Gly Phe Trp Ile
                 85                  90                  95
Arg Glu Ile Gly Leu Gln Asp Ala Asp Gly Lys Phe Val Ala Val Ser
                100                 105                 110
Asn Cys Pro Pro Ser Tyr Lys Ala Ala Met Glu Ser Gly Ser Ala Arg
                115                 120                 125
Thr Gln Thr Ile Arg Val Asn Ile Ala Leu Ser Gly Leu Glu Asn Val
                130                 135                 140
Gln Leu Leu Ile Asp Asn Gly Ile Ile Tyr Ala Thr Gln Asp Trp Val
145                 150                 155                 160
Lys Glu Lys Val Ala Ala Asp Phe Lys Gly Arg Lys Ile Leu Ala Gly
                165                 170                 175
Asn Gly Leu Val Gly Gly Asp Leu Ser Ala Asp Arg Ser Ile Gly
                180                 185                 190
Leu Ala Pro Ser Gly Val Thr Ala Gly Ser Tyr Arg Ser Val Thr Val
                195                 200                 205
Asn Ala Asn Gly Val Val Thr Gln Gly Ser Asn Pro Thr Thr Leu Ala
                210                 215                 220
Gly Tyr Ala Ile Gly Asp Ala Tyr Thr Lys Ala Asp Thr Asp Gly Lys
225                 230                 235                 240
Leu Ala Gln Lys Ala Asn Lys Ala Thr Thr Leu Ala Gly Tyr Gly Ile
                245                 250                 255
Thr Asp Ala Leu Arg Val Asp Gly Asn Ala Val Ser Ser Ser Arg Leu
                260                 265                 270
Ala Ala Pro Arg Ser Leu Ala Ala Ser Gly Asp Ala Ser Trp Ser Val
                275                 280                 285
Thr Phe Asp Gly Ser Ala Asn Val Ser Ala Pro Leu Ser Leu Ser Ala
                290                 295                 300
Thr Gly Val Ala Ala Gly Ser Tyr Pro Lys Val Thr Val Asp Thr Lys
305                 310                 315                 320
Gly Arg Val Thr Ala Gly Met Ala Leu Ala Thr Asp Ile Pro Gly
                325                 330                 335
Leu Asp Ala Ser Lys Leu Val Ser Gly Val Leu Ala Glu Gln Arg Leu
                340                 345                 350
Pro Val Phe Ala Arg Gly Leu Ala Thr Ala Val Ser Asn Ser Ser Asp
                355                 360                 365
Pro Asn Thr Ala Thr Val Pro Leu Met Leu Thr Asn His Ala Asn Gly
                370                 375                 380
Pro Val Ala Gly Arg Tyr Phe Tyr Ile Gln Ser Met Phe Tyr Pro Asp
385                 390                 395                 400
Gln Asn Gly Asn Ala Ser Gln Ile Ala Thr Ser Tyr Asn Ala Thr Ser
                405                 410                 415
Glu Met Tyr Val Arg Val Ser Tyr Ala Ala Asn Pro Ser Ile Arg Glu
                420                 425                 430
Trp Leu Pro Trp Gln Arg Cys Asp Ile Gly Gly Ser Phe Thr Lys Thr
                435                 440                 445
```

```
Thr Asp Gly Ser Ile Gly Asn Gly Val Asn Ile Asn Ser Phe Val Asn
    450                 455                 460

Ser Gly Trp Trp Leu Gln Ser Thr Ser Glu Trp Ala Ala Gly Gly Ala
465                 470                 475                 480

Asn Tyr Pro Val Gly Leu Ala Gly Leu Leu Ile Val Tyr Arg Ala His
                485                 490                 495

Ala Asp His Ile Tyr Gln Thr Tyr Val Thr Leu Asn Gly Ser Thr Tyr
            500                 505                 510

Ser Arg Cys Cys Tyr Ala Gly Ser Trp Arg Pro Trp Arg Gln Asn Trp
        515                 520                 525

Asp Asp Gly Asn Phe Asp Pro Ala Ser Tyr Leu Pro Lys Ala Gly Phe
    530                 535                 540

Thr Trp Ala Ala Leu Pro Gly Lys Pro Ala Thr Phe Pro Pro Ser Gly
545                 550                 555                 560

His Asn His Asp Thr Ser Gln Ile Thr Ser Gly Ile Leu Pro Leu Ala
                565                 570                 575

Arg Gly Gly Leu Gly Ala Asn Thr Ala Gly Ala Arg Asn Asn Ile
            580                 585                 590

Gly Ala Gly Val Pro Ala Thr Ala Ser Arg Ala Leu Asn Gly Trp Trp
        595                 600                 605

Lys Asp Asn Asp Thr Gly Leu Ile Val Gln Trp Met Gln Val Asn Val
    610                 615                 620

Gly Asp His Pro Gly Gly Ile Ile Asp Arg Thr Leu Thr Phe Pro Ile
625                 630                 635                 640

Ala Phe Pro Ser Ala Cys Leu His Val Val Pro Thr Val Lys Glu Val
                645                 650                 655

Gly Arg Pro Ala Thr Ser Ala Ser Thr Val Thr Val Ala Asp Val Ser
            660                 665                 670

Val Ser Asn Thr Gly Cys Val Ile Val Ser Ser Glu Tyr Tyr Gly Leu
        675                 680                 685

Ala Gln Asn Tyr Gly Ile Arg Val Met Ala Ile Gly Tyr
    690                 695                 700

<210> SEQ ID NO 2
<211> LENGTH: 146
<212> TYPE: PRT
<213> ORGANISM: Pseudomonas aeruginosa

<400> SEQUENCE: 2

Met Ile Phe Phe His Ala Ala Thr Gly Gly Phe Tyr Ser Lys Glu Ile
1               5                   10                  15

His Gly Ser Arg Met Pro Leu Glu Asp Glu Met His Pro Leu Glu Asp
                20                  25                  30

Ala Glu Tyr Gln Ala Leu Leu Arg Ala Gln Ser Glu Gly Lys Arg Ile
            35                  40                  45

Val Thr Asp His Thr Gly Arg Pro Ile Cys Val Asp Pro Pro Ala Pro
        50                  55                  60

Ala Lys Asp Ile Leu Val Gln Arg Glu Arg Ile Trp Arg Asp Arg Gln
65                  70                  75                  80

Leu Gln Leu Thr Asp Gly Pro Leu Ala Arg His Arg Asp Glu Gln Asp
                85                  90                  95

Leu Gly Lys Thr Thr Thr Leu Ser Gln Glu Gln Leu Arg Glu Leu Thr
            100                 105                 110

Leu Tyr Arg Ala Val Leu Arg Asp Trp Pro Ile Ala Ala Glu Phe Pro
        115                 120                 125
```

Asp Leu Asn Ala Arg Pro Glu Pro Ala Trp Leu Gln Ser Leu Ile
            130                 135                 140

Thr Pro
145

<210> SEQ ID NO 3
<211> LENGTH: 691
<212> TYPE: PRT
<213> ORGANISM: Pseudomonas aeruginosa

<400> SEQUENCE: 3

Met Ala Thr Asn Thr Pro Lys Tyr Gly Gly Leu Leu Thr Asp Ile Gly
1               5                   10                  15

Ala Ala Ala Leu Ala Thr Ala Ser Ala Ala Gly Lys Lys Trp Gln Pro
            20                  25                  30

Thr His Met Leu Ile Gly Asp Ala Gly Ala Pro Gly Asp Thr Pro
            35                  40                  45

Asp Pro Leu Pro Ser Ala Ala Gln Lys Ser Leu Ile Asn Gln Arg His
    50                  55                  60

Arg Ala Gln Leu Asn Arg Leu Phe Val Ser Asp Lys Asn Ala Asn Thr
65                  70                  75                  80

Leu Val Ala Glu Val Val Leu Pro Val Glu Val Gly Gly Phe Trp Ile
                85                  90                  95

Arg Glu Ile Gly Leu Gln Asp Ala Asp Gly Lys Phe Val Ala Val Ser
            100                 105                 110

Asn Cys Pro Pro Ser Tyr Lys Ala Ala Met Glu Ser Gly Ser Ala Arg
        115                 120                 125

Thr Gln Thr Ile Arg Val Asn Ile Ala Leu Ser Gly Leu Glu Asn Val
    130                 135                 140

Gln Leu Leu Ile Asp Asn Gly Ile Ile Tyr Ala Thr Gln Asp Trp Val
145                 150                 155                 160

Lys Glu Lys Val Ala Ala Asp Phe Lys Gly Arg Lys Ile Leu Ala Gly
                165                 170                 175

Asn Gly Leu Leu Gly Gly Gly Asp Leu Ser Ala Asp Arg Ser Ile Gly
            180                 185                 190

Leu Ala Pro Ser Gly Val Thr Ala Gly Ser Tyr Arg Ser Val Thr Val
        195                 200                 205

Asn Ala Asn Gly Val Val Thr Gln Gly Ser Asn Pro Thr Thr Leu Ala
    210                 215                 220

Gly Tyr Ala Ile Gly Asp Ala Tyr Thr Lys Ala Asp Thr Asp Gly Lys
225                 230                 235                 240

Leu Ala Gln Lys Ala Asn Lys Ala Thr Thr Leu Ala Gly Tyr Gly Ile
                245                 250                 255

Thr Asp Ala Leu Arg Val Asp Gly Asn Ala Val Ser Ser Ser Arg Leu
            260                 265                 270

Ala Ala Pro Arg Ser Leu Ala Ala Ser Gly Asp Ala Ser Trp Ser Val
        275                 280                 285

Thr Phe Asp Gly Ser Ala Asn Val Ser Ala Pro Leu Ser Leu Ser Ala
    290                 295                 300

Thr Gly Val Ala Ala Gly Ser Tyr Pro Lys Val Thr Val Asp Thr Lys
305                 310                 315                 320

Gly Arg Val Thr Ala Gly Met Ala Leu Ala Ala Thr Asp Ile Pro Gly
                325                 330                 335

Leu Asp Ala Ser Lys Leu Val Ser Gly Val Leu Ala Glu Gln Arg Leu
            340                 345                 350

```
Pro Val Phe Ala Arg Gly Leu Ala Thr Ala Val Ser Asn Ser Ser Asp
        355                 360                 365

Pro Asn Thr Ala Thr Val Pro Leu Met Leu Thr Asn His Ala Asn Gly
        370                 375                 380

Pro Val Ala Gly Arg Tyr Phe Tyr Ile Gln Ser Met Phe Tyr Pro Asp
385                 390                 395                 400

Gln Asn Gly Asn Ala Ser Gln Ile Ala Thr Ser Tyr Asn Ala Thr Ser
                405                 410                 415

Glu Met Tyr Val Arg Val Ser Tyr Ala Ala Asn Pro Ser Ile Arg Glu
                420                 425                 430

Trp Leu Pro Trp Gln Arg Cys Asp Ile Gly Gly Ser Phe Thr Lys Glu
        435                 440                 445

Ala Asp Gly Glu Leu Pro Gly Gly Val Asn Leu Asp Ser Met Val Thr
        450                 455                 460

Ser Gly Trp Trp Ser Gln Ser Phe Thr Ala Gln Ala Ala Ser Gly Ala
465                 470                 475                 480

Asn Tyr Pro Ile Val Arg Ala Gly Leu Leu His Val Tyr Ala Ala Ser
                485                 490                 495

Ser Asn Phe Ile Tyr Gln Thr Tyr Gln Ala Tyr Asp Gly Glu Ser Phe
                500                 505                 510

Tyr Phe Arg Cys Arg His Ser Asn Thr Trp Phe Pro Trp Arg Arg Met
        515                 520                 525

Trp His Gly Asp Phe Asn Pro Ser Asp Tyr Leu Leu Lys Ser Gly
        530                 535                 540

Phe Tyr Trp Asn Ala Leu Pro Gly Lys Pro Ala Thr Phe Pro Pro Ser
545                 550                 555                 560

Ala His Asn His Asp Val Gly Gln Leu Thr Ser Gly Ile Leu Pro Leu
                565                 570                 575

Ala Arg Gly Gly Val Gly Ser Asn Thr Ala Gly Ala Arg Ser Thr
                580                 585                 590

Ile Gly Ala Gly Val Pro Ala Thr Ala Ser Leu Gly Ala Ser Gly Trp
        595                 600                 605

Trp Arg Asp Asn Asp Thr Gly Leu Ile Arg Gln Trp Gly Gln Val Thr
        610                 615                 620

Cys Pro Ala Asp Ala Asp Ala Ser Ile Thr Phe Pro Ile Pro Phe Pro
625                 630                 635                 640

Thr Leu Cys Leu Gly Gly Tyr Ala Asn Gln Thr Ser Ala Phe His Pro
                645                 650                 655

Gly Thr Asp Ala Ser Thr Gly Phe Arg Gly Ala Thr Thr Thr Thr Ala
                660                 665                 670

Val Ile Arg Asn Gly Tyr Phe Ala Gln Ala Val Leu Ser Trp Glu Ala
                675                 680                 685

Phe Gly Arg
    690

<210> SEQ ID NO 4
<211> LENGTH: 152
<212> TYPE: PRT
<213> ORGANISM: Pseudomonas aeruginosa

<400> SEQUENCE: 4

Met Lys Gly Glu Tyr Tyr Phe Ser Pro Ser Gln Val Ala Phe Tyr Pro
1               5                   10                  15

Ala Ser Leu Arg Glu Val Tyr Glu Tyr Ala Gly Cys Trp Pro Val Asp
            20                  25                  30
```

```
Gly Glu Trp Val Ser Ala Glu Leu His Glu Gln Leu Met Asn Glu Gln
            35                  40                  45

Ala Ala Gly Arg Ala Ile Ser Ser Asp Val Asn Gly Asn Pro Val Ala
         50                  55                  60

Ile Glu Arg Pro Pro Leu Ser Arg Gln Gln Arg Ser Thr His Glu Arg
 65                  70                  75                  80

Arg Trp Arg Asp Ser Gln Leu Leu Ala Thr Asp Gly Leu Val Val Arg
                 85                  90                  95

His Arg Asp Gln Leu Glu Thr Gly Lys Glu Thr Thr Leu Leu Pro Val
            100                 105                 110

Gln Tyr His Glu Leu Met Ser Tyr Arg Ala Ser Leu Arg Asp Trp Pro
            115                 120                 125

Glu Glu Pro Leu Phe Pro Asp Ser Gly Gly Arg Pro Ser Val Pro Asp
            130                 135                 140

Trp Leu Arg Arg Tyr Val Thr Pro
145                 150
```

<210> SEQ ID NO 5
<211> LENGTH: 691
<212> TYPE: PRT
<213> ORGANISM: Pseudomonas aeruginosa
<220> FEATURE:
<221> NAME/KEY: MISC_FEATURE
<222> LOCATION: (324)..(324)
<223> OTHER INFORMATION: Other

<400> SEQUENCE: 5

```
Met Thr Thr Asn Thr Pro Lys Tyr Gly Gly Leu Leu Thr Asp Ile Gly
 1               5                  10                  15

Ala Ala Ala Leu Ala Ala Ala Ser Ala Ala Gly Lys Lys Trp Gln Pro
             20                  25                  30

Thr His Met Leu Ile Gly Asp Ala Gly Gly Ala Pro Gly Asp Thr Leu
             35                  40                  45

Asp Pro Leu Pro Ser Ala Ala Gln Lys Ser Leu Ile Asn Gln Arg His
         50                  55                  60

Arg Ala Gln Leu Asn Arg Leu Phe Val Ser Asp Lys Asn Ala Asn Thr
 65                  70                  75                  80

Leu Val Ala Glu Val Val Leu Pro Val Glu Val Gly Gly Phe Trp Ile
                 85                  90                  95

Arg Glu Ile Gly Leu Gln Asp Ala Asp Gly Lys Phe Val Ala Val Ser
            100                 105                 110

Asn Cys Pro Pro Ser Tyr Lys Ala Met Glu Ser Gly Ser Ala Arg
            115                 120                 125

Thr Gln Thr Ile Arg Val Asn Ile Ala Leu Ser Gly Leu Glu Asn Val
        130                 135                 140

Gln Leu Leu Ile Asp Asn Gly Ile Ile Tyr Ala Thr Gln Asp Trp Val
145                 150                 155                 160

Lys Glu Lys Val Ala Ala Asp Phe Lys Gly Arg Lys Ile Leu Ala Gly
                165                 170                 175

Asn Gly Leu Leu Gly Gly Asp Leu Ser Ala Asp Arg Ser Ile Gly
            180                 185                 190

Leu Ala Pro Ser Gly Val Thr Ala Gly Ser Tyr Arg Ser Val Thr Val
            195                 200                 205

Asn Ala Asn Gly Val Val Thr Gln Gly Ser Asn Pro Thr Thr Leu Ala
        210                 215                 220

Gly Tyr Ala Ile Gly Asp Ala Tyr Thr Lys Ala Asp Thr Asp Gly Lys
225                 230                 235                 240
```

```
Leu Ala Gln Lys Ala Asn Lys Ala Thr Thr Leu Ala Gly Tyr Gly Ile
                245                 250                 255

Thr Asp Ala Leu Arg Val Asp Gly Asn Ala Val Ser Ser Ser Arg Leu
            260                 265                 270

Ala Ala Pro Arg Ser Leu Ala Ala Ser Gly Asp Ala Ser Trp Ser Val
        275                 280                 285

Thr Phe Asp Gly Ser Ala Asn Val Ser Ala Pro Leu Ser Leu Ser Ala
    290                 295                 300

Thr Gly Val Ala Ala Gly Ser Tyr Pro Lys Val Thr Val Asp Thr Lys
305                 310                 315                 320

Gly Arg Val Xaa Ala Gly Met Ala Leu Ala Ala Thr Asp Ile Pro Gly
                325                 330                 335

Leu Asp Ala Ser Lys Leu Val Ser Gly Val Leu Ala Glu Gln Arg Leu
            340                 345                 350

Pro Val Phe Ala Arg Gly Leu Ala Thr Ala Val Ser Asn Ser Ser Asp
        355                 360                 365

Pro Asn Thr Ala Thr Val Pro Leu Met Leu Thr Asn His Ala Asn Gly
    370                 375                 380

Pro Val Ala Gly Arg Tyr Phe Tyr Ile Gln Ser Met Phe Tyr Pro Asp
385                 390                 395                 400

Gln Asn Gly Asn Ala Ser Gln Ile Ala Thr Ser Tyr Asn Ala Thr Ser
                405                 410                 415

Glu Met Tyr Val Arg Val Ser Tyr Ala Ala Asn Pro Ser Ile Arg Glu
            420                 425                 430

Trp Leu Pro Trp Gln Arg Cys Asp Ile Gly Gly Ser Phe Thr Lys Glu
        435                 440                 445

Ala Asp Gly Glu Leu Pro Gly Gly Val Asn Leu Asp Ser Met Val Thr
    450                 455                 460

Ser Gly Trp Trp Ser Gln Ser Phe Thr Ala Gln Ala Ala Ser Gly Ala
465                 470                 475                 480

Asn Tyr Pro Ile Ala Arg Ala Gly Leu Leu His Val Tyr Ala Ala Ser
                485                 490                 495

Ser Asn Phe Ile Tyr Gln Thr Tyr Gln Ala Tyr Asp Gly Glu Ser Phe
            500                 505                 510

Tyr Phe Arg Cys Arg Tyr Ser Asn Thr Trp Leu Pro Trp Arg Arg Met
        515                 520                 525

Trp His Gly Gly Asp Phe Asn Pro Ser Asp Tyr Leu Leu Lys Ser Gly
    530                 535                 540

Phe Tyr Trp Asn Ala Leu Pro Gly Lys Pro Ala Thr Phe Pro Pro Ser
545                 550                 555                 560

Ala His Asn His Asp Val Gly Gln Leu Thr Ser Gly Ile Leu Pro Leu
                565                 570                 575

Ala Arg Gly Gly Val Gly Ser Asn Thr Ala Gly Ala Arg Ser Thr
            580                 585                 590

Ile Gly Ala Gly Val Pro Ala Thr Ala Ser Leu Gly Ala Ser Gly Trp
        595                 600                 605

Trp Arg Asp Asn Asp Thr Gly Leu Ile Arg Gln Trp Gly Gln Val Thr
    610                 615                 620

Cys Pro Ala Asp Ala Asp Ala Ser Ile Thr Phe Pro Ile Pro Phe Pro
625                 630                 635                 640

Thr Leu Cys Leu Gly Gly Tyr Ala Asn Gln Thr Ser Ala Phe Gln Pro
                645                 650                 655

Gly Thr Asp Ala Ser Thr Gly Phe Arg Gly Ala Thr Thr Thr Thr Ala
```

```
                        660                 665                 670
Val Ile Arg Asn Gly Tyr Phe Ala Gln Ala Val Leu Ser Trp Glu Ala
            675                 680                 685

Phe Gly Arg
    690

<210> SEQ ID NO 6
<211> LENGTH: 152
<212> TYPE: PRT
<213> ORGANISM: Pseudomonas aeruginosa

<400> SEQUENCE: 6

Met Lys Gly Glu Tyr Tyr Phe Ser Pro Ser Gln Val Ala Phe Tyr Pro
1               5                   10                  15

Ala Ser Leu Arg Glu Val Tyr Glu His Ala Gly Cys Trp Pro Val Asp
            20                  25                  30

Gly Glu Trp Val Ser Ala Glu Leu His Glu Gln Leu Met Asn Glu Gln
        35                  40                  45

Ala Ala Gly Arg Ala Ile Ser Ser Asp Val Asn Gly Asn Pro Val Ala
    50                  55                  60

Ile Glu Arg Pro Pro Leu Ser Arg Gln Gln Arg Ser Thr His Glu Arg
65                  70                  75                  80

Arg Trp Arg Asp Ser Gln Leu Leu Ala Thr Asp Gly Leu Val Val Arg
                85                  90                  95

His Arg Asp Gln Leu Glu Thr Gly Lys Glu Thr Thr Leu Leu Pro Val
            100                 105                 110

Gln Tyr His Glu Leu Met Ser Tyr Arg Ala Ser Leu Arg Asp Trp Pro
        115                 120                 125

Glu Glu Pro Leu Phe Pro Asp Ser Gly Gly Arg Pro Ser Val Pro Asp
    130                 135                 140

Trp Leu Arg Arg Tyr Val Thr Pro
145                 150

<210> SEQ ID NO 7
<211> LENGTH: 691
<212> TYPE: PRT
<213> ORGANISM: Pseudomonas aeruginosa

<400> SEQUENCE: 7

Met Thr Thr Asn Thr Pro Lys Tyr Gly Gly Leu Leu Thr Asp Ile Gly
1               5                   10                  15

Ala Ala Ala Leu Ala Ala Ala Ser Ala Ala Gly Lys Lys Trp Gln Pro
            20                  25                  30

Thr His Met Leu Ile Gly Asp Ala Gly Gly Ala Pro Gly Asp Thr Pro
        35                  40                  45

Asp Pro Leu Pro Ser Ala Ala Gln Lys Ser Leu Ile Asn Gln Arg His
    50                  55                  60

Arg Ala Gln Leu Asn Arg Leu Phe Val Ser Asp Lys Asn Ala Asn Thr
65                  70                  75                  80

Leu Val Ala Glu Val Val Leu Pro Val Glu Val Gly Gly Phe Trp Ile
                85                  90                  95

Arg Glu Ile Gly Leu Gln Asp Ala Asp Gly Lys Phe Val Ala Val Ser
            100                 105                 110

Asn Cys Pro Pro Ser Tyr Lys Ala Ala Met Glu Ser Gly Ser Ala Arg
        115                 120                 125

Thr Gln Thr Ile Arg Val Asn Ile Ala Leu Ser Gly Leu Glu Asn Val
    130                 135                 140
```

```
Gln Leu Leu Ile Asp Asn Gly Ile Ile Tyr Ala Thr Gln Asp Trp Val
145                 150                 155                 160

Lys Glu Lys Val Ala Ala Asp Phe Lys Gly Arg Lys Ile Leu Ala Gly
            165                 170                 175

Asn Gly Leu Val Gly Gly Asp Leu Ser Ala Asp Arg Ser Ile Gly
        180                 185                 190

Leu Ala Pro Ser Gly Val Thr Ala Gly Ser Tyr Arg Ser Val Thr Val
            195                 200                 205

Asn Ala Asn Gly Val Val Thr Gln Gly Ser Asn Pro Thr Thr Leu Ala
210                 215                 220

Gly Tyr Ala Ile Gly Asp Ala Tyr Thr Lys Ala Asp Thr Asp Gly Lys
225                 230                 235                 240

Leu Ala Gln Lys Ala Asn Lys Ala Thr Thr Leu Ala Gly Tyr Gly Ile
            245                 250                 255

Thr Asp Ala Leu Arg Val Asp Gly Asn Ala Val Ser Ser Ser Arg Leu
            260                 265                 270

Ala Ala Pro Arg Ser Leu Ala Ala Ser Gly Asp Ala Ser Trp Ser Val
            275                 280                 285

Thr Phe Asp Gly Ser Ala Asn Val Ser Ala Pro Leu Ser Leu Ser Ala
            290                 295                 300

Thr Gly Val Ala Ala Gly Ser Tyr Pro Lys Val Thr Val Asp Thr Lys
305                 310                 315                 320

Gly Arg Val Thr Ala Gly Met Ala Leu Ala Ala Thr Asp Ile Pro Gly
                325                 330                 335

Leu Asp Ala Ser Lys Leu Val Ser Gly Val Leu Ala Glu Gln Arg Leu
            340                 345                 350

Pro Val Phe Ala Arg Gly Leu Ala Thr Ala Val Ser Asn Ser Ser Asp
            355                 360                 365

Pro Asn Thr Ala Thr Val Pro Leu Met Leu Thr Asn His Ala Asn Gly
370                 375                 380

Pro Val Ala Gly Arg Tyr Phe Tyr Ile Gln Ser Met Phe Tyr Pro Asp
385                 390                 395                 400

Gln Asn Gly Asn Ala Ser Gln Ile Ala Thr Ser Tyr Asn Ala Thr Ser
            405                 410                 415

Glu Met Tyr Val Arg Val Ser Tyr Ala Ala Asn Pro Ser Ile Arg Glu
            420                 425                 430

Trp Leu Pro Trp Gln Arg Cys Asp Ile Gly Gly Ser Phe Thr Lys Glu
            435                 440                 445

Ala Asp Gly Glu Leu Pro Gly Gly Val Asn Leu Asp Ser Met Val Thr
450                 455                 460

Ser Gly Trp Trp Ser Gln Ser Phe Thr Ala Gln Ala Thr Gly Ala
465                 470                 475                 480

Asn Tyr Pro Ile Val Arg Ala Gly Leu Leu His Val Tyr Ala Ala Ser
            485                 490                 495

Ser Asn Phe Ile Tyr Gln Thr Tyr Gln Ala Tyr Asp Gly Glu Ser Phe
            500                 505                 510

Tyr Phe Arg Cys Arg His Ser Asn Thr Trp Phe Pro Trp Arg Arg Met
            515                 520                 525

Trp His Gly Gly Asp Phe Asn Pro Ser Asp Tyr Leu Leu Lys Ser Gly
            530                 535                 540

Phe Tyr Trp Asn Ala Leu Pro Gly Lys Pro Ala Thr Phe Pro Pro Ser
545                 550                 555                 560

Ala His Asn His Asp Val Gly Gln Leu Thr Ser Gly Ile Leu Pro Leu
```

```
                        565                 570                 575

Ala Arg Gly Gly Val Gly Ser Asn Thr Ala Ala Gly Arg Ser Thr
                580                 585                 590

Ile Gly Ala Gly Val Pro Ala Thr Ala Ser Leu Gly Ala Ser Gly Trp
            595                 600                 605

Trp Arg Asp Asn Asp Thr Gly Leu Ile Arg Gln Trp Gly Gln Val Thr
            610                 615                 620

Cys Pro Ala Asp Ala Asp Ala Ser Ile Thr Phe Pro Ile Pro Phe Pro
625                 630                 635                 640

Thr Leu Cys Leu Gly Gly Tyr Ala Asn Gln Thr Ser Ala Phe His Pro
                645                 650                 655

Gly Thr Asp Ala Ser Thr Gly Phe Arg Gly Ala Thr Thr Thr Thr Ala
                660                 665                 670

Val Ile Arg Asn Gly Tyr Phe Ala Gln Ala Val Leu Ser Trp Glu Ala
                675                 680                 685

Phe Gly Arg
        690

<210> SEQ ID NO 8
<211> LENGTH: 152
<212> TYPE: PRT
<213> ORGANISM: Pseudomonas aeruginosa
<220> FEATURE:
<221> NAME/KEY: MISC_FEATURE
<222> LOCATION: (17)..(17)
<223> OTHER INFORMATION: Other

<400> SEQUENCE: 8

Met Lys Gly Glu Tyr Tyr Phe Ser Pro Ser Gln Val Ala Phe Tyr Pro
1               5                   10                  15

Xaa Ser Leu Arg Glu Val Tyr Glu Tyr Ala Gly Cys Trp Pro Val Asp
                20                  25                  30

Gly Glu Trp Val Ser Ala Glu Leu His Glu Gln Leu Met Asn Glu Gln
            35                  40                  45

Ala Ala Gly Arg Ala Ile Ser Ser Asp Val Asn Gly Asn Pro Val Ala
        50                  55                  60

Ile Glu Arg Pro Pro Leu Ser Arg Gln Gln Arg Ser Ala His Glu Arg
65                  70                  75                  80

Arg Trp Arg Asp Ser Gln Leu Leu Ala Thr Asp Gly Leu Val Val Arg
                85                  90                  95

His Arg Asp Gln Leu Glu Thr Gly Lys Glu Thr Thr Leu Leu Pro Val
            100                 105                 110

Gln Tyr His Glu Leu Met Ser Tyr Arg Ala Ser Leu Arg Asp Trp Pro
        115                 120                 125

Glu Glu Pro Leu Phe Pro Asp Ser Gly Gly Arg Pro Ser Val Pro Asp
    130                 135                 140

Trp Leu Arg Arg Tyr Val Thr Pro
145                 150

<210> SEQ ID NO 9
<211> LENGTH: 702
<212> TYPE: PRT
<213> ORGANISM: Pseudomonas aeruginosa

<400> SEQUENCE: 9

Met Thr Thr Asn Thr Pro Lys Tyr Gly Gly Leu Leu Thr Asp Ile Gly
1               5                   10                  15

Ala Ala Ala Leu Ala Ala Ala Ser Ala Ala Gly Lys Lys Trp Gln Pro
```

```
                    20                  25                  30
Thr His Met Leu Ile Gly Asp Ala Gly Gly Pro Gly Ala Thr Pro
                35                  40                  45
Asp Pro Ile Pro Ala Ala Thr Gln Thr Lys Leu Ile Asn Gln Arg Tyr
        50                  55                  60
Arg Ala Gln Leu Asn Arg Leu Phe Val Ser Asp Lys Asn Ile Asn Thr
65                  70                  75                  80
Leu Val Ala Glu Val Val Leu Pro Val Glu Val Gly Gly Phe Trp Ile
                85                  90                  95
Arg Glu Ile Gly Leu Gln Asp Ala Asp Gly Lys Phe Val Ala Val Ser
                100                 105                 110
Asn Cys Pro Pro Ser Tyr Lys Ala Ala Met Glu Ser Gly Ser Ala Arg
                115                 120                 125
Thr Gln Thr Ile Arg Val Asn Ile Ala Leu Ser Gly Leu Glu Asn Val
        130                 135                 140
Gln Leu Leu Ile Asp Asn Gly Ile Ile Tyr Ala Thr Gln Asp Trp Val
145                 150                 155                 160
Lys Glu Lys Val Ala Ala Asp Phe Lys Gly Arg Lys Ile Leu Ala Gly
                165                 170                 175
Asn Gly Leu Val Gly Gly Gly Asp Leu Ser Ala Asp Arg Ser Ile Gly
                180                 185                 190
Leu Ala Pro Ser Gly Val Thr Ala Gly Ser Tyr Arg Ser Val Thr Val
                195                 200                 205
Asn Ala Asn Gly Val Val Thr Gln Gly Ser Asn Pro Ser Thr Leu Ala
        210                 215                 220
Gly Tyr Ala Ile Gly Asp Ala Tyr Thr Lys Ala Asp Thr Asp Gly Lys
225                 230                 235                 240
Leu Ala Gln Lys Ala Asn Lys Ala Thr Thr Leu Ala Gly Tyr Gly Ile
                245                 250                 255
Thr Asp Ala Leu Arg Val Asp Gly Asn Ala Val Ser Ser Ser Arg Leu
                260                 265                 270
Ala Ala Pro Arg Ser Leu Ala Ala Ser Gly Asp Ala Ser Trp Ser Val
                275                 280                 285
Thr Phe Asp Gly Ser Ala Asn Val Ser Ala Pro Leu Ser Leu Ser Ala
        290                 295                 300
Thr Gly Val Ala Ala Gly Ser Tyr Pro Lys Val Thr Val Asp Thr Lys
305                 310                 315                 320
Gly Arg Val Thr Ala Gly Met Ala Leu Ala Ala Thr Asp Ile Pro Gly
                325                 330                 335
Leu Asp Ala Ser Lys Leu Val Ser Gly Val Leu Ala Glu Gln Arg Leu
                340                 345                 350
Pro Val Phe Ala Arg Gly Leu Ala Thr Ala Val Ser Thr Thr Ser Asp
                355                 360                 365
Pro Asn Thr Ala Thr Val Pro Leu Met Leu Thr Asn His Ala Asn Gly
        370                 375                 380
Pro Val Ala Gly Arg Tyr Phe Tyr Ile Gln Ser Met Phe Tyr Pro Asp
385                 390                 395                 400
Gln Asn Gly Asn Ala Ser Gln Ile Ala Thr Ser Tyr Asn Ala Thr Ser
                405                 410                 415
Glu Met Tyr Val Arg Val Ser Tyr Ala Ala Asn Pro Ser Ala Arg Asp
                420                 425                 430
Trp Leu Pro Trp Lys Arg Cys Asp Ile Gly Gly Ser Phe Ser Lys Glu
        435                 440                 445
```

```
Ala Asp Gly Ala Leu Gly Gly Ala Val Asn Leu Asn Ser Leu Ile Thr
    450                 455                 460

Ser Gly Trp Trp Tyr Gln Thr Ala Asn Ala Gln Ala Glu Ser Gly Ala
465                 470                 475                 480

Asn Tyr Pro Val Pro Arg Ala Gly Leu Leu Gln Val His Asn Ala Gly
                485                 490                 495

Thr Asn Phe Ile Tyr Gln Thr Tyr Gln Val Tyr Asp Gly Glu Gly Phe
            500                 505                 510

Tyr Phe Arg Cys Arg Tyr Thr Asn Thr Trp Tyr Pro Trp Arg Arg Val
        515                 520                 525

Trp His Gly Ala Asp Phe Asn Pro Asn Asp Tyr Leu Leu Lys Ser Gly
    530                 535                 540

Phe Thr Trp Ala Ala Leu Pro Gly Lys Pro Ala Thr Phe Pro Pro Thr
545                 550                 555                 560

Gly His Asn His Asp Ala Ala Gln Ile Thr Ser Gly Ile Leu Pro Leu
                565                 570                 575

Ala Arg Gly Gly Leu Gly Ser Asn Thr Ala Gly Ala Arg Asn Asn
            580                 585                 590

Ile Gly Ala Gly Val Pro Ala Thr Ala Asn Arg Ser Leu Asn Gly Trp
        595                 600                 605

Trp Lys Asp Asn Asp Thr Gly Leu Ile Val Gln Trp Met Thr Val Ser
    610                 615                 620

Val Gly Asp His Pro Gly Gly Ile Val Asn Arg Ser Leu Thr Phe Pro
625                 630                 635                 640

Ile Ala Phe Pro Thr Thr Cys Leu His Val Val Pro Ser Val Lys Glu
                645                 650                 655

Leu Gly Arg Pro Ala Thr Ser Ala Ser Thr Val Thr Leu Ala Asp Val
            660                 665                 670

Ser Val Ser Thr Thr Gly Cys Val Ile Val Ala Thr Glu Tyr His Gly
        675                 680                 685

Ala Val Gln Asn Tyr Ala Ile Arg Leu Val Ala Ile Gly Cys
    690                 695                 700

<210> SEQ ID NO 10
<211> LENGTH: 146
<212> TYPE: PRT
<213> ORGANISM: Pseudomonas aeruginosa

<400> SEQUENCE: 10

Met Ile Phe Phe His Ala Ala Thr Gly Gly Phe Tyr Ser Lys Asp Val
1               5                   10                  15

His Gly Asp Arg Met Pro Ile Asp Ala Arg Met Tyr Pro Leu Glu Glu
            20                  25                  30

Ala Glu Tyr Leu Ala Leu Leu Val Ala Gln Ser Glu Gly Lys Gln Ile
        35                  40                  45

Val Ala Asp Ala Ala Gly Arg Pro Phe Cys Ile Asp Pro Pro Ala Pro
    50                  55                  60

Ala Glu Glu Val Leu Ala His Arg Glu Arg Ile Trp Arg Asp Arg Gln
65                  70                  75                  80

Leu Thr Leu Thr Asp Gly Pro Ile Ala Arg His Arg Asp Glu Leu Asp
            85                  90                  95

Leu Gly Lys Ile Thr Thr Leu Asn Gln Ala Gln Leu Leu Glu Leu Thr
        100                 105                 110

Leu Tyr Arg Ala Ser Leu Arg Asp Trp Pro Ala Ser Ala Ala Phe Pro
    115                 120                 125
```

```
Asp Leu Gly Ala Arg Pro Glu Pro Leu Trp Leu Glu Pro Leu Ile
        130                 135                 140

Thr Pro
145

<210> SEQ ID NO 11
<211> LENGTH: 485
<212> TYPE: PRT
<213> ORGANISM: Pseudomonas aeruginosa

<400> SEQUENCE: 11

Met Lys Arg Ser Phe Leu Ser Leu Ala Val Ala Val Val Leu Ser
1               5                   10                  15

Gly Cys Ser Leu Ile Pro Asp Tyr Gln Arg Pro Glu Ala Pro Val Ala
                20                  25                  30

Ala Ala Tyr Pro Gln Gly Gln Ala Tyr Gly Gln Asn Thr Gly Ala Ala
                35                  40                  45

Ala Val Pro Ala Ala Asp Ile Gly Trp Arg Glu Phe Phe Arg Asp Pro
50                  55                  60

Gln Leu Gln Gln Leu Ile Gly Val Ala Leu Glu Asn Asn Arg Asp Leu
65                  70                  75                  80

Arg Val Ala Ala Leu Asn Val Glu Ala Phe Arg Ala Gln Tyr Arg Ile
                85                  90                  95

Gln Arg Ala Asp Leu Phe Pro Arg Ile Gly Val Asp Gly Ser Gly Thr
                100                 105                 110

Arg Gln Arg Leu Pro Gly Asp Leu Ser Thr Thr Gly Ser Pro Ala Ile
                115                 120                 125

Ser Ser Gln Tyr Gly Val Thr Leu Gly Thr Thr Ala Trp Glu Leu Asp
130                 135                 140

Leu Phe Gly Arg Leu Arg Ser Leu Arg Asp Gln Ala Leu Glu Gln Tyr
145                 150                 155                 160

Leu Ala Thr Glu Gln Ala Gln Arg Ser Ala Gln Thr Thr Leu Val Ala
                165                 170                 175

Ser Val Ala Thr Ala Tyr Leu Thr Leu Lys Ala Asp Gln Ala Gln Leu
                180                 185                 190

Gln Leu Thr Lys Asp Thr Leu Gly Thr Tyr Gln Lys Ser Phe Asp Leu
                195                 200                 205

Thr Gln Arg Ser Tyr Asp Val Gly Val Ala Ser Ala Leu Asp Leu Arg
210                 215                 220

Gln Ala Gln Thr Ala Val Glu Gly Ala Arg Ala Thr Leu Ala Gln Tyr
225                 230                 235                 240

Thr Arg Leu Val Ala Gln Asp Gln Asn Ala Leu Val Leu Leu Leu Gly
                245                 250                 255

Ser Gly Ile Pro Ala Asn Leu Pro Gln Gly Leu Gly Leu Asp Gln Thr
                260                 265                 270

Leu Leu Thr Glu Val Pro Ala Gly Leu Pro Ser Asp Leu Leu Gln Arg
                275                 280                 285

Arg Pro Asp Ile Leu Glu Ala Glu His Gln Leu Met Ala Ala Asn Ala
290                 295                 300

Ser Ile Gly Ala Ala Arg Ala Ala Phe Phe Pro Ser Ile Ser Leu Thr
305                 310                 315                 320

Ala Asn Ala Gly Thr Met Ser Arg Gln Leu Ser Gly Leu Phe Asp Ala
                325                 330                 335

Gly Ser Gly Ser Trp Leu Phe Gln Pro Ser Ile Asn Leu Pro Ile Phe
                340                 345                 350
```

```
Thr Ala Gly Ser Leu Arg Ala Ser Leu Asp Tyr Ala Lys Ile Gln Lys
            355                 360                 365

Asp Ile Asn Val Ala Gln Tyr Glu Lys Ala Ile Gln Thr Ala Phe Gln
        370                 375                 380

Glu Val Ala Asp Gly Leu Ala Ala Arg Gly Thr Phe Thr Glu Gln Leu
385                 390                 395                 400

Gln Ala Gln Arg Asp Leu Val Lys Ala Ser Asp Glu Tyr Tyr Gln Leu
                405                 410                 415

Ala Asp Lys Arg Tyr Arg Thr Gly Val Asp Asn Tyr Leu Thr Leu Leu
            420                 425                 430

Asp Ala Gln Arg Ser Leu Phe Thr Ala Gln Gln Leu Ile Thr Asp
        435                 440                 445

Arg Leu Asn Gln Leu Thr Ser Glu Val Asn Leu Tyr Lys Ala Leu Gly
    450                 455                 460

Gly Gly Trp Asn Gln Gln Thr Val Thr Gln Gln Thr Ala Lys Lys
465                 470                 475                 480

Glu Asp Pro Gln Ala
            485

<210> SEQ ID NO 12
<211> LENGTH: 479
<212> TYPE: PRT
<213> ORGANISM: Pseudomonas aeruginosa

<400> SEQUENCE: 12

Met Arg Lys Pro Ala Phe Gly Val Ser Ala Leu Leu Ile Ala Leu Thr
1               5                   10                  15

Leu Gly Ala Cys Ser Met Ala Pro Thr Tyr Glu Arg Pro Ala Ala Pro
            20                  25                  30

Val Ala Asp Ser Trp Ser Gly Ala Ala Ala Gln Arg Gln Gly Ala Ala
        35                  40                  45

Ile Asp Thr Leu Asp Trp Lys Ser Phe Ile Val Asp Ala Glu Leu Arg
    50                  55                  60

Arg Leu Val Asp Met Ala Leu Asp Asn Asn Arg Ser Leu Arg Gln Thr
65                  70                  75                  80

Leu Leu Asp Ile Glu Ala Ala Arg Ala Gln Tyr Arg Ile Gln Arg Ala
                85                  90                  95

Asp Arg Val Pro Gly Leu Asn Ala Ala Ala Thr Gly Asn Arg Gln Arg
            100                 105                 110

Gln Pro Ala Asp Leu Ser Ala Gly Asn Arg Ser Glu Val Ala Ser Ser
        115                 120                 125

Tyr Gln Val Gly Leu Ala Leu Pro Glu Tyr Glu Leu Asp Leu Phe Gly
    130                 135                 140

Arg Val Lys Ser Leu Thr Asp Ala Ala Leu Gln Gln Tyr Leu Ala Ser
145                 150                 155                 160

Glu Glu Ala Ala Arg Ala Ala Arg Ile Ala Leu Val Ala Glu Val Ser
                165                 170                 175

Gln Ala Tyr Leu Ser Tyr Asp Gly Ala Leu Arg Arg Leu Ala Leu Thr
            180                 185                 190

Arg Gln Thr Leu Val Ser Arg Glu Tyr Ser Phe Ala Leu Ile Asp Gln
        195                 200                 205

Arg Arg Ala Ala Gly Ala Ala Thr Ala Leu Asp Tyr Gln Glu Ala Leu
    210                 215                 220

Gly Leu Val Glu Gln Ala Arg Ala Glu Gln Glu Arg Asn Leu Arg Gln
225                 230                 235                 240
```

```
Lys Gln Gln Ala Phe Asn Ala Leu Val Leu Leu Leu Gly Ser Asp Asp
                245                 250                 255

Ala Ala Gln Ala Ile Pro Arg Ser Pro Gly Gln Arg Pro Lys Leu Leu
            260                 265                 270

Gln Asp Ile Ala Pro Gly Thr Pro Ser Glu Leu Ile Glu Arg Arg Pro
        275                 280                 285

Asp Ile Leu Ala Ala Glu His Arg Leu Arg Ala Arg Asn Ala Asp Ile
    290                 295                 300

Gly Ala Ala Arg Ala Ala Phe Phe Pro Arg Ile Ser Leu Thr Gly Ser
305                 310                 315                 320

Phe Gly Thr Ser Ser Ala Glu Met Ser Gly Leu Phe Asp Gly Gly Ser
                325                 330                 335

Arg Ser Trp Ser Phe Leu Pro Thr Leu Thr Leu Pro Ile Phe Asp Gly
            340                 345                 350

Gly Arg Asn Arg Ala Asn Leu Ser Leu Ala Glu Ala Arg Lys Asp Ser
        355                 360                 365

Ala Val Ala Ala Tyr Glu Gly Thr Ile Gln Thr Ala Phe Arg Glu Val
    370                 375                 380

Ala Asp Ala Leu Ala Ala Ser Asp Thr Leu Arg Arg Glu Glu Lys Ala
385                 390                 395                 400

Leu Arg Ala Leu Ala Asn Ser Ser Asn Glu Ala Leu Lys Leu Ala Lys
                405                 410                 415

Ala Arg Tyr Glu Ser Gly Val Asp Asn His Leu Arg Tyr Leu Asp Ala
            420                 425                 430

Gln Arg Ser Ser Phe Leu Asn Glu Ile Ala Phe Ile Asp Gly Ser Thr
        435                 440                 445

Gln Arg Gln Ile Ala Leu Val Asp Leu Phe Arg Ala Leu Gly Gly Gly
    450                 455                 460

Trp Asp Glu Gly Arg Ser Leu Val Val His Arg Gly Gly Arg Ser
465                 470                 475

<210> SEQ ID NO 13
<211> LENGTH: 472
<212> TYPE: PRT
<213> ORGANISM: Pseudomonas aeruginosa

<400> SEQUENCE: 13

Met Ile His Ala Gln Ser Ile Arg Ser Gly Leu Ala Ser Ala Leu Gly
1               5                   10                  15

Leu Phe Ser Leu Leu Ala Leu Ser Ala Cys Thr Val Gly Pro Asp Tyr
            20                  25                  30

Arg Thr Pro Asp Thr Ala Ala Lys Ile Asp Ala Thr Ala Ser Lys
        35                  40                  45

Pro Tyr Asp Arg Ser Arg Phe Glu Ser Leu Trp Trp Lys Gln Phe Asp
    50                  55                  60

Asp Pro Thr Leu Asn Gln Leu Val Glu Gln Ser Leu Ser Gly Asn Arg
65                  70                  75                  80

Asp Leu Arg Val Ala Phe Ala Arg Leu Arg Ala Arg Ala Leu Arg
                85                  90                  95

Asp Asp Val Ala Asn Asp Arg Phe Pro Val Val Thr Ser Arg Ala Ser
            100                 105                 110

Ala Asp Ile Gly Lys Gly Gln Gln Pro Gly Val Thr Glu Asp Arg Val
        115                 120                 125

Asn Ser Glu Arg Tyr Asp Leu Gly Leu Asp Ser Ala Trp Glu Leu Asp
    130                 135                 140
```

```
Leu Phe Gly Arg Ile Arg Arg Gln Leu Glu Ser Ser Asp Ala Leu Ser
145                 150                 155                 160

Glu Ala Ala Glu Ala Asp Leu Gln Gln Leu Gln Val Ser Leu Ile Ala
            165                 170                 175

Glu Leu Val Asp Ala Tyr Gly Gln Leu Arg Gly Ala Gln Leu Arg Glu
        180                 185                 190

Lys Ile Ala Leu Ser Asn Leu Glu Asn Gln Lys Glu Ser Arg Gln Leu
    195                 200                 205

Thr Glu Gln Leu Arg Asp Ala Gly Val Gly Ala Glu Leu Asp Val Leu
210                 215                 220

Arg Ala Asp Ala Arg Leu Ala Ala Thr Ala Ala Ser Val Pro Gln Leu
225                 230                 235                 240

Gln Ala Glu Ala Glu Arg Ala Arg His Arg Ile Ala Thr Leu Leu Gly
            245                 250                 255

Gln Arg Pro Glu Glu Leu Thr Val Asp Leu Ser Pro Arg Asp Leu Pro
        260                 265                 270

Ala Ile Thr Lys Ala Leu Pro Ile Gly Asp Pro Gly Glu Leu Leu Arg
    275                 280                 285

Arg Arg Pro Asn Ile Arg Ala Ala Glu Arg Arg Val Ala Ala Ser Thr
290                 295                 300

Ala Asp Val Gly Val Ala Thr Ala Asp Leu Phe Pro Ala Gly Gln Pro
305                 310                 315                 320

Gln Arg Leu Pro Arg Leu His Arg Arg Ala Gly Ser Gln Ile Gly Ser
            325                 330                 335

Ser Ala Ala Arg Ala Trp Ser Val Gly Pro Ser Ile Ser Trp Ala Ala
        340                 345                 350

Phe Asp Leu Gly Ser Val Arg Ala Arg Leu Arg Gly Ala Lys Ala Asp
    355                 360                 365

Ala Asp Ala Ala Leu Ala Ser Tyr Glu Gln Gln Val Leu Leu Ala Leu
370                 375                 380

Glu Glu Ser Ala Asn Ala Phe Ser Asp Tyr Gly Lys Arg Gln Glu Arg
385                 390                 395                 400

Leu Val Ser Leu Val Arg Gln Ser Glu Ala Ser Arg Ala Ala Ala Gln
            405                 410                 415

Gln Ala Ala Ile Arg Tyr Arg Glu Gly Thr Thr Asp Phe Leu Val Leu
        420                 425                 430

Leu Asp Ala Glu Arg Glu Gln Leu Ser Ala Glu Asp Ala Gln Ala Gln
    435                 440                 445

Ala Glu Val Glu Leu Tyr Arg Gly Ile Val Ala Ile Tyr Arg Ser Leu
450                 455                 460

Gly Gly Gly Trp Gln Pro Ser Ala
465                 470

<210> SEQ ID NO 14
<211> LENGTH: 472
<212> TYPE: PRT
<213> ORGANISM: Pseudomonas aeruginosa

<400> SEQUENCE: 14

Met Ile His Ala Gln Ser Ile Arg Ser Gly Leu Ala Ser Ala Leu Gly
1               5                   10                  15

Leu Phe Ser Leu Leu Ala Leu Ser Ala Cys Thr Val Gly Pro Asp Tyr
            20                  25                  30

Arg Thr Pro Asp Thr Ala Ala Ala Lys Ile Asp Ala Thr Ala Ser Lys
        35                  40                  45
```

```
Pro Tyr Asp Arg Ser Arg Phe Glu Ser Leu Trp Trp Lys Gln Phe Asp
 50                  55                  60

Asp Pro Thr Leu Asn Gln Leu Val Glu Gln Ser Leu Ser Gly Asn Arg
 65                  70                  75                  80

Asp Leu Arg Val Ala Phe Ala Arg Leu Arg Ala Arg Ala Leu Arg
                 85                  90                  95

Asp Asp Val Ala Asn Asp Arg Phe Pro Val Val Thr Ser Arg Ala Ser
                100                 105                 110

Ala Asp Ile Gly Lys Gly Gln Gln Pro Gly Val Thr Glu Asp Arg Val
            115                 120                 125

Asn Ser Glu Arg Tyr Asp Leu Gly Leu Asp Ser Ala Trp Glu Leu Asp
130                 135                 140

Leu Phe Gly Arg Ile Arg Arg Gln Leu Glu Ser Ser Asp Ala Leu Ser
145                 150                 155                 160

Glu Ala Ala Glu Ala Asp Leu Gln Gln Leu Gln Val Ser Leu Ile Ala
            165                 170                 175

Glu Leu Val Asp Ala Tyr Gly Gln Leu Arg Gly Ala Gln Leu Arg Glu
            180                 185                 190

Lys Ile Ala Leu Ser Asn Leu Glu Asn Gln Lys Glu Ser Arg Gln Leu
            195                 200                 205

Thr Glu Gln Leu Arg Asp Ala Gly Val Gly Ala Glu Leu Asp Val Leu
210                 215                 220

Arg Ala Asp Ala Arg Leu Ala Ala Thr Ala Ala Ser Val Pro Gln Leu
225                 230                 235                 240

Gln Ala Glu Ala Glu Arg Ala Arg His Arg Ile Ala Thr Leu Leu Gly
            245                 250                 255

Gln Arg Pro Glu Glu Leu Thr Val Asp Leu Ser Pro Arg Asp Leu Pro
            260                 265                 270

Ala Ile Thr Lys Ala Leu Pro Ile Gly Asp Pro Gly Glu Leu Leu Arg
            275                 280                 285

Arg Arg Pro Asn Ile Arg Ala Ala Glu Arg Arg Val Ala Ala Ser Thr
290                 295                 300

Ala Asp Val Gly Val Ala Thr Ala Asp Leu Phe Pro Ala Gly Gln Pro
305                 310                 315                 320

Gln Arg Leu Pro Arg Leu His Arg Arg Ala Gly Ser Gln Ile Gly Ser
            325                 330                 335

Ser Ala Ala Arg Ala Trp Ser Val Gly Pro Ser Ile Ser Trp Ala Ala
            340                 345                 350

Phe Asp Leu Gly Ser Val Arg Ala Arg Leu Arg Gly Ala Lys Ala Asp
            355                 360                 365

Ala Asp Ala Ala Leu Ala Ser Tyr Glu Gln Gln Val Leu Leu Ala Leu
370                 375                 380

Glu Glu Ser Ala Asn Ala Phe Ser Asp Tyr Gly Lys Arg Gln Glu Arg
385                 390                 395                 400

Leu Val Ser Leu Val Arg Gln Ser Glu Ala Ser Arg Ala Ala Ala Gln
            405                 410                 415

Gln Ala Ala Ile Arg Tyr Arg Glu Gly Thr Thr Asp Phe Leu Val Leu
            420                 425                 430

Leu Asp Ala Glu Arg Glu Gln Leu Ser Ala Glu Asp Ala Gln Ala Gln
            435                 440                 445

Ala Glu Val Glu Leu Tyr Arg Gly Ile Val Ala Ile Tyr Arg Ser Leu
            450                 455                 460

Gly Gly Gly Trp Gln Pro Ser Ala
465                 470
```

<210> SEQ ID NO 15
<211> LENGTH: 451
<212> TYPE: PRT
<213> ORGANISM: Pseudomonas aeruginosa

<400> SEQUENCE: 15

Met Asn Arg Leu Arg Ala Cys Leu Leu Ser Ser Ala Leu Leu Ser Ala
1               5                   10                  15

Ser Ser Ala Gln Ala Leu Gly Leu Leu Asp Ala Tyr Gln Leu Ala Val
            20                  25                  30

Arg His Asp Pro Thr Phe Gln Ala Ala Leu His Glu Arg Arg Ala Gly
        35                  40                  45

Ser Glu Asn Arg Ala Ile Gly Arg Ala Gly Leu Leu Pro Ser Leu Arg
    50                  55                  60

Tyr Asp Tyr Asn Lys Ala Arg Asn Asp Ser Thr Val Ser Gln Gly Asp
65                  70                  75                  80

Ala Arg Val Glu Arg Asp Tyr Arg Ser Tyr Ala Ser Thr Leu Ser Leu
                85                  90                  95

Glu Gln Pro Leu Phe Asp Tyr Glu Ala Tyr Ala Arg Tyr Arg Gln Gly
            100                 105                 110

Glu Ala Gln Ala Leu Phe Ala Asp Glu Gln Phe Arg Gly Arg Ser Gln
        115                 120                 125

Glu Leu Ala Val Arg Leu Phe Ala Ala Tyr Ser Glu Thr Leu Phe Ala
    130                 135                 140

Arg Glu Gln Val Val Leu Ala Glu Ala Gln Arg Arg Ala Leu Glu Thr
145                 150                 155                 160

Gln Leu Ala Phe Asn Gln Arg Ala Phe Glu Glu Gly Glu Gly Thr Arg
                165                 170                 175

Thr Asp Leu Leu Glu Thr Arg Ala Arg Leu Ser Leu Thr Arg Ala Glu
            180                 185                 190

Glu Ile Ala Ala Ser Asp Arg Ala Ala Ala Arg Arg Thr Leu Glu
        195                 200                 205

Ala Met Leu Gly Gln Ala Leu Glu Asp Arg Glu Leu Ala Ala Pro Ile
    210                 215                 220

Glu Arg Phe Pro Ala Leu Arg Leu Gln Pro Ala Thr Phe Glu Gly Trp
225                 230                 235                 240

Arg Gln Val Ala Leu Gln Arg Ser Ala Glu Leu Gly Ala Gln Arg His
                245                 250                 255

Ala Leu Glu Ala Ala Ala Tyr Glu Val Glu Arg Asn Arg Ala Gly His
            260                 265                 270

Leu Pro Arg Leu Ser Leu Tyr Ala Ser Ser Ser Lys Thr His Ser Ala
        275                 280                 285

Ser Glu Ser Thr Tyr Glu Gln Lys Tyr Asp Thr Asp Ser Val Gly Leu
    290                 295                 300

Arg Leu Ser Leu Pro Leu Phe Glu Gly Gly Arg Val Ser Ala Ala Thr
305                 310                 315                 320

Arg Gln Ala Gly Asp Lys Tyr Ala Gln Ala Gln Ala Glu Leu Asp Ala
                325                 330                 335

Gln Val Ala Ser Val Ile Asn Asp Leu His Ser Gln Phe Asp Leu Thr
            340                 345                 350

Ala Ser Ser Leu Ala Lys Val Arg Ala Tyr Glu Met Ala Val Ala Ala
        355                 360                 365

Ala Arg Glu Gln Val Thr Ala Thr Arg Arg Ser Val Ala Gly Gly Glu
    370                 375                 380

```
Arg Val Asn Arg Asp Val Leu Asp Ala Glu Gln Gln Phe Tyr Gly Ala
385                 390                 395                 400

Arg Arg Asp Leu Ala Glu Ala Arg Tyr Ala Tyr Leu Asn Ala Trp Leu
            405                 410                 415

Arg Leu Arg Gln Leu Ala Gly Val Leu Glu Asp Arg Asp Leu Ala Val
            420                 425                 430

Leu Ala Ala Tyr Phe Gly Ala Gly Glu Gly Arg Ala Gln Val Thr Ala
            435                 440                 445

Ala Ile Arg
    450

<210> SEQ ID NO 16
<211> LENGTH: 479
<212> TYPE: PRT
<213> ORGANISM: Pseudomonas aeruginosa

<400> SEQUENCE: 16

Met Lys Gly Thr Pro Leu Leu Ile Ala Ser Leu Ala Leu Gly Ala
1               5                   10                  15

Cys Ser Leu Gly Pro Asp Phe Thr Arg Pro Asp Arg Pro Ala Pro Gly
            20                  25                  30

Glu Trp Ser Leu Gln Ala Ala Gly Asn Pro Ser His Leu Ala Ala
            35                  40                  45

Ala Pro Leu Ala Ala Gln Trp Trp Thr Leu Phe Asp Asp Ala Gln Leu
    50                  55                  60

Asn Ala Leu Leu Gln Arg Val Gln Arg Ala Asn Leu Asp Leu Arg Ser
65                  70                  75                  80

Ala Ala Ala Arg Leu Gln Gln Ser Arg Ala Ile Arg Arg Ser Leu Gly
                85                  90                  95

Gly Asp Ala Leu Pro Ser Val Asp Ala Ser Gly Asn Tyr Gln Arg Gln
            100                 105                 110

Arg Thr Thr Ser Ala Gly Leu Phe Asp Pro Ser Gly Lys Ala Gly Lys
        115                 120                 125

Gly Asn Tyr Asn His Ala Leu Ala Gly Phe Asp Ala Ser Trp Glu Leu
    130                 135                 140

Asp Phe Trp Gly Arg Val Arg Arg Glu Leu Glu Ala Ala Asp Ala Thr
145                 150                 155                 160

Val Glu Ala Ser Glu Asn Glu Leu Arg Asp Val Gln Val Ser Val Leu
                165                 170                 175

Ala Glu Ala Ala Arg Asp Tyr Ile Gln Leu Arg Gly Glu Gln Asn Arg
            180                 185                 190

Ala Ala Ile Ile Arg Asp Asn Leu Glu Thr Ala Arg Arg Ser Leu Glu
        195                 200                 205

Leu Thr Arg Thr Arg Leu Ala Asn Gly Val Ala Thr Asp Leu Glu Val
    210                 215                 220

Ala Gln Ala Leu Ala Gln Val Ala Ser Met Glu Ala Arg Leu Pro Glu
225                 230                 235                 240

Val Glu Lys Asn Gln Ala His Leu Val Asn Ala Leu Gly Tyr Leu Val
                245                 250                 255

Gly Ala Ser Pro Gly Ser Leu Leu Ala Glu Leu Gly Pro Ala Arg Ala
            260                 265                 270

Ile Pro Arg Pro Pro Gly Ser Val Pro Val Gly Leu Pro Ser Glu Leu
        275                 280                 285

Ala Gln Arg Arg Pro Asp Ile Arg Arg Ala Glu Ala Arg Leu His Ala
    290                 295                 300
```

Ala Thr Ala Ser Ile Gly Val Ala Lys Ala Asp Phe Tyr Pro Arg Ile
305                 310                 315                 320

Thr Leu Asn Gly Asn Phe Gly Phe Glu Ser Leu Gln Leu Ser Ser Leu
            325                 330                 335

Gly Asp Trp Asp His Arg Gln Phe Ala Ile Gly Pro Ala Phe Ser Leu
            340                 345                 350

Pro Ile Phe Glu Gly Gly Arg Leu Arg Gly Arg Leu Glu Leu Arg Glu
            355                 360                 365

Ala Gln Gln Gln Glu Ala Ala Ile Asp Tyr Gln Arg Thr Val Leu Arg
            370                 375                 380

Ala Trp Gln Glu Val Asp Asp Ala Met His Asp Tyr Ala Ala Asn Gln
385                 390                 395                 400

Arg Arg Gln Glu Arg Leu Gly Glu Ala Val Ala Gln Asn Arg Arg Ala
            405                 410                 415

Leu Gln Ser Ala Arg Glu Gln Tyr Arg Ala Gly Ala Val Asp Phe Leu
            420                 425                 430

Ser Val Leu Asp Ser Gln Arg Gln Leu Leu Asp Asn Gln Glu Gln Gln
            435                 440                 445

Val Ala Ser Asp Glu Ala Val Ser Leu Thr Leu Val Asn Leu Tyr Lys
450                 455                 460

Ala Leu Gly Gly Gly Trp Ser Pro Thr Ser Asp Pro Ala Ser Gly
465                 470                 475

<210> SEQ ID NO 17
<211> LENGTH: 487
<212> TYPE: PRT
<213> ORGANISM: Pseudomonas aeruginosa

<400> SEQUENCE: 17

Met Lys Arg Ser Tyr Pro Asn Leu Ser Arg Leu Ala Leu Ala Leu Ala
1               5                   10                  15

Val Gly Thr Gly Leu Ala Ala Cys Ser Val Gly Pro Asp Tyr Gln Arg
            20                  25                  30

Pro Gln Ser Pro Pro Pro Arg Val Ala Ser Glu His Leu Gly Glu Phe
        35                  40                  45

Ser Gly Glu Arg Arg Glu Ala Pro Trp Trp Ser Phe Phe Asp Asp Pro
50                  55                  60

Gln Leu Val Arg Leu Val Asp Gln Ala Leu Ala Arg Asn His Asp Ile
65                  70                  75                  80

Arg Glu Ala Arg Ala Asn Leu Arg Ser Ala Arg Ala Leu Phe Asp Asp
            85                  90                  95

Arg Trp Leu Asp Gln Leu Pro Gln Val Thr Ser Gln Ala Gly Tyr Ser
            100                 105                 110

Arg Ser Ile Glu Gln Gln Leu Asp Tyr Asp Gly Glu Pro Arg Arg Arg
            115                 120                 125

Leu Ala Glu Ser Tyr Arg Ala Gly Phe Asp Ala Gln Trp Glu Ile Asp
            130                 135                 140

Leu Phe Gly Arg Leu Gly Arg Leu Ser Asp Ala Ala Leu Ala Arg Ala
145                 150                 155                 160

Glu Ala Ala Asp Ala Asp Leu Arg Leu Val Arg Leu Ser Ile Ala Ala
            165                 170                 175

Asp Thr Ala Arg Ala Tyr Phe Glu Ile Gln Gly Tyr Gln Arg Arg Leu
            180                 185                 190

Asp Val Ala Arg Ala Gln Val Arg Ser Trp Arg Asp Thr Leu Glu Leu
            195                 200                 205

```
Thr Arg Ser Ser Leu Gln Leu Gly Ser Gly Leu Pro Glu Asp Val Glu
    210                 215                 220
Asn Ala Gln Ala Asn Leu Leu Arg Ser Glu Ala Ala Ile Pro Pro Leu
225                 230                 235                 240
Thr Thr Ala Leu Glu Ser Ala Arg Tyr Arg Leu Asp Val Leu Arg Gly
                245                 250                 255
Glu Ala Pro Gly Ser Gly Ala Pro Ile Leu Asp Gly Gly Ala Ala Ala
            260                 265                 270
Pro Leu Ala Lys Asn Leu Pro Leu Gly Asp Val Asp Arg Leu Ile Leu
        275                 280                 285
Gln Arg Pro Asp Val Val Ser Ala Glu Arg Gln Leu Ala Ala Ser Thr
    290                 295                 300
Glu Asp Val Gly Ala Ala Thr Ala Glu Leu Tyr Pro Arg Leu Asp Leu
305                 310                 315                 320
Gly Gly Phe Ile Gly Phe Phe Ala Leu Arg Ser Gly Asp Leu Gly Ser
                325                 330                 335
Ala Ser Arg Ala Phe Glu Leu Ala Pro Ser Val Ser Trp Pro Ala Phe
            340                 345                 350
Arg Leu Gly Asn Val Arg Ala Arg Leu Arg Ala Val Glu Ala Gln Ser
        355                 360                 365
Asp Ala Ala Leu Ala Arg Tyr Gln Arg Ser Leu Leu Leu Ala Gln Glu
    370                 375                 380
Asp Val Gly Asn Ala Leu Asn Gln Leu Ala Glu His Gln Arg Arg Leu
385                 390                 395                 400
Val Ala Leu Phe Gln Ser Ala Thr His Gly Ala Asn Ala Leu Glu Ile
                405                 410                 415
Ala Asn Glu Arg Tyr Arg Ala Gly Ala Gly Ser Tyr Leu Ala Val Leu
            420                 425                 430
Glu Asn Gln Arg Ala Leu Tyr Gln Ile Arg Glu Glu Leu Ala Gln Ala
        435                 440                 445
Glu Thr Ala Ser Phe Val Asn Val Ile Ala Leu Tyr Lys Ala Leu Gly
    450                 455                 460
Trp Gly Ser Gly Asp Leu Ala Pro Gly Ala Gly Gln Leu Ala Ala Gly
465                 470                 475                 480
Glu Thr Ala Gly Ala Asn Arg
                485

<210> SEQ ID NO 18
<211> LENGTH: 491
<212> TYPE: PRT
<213> ORGANISM: Pseudomonas aeruginosa

<400> SEQUENCE: 18

Met Lys Pro Tyr Leu Arg Ser Ser Leu Ser Ala Leu Ile Leu Leu Gly
1               5                   10                  15
Gly Cys Ala Ala Val Gly Pro Asp Tyr Ala Pro Pro Ser Ala Ser Ala
            20                  25                  30
Pro Ala Ser Phe Gly Ala Met Pro Ala Gly Ile Asp Gly Ser Gly Val
        35                  40                  45
Glu Ile Glu Trp Trp Arg Gly Phe Asp Glu Pro Ala Leu Glu Ser Leu
    50                  55                  60
Ile Gln Arg Ala Leu Ala Ala Asn Leu Asp Ile Ala Leu Ala Gly Ala
65                  70                  75                  80
Arg Leu Asp Glu Ala Lys Ala Leu Leu Arg Glu Asn Arg Glu Glu Phe
                85                  90                  95
```

-continued

Leu Pro Arg Gly Gly Pro Ala Phe Asp Tyr Gln Ala Arg Arg Gly
        100                 105                 110

Glu Val Glu Thr Pro Ala Gly Gln Gln Arg Asp Ile Glu Thr Tyr Arg
    115                 120                 125

Gly Ala Leu Asp Ala Ser Trp Glu Ile Asp Leu Phe Gly Arg Val Arg
130                 135                 140

Arg Ser Val Glu Ala Ala Glu Ala Gln Ala Gly Ser Arg Glu Ala Leu
145                 150                 155                 160

Leu Arg Asn Val Gln Ala Ser Val Ala Ala Thr Val Ala Met Ser Trp
                165                 170                 175

Phe Gln Leu Gln Gly Ile Glu Ala Glu Leu Ala Val Val His Asp Ile
            180                 185                 190

Ala Gly Asn Gln Arg Asp Ser Leu Glu Met Val Glu Arg Leu Val Ser
        195                 200                 205

Ala Gly Ser Ala His Glu Phe Asp Arg Leu Arg Ala Glu Ala Leu Leu
    210                 215                 220

His Asn Val Glu Ala Ala Val Pro Asp Leu Glu Arg Arg Arg Ala Ala
225                 230                 235                 240

Thr Arg Asn Ala Leu Ala Val Leu Leu Ala Glu Ala Pro Gln Ala Phe
                245                 250                 255

Ser Pro Pro Val Ala Arg Ala Ser Gly Glu Arg Leu Thr Leu Arg Thr
            260                 265                 270

Leu Gly Val Gly Asp Pro Ala Gly Leu Leu Ala Arg Arg Ala Asp Ile
        275                 280                 285

Ala Ala Ala Glu Arg Asn Leu Ala Ala Ala Thr Ala Arg Ile Gly Val
    290                 295                 300

Glu Thr Ala Gly Leu Tyr Pro Gln Val Glu Val Arg Gly Ser Ile Gly
305                 310                 315                 320

Leu Val Ala Gly Asn Leu Asp Ala Leu Asp Glu Ser Gly Thr Ser Phe
                325                 330                 335

Asn Val Leu Asn Pro Val Ile Arg Trp Ala Leu Leu Asp Arg Gly Arg
            340                 345                 350

Val Trp Ala Arg Ile Ala Ala Ser Glu Ala Arg Ala Gln Glu Ala Leu
        355                 360                 365

Ile Leu Tyr Asp Arg Thr Val Leu Arg Ala Leu Gln Glu Thr Asp Asp
    370                 375                 380

Ala Phe Asn Gly Tyr Gly Ala Ala Asp Arg Leu Arg Leu Arg Leu
385                 390                 395                 400

Leu Glu Ala Thr Ala Asn Arg Glu Ala Ala Arg Leu Ala Arg Glu Arg
                405                 410                 415

Phe Val Gln Gly Asp Gly Glu Tyr Leu Asp Val Leu Glu Ala Glu Arg
            420                 425                 430

Ser Asp Tyr Leu Ser Arg Arg Ala Leu Ser Ile Ala Arg Thr Glu Gln
        435                 440                 445

Arg Leu Ala Val Val Gly Ile Tyr Lys Ala Leu Gly Gly Gly Trp Glu
    450                 455                 460

Ala Cys Ala Gly Ala Arg Arg Cys Gly Val Ala Thr Asp Asp Thr Ser
465                 470                 475                 480

Pro Gly Val Ala Arg Gln Arg Asp Ser Arg Ser
                485                 490

<210> SEQ ID NO 19
<211> LENGTH: 779
<212> TYPE: PRT

<213> ORGANISM: Phage PS17

<400> SEQUENCE: 19

Met Ser Thr Asn Gln Tyr Gly Gly Phe Leu Thr Asp Lys Gly Ala Ala
1               5                   10                  15

Lys Gln Val Glu Ala Ala Ser Gly Gly Leu Arg Arg Asn Ile Thr His
            20                  25                  30

Met Leu Ile Gly Asp Ala Gly Ala Pro Gly Gln Thr Pro Asp Pro
        35                  40                  45

Val Pro Ser Pro Leu Gln Thr Lys Leu Val Arg Gln Arg Tyr Arg Val
    50                  55                  60

Lys Leu Asn Arg Leu Val Ala Ala Asp Asn Ser Pro Ser Val Leu Ile
65                  70                  75                  80

Ala Glu Ala Ile Leu Pro Gln Asp Val Gly Gly Trp Trp Met Arg Glu
                85                  90                  95

Leu Gly Leu Glu Asp Ser Asp Gly Asp Met Ile Ala Val Ala Asn Cys
            100                 105                 110

Ala Pro Ser Tyr Lys Pro Leu Val Asn Glu Gly Ser Gly Arg Thr Gln
        115                 120                 125

Thr Val Arg Leu His Ile Ala Phe Ser His Ala Glu Thr Val Asp Leu
    130                 135                 140

Leu Ile Asp Pro Asn Val Val Thr Ala Thr Val Ala Asp Leu Gln Asn
145                 150                 155                 160

Ala Leu Leu Glu Val Arg Ala Thr Asn Asp Ala Thr Gly Gln Met Thr
                165                 170                 175

Arg Gly Thr Asp Gly Lys Leu Ala Leu Pro Leu Ser Leu Ser Leu Thr
            180                 185                 190

Gly Ile Ala Ala Gly Thr Tyr Arg Ser Leu Thr Val Asp Ala Lys Gly
        195                 200                 205

Arg Ala Thr Ser Gly Ser Asn Pro Thr Thr Leu Gly Gly Tyr Gly Ile
    210                 215                 220

Thr Asp Ala Leu Ala Lys Ser Asp Ala Val Asp Val Pro Ala Pro Asn
225                 230                 235                 240

Lys Leu Leu Arg Leu Asn Ala Ala Ser Gln Leu Pro Ala Ser Ile Thr
                245                 250                 255

Gly Asn Ala Ala Thr Ala Thr Lys Leu Ala Val Pro Arg Met Leu Ser
            260                 265                 270

Phe Thr Gly Asp Ala Thr Gly Gly Ala Ser Phe Asp Gly Ser Ala Asn
        275                 280                 285

Ala Ala Val Ala Leu Thr Leu Ala Asn Ser Gly Val Thr Ala Gly Thr
    290                 295                 300

Tyr Ala Lys Val Thr Val Asn Gly Lys Gly Leu Val Thr Gly Gly Ala
305                 310                 315                 320

Gln Leu Thr Ala Ala Asp Ile Pro Ala Leu Asp Ala Gly Lys Val Val
                325                 330                 335

Ser Gly Val Leu Pro Ile Ala Arg Gly Gly Thr Gly Asn Ala Ile Gly
            340                 345                 350

Gln Ala Ala Thr Ala Val Lys Leu Ala Ser Pro Arg Thr Leu Ala Ile
        355                 360                 365

Ala Gly Asp Ala Thr Gly Ser Ala Ala Phe Asp Gly Ser Ala Asn Ala
    370                 375                 380

Ser Ile Ser Val Thr Leu Ala Asn Thr Gly Val Ala Val Gly Thr Tyr
385                 390                 395                 400

Thr Lys Val Arg Val Asn Ala Lys Gly Leu Val Thr Ser Ala Ala Ser

```
                    405                 410                 415
Leu Thr Ala Asp Asp Val Pro Trp Leu Asp Ala Ser Lys Val Thr Ser
                420                 425                 430

Gly Met Phe Ala Asp Ala Arg Leu Pro Trp Tyr Ala Gln Gly Leu Cys
            435                 440                 445

Thr Ser Ala Pro Asn Thr Thr Asp Pro Asn Thr Thr Asn Ile Pro Leu
        450                 455                 460

Ile Leu Thr Asn His Glu Asn Gly Pro Ile Pro Gly Thr Phe Phe Tyr
465                 470                 475                 480

Ile Gln Thr Met Met Tyr Asn Gln Arg Asn Gly Asn Ala Ala Gln Ile
                485                 490                 495

Ala Val Arg Tyr Ala Ala Asn Ala Glu Met Tyr Val Arg Tyr Met Tyr
            500                 505                 510

Asp Val Gly Asn Lys Arg Gly Val Trp Ser Ala Trp Lys Arg Cys Asp
        515                 520                 525

Val Gly Gly Ser Phe Ala Lys Glu Ala Asp Gly Glu Leu Gly Gly Gly
    530                 535                 540

Val Asn Leu Asp Thr Met Ile Ala Ser Gly Trp Trp His Gln Pro Phe
545                 550                 555                 560

Ser Ala Asn Ala Lys Asn Gly Thr Asn Tyr Pro Val Gly Glu Ala Gly
                565                 570                 575

Leu Leu Thr Val His Ala Pro Thr Ser Thr Met Ile Tyr Gln Thr Tyr
            580                 585                 590

Arg Gly Tyr Ala Ala Gly Gly Leu Tyr Trp Arg Cys Arg Tyr Asn Gly
        595                 600                 605

Thr Trp Ser Ala Trp Tyr Arg Ala Trp Asp Ser Gly Asn Phe Asn Pro
    610                 615                 620

Ala Asn Tyr Val Ala Arg Ser Glu Tyr Ser Trp Ala Ser Leu Pro Gly
625                 630                 635                 640

Lys Pro Ala Thr Phe Pro Pro Ser Gly His Asn His Asp Ala Thr Gln
                645                 650                 655

Ile Thr Ser Gly Ile Leu Pro Leu Ala Arg Gly Gly Leu Gly Ala Asn
            660                 665                 670

Asn Ala Val Thr Ala Arg Ser Asn Ile Gly Ala Gly Thr Ile Ala Thr
        675                 680                 685

Ala Ser Leu Gly Ser Ser Gly Trp Trp Arg Asp Asn Asp Thr Gly Tyr
    690                 695                 700

Ile Arg Gln Trp Gly Arg Val Thr Val Pro Gly Asp Gly Ser Ala Ala
705                 710                 715                 720

Ile Thr Phe Pro Ile Ala Phe Pro Ser Val Cys Leu Gly Gly Phe Ala
                725                 730                 735

Gly Gln Thr Ala Asn Phe His Pro Gly Thr Asp Ala Ser Thr Ser Phe
            740                 745                 750

Tyr Asn Gln Ser Thr Thr Gly Ala Thr Leu Glu Asn Gly Tyr Gln Phe
        755                 760                 765

Gln Ala Val Leu Leu Trp Glu Ala Phe Gly Arg
    770                 775

<210> SEQ ID NO 20
<211> LENGTH: 153
<212> TYPE: PRT
<213> ORGANISM: Phage PS17

<400> SEQUENCE: 20

Met Ser Ala Ser Asp Tyr Val Phe Ser Pro Ser Ala Arg Val Phe Tyr
```

```
                 1               5                  10                 15
Pro Val Ala Leu Arg Glu Val Tyr Glu Thr Gly Glu Gly Trp Pro Ala
                20                 25                 30

Asp Ala Val Pro Val Ser Asn Glu Arg Tyr Leu His Leu Leu Ala Gly
                35                 40                 45

Gln Glu Ala Gly Met Arg Ile Ala Asn Ala Ser Gly Gln Pro Val
                50                 55                 60

Leu Val Asp Pro Pro Leu Thr Glu Ala Glu Arg Arg Thr Lys Ala
65                  70                 75                 80

Arg Ala Trp Arg Asp Ala Gln Leu Ala Gln Thr Asp Gly Met Val Ala
                85                 90                 95

Arg His Arg Asp Glu Arg Asp Leu Gly Asn Asp Thr Thr Leu Gln Pro
                100                105                110

Glu Gln Phe Val Glu Val Met Asn Tyr Arg Ala Ala Leu Arg Asn Trp
                115                120                125

Pro Asp Asp Pro Ala Phe Pro Asp Pro Ala Ser Arg Pro Glu Pro Pro
                130                135                140

Ala Trp Leu Ala Glu Glu Gly Thr Asn
145                 150

<210> SEQ ID NO 21
<211> LENGTH: 178
<212> TYPE: PRT
<213> ORGANISM: Vibrio harveyi

<400> SEQUENCE: 21

Met Ala Gly Leu Lys Leu Gln Phe Thr Glu Ala Gly Leu Ala Glu Leu
1               5                   10                  15

Ile Ser Ala Lys Glu Gln Gly Ile Lys Gly Ala Ile Ser His Leu Ala
                20                  25                  30

Phe Gly Asp Met Ala Tyr Thr Pro Asn Lys Ser Gln Thr Arg Leu Gln
                35                  40                  45

Arg Glu Gln Glu Arg Val Glu Ile Ala Asp Tyr Gln Asp Gly Gly Leu
                50                  55                  60

Ser Leu Arg Met Ala Ala Val Phe Ser Gly Glu Lys Glu Tyr Ala Ile
65                  70                  75                  80

Arg Glu Ile Gly Val Phe Leu Ser Thr Gly Thr Leu Leu Gly Val Tyr
                85                  90                  95

Ser Gln Ser Gly Lys Thr Ile Gly Tyr Arg Thr Pro Ser Val Lys Val
                100                 105                 110

Met Gln Trp Leu Thr Leu Asn Ile Thr Ala Leu Pro Ser Asp Ser Val
                115                 120                 125

Thr Val Val Val Gly Thr Glu Asn Leu Asn Leu Ile Leu Asp Ala Glu
                130                 135                 140

Phe Met Glu Ser Ala Ala Ser Phe Met Arg Leu Gly Ala Ala Thr Ile
145                 150                 155                 160

Arg Gln Ala Leu Trp Asn Leu Gln Leu Ser Glu Lys Ile Arg Ala Leu
                165                 170                 175

Glu Ser

<210> SEQ ID NO 22
<211> LENGTH: 410
<212> TYPE: PRT
<213> ORGANISM: Vibrio harveyi
<220> FEATURE:
<221> NAME/KEY: MISC_FEATURE
<222> LOCATION: (18)..(18)
```

```
<223> OTHER INFORMATION: Other
<220> FEATURE:
<221> NAME/KEY: MISC_FEATURE
<222> LOCATION: (22)..(22)
<223> OTHER INFORMATION: Other
<220> FEATURE:
<221> NAME/KEY: MISC_FEATURE
<222> LOCATION: (340)..(340)
<223> OTHER INFORMATION: Other

<400> SEQUENCE: 22

Met Gly Thr Ile Thr Glu Gln Ile Glu Ser Leu Lys Thr Ala Ser Ala
1               5                  10                  15

Glu Xaa Thr Ala Ala Xaa Gln Ala Leu Ala Gln Glu Val Ser Gly Lys
            20                  25                  30

Met Ala Ala Ile Asp Lys Lys Thr Asn Asp Ser Ile Ala Lys Val Lys
        35                  40                  45

Ser Thr Tyr Asp Gln Lys Ala Asn Gly Leu Thr Ile Ala Thr Asp
 50                  55                  60

Gly Tyr Arg Lys Ala Val Glu His Asn Ser Gly Arg Asn Thr Val
65                  70                  75                  80

Ile Tyr Asp Ala Gln Gly Asn Pro Asn Ile Met Cys Val Ile Pro Arg
                85                  90                  95

Phe Asn Ile Glu Asp Leu Gly Leu Thr Glu Leu Asp Leu Gly Thr Gly
            100                 105                 110

Val His Pro Ala Phe Val Thr Asn Gly Ala Pro Arg Gly Glu Ile Leu
        115                 120                 125

Val Gly Lys Tyr Leu Ala Ser Ser Ala Ala Gly Gly Ser Ala Val Ile
130                 135                 140

Gly Gly Pro Gln Pro Arg Thr Ser Val Asn Tyr Asp Thr Ala Lys Gln
145                 150                 155                 160

Leu Cys Thr Gln Lys Gly Asp Asn Trp His Leu Met Ser Ile His Glu
                165                 170                 175

Trp Ala Ala Ile Ala Leu Trp Ser Leu Ala Asn Gly Thr Val Pro Arg
            180                 185                 190

Gly Asn Thr Asn Tyr Gly Arg Ser His Glu Ala Lys Trp Glu Thr Ala
        195                 200                 205

Arg Arg Ala Asp Asn Gly Leu Pro Gly Asp Thr Ser Gly Thr Gly Arg
210                 215                 220

Thr Asp Thr Gly Lys Gly Pro Ala Thr Trp Asn His Asp His Thr Glu
225                 230                 235                 240

Phe Gly Val Cys Asp Leu Val Gly Asn Val Trp Glu Trp Ile Asp Gln
                245                 250                 255

Met Lys Leu Asp Asp Gly Gln Ile Leu Thr Thr Leu Asp Asn Asn Pro
            260                 265                 270

Gly Val Ala Glu Ala Asn Trp His Arg His Pro Ala Tyr Phe Asp Ser
        275                 280                 285

Thr Ser Asp Asn Gln Ser Gly Ala Gly Asn Asn Gly Ser Pro Val Leu
290                 295                 300

Ser Asn Ser Val Thr Lys Arg Asn Gly Pro Ala Asp Asp Asp Ser His
305                 310                 315                 320

Asp Tyr Pro Tyr Met His Asn Pro His Phe Ala Ala Ile Thr Lys Ser
                325                 330                 335

Ala Gly Tyr Xaa Pro Asn Glu Leu Leu Arg Arg Leu Leu Ile Glu Ser
            340                 345                 350

Ala Thr Ala Thr Thr Val Gly Gly Gly Leu Trp Cys Arg Asn Tyr Gly
        355                 360                 365
```

```
Asp Arg Phe Pro Leu Arg Gly Tyr Trp Asn Asn Gly Ser Ser Ala
    370                 375                 380

Gly Leu Gly Ala Leu Tyr Leu Ser Tyr Ala Arg Ser Asn Ser Asn Ser
385                 390                 395                 400

Ser Ile Gly Phe Arg Pro Ala Phe Phe Val
            405                 410

<210> SEQ ID NO 23
<211> LENGTH: 91
<212> TYPE: PRT
<213> ORGANISM: Vibrio harveyi

<400> SEQUENCE: 23

Met Phe Ser Tyr Ile Phe Gln Gly Arg Thr His Thr Asp Thr Thr Arg
1               5                   10                  15

Ser Tyr Met Asn Ser Leu Gly Met Thr Gln Glu Gln Val Asp Ser Val
            20                  25                  30

Leu Gln Gln Lys Asp Phe Glu Ala Gln Asn Leu Val Lys Arg Gln
        35                  40                  45

Glu Ala Tyr Arg Leu Glu Ser Asp Pro Leu Phe Met Glu Trp Gln Tyr
50                  55                  60

Asp Asn Thr Pro Glu Ser Glu Gln Ala Trp Arg Asp Lys Val Ala Glu
65                  70                  75                  80

Ile Lys Ala Arg Tyr Pro Leu Pro Ser Glu Ser
            85                  90

<210> SEQ ID NO 24
<211> LENGTH: 381
<212> TYPE: PRT
<213> ORGANISM: Bordetella phage BPP-1

<400> SEQUENCE: 24

Met Ser Thr Ala Val Gln Phe Arg Gly Gly Thr Thr Ala Gln His Ala
1               5                   10                  15

Thr Phe Thr Gly Ala Ala Arg Glu Ile Thr Val Asp Thr Asp Lys Asn
            20                  25                  30

Thr Val Val His Asp Gly Ala Thr Ala Gly Gly Phe Pro Leu Ala
        35                  40                  45

Arg His Asp Leu Val Lys Thr Ala Phe Ile Lys Ala Asp Lys Ser Ala
50                  55                  60

Val Ala Phe Thr Arg Thr Gly Asn Ala Thr Ala Ser Ile Lys Ala Gly
65                  70                  75                  80

Thr Ile Val Glu Val Asn Gly Lys Leu Val Gln Phe Thr Ala Asp Thr
            85                  90                  95

Ala Ile Thr Met Pro Ala Leu Thr Ala Gly Thr Asp Tyr Ala Ile Tyr
            100                 105                 110

Val Cys Asp Asp Gly Thr Val Arg Ala Asp Ser Asn Phe Ser Ala Pro
        115                 120                 125

Thr Gly Tyr Thr Ser Thr Thr Ala Arg Lys Val Gly Gly Phe His Tyr
    130                 135                 140

Ala Pro Gly Ser Asn Ala Ala Ala Gln Ala Gly Gly Asn Thr Thr Ala
145                 150                 155                 160

Gln Ile Asn Glu Tyr Ser Leu Trp Asp Ile Lys Phe Arg Pro Ala Ala
                165                 170                 175

Leu Asp Pro Arg Gly Met Thr Leu Val Ala Gly Ala Phe Trp Ala Asp
            180                 185                 190
```

```
Ile Tyr Leu Leu Gly Val Asn His Leu Thr Asp Gly Thr Ser Lys Tyr
        195                 200                 205

Asn Val Thr Ile Ala Asp Gly Ser Ala Ser Pro Lys Lys Ser Thr Lys
    210                 215                 220

Phe Gly Asp Gly Ser Ala Ala Tyr Ser Asp Gly Ala Trp Tyr Asn
225                 230                 235                 240

Phe Ala Glu Val Met Thr His His Gly Lys Arg Leu Pro Asn Tyr Asn
                245                 250                 255

Glu Phe Gln Ala Leu Ala Phe Gly Thr Thr Glu Ala Thr Ser Ser Gly
                260                 265                 270

Gly Thr Asp Val Pro Thr Thr Gly Val Asn Gly Thr Gly Ala Thr Ser
            275                 280                 285

Ala Trp Asn Ile Phe Thr Ser Lys Trp Gly Val Val Gln Ala Ser Gly
        290                 295                 300

Cys Leu Trp Thr Trp Gly Asn Glu Phe Gly Gly Val Asn Gly Ala Ser
305                 310                 315                 320

Glu Tyr Thr Ala Asn Thr Gly Gly Arg Gly Ser Val Tyr Ala Gln Pro
                325                 330                 335

Ala Ala Ala Leu Phe Gly Ala Trp Asn Gly Thr Ser Leu Ser Gly
                340                 345                 350

Ser Arg Ala Ala Leu Trp Tyr Ser Gly Pro Ser Phe Ser Phe Ala Phe
            355                 360                 365

Phe Gly Ala Arg Gly Val Cys Asp His Leu Ile Leu Glu
            370                 375                 380

<210> SEQ ID NO 25
<211> LENGTH: 669
<212> TYPE: PRT
<213> ORGANISM: Bacteriophage P2

<400> SEQUENCE: 25

Met Ser Ile Lys Phe Arg Thr Val Ile Thr Thr Ala Gly Ala Ala Lys
1               5                   10                  15

Leu Ala Ala Ala Thr Ala Pro Gly Arg Arg Lys Val Gly Ile Thr Thr
                20                  25                  30

Met Ala Val Gly Asp Gly Gly Lys Leu Pro Val Pro Asp Ala Gly
            35                  40                  45

Gln Thr Gly Leu Ile His Glu Val Trp Arg His Ala Leu Asn Lys Ile
    50                  55                  60

Ser Gln Asp Lys Arg Asn Ser Asn Tyr Ile Ile Ala Glu Leu Val Ile
65                  70                  75                  80

Pro Pro Glu Val Gly Gly Phe Trp Met Arg Glu Leu Gly Leu Tyr Asp
                85                  90                  95

Asp Ala Gly Thr Leu Ile Ala Val Ala Asn Met Ala Glu Ser Tyr Lys
                100                 105                 110

Pro Ala Leu Ala Glu Gly Ser Gly Arg Trp Gln Thr Cys Arg Met Val
            115                 120                 125

Ile Ile Val Ser Ser Val Ala Ser Val Glu Leu Thr Ile Asp Thr Thr
130                 135                 140

Thr Val Met Ala Thr Gln Asp Tyr Val Asp Lys Ile Ala Glu His
145                 150                 155                 160

Glu Gln Ser Arg Arg His Pro Asp Ala Ser Leu Thr Ala Lys Gly Phe
                165                 170                 175

Thr Gln Leu Ser Ser Ala Thr Asn Ser Thr Ser Glu Thr Leu Ala Ala
            180                 185                 190
```

```
Thr Pro Lys Ala Val Lys Ala Ala Tyr Asp Leu Ala Asn Gly Lys Tyr
        195                 200                 205
Thr Ala Gln Asp Ala Thr Thr Ala Arg Lys Gly Leu Val Gln Leu Ser
        210                 215                 220
Ser Ala Thr Asn Ser Thr Ser Glu Thr Leu Ala Ala Thr Pro Lys Ala
225                 230                 235                 240
Val Lys Thr Val Met Asp Glu Thr Asn Lys Lys Ala Pro Leu Asn Ser
                245                 250                 255
Pro Ala Leu Thr Gly Thr Pro Thr Thr Pro Thr Ala Arg Gln Gly Thr
            260                 265                 270
Asn Asn Thr Gln Ile Ala Asn Thr Ala Phe Val Met Ala Ala Ile Ala
        275                 280                 285
Ala Leu Val Asp Ser Ser Pro Asp Ala Leu Asn Thr Leu Asn Glu Leu
        290                 295                 300
Ala Ala Ala Leu Gly Asn Asp Pro Asn Phe Ala Thr Thr Met Thr Asn
305                 310                 315                 320
Ala Leu Ala Gly Lys Gln Pro Lys Asp Ala Thr Leu Thr Ala Leu Ala
                325                 330                 335
Gly Leu Ala Thr Ala Ala Asp Arg Phe Pro Tyr Phe Thr Gly Asn Asp
            340                 345                 350
Val Ala Ser Leu Ala Thr Leu Thr Lys Val Gly Arg Asp Ile Leu Ala
        355                 360                 365
Lys Ser Thr Val Ala Ala Val Ile Glu Tyr Leu Gly Leu Gln Glu Thr
        370                 375                 380
Val Asn Arg Ala Gly Asn Ala Val Gln Lys Asn Gly Asp Thr Leu Ser
385                 390                 395                 400
Gly Gly Leu Thr Phe Glu Asn Asp Ser Ile Leu Ala Trp Ile Arg Asn
                405                 410                 415
Thr Asp Trp Ala Lys Ile Gly Phe Lys Asn Asp Ala Asp Gly Asp Thr
            420                 425                 430
Asp Ser Tyr Met Trp Phe Glu Thr Gly Asp Asn Gly Asn Glu Tyr Phe
        435                 440                 445
Lys Trp Arg Ser Arg Gln Ser Thr Thr Thr Lys Asp Leu Met Thr Leu
        450                 455                 460
Lys Trp Asp Ala Leu Asn Ile Leu Val Asn Ala Val Ile Asn Gly Cys
465                 470                 475                 480
Phe Gly Val Gly Thr Thr Asn Ala Leu Gly Gly Ser Ser Ile Val Leu
                485                 490                 495
Gly Asp Asn Asp Thr Gly Phe Lys Gln Asn Gly Asp Gly Ile Leu Asp
            500                 505                 510
Val Tyr Ala Asn Ser Gln Arg Val Phe Arg Phe Gln Asn Gly Val Ala
        515                 520                 525
Ile Ala Phe Lys Asn Ile Gln Ala Gly Asp Ser Lys Lys Phe Ser Leu
        530                 535                 540
Ser Ser Ser Asn Thr Ser Thr Lys Asn Ile Thr Phe Asn Leu Trp Gly
545                 550                 555                 560
Ala Ser Thr Arg Pro Val Val Ala Glu Leu Gly Asp Glu Ala Gly Trp
                565                 570                 575
His Phe Tyr Ser Gln Arg Asn Thr Asp Asn Ser Val Ile Phe Ala Val
            580                 585                 590
Asn Gly Gln Met Gln Pro Ser Asn Trp Gly Asn Phe Asp Ser Arg Tyr
        595                 600                 605
Val Lys Asp Val Arg Leu Gly Thr Arg Val Val Gln Leu Met Ala Arg
610                 615                 620
```

```
Gly Gly Arg Tyr Glu Lys Ala Gly His Thr Ile Thr Gly Leu Arg Ile
625                 630                 635                 640

Ile Gly Glu Val Asp Gly Asp Glu Ala Ile Phe Arg Pro Ile Gln
            645                 650                 655

Lys Tyr Ile Asn Gly Thr Trp Tyr Asn Val Ala Gln Val
            660                 665
```

<210> SEQ ID NO 26
<211> LENGTH: 175
<212> TYPE: PRT
<213> ORGANISM: Bacteriophage P2

<400> SEQUENCE: 26

```
Met Gln His Leu Lys Asn Ile Lys Ser Gly Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Glu Val Lys Asn Phe Gln Pro Asp Thr
        35                  40                  45

Ile Lys Ile Val Tyr Asp Glu Asn Asn Ile Ile Val Ala Ile Thr Arg
50                  55                  60

Asp Ala Ser Thr Leu Asn Pro Glu Gly Phe Ser Val Val Glu Val Pro
65                  70                  75                  80

Asp Ile Thr Ser Asn Arg Arg Ala Asp Ser Gly Lys Trp Met Phe
                85                  90                  95

Lys Asp Gly Ala Val Val Lys Arg Ile Tyr Thr Ala Glu Gln Gln
            100                 105                 110

Gln Gln Ala Glu Ser Gln Lys Ala Ala Leu Leu Ser Glu Ala Glu Asn
        115                 120                 125

Val Ile Gln Pro Leu Glu Arg Ala Val Arg Leu Asn Met Ala Thr Asp
130                 135                 140

Glu Glu Arg Ala Arg Leu Glu Ser Trp Glu Arg Tyr Ser Val Leu Val
145                 150                 155                 160

Ser Arg Val Asp Pro Ala Asn Pro Glu Trp Pro Glu Met Pro Gln
                165                 170                 175
```

<210> SEQ ID NO 27
<211> LENGTH: 676
<212> TYPE: PRT
<213> ORGANISM: Podoviridae bacteriophage

<400> SEQUENCE: 27

```
Met Ala Thr Asn Thr Pro Lys Tyr Gly Gly Leu Leu Thr Asp Ile Gly
1               5                   10                  15

Ala Ala Ala Leu Ala Thr Ala Ser Ala Ala Gly Lys Lys Trp Gln Pro
            20                  25                  30

Thr His Met Leu Ile Gly Asp Ala Gly Ala Pro Gly Asp Thr Pro
        35                  40                  45

Asp Pro Leu Pro Ser Ala Ala Gln Lys Ser Leu Ile Asn Gln Arg His
50                  55                  60

Arg Ala Gln Leu Asn Arg Leu Phe Val Ser Asp Lys Asn Ala Asn Thr
65                  70                  75                  80

Leu Val Ala Glu Val Val Leu Pro Val Glu Val Gly Phe Trp Ile
                85                  90                  95

Arg Glu Ile Gly Leu Gln Asp Ala Asp Gly Lys Phe Val Ala Val Ser
            100                 105                 110
```

```
Asn Cys Pro Pro Ser Tyr Lys Ala Ala Met Glu Ser Gly Ser Ala Arg
    115                 120                 125

Thr Gln Thr Ile Arg Val Asn Ile Ala Leu Ser Gly Leu Glu Asn Val
130                 135                 140

Gln Leu Leu Ile Asp Asn Gly Ile Ile Tyr Ala Thr Gln Asp Trp Val
145                 150                 155                 160

Lys Glu Lys Leu Ala Glu His Glu Gln Ser Arg Arg His Pro Asp Ala
                165                 170                 175

Ser Leu Thr Ala Lys Gly Phe Thr Gln Leu Ser Ser Ala Thr Asn Ser
                180                 185                 190

Thr Ser Glu Thr Leu Ala Ala Thr Pro Lys Ala Val Lys Ala Ala Tyr
            195                 200                 205

Asp Leu Ala Asn Gly Lys Tyr Thr Ala Gln Asp Ala Thr Thr Ala Arg
210                 215                 220

Lys Gly Leu Val Gln Leu Ser Ser Ala Thr Asn Ser Thr Ser Glu Thr
225                 230                 235                 240

Leu Ala Ala Thr Pro Lys Ala Val Lys Thr Val Met Asp Glu Thr Asn
                245                 250                 255

Lys Lys Ala Pro Leu Asn Ser Pro Ala Leu Thr Gly Thr Pro Thr Thr
            260                 265                 270

Pro Thr Ala Arg Gln Gly Thr Asn Asn Thr Gln Ile Ala Asn Thr Ala
            275                 280                 285

Phe Val Met Ala Ala Ile Ala Ala Leu Val Asp Ser Ser Pro Asp Ala
            290                 295                 300

Leu Asn Thr Leu Asn Glu Leu Ala Ala Leu Gly Asn Asp Pro Asn
305                 310                 315                 320

Phe Ala Thr Thr Met Thr Asn Ala Leu Ala Gly Lys Gln Pro Lys Asp
                325                 330                 335

Ala Thr Leu Thr Ala Leu Ala Gly Leu Ala Thr Ala Ala Asp Arg Phe
            340                 345                 350

Pro Tyr Phe Thr Gly Asn Asp Val Ala Ser Leu Ala Thr Leu Thr Lys
            355                 360                 365

Val Gly Arg Asp Ile Leu Ala Lys Ser Thr Val Ala Ala Val Ile Glu
370                 375                 380

Tyr Leu Gly Leu Gln Glu Thr Val Asn Arg Ala Gly Asn Ala Val Gln
385                 390                 395                 400

Lys Asn Gly Asp Thr Leu Ser Gly Gly Leu Thr Phe Glu Asn Asp Ser
                405                 410                 415

Ile Leu Ala Trp Ile Arg Asn Thr Asp Trp Ala Lys Ile Gly Phe Lys
                420                 425                 430

Asn Asp Ala Asp Gly Asp Thr Asp Ser Tyr Met Trp Phe Glu Thr Gly
            435                 440                 445

Asp Asn Gly Asn Glu Tyr Phe Lys Trp Arg Ser Arg Gln Ser Thr Thr
450                 455                 460

Thr Lys Asp Leu Met Thr Leu Lys Trp Asp Ala Leu Asn Ile Leu Val
465                 470                 475                 480

Asn Ala Val Ile Asn Gly Cys Phe Gly Val Gly Thr Thr Asn Ala Leu
                485                 490                 495

Gly Gly Ser Ser Ile Val Leu Gly Asp Asn Asp Thr Gly Phe Lys Gln
            500                 505                 510

Asn Gly Asp Gly Ile Leu Asp Val Tyr Ala Asn Ser Gln Arg Val Phe
            515                 520                 525

Arg Phe Gln Asn Gly Val Ala Ile Ala Phe Lys Asn Ile Gln Ala Gly
530                 535                 540
```

```
Asp Ser Lys Lys Phe Ser Leu Ser Ser Asn Thr Ser Thr Lys Asn
545                 550                 555                 560

Ile Thr Phe Asn Leu Trp Gly Ala Ser Thr Arg Pro Val Val Ala Glu
                565                 570                 575

Leu Gly Asp Glu Ala Gly Trp His Phe Tyr Ser Gln Arg Asn Thr Asp
            580                 585                 590

Asn Ser Val Ile Phe Ala Val Asn Gly Gln Met Gln Pro Ser Asn Trp
        595                 600                 605

Gly Asn Phe Asp Ser Arg Tyr Val Lys Asp Val Arg Leu Gly Thr Arg
    610                 615                 620

Val Val Gln Leu Met Ala Arg Gly Gly Arg Tyr Glu Lys Ala Gly His
625                 630                 635                 640

Thr Ile Thr Gly Leu Arg Ile Ile Gly Glu Val Asp Gly Asp Glu
                645                 650                 655

Ala Ile Phe Arg Pro Ile Gln Lys Tyr Ile Asn Gly Thr Trp Tyr Asn
                660                 665                 670

Val Ala Gln Val
        675

<210> SEQ ID NO 28
<211> LENGTH: 913
<212> TYPE: PRT
<213> ORGANISM: Bacteriophage L-413c

<400> SEQUENCE: 28

Met Ser Thr Lys Phe Lys Thr Val Ile Thr Thr Ala Gly Ala Ala Lys
1               5                   10                  15

Leu Ala Ala Ala Thr Val Pro Gly Gly Lys Lys Val Asn Leu Ser Ala
                20                  25                  30

Met Ala Val Gly Asp Gly Asn Gly Lys Leu Pro Val Pro Asp Ala Gly
            35                  40                  45

Gln Thr Lys Leu Val His Glu Val Trp Arg His Ala Leu Asn Lys Val
    50                  55                  60

Ser Val Asp Asn Lys Asn Lys Asn Tyr Ile Val Ala Glu Leu Val Val
65                  70                  75                  80

Pro Pro Glu Val Gly Gly Phe Trp Met Arg Glu Leu Gly Leu Tyr Asp
                85                  90                  95

Asp Ala Gly Thr Leu Ile Ala Val Ser Asn Met Ala Glu Ser Tyr Lys
            100                 105                 110

Pro Glu Leu Ala Glu Gly Ser Gly Arg Ala Gln Thr Cys Arg Met Val
        115                 120                 125

Ile Ile Leu Ser Asn Val Ala Ser Val Glu Leu Ser Ile Asp Ala Ser
    130                 135                 140

Thr Val Met Ala Thr Gln Asp Tyr Val Asp Asp Lys Ile Ala Glu His
145                 150                 155                 160

Glu Gln Ser Arg Arg His Pro Asp Ala Thr Leu Thr Glu Lys Gly Phe
                165                 170                 175

Thr Gln Leu Ser Ser Ala Thr Asn Ser Thr Ser Glu Lys Leu Ala Ala
            180                 185                 190

Thr Pro Lys Ala Val Lys Ala Ala Asn Asp Asn Ala Asn Ser Arg Leu
        195                 200                 205

Ala Lys Asn Gln Asn Gly Ala Asp Ile Gln Asp Lys Ser Ala Phe Leu
    210                 215                 220

Asp Asn Ile Gly Val Thr Ser Leu Thr Phe Met Lys His Asn Gly Met
225                 230                 235                 240
```

```
Ile Pro Thr Thr Asp Asn Leu Asp Ser Tyr Gly Pro Glu Glu Lys Tyr
            245                 250                 255

Leu Gly Thr Trp Ser Cys Pro Ser Gln Ser Thr Ala Lys Pro Glu Ser
            260                 265                 270

Gly Tyr Pro Glu Asp Lys Gly Asn Gly Val Leu Glu Val Phe Asn Ala
            275                 280                 285

Gly Arg Phe His Cys Thr Gln Arg Tyr Thr Arg Thr Gly Asn Ile
290                 295                 300

Tyr Ile Arg Met Leu Asp Ala Glu Trp Asn Pro Ala Ser Pro Thr Trp
305                 310                 315                 320

Ser Ala Trp Arg Val Ile Thr Ser Gly Thr Arg Pro Leu Ser Thr Ser
                325                 330                 335

Ile Asp Leu Asn Ser Leu Gly Gly Ala Glu His Leu Gly Ile Trp Arg
            340                 345                 350

Asn Ser Ser Thr Ser Ile Ala Ser Phe Glu Arg His Phe Pro Glu Asp
            355                 360                 365

Gly Ser Phe Gly Gln Gly Ile Leu Glu Val Phe Glu Gly Gly Leu Tyr
        370                 375                 380

Gly Arg Met Gln Arg Tyr Thr Thr Arg Ser Gly Thr Met Tyr Ile Arg
385                 390                 395                 400

Gly Leu Thr Ala Ser Trp Asp Ala Glu Asn Pro Gln Trp Glu Asp Trp
                405                 410                 415

Ile Ala Val Gly Tyr Gln Ser Thr Gly Trp Thr Tyr Ser Gly Asp Leu
            420                 425                 430

Asp Asp Leu Leu Lys Pro Gly Ile Tyr Ser Val Thr Lys Gln Ala Thr
            435                 440                 445

Asn Ala Pro Val Thr Asp Ser Lys Asp Leu Ala Val Gly Ser Ile Val
    450                 455                 460

Glu Val Lys Lys Arg Cys Asp Ile Glu Ser Tyr Ile Gln Thr Tyr Thr
465                 470                 475                 480

Thr Val Ser Ala Thr Asp Ala Tyr Lys Asn Arg Thr Phe Gln Arg Thr
                485                 490                 495

Arg Ala Ser Gly Glu Ala Asp Trp Gly Glu Trp Ala Glu Val Tyr Asn
            500                 505                 510

Ser Lys Ser Leu Leu Thr Lys Leu Gly Val Gly Val Thr Asp Arg
    515                 520                 525

Leu Ser Ser Leu Asp Trp Gln Thr Tyr Asp Phe Val Pro Gly Ser Met
    530                 535                 540

Ile Thr Val Arg Leu Ser Asp Met Thr Asn Ile Pro Asp Gly Met Glu
545                 550                 555                 560

Trp Gly Val Ile Asp Thr Asn Leu Ile Asn Ile Thr Val Gly Pro Ser
                565                 570                 575

Glu Gly Gly Gly Val Ala Arg Ser Met Gln Val Trp Arg Ser Thr Ser
            580                 585                 590

Asn Lys Thr Asn Tyr Arg Phe Phe Thr Val Arg Leu Tyr Gly Asn Pro
        595                 600                 605

Gly Glu Arg Ser Phe Asn Ile Arg Arg Leu Pro Ile Ile Asp Glu Ala
            610                 615                 620

Gln Thr Trp Glu Ala Lys Gln Thr Phe Ser Ala Gly Leu Ser Gly Glu
625                 630                 635                 640

Leu Ser Gly Asn Ala Ala Thr Ala Thr Lys Leu Lys Thr Ala Arg Lys
                645                 650                 655

Ile Asn Asn Val Ser Phe Asp Gly Thr Ser Asp Ile Asn Leu Thr Pro
```

```
                    660             665             670
Lys Asn Ile Gly Ala Phe Ala Ser Gly Lys Thr Gly Asp Thr Val Ala
            675                 680                 685

Asn Asp Lys Ala Val Gly Trp Asn Trp Ser Ser Gly Ala Tyr Asn Ala
690                 695                 700

Thr Thr Gly Gly Ala Ser Thr Leu Ile Leu His Phe Asn Ile Gly Glu
705                 710                 715                 720

Gly Ser Cys Pro Ala Ala Gln Phe Arg Val Asn Tyr Lys Asn Gly Gly
                725                 730                 735

Ile Phe Tyr Arg Ser Ala Arg Asp Gly Tyr Gly Phe Glu Ala Asp Trp
            740                 745                 750

Ser Glu Phe Tyr Thr Thr Thr Arg Lys Pro Thr Ala Gly Asp Val Gly
            755                 760                 765

Ala Leu Ser Leu Ser Gly Gly Gln Leu Asn Gly Ala Leu Gly Ile Gly
            770                 775                 780

Thr Ser Ser Asp Leu Gly Gly Asn Ser Ile Val Leu Gly Asp Asn Asp
785                 790                 795                 800

Thr Gly Phe Lys Gln Asn Gly Asp Gly Asn Leu Asp Val Tyr Ala Asn
                805                 810                 815

Ser Val His Val Met Arg Phe Val Ser Gly Ser Ile Gln Ser Asn Lys
                820                 825                 830

Thr Ile Asn Ile Thr Gly Arg Val Asn Pro Ser Asp Tyr Gly Asn Phe
                835                 840                 845

Asp Ser Arg Tyr Val Arg Asp Val Arg Leu Gly Thr Arg Val Val Gln
850                 855                 860

Thr Met Gln Lys Gly Val Met Tyr Glu Lys Ser Gly His Val Ile Thr
865                 870                 875                 880

Gly Leu Gly Ile Val Gly Glu Val Asp Gly Asp Pro Ala Val Phe
                885                 890                 895

Arg Pro Ile Gln Lys Tyr Ile Asn Gly Thr Trp Tyr Asn Val Ala Gln
                900                 905                 910

Val

<210> SEQ ID NO 29
<211> LENGTH: 175
<212> TYPE: PRT
<213> ORGANISM: Bacteriophage L-413c

<400> SEQUENCE: 29

Met Gln His Leu Lys Asn Ile Lys Ser Gly Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Glu Val Ser Asn Phe Gln Glu Asp Thr
        35                  40                  45

Ile Lys Ile Val Tyr Asp Glu Asn Asn Ile Ile Val Gly Ile Thr Arg
    50                  55                  60

Asp Ala Ser Thr Phe Asn Pro Glu Gly Phe Ser Val Val Glu Val Pro
65                  70                  75                  80

Asp Ile Thr Ala Asn Arg Arg Ala Asp Ser Gly Lys Trp Met Phe
                85                  90                  95

Lys Asp Gly Ala Val Ile Lys Arg Ile Tyr Thr Ala Asp Glu Gln Gln
                100                 105                 110

Gln Gln Ala Glu Ser Gln Lys Ala Ala Leu Leu Ser Glu Ala Glu Ser
            115                 120                 125
```

-continued

```
Val Ile Gln Pro Leu Glu Arg Ala Val Arg Leu Asn Met Ala Thr Asp
    130                 135                 140

Glu Glu Arg Ser Arg Leu Glu Ala Trp Glu Arg Tyr Ser Val Leu Val
145                 150                 155                 160

Ser Arg Val Asp Pro Ala Asn Pro Glu Trp Pro Glu Met Pro Gln
                165                 170                 175

<210> SEQ ID NO 30
<211> LENGTH: 920
<212> TYPE: PRT
<213> ORGANISM: Artificial Sequence
<220> FEATURE:
<223> OTHER INFORMATION: Synthetic construct - modified hmw
      bacteriocin - R2 - L413c fusion protein

<400> SEQUENCE: 30

Met Ala Thr Asn Thr Pro Lys Tyr Gly Gly Leu Leu Thr Asp Ile Gly
1               5                   10                  15

Ala Ala Ala Leu Ala Thr Ala Ser Ala Ala Gly Lys Lys Trp Gln Pro
                20                  25                  30

Thr His Met Leu Ile Gly Asp Ala Gly Ala Pro Gly Asp Thr Pro
            35                  40                  45

Asp Pro Leu Pro Ser Ala Ala Gln Lys Ser Leu Ile Asn Gln Arg His
    50                  55                  60

Arg Ala Gln Leu Asn Arg Leu Phe Val Ser Asp Lys Asn Ala Asn Thr
65                  70                  75                  80

Leu Val Ala Glu Val Leu Pro Val Glu Val Gly Gly Phe Trp Ile
                85                  90                  95

Arg Glu Ile Gly Leu Gln Asp Ala Asp Gly Lys Phe Val Ala Val Ser
                100                 105                 110

Asn Cys Pro Pro Ser Tyr Lys Ala Ala Met Glu Ser Gly Ser Ala Arg
            115                 120                 125

Thr Gln Thr Ile Arg Val Asn Ile Ala Leu Ser Gly Leu Glu Asn Val
    130                 135                 140

Gln Leu Leu Ile Asp Asn Gly Ile Ile Tyr Ala Thr Gln Asp Trp Val
145                 150                 155                 160

Lys Glu Lys Val Ala Glu His Glu Gln Ser Arg Arg His Pro Asp Ala
                165                 170                 175

Thr Leu Thr Glu Lys Gly Phe Thr Gln Leu Ser Ser Ala Thr Asn Ser
            180                 185                 190

Thr Ser Glu Lys Leu Ala Ala Thr Pro Lys Ala Val Lys Ala Ala Asn
    195                 200                 205

Asp Asn Ala Asn Ser Arg Leu Ala Lys Asn Gln Asn Gly Ala Asp Ile
    210                 215                 220

Gln Asp Lys Ser Ala Phe Leu Asp Asn Ile Gly Val Thr Ser Leu Thr
225                 230                 235                 240

Phe Met Lys His Asn Gly Met Ile Pro Thr Thr Asp Asn Leu Asp Ser
                245                 250                 255

Tyr Gly Pro Glu Glu Lys Tyr Leu Gly Thr Trp Ser Cys Pro Ser Gln
            260                 265                 270

Ser Thr Ala Lys Pro Glu Ser Gly Tyr Pro Glu Asp Lys Gly Asn Gly
    275                 280                 285

Val Leu Glu Val Phe Asn Ala Gly Arg Phe His Cys Thr Gln Arg Tyr
    290                 295                 300

Thr Thr Arg Thr Gly Asn Ile Tyr Ile Arg Met Leu Asp Ala Glu Trp
305                 310                 315                 320
```

```
Asn Pro Ala Ser Pro Thr Trp Ser Ala Trp Arg Val Ile Thr Ser Gly
            325                 330                 335

Thr Arg Pro Leu Ser Thr Ser Ile Asp Leu Asn Ser Leu Gly Gly Ala
            340                 345                 350

Glu His Leu Gly Ile Trp Arg Asn Ser Ser Thr Ser Ile Ala Ser Phe
            355                 360                 365

Glu Arg His Phe Pro Glu Asp Gly Ser Phe Gln Gly Ile Leu Glu
            370                 375                 380

Val Phe Glu Gly Gly Leu Tyr Gly Arg Met Gln Arg Tyr Thr Thr Arg
385                 390                 395                 400

Ser Gly Thr Met Tyr Ile Arg Gly Leu Thr Ala Ser Trp Asp Ala Glu
                405                 410                 415

Asn Pro Gln Trp Glu Asp Trp Ile Ala Val Gly Tyr Gln Ser Thr Gly
            420                 425                 430

Trp Thr Tyr Ser Gly Asp Leu Asp Asp Leu Leu Lys Pro Gly Ile Tyr
            435                 440                 445

Ser Val Thr Lys Gln Ala Thr Asn Ala Pro Val Thr Asp Ser Lys Asp
            450                 455                 460

Leu Ala Val Gly Ser Ile Val Glu Val Lys Lys Arg Cys Asp Ile Glu
465                 470                 475                 480

Ser Tyr Ile Gln Thr Tyr Thr Thr Val Ser Ala Thr Asp Ala Tyr Lys
                485                 490                 495

Asn Arg Thr Phe Gln Arg Thr Arg Ala Ser Gly Glu Ala Asp Trp Gly
            500                 505                 510

Glu Trp Ala Glu Val Tyr Asn Ser Lys Ser Leu Leu Thr Lys Leu Gly
            515                 520                 525

Val Gly Gly Val Thr Asp Arg Leu Ser Ser Leu Asp Trp Gln Thr Tyr
            530                 535                 540

Asp Phe Val Pro Gly Ser Met Ile Thr Val Arg Leu Ser Asp Met Thr
545                 550                 555                 560

Asn Ile Pro Asp Gly Met Glu Trp Gly Val Ile Asp Thr Asn Leu Ile
            565                 570                 575

Asn Ile Thr Val Gly Pro Ser Glu Gly Gly Val Ala Arg Ser Met
            580                 585                 590

Gln Val Trp Arg Ser Thr Ser Asn Lys Thr Asn Tyr Arg Phe Phe Thr
            595                 600                 605

Val Arg Leu Tyr Gly Asn Pro Gly Glu Arg Ser Phe Asn Ile Arg Arg
610                 615                 620

Leu Pro Ile Ile Asp Glu Ala Gln Thr Trp Glu Ala Lys Gln Thr Phe
625                 630                 635                 640

Ser Ala Gly Leu Ser Gly Glu Leu Ser Gly Asn Ala Ala Thr Ala Thr
                645                 650                 655

Lys Leu Lys Thr Ala Arg Lys Ile Asn Asn Val Ser Phe Asp Gly Thr
            660                 665                 670

Ser Asp Ile Asn Leu Thr Pro Lys Asn Ile Gly Ala Phe Ala Ser Gly
            675                 680                 685

Lys Thr Gly Asp Thr Val Ala Asn Asp Lys Ala Val Gly Trp Asn Trp
            690                 695                 700

Ser Ser Gly Ala Tyr Asn Ala Thr Thr Gly Gly Ala Ser Thr Leu Ile
705                 710                 715                 720

Leu His Phe Asn Ile Gly Glu Gly Ser Cys Pro Ala Ala Gln Phe Arg
            725                 730                 735

Val Asn Tyr Lys Asn Gly Gly Ile Phe Tyr Arg Ser Ala Arg Asp Gly
```

```
            740                 745                 750
Tyr Gly Phe Glu Ala Asp Trp Ser Glu Phe Tyr Thr Thr Thr Arg Lys
        755                 760                 765
Pro Thr Ala Gly Asp Val Gly Ala Leu Ser Leu Ser Gly Gly Gln Leu
    770                 775                 780
Asn Gly Ala Leu Gly Ile Gly Thr Ser Ser Asp Leu Gly Gly Asn Ser
785                 790                 795                 800
Ile Val Leu Gly Asp Asn Asp Thr Gly Phe Lys Gln Asn Gly Asp Gly
                805                 810                 815
Asn Leu Asp Val Tyr Ala Asn Ser Val His Val Met Arg Phe Val Ser
                820                 825                 830
Gly Ser Ile Gln Ser Asn Lys Thr Ile Asn Ile Thr Gly Arg Val Asn
                835                 840                 845
Pro Ser Asp Tyr Gly Asn Phe Asp Ser Arg Tyr Val Arg Asp Val Arg
            850                 855                 860
Leu Gly Thr Arg Val Val Gln Thr Met Gln Lys Gly Val Met Tyr Glu
865                 870                 875                 880
Lys Ser Gly His Val Ile Thr Gly Leu Gly Ile Val Gly Glu Val Asp
                885                 890                 895
Gly Asp Asp Pro Ala Val Phe Arg Pro Ile Gln Lys Tyr Ile Asn Gly
                900                 905                 910
Thr Trp Tyr Asn Val Ala Gln Val
                915                 920

<210> SEQ ID NO 31
<211> LENGTH: 1026
<212> TYPE: PRT
<213> ORGANISM: Bacteriophage AV17

<400> SEQUENCE: 31

Met Ala Thr Leu Lys Gln Ile Gln Phe Lys Arg Ser Lys Ile Ala Gly
1               5                   10                  15
Thr Arg Pro Ala Ala Ser Val Leu Ala Glu Gly Glu Leu Ala Ile Asn
                20                  25                  30
Leu Lys Asp Arg Thr Ile Phe Thr Lys Asp Asp Ser Gly Asn Ile Ile
                35                  40                  45
Asp Leu Gly Phe Ala Lys Gly Gly Gln Val Asp Gly Asn Val Thr Ile
    50                  55                  60
Asn Gly Leu Leu Arg Leu Asn Gly Asp Tyr Val Gln Thr Gly Gly Met
65              70                  75                  80
Thr Val Asn Gly Pro Ile Gly Ser Thr Asp Val Thr Gly Lys Ile
                85                  90                  95
Phe Arg Ser Thr Gln Gly Ser Phe Tyr Ala Arg Ala Thr Asn Asp Thr
                100                 105                 110
Ser Asn Ala His Leu Trp Phe Glu Asn Ala Asp Gly Thr Glu Arg Gly
                115                 120                 125
Val Ile Tyr Ala Arg Pro Gln Thr Thr Thr Asp Gly Glu Ile Arg Leu
    130                 135                 140
Arg Val Arg Gln Gly Thr Gly Ser Thr Ala Asn Ser Glu Phe Tyr Phe
145                 150                 155                 160
Arg Ser Ile Asn Gly Gly Glu Phe Gln Ala Asn Arg Ile Leu Ala Ser
                165                 170                 175
Asp Ser Leu Val Thr Lys Arg Ile Ala Val Asp Thr Val Ile His Asp
                180                 185                 190
Ala Lys Ala Phe Gly Gln Tyr Asp Ser His Ser Leu Val Asn Tyr Val
```

-continued

```
            195                 200                 205
Tyr Pro Gly Thr Gly Glu Thr Asn Gly Val Asn Tyr Leu Arg Lys Val
210                 215                 220

Arg Ala Lys Ser Gly Gly Thr Ile Tyr His Glu Ile Val Thr Ala Gln
225                 230                 235                 240

Thr Gly Leu Ala Asp Glu Val Ser Trp Trp Ser Gly Asp Thr Pro Val
                245                 250                 255

Phe Lys Leu Tyr Gly Ile Arg Asp Asp Gly Arg Met Ile Ile Arg Asn
                260                 265                 270

Ser Leu Ala Leu Gly Thr Phe Thr Thr Asn Phe Pro Ser Ser Asp Tyr
                275                 280                 285

Gly Asn Val Gly Val Met Gly Asp Lys Tyr Leu Val Leu Gly Asp Thr
            290                 295                 300

Val Thr Gly Leu Ser Tyr Lys Lys Thr Gly Val Phe Asp Leu Val Gly
305                 310                 315                 320

Gly Gly Tyr Ser Val Ala Ser Ile Thr Pro Asp Ser Phe Arg Ser Thr
                325                 330                 335

Arg Lys Gly Ile Phe Gly Arg Ser Glu Asp Gln Gly Ala Thr Trp Ile
                340                 345                 350

Met Pro Gly Thr Asn Ala Ala Leu Leu Ser Val Gln Thr Gln Ala Asp
                355                 360                 365

Asn Asn Asn Ala Gly Asp Gly Gln Thr His Ile Gly Tyr Asn Ala Gly
            370                 375                 380

Gly Lys Met Asn His Tyr Phe Arg Gly Thr Gly Gln Met Asn Ile Asn
385                 390                 395                 400

Thr Gln Gln Gly Met Glu Ile Asn Pro Gly Ile Leu Lys Leu Val Thr
                405                 410                 415

Gly Ser Asn Asn Val Gln Phe Tyr Ala Asp Gly Thr Ile Ser Ser Ile
                420                 425                 430

Gln Pro Ile Lys Leu Asp Asn Glu Ile Phe Leu Thr Lys Ser Asn Asn
                435                 440                 445

Thr Ala Gly Leu Lys Phe Gly Ala Pro Ser Gln Val Asp Gly Thr Arg
450                 455                 460

Thr Ile Gln Trp Asn Gly Gly Thr Arg Glu Gly Gln Asn Lys Asn Tyr
465                 470                 475                 480

Val Ile Ile Lys Ala Trp Gly Asn Ser Phe Asn Ala Thr Gly Asp Arg
                485                 490                 495

Ser Arg Glu Thr Val Phe Gln Val Ser Asp Ser Gln Tyr Tyr Phe
                500                 505                 510

Tyr Ala His Arg Lys Ala Pro Thr Gly Asp Glu Thr Ile Gly Arg Ile
                515                 520                 525

Glu Ala Gln Phe Ala Gly Asp Val Tyr Ala Lys Gly Ile Ile Ala Asn
                530                 535                 540

Gly Asn Phe Arg Val Val Gly Ser Ser Ala Leu Ala Gly Asn Val Thr
545                 550                 555                 560

Met Ser Asn Gly Leu Phe Val Gln Gly Ser Ser Ile Thr Gly Gln
                565                 570                 575

Val Lys Ile Gly Gly Thr Ala Asn Ala Leu Arg Ile Trp Asn Ala Glu
                580                 585                 590

Tyr Gly Ala Ile Phe Arg Arg Ser Glu Ser Asn Phe Tyr Ile Ile Pro
                595                 600                 605

Thr Asn Gln Asn Glu Gly Glu Ser Gly Asp Ile His Ser Ser Leu Arg
                610                 615                 620
```

Pro Val Arg Ile Gly Leu Asn Asp Gly Met Val Gly Leu Gly Arg Asp
625                 630                 635                 640

Ser Phe Ile Val Asp Gln Asn Asn Ala Leu Thr Thr Ile Asn Ser Asn
            645                 650                 655

Ser Arg Ile Asn Ala Asn Phe Arg Met Gln Leu Gly Gln Ser Ala Tyr
        660                 665                 670

Ile Asp Ala Glu Cys Thr Asp Ala Val Arg Pro Ala Gly Ala Gly Ser
    675                 680                 685

Phe Ala Ser Gln Asn Asn Glu Asp Val Arg Ala Pro Phe Tyr Met Asn
690                 695                 700

Ile Asp Arg Thr Asp Ala Ser Ala Tyr Val Pro Ile Leu Lys Gln Arg
705                 710                 715                 720

Tyr Val Gln Gly Asn Gly Cys Tyr Ser Leu Gly Thr Leu Ile Asn Asn
            725                 730                 735

Gly Asn Phe Arg Val His Tyr His Gly Gly Asp Asn Gly Ser Thr
        740                 745                 750

Gly Pro Gln Thr Ala Asp Phe Gly Trp Glu Phe Ile Lys Asn Gly Asp
    755                 760                 765

Phe Ile Ser Pro Arg Asp Leu Ile Ala Gly Lys Val Arg Phe Asp Arg
770                 775                 780

Thr Gly Asn Ile Thr Gly Gly Ser Gly Asn Phe Ala Asn Leu Asn Ser
785                 790                 795                 800

Thr Ile Glu Ser Leu Lys Thr Asp Ile Met Ser Ser Tyr Pro Ile Gly
            805                 810                 815

Ala Pro Ile Pro Trp Pro Ser Asp Ser Val Pro Ala Gly Phe Ala Leu
        820                 825                 830

Met Glu Gly Gln Thr Phe Asp Lys Ser Ala Tyr Pro Lys Leu Ala Val
    835                 840                 845

Ala Tyr Pro Ser Gly Val Ile Pro Asp Met Arg Gly Gln Thr Ile Lys
850                 855                 860

Gly Lys Pro Ser Gly Arg Ala Val Leu Ser Ala Glu Ala Asp Gly Val
865                 870                 875                 880

Lys Ala His Ser His Ser Ala Ser Ala Ser Ser Thr Asp Leu Gly Thr
            885                 890                 895

Lys Thr Thr Ser Ser Phe Asp Tyr Gly Thr Lys Gly Thr Asn Ser Thr
        900                 905                 910

Gly Gly His Thr His Ser Gly Ser Gly Ser Thr Ser Thr Asn Gly Glu
    915                 920                 925

His Ser His Tyr Ile Glu Ala Trp Asn Gly Thr Gly Val Gly Gly Asn
930                 935                 940

Lys Met Ser Ser Tyr Ala Ile Ser Tyr Arg Ala Gly Gly Ser Asn Thr
945                 950                 955                 960

Asn Ala Ala Gly Asn His Ser His Thr Phe Ser Phe Gly Thr Ser Ser
            965                 970                 975

Ala Gly Asp His Ser His Ser Val Gly Ile Gly Ala His Thr His Thr
        980                 985                 990

Val Ala Ile Gly Ser His Gly His Thr Ile Thr Val Asn Ser Thr Gly
    995                 1000                1005

Asn Thr Glu Asn Thr Val Lys Asn Ile Ala Phe Asn Tyr Ile Val
    1010                1015                1020

Arg Leu Ala
    1025

<210> SEQ ID NO 32

```
<211> LENGTH: 183
<212> TYPE: PRT
<213> ORGANISM: Bacteriophage T4

<400> SEQUENCE: 32

Met Lys Ile Tyr His Tyr Tyr Phe Asp Thr Lys Glu Phe Tyr Lys Glu
1               5                   10                  15

Glu Asn Tyr Lys Pro Val Lys Gly Leu Gly Leu Pro Ala His Ser Thr
            20                  25                  30

Ile Lys Lys Pro Leu Glu Pro Lys Glu Gly Tyr Ala Val Val Phe Asp
        35                  40                  45

Glu Arg Thr Gln Asp Trp Ile Tyr Glu Glu Asp His Arg Gly Lys Arg
    50                  55                  60

Ala Trp Thr Phe Asn Lys Glu Glu Ile Phe Ile Ser Asp Ile Gly Ser
65                  70                  75                  80

Pro Val Gly Ile Thr Phe Asp Glu Pro Gly Glu Phe Asp Ile Trp Thr
                85                  90                  95

Asp Asp Gly Trp Lys Glu Asp Glu Thr Tyr Lys Arg Val Leu Ile Arg
            100                 105                 110

Asn Arg Lys Ile Glu Glu Leu Tyr Lys Glu Phe Gln Val Leu Asn Asn
        115                 120                 125

Met Ile Glu Ala Ser Val Ala Asn Lys Lys Lys Phe Tyr Tyr Lys
    130                 135                 140

Asn Leu Lys Arg Phe Phe Ala Leu Leu Glu Lys His Glu His Leu Gly
145                 150                 155                 160

Gly Glu Phe Pro Ser Trp Pro Glu Lys Glu Lys Pro Trp Tyr Lys
                165                 170                 175

Arg Leu Phe Lys His Tyr Val
            180

<210> SEQ ID NO 33
<211> LENGTH: 1083
<212> TYPE: PRT
<213> ORGANISM: Bacteriophage AV17

<400> SEQUENCE: 33

Met Ala Thr Leu Lys Gln Ile Gln Phe Lys Arg Ser Lys Thr Ala Gly
1               5                   10                  15

Ala Arg Pro Ala Ala Ser Val Leu Ala Glu Gly Glu Leu Ala Ile Asn
            20                  25                  30

Leu Lys Asp Arg Val Leu Phe Thr Lys Asp Asp Gln Gly Asn Ile Ile
        35                  40                  45

Asp Leu Gly Phe Ala Lys Gly Gly Ser Ile Asp Gly Asn Val Ile His
    50                  55                  60

Thr Gly Asn Tyr Asn Gln Thr Gly Asp Tyr Thr Leu Asn Gly Val Phe
65                  70                  75                  80

Thr Gln Thr Gly Asn Phe Asn Leu Thr Gly Ile Ala Arg Val Thr Arg
                85                  90                  95

Asp Ile Ile Ala Ala Gly Gln Ile Met Thr Glu Gly Gly Leu Ile
            100                 105                 110

Thr Lys Ser Ser Gly Thr Ala His Val Arg Phe Phe Asp Asn Asn Ser
        115                 120                 125

Arg Glu Arg Gly Ile Ile Tyr Ala Pro Ala Asn Asp Gly Leu Thr Thr
    130                 135                 140

Gln Val Leu Asn Ile Arg Val Gln Asp Tyr Ala Ala Gly Ser Glu Ser
145                 150                 155                 160
```

-continued

```
Thr Tyr Ala Phe Ser Gly Ser Gly Leu Phe Thr Ser Pro Glu Val Ser
                165                 170                 175

Ala Trp Lys Ser Ile Ser Ser Pro Gln Ile Leu Thr Asn Lys Val Ile
            180                 185                 190

Thr Asn Asn Lys Ser Thr Gly Asp Tyr Asp Ile Tyr Ser Met Ala Asp
        195                 200                 205

Asn Val Pro Leu Ser Glu Ser Thr Thr Ala Ile Asn His Leu Arg Val
    210                 215                 220

Met Arg Asn Ala Val Gly Ser Gly Ile Phe His Glu Val Lys Asp Asn
225                 230                 235                 240

Asp Gly Ile Thr Trp Tyr Ser Gly Asp Leu Asp Ala Tyr Leu Trp
                245                 250                 255

Ser Phe Thr Trp Ser Gly Gly Ile Lys Ser Ser His Ser Ile Ser Ile
            260                 265                 270

Gly Leu Thr Pro Gly Asn Lys Asp Tyr Ser Ile Leu Gly Pro Ser Ser
        275                 280                 285

Ile Ala Leu Gly Asp Asn Asp Thr Gly Phe Lys Trp His Gln Asp Gly
    290                 295                 300

Tyr Tyr Phe Ser Val Asn Asn Gly Thr Lys Thr Phe Leu Phe Asn Pro
305                 310                 315                 320

Ser Glu Thr Thr Ser Leu Arg Lys Phe Val Ala Gly Tyr Ser Thr Asn
                325                 330                 335

Gly Thr Asp Leu Thr Thr Pro Pro Thr Glu Asn Tyr Ala Leu Ala Thr
            340                 345                 350

Val Val Thr Tyr His Asp Asn Asn Ala Phe Gly Asp Gly Gln Thr Leu
        355                 360                 365

Leu Gly Tyr Tyr Gln Gly Gly Asn Tyr His His Tyr Phe Arg Gly Lys
    370                 375                 380

Gly Thr Thr Asn Ile Asn Thr His Gly Gly Leu Leu Val Thr Pro Gly
385                 390                 395                 400

Asn Ile Asp Val Ile Gly Gly Ser Val Asn Ile Asp Gly Arg Asn Asn
                405                 410                 415

Ser Ser Thr Leu Met Phe Arg Gly Asn Thr Thr Gly Tyr Ser Ser Val
            420                 425                 430

Asp Asn Met Asp Ile Lys Val Trp Gly Asn Thr Phe Val Asp Pro Ser
        435                 440                 445

Gly Gly Ile Arg Lys Asn Ile Met Glu Ile Ser Asp Ala Thr Ser Trp
    450                 455                 460

Met Ser Tyr Ile Gln Arg Leu Thr Thr Gly Glu Val Glu Met Asn Val
465                 470                 475                 480

Asn Gly Ser Phe Glu Ser Ser Gly Val Thr Ala Gly Asp Arg Gly Val
                485                 490                 495

His Thr Thr Gly Glu Ile Ser Ser Gly Ala Val Asn Ala Leu Arg Ile
            500                 505                 510

Trp Asn Ala Asp Tyr Gly Ala Ile Phe Arg Arg Ser Glu Gly Ser Leu
        515                 520                 525

His Ile Ile Pro Thr Ala Tyr Gly Glu Gly Lys Asn Gly Asp Ile Gly
    530                 535                 540

Pro Leu Arg Pro Phe Ser Leu Ala Leu Asp Thr Gly Lys Val Thr Ile
545                 550                 555                 560

Pro Asp Leu Gln Ser Ser Tyr Asn Thr Phe Ala Ala Asn Gly Tyr Ile
                565                 570                 575

Lys Phe Val Gly His Gly Ala Gly Ala Gly Gly Tyr Asp Ile Gln Tyr
            580                 585                 590
```

```
Ala Gln Ala Ala Pro Ile Phe Gln Glu Ile Asp Asp Ala Val Ser
        595                 600                 605

Lys Tyr Tyr Pro Ile Val Lys Gln Lys Phe Leu Asn Gly Lys Ala Val
        610                 615                 620

Trp Ser Leu Gly Thr Glu Ile Asn Ser Gly Thr Phe Val Ile His His
625                 630                 635                 640

Leu Lys Glu Asp Gly Ser Gln Gly His Thr Ser Arg Phe Asn Gln Asp
        645                 650                 655

Gly Thr Val Asn Phe Pro Asp Asn Val Ser Val Gly Gly Gly Glu Ala
        660                 665                 670

Thr Ile Ala Arg Asn Gly Asn Ile Trp Ser Asp Ile Trp Lys Thr Phe
        675                 680                 685

Thr Ser Ala Gly Asp Thr Thr Asn Ile Arg Asp Ala Ile Ala Thr Arg
        690                 695                 700

Val Ser Lys Glu Gly Asp Thr Met Thr Gly Thr Leu Trp Ile Asn Lys
705                 710                 715                 720

Asp Ala Ala Gly Ile Val Leu Asn Pro Pro Leu Thr Ser Asp Ser Ser
        725                 730                 735

Phe Ile Arg Ser Asp Thr Ala Gly Ala Asn Asn Trp Tyr Ile Gly Lys
        740                 745                 750

Gly Gly Ala Asp Asn Gly Leu Gly Phe Tyr Ser Tyr Val Thr Gln Gly
        755                 760                 765

Gly Val Tyr Ile Thr Asn Asn Gly Glu Ile Ser Leu Ser Pro Gln Gly
        770                 775                 780

Gln Gly Thr Phe Asn Phe Asn Arg Asp Arg Leu His Ile Asn Gly Thr
785                 790                 795                 800

Gln Trp Ala Ala His Gln Gly Gly Trp Gly Asn Gln Trp Asn Gln
        805                 810                 815

Glu Ala Pro Val Phe Val Asp Phe Gly Asn Val Gly Asn Asp Ser Tyr
        820                 825                 830

Tyr Pro Ile Ile Lys Gly Lys Ser Gly Ile Thr Asn Glu Gly Tyr Ile
        835                 840                 845

Ser Gly Val Asp Phe Gly Met Arg Arg Ile Thr Asn Thr Trp Ala Gln
        850                 855                 860

Gly Ile Ile Arg Val Gly Asn Gln Glu Asn Gly Tyr Asp Pro Gln Ala
865                 870                 875                 880

Val Tyr Glu Phe His His Asn Gly Thr Phe Tyr Ala Pro Ser Leu Leu
        885                 890                 895

Lys Ser Ser Arg Val Ser Ala Gly Gly Gly Asp Pro Ala Trp Gly Gly
        900                 905                 910

Pro Cys Ile Val Leu Gly Asp Asn Asp Thr Gly Leu Leu Trp Glu Asn
        915                 920                 925

Asp Gly Ile Phe Asn Ala Tyr Ala Asn Gly Gln Gly Val Phe Ser Phe
        930                 935                 940

Arg Pro Gly Leu Ala Gln Thr Phe Gly Asp Val Asn Phe His Cys Asn
945                 950                 955                 960

Ala Gly Met Tyr Val Arg Asp Asn Ile Asp Val Asn Asp Val Tyr Ile
        965                 970                 975

Arg Ser Asp Ile Arg Cys Lys Ser Glu Ile Lys Leu Ile Lys Asn Ala
        980                 985                 990

Gln Glu Lys Ser Lys Leu Leu Gly Gly Tyr Thr Tyr Leu Leu Lys Asn
        995                 1000                1005

Ser Val Thr Asp Glu Val Lys Pro Ser Ala Gly Leu Ile Ala Gln
```

-continued

```
                1010                1015                1020

Glu Val Gln Glu Val Leu Pro Glu Leu Val Ser Glu Asp Lys Glu
            1025                1030                1035

Thr Gly Leu Leu Arg Leu Asn Tyr Asn Gly Ile Ile Gly Leu Asn
            1040                1045                1050

Thr Ala Ala Ile Asn Glu His Thr Asp Glu Ile Lys Glu Leu Lys
            1055                1060                1065

Ser Glu Ile Thr Glu Leu Lys Ala Leu Ile Lys Ser Leu Ile Lys
            1070                1075                1080

<210> SEQ ID NO 34
<211> LENGTH: 259
<212> TYPE: PRT
<213> ORGANISM: Bacteriophage AV17
<220> FEATURE:
<221> NAME/KEY: MISC_FEATURE
<222> LOCATION: (164)..(164)
<223> OTHER INFORMATION: Other

<400> SEQUENCE: 34

Met Ala Val Val Gly Ile Pro Gly Trp Ile Gly Thr Ser Ala Val Ala
1               5                   10                  15

Glu Thr Gly Gln Arg Trp Met Thr Ala Ala Ser Arg Glu Leu Arg Leu
            20                  25                  30

Gly Asn Pro Ser Trp Met Ser Gln Phe Ala Gly Arg Ser Arg Glu Ile
        35                  40                  45

Ile His Thr Leu Gly Ala Asp His Asn Phe Asn Gly Gln Trp Phe Arg
    50                  55                  60

Asp Arg Cys Phe Glu Ala Gly Ser Ala Pro Ile Val Phe Asn Ile Thr
65                  70                  75                  80

Gly Asn Leu Val Ser Tyr Ser Lys Asp Val Pro Leu Phe Phe Met Tyr
                85                  90                  95

Gly Asp Thr Pro Asn Glu Tyr Val Thr Leu Asn Ile His Gly Gly Val
            100                 105                 110

His Met Trp Gly Arg Gly Gly Asn Gly Thr Val Asn Gly Asn Pro Gly
        115                 120                 125

Thr Asn Gly Gly Asp Val Ile Gln Asn Asp Ile Gly Gly Arg Leu Arg
    130                 135                 140

Ile Trp Asn Tyr Gly Val Ile Ala Ser Gly Gly Gly Gly Gly Gly Ala
145                 150                 155                 160

Val Ser Leu Xaa Asn Ser Trp Ala Pro Asn Ala Thr Ala Gly Gly Gly
                165                 170                 175

Gly Gly Arg Pro Phe Gly Ile Gly Gly Gly Val Asn Trp Pro Gly
        180                 185                 190

Gly Asn Ala Ser Tyr Asp Ala Pro Gly Gly Ala Gly Tyr Thr Ser Gln
    195                 200                 205

Phe Gly Gly Gly Asn Gly Gly Asp Ala Gly Gly Arg Gly Gly Asp Gly
210                 215                 220

Trp Gly Asn His Leu Ser Arg Ser Gly Gly Ala Pro Gly Arg Ala
225                 230                 235                 240

Val Phe Gly Ser Ser Pro Ser Trp Gly Ala Thr Gly Thr Ile Tyr Gly
                245                 250                 255

Ser Trp Ile

<210> SEQ ID NO 35
<211> LENGTH: 472
<212> TYPE: PRT
```

<213> ORGANISM: Pseudomonas aeruginosa

<400> SEQUENCE: 35

```
Met Lys Asn Leu Ser Leu Ile Ser Ala Cys Leu Leu Gly Ala Cys
1               5                   10                  15

Gly Ser Thr Pro Ala Pro Leu Asp Ser Gly Leu Ala Ala Pro Ser Gln
            20                  25                  30

Trp Arg Tyr Leu Ala Ala Gly Arg Ser Asp Ala Ser Asp Ile Arg Gln
        35                  40                  45

Trp Trp Lys Ala Phe Gly Ala Pro Glu Leu Asp Ser Leu Leu Gln Arg
    50                  55                  60

Ala Leu Leu Asn Ser Gln Asp Leu Gly Ala Ala Val Ala Arg Val Arg
65                  70                  75                  80

Gln Ala Gln Ala Ser Ala Val Ile Ala Gly Ala Pro Leu Leu Pro Glu
                85                  90                  95

Leu Asn Ala Thr Leu Gly Ala Ser Arg Gln Lys Leu Leu Arg Asp Ser
            100                 105                 110

Gly Tyr Ser Gly Thr Asp Ala Thr Ser Asp Asn Asp Ala Val Asp Ser
        115                 120                 125

Phe Ser Ala Gly Leu Ser Ala Ser Tyr Glu Val Asp Phe Trp Gly Gly
    130                 135                 140

Arg Gln Ala Ala Tyr Arg Ser Ala Leu Glu Ser Leu Lys Ala Ser Glu
145                 150                 155                 160

Tyr Asp Arg Ala Thr Val Glu Leu Thr Leu Leu Ser Gly Val Ala Asn
                165                 170                 175

Ser Tyr Leu Gln Val Leu Ala Leu Arg Glu Gln Arg Ile Ala Arg
            180                 185                 190

Leu Asn Leu Asp Asn Ala Glu His Val Leu Arg Leu Val Glu Thr Arg
        195                 200                 205

His Ala Ala Gly Ser Ala Thr Ala Leu Glu Val Ala Gln Gln Ser Ser
210                 215                 220

Leu Val Ala Ser Gln Arg Lys Gln Leu Pro Leu Leu Glu Gln Gln Ala
225                 230                 235                 240

His Glu Ala Leu Ile Thr Leu Ala Thr Leu Ile Gly Glu Pro Val Gln
                245                 250                 255

Ala Leu Gln Val Ala Glu Arg Pro Phe Asp Ser Leu Arg Trp Pro Glu
            260                 265                 270

Thr Gly Ala Gly Leu Pro Ser Glu Leu Leu Ser Arg Arg Pro Asp Ile
        275                 280                 285

Ala Asn Ala Glu Ala Gln Leu Ala Ala Ala Gln Ala Asp Val Gln Val
290                 295                 300

Ala Arg Ala Ala Leu Phe Pro Lys Leu Thr Leu Ser Ala Ser Leu Ser
305                 310                 315                 320

Ser Gly Ala Asn Arg Ala Ala Asp Thr Phe Arg Asn Pro Tyr Tyr Asn
                325                 330                 335

Leu Gly Ala Asn Leu Leu Ala Pro Ile Phe Asn His Gly Arg Leu Arg
            340                 345                 350

Ala Glu Arg Asp Arg Ser Leu Ala Arg Gln Glu Leu Leu Glu Thr
        355                 360                 365

Tyr Arg Lys Ala Ile Leu Thr Ala Phe Ala Asp Thr Glu Arg Ser Leu
370                 375                 380

Asn Ser Ile Asp Gly Leu Asp Arg Gln Leu His Trp Gln Gln Gln Glu
385                 390                 395                 400

Leu Glu Gln Ala Gln Arg Ala Phe Asp Leu Ser Asp Ser Arg Tyr Gln
```

```
                       405                 410                 415
Ala Gly Ala Glu Thr Leu Leu Thr Val Leu Glu Thr Gln Arg Thr Leu
                420                 425                 430

Tyr Ala Ala Gln Asp Ala Ala Val Gln Leu Arg Leu Ala Arg Leu Gln
            435                 440                 445

Ala Ser Val Gly Leu Tyr Lys Ala Leu Gly Gly Trp Gln Ser Asp
        450                 455                 460

Arg Gln Gly Leu Ala Arg Lys Asp
465                 470

<210> SEQ ID NO 36
<211> LENGTH: 498
<212> TYPE: PRT
<213> ORGANISM: Pseudomonas aeruginosa

<400> SEQUENCE: 36

Met Lys His Thr Pro Ser Leu Leu Ala Leu Ala Leu Val Ala Ala Leu
1               5                   10                  15

Gly Gly Cys Ala Ile Gly Pro Asp Tyr Gln Arg Pro Asp Leu Ala Val
            20                  25                  30

Pro Ala Glu Phe Lys Glu Ala Glu Gly Trp Arg Arg Ala Glu Pro Arg
        35                  40                  45

Asp Val Phe Gln Arg Gly Ala Trp Trp Glu Leu Tyr Gly Asp Gln Thr
    50                  55                  60

Leu Asn Asp Leu Gln Met His Leu Glu Arg Ser Asn Gln Thr Leu Ala
65                  70                  75                  80

Gln Ser Val Ala Gln Phe Arg Gln Ala Glu Ala Leu Val Arg Gly Ala
                85                  90                  95

Arg Ala Ala Phe Phe Pro Ser Ile Thr Gly Asn Val Gly Lys Thr Arg
            100                 105                 110

Ser Gly Gln Gly Gly Gly Asp Ser Thr Val Leu Leu Pro Gly Gly Ser
        115                 120                 125

Thr Val Ser Ser Gly Gly Ser Gly Ala Ile Ser Thr Ser Tyr Ser Thr
    130                 135                 140

Asn Leu Ser Val Ser Trp Glu Val Asp Leu Trp Gly Lys Leu Arg Arg
145                 150                 155                 160

Gln Leu Glu Ala Asn Gln Ala Ser Leu His Ala Ser Ala Ala Asp Leu
                165                 170                 175

Ala Ala Val Arg Leu Ser Gln Gln Ser Gln Leu Ala Gln Asn Tyr Leu
            180                 185                 190

Gln Leu Arg Val Met Asp Glu Gln Ile Arg Leu Leu Asn Asp Thr Val
        195                 200                 205

Thr Ala Tyr Glu Arg Ser Leu Lys Val Ala Glu Asn Lys Tyr Arg Ala
    210                 215                 220

Gly Ile Val Thr Arg Ala Asp Val Ala Gln Ala Arg Thr Gln Leu Lys
225                 230                 235                 240

Ser Thr Gln Ala Gln Ala Ile Asp Leu Lys Tyr Gln Arg Ala Gln Leu
                245                 250                 255

Glu His Ala Ile Ala Val Leu Val Gly Leu Pro Pro Ala Gln Phe Asn
            260                 265                 270

Leu Pro Pro Val Ala Ser Val Pro Lys Leu Pro Asp Leu Pro Ala Val
        275                 280                 285

Val Pro Ser Gln Leu Leu Glu Arg Arg Pro Asp Ile Ala Ser Ala Glu
    290                 295                 300

Arg Lys Val Ile Ser Ala Asn Ala Gln Ile Gly Val Ala Lys Ala Ala
```

```
            305                 310                 315                 320
Tyr Phe Pro Asp Leu Thr Leu Ser Ala Ala Gly Gly Tyr Arg Ser Gly
                325                 330                 335

Ser Leu Ser Asn Trp Ile Ser Thr Pro Asn Arg Phe Trp Ser Ile Gly
                340                 345                 350

Pro Gln Phe Ala Met Thr Leu Phe Asp Gly Gly Leu Ile Gly Ser Gln
                355                 360                 365

Val Asp Gln Ala Glu Ala Thr Tyr Asp Gln Thr Val Ala Thr Tyr Arg
            370                 375                 380

Gln Thr Val Leu Asp Gly Phe Arg Glu Val Glu Asp Tyr Leu Val Gln
385                 390                 395                 400

Leu Ser Val Leu Asp Glu Glu Ser Gly Val Gln Arg Glu Ala Leu Glu
                405                 410                 415

Ser Ala Arg Glu Ala Leu Arg Leu Ala Glu Asn Gln Tyr Lys Ala Gly
                420                 425                 430

Thr Val Asp Tyr Thr Asp Val Val Thr Asn Ala Thr Ala Leu Ser
            435                 440                 445

Asn Glu Arg Thr Val Leu Thr Leu Gly Ser Arg Leu Thr Ala Ser
450                 455                 460

Val Gln Leu Ile Ala Ala Met Gly Gly Gly Trp Asp Ser Ala Asp Ile
465                 470                 475                 480

Glu Arg Thr Asp Glu Arg Leu Gly Arg Val Glu Glu Gly Leu Pro Pro
                485                 490                 495

Ser Pro

<210> SEQ ID NO 37
<211> LENGTH: 482
<212> TYPE: PRT
<213> ORGANISM: Pseudomonas aeruginosa

<400> SEQUENCE: 37

Met Pro Leu Ala Ser His Leu Arg Cys Val Ala Leu Ala Leu Gly Ile
1               5                   10                  15

Ser Thr Ala Leu Gly Cys Ala Asn Arg Asn Gln Pro Ala Pro Arg Ala
                20                  25                  30

Glu Ser Leu Asp Pro Gly Leu Ser Arg Val Ala Gly Thr Arg Gly Asp
            35                  40                  45

Ala Leu Pro Ala Gln Trp Trp Thr Leu Tyr Gln Asp Pro Gly Leu Asn
        50                  55                  60

His Leu Val Ala Ala Ala Leu Arg His Asn Arg Asp Leu Ala Ala Ala
65                  70                  75                  80

Asp Ala His Ala Arg Ala Leu Leu Gly His Leu Arg Gly Ala Gln Gly
                85                  90                  95

Glu Arg Trp Pro Arg Thr Glu Val Gly Tyr Gly Tyr Gln Tyr Gly Arg
            100                 105                 110

Asp Gly Asp Asp Gln Thr Leu Ala Glu Ala Thr Asp Glu Asp Leu His
        115                 120                 125

Ser Gln Trp Lys His Thr Val Arg Leu Asp Leu Ser Tyr Gln Leu Asp
    130                 135                 140

Leu Trp Gly Glu Val Arg Ala Arg Ile Ala Ala Ala Lys Ala Asp Ala
145                 150                 155                 160

Glu Ala Ala Gln Ala Ala Arg Asp Leu Leu Arg Val Ser Val Ala Ser
                165                 170                 175

Gln Thr Thr Leu Ala Tyr Val Arg Ala Cys Ala Leu Ala Arg Arg Ala
            180                 185                 190
```

Glu Val Gln Arg Arg Ser Val Gly Leu Leu Asp Ala Ser Leu Ala Leu
            195                 200                 205

Ser Glu Arg Gln Leu Ala Ala Gly Leu Ser Ser Glu Leu Gln Arg Arg
        210                 215                 220

Arg Leu Leu Ala Leu Glu Arg Thr Arg Ala Ala Leu Pro Met Leu
225                 230                 235                 240

Glu Ala Arg Arg Ala Ala Leu Tyr Glu Leu Ala Leu Leu Ser Gly
                245                 250                 255

Arg Ser Pro Arg Gln Leu Asp Ala Pro Ala Ala Thr Cys Ala Gly Ile
                260                 265                 270

Pro Gln Leu Arg Arg Ala Leu Pro Thr Gly Asp Gly Trp Ser Leu Leu
            275                 280                 285

Ala Arg Arg Pro Asp Val Arg Ala Ala Glu Arg Leu Ala Ala Ala
        290                 295                 300

Asp Ala Arg Arg Ala Leu Ala Glu Ala Glu Leu Tyr Pro Arg Ile Ser
305                 310                 315                 320

Phe Ala Val Gly Ala Glu Thr Ser Ala Ala Thr Leu Ala Gly Leu Gly
                325                 330                 335

Gly Ser Gly Ala Leu Ala Tyr Ala Ala Gly Pro Leu Leu Ser Trp Arg
            340                 345                 350

Phe Pro Asn Arg Glu Ser Ala Arg Gly Arg Leu Asp Ser Ala Ala Ala
        355                 360                 365

Glu Arg Asp Ala Ala Leu Ala Arg Phe Asp Gly Ala Val Leu Gly Ala
    370                 375                 380

Leu Arg Glu Val Glu Arg Ala Leu Ala Leu Tyr Ala Gly Glu Arg Gln
385                 390                 395                 400

Arg Arg Ala Asp Leu Gln Arg Ala Leu Asp Glu Gln Arg His Ala Tyr
                405                 410                 415

Arg Leu Ala Arg Ser Asn Tyr Arg Ala Gly Ala Leu Asp Ala Leu Glu
            420                 425                 430

Leu Leu Asp Ser Gln Arg Ser Leu Val Ala Asp Arg Ala Arg Leu Val
        435                 440                 445

Asp Ala Glu Met Arg Val Ala Glu Arg Gln Val Glu Leu Phe Arg Ala
    450                 455                 460

Leu Gly Gly Gly Trp Gln Ala Ala Ser Ser Pro Ser His Gln Glu Asn
465                 470                 475                 480

Gly Gln

<210> SEQ ID NO 38
<211> LENGTH: 492
<212> TYPE: PRT
<213> ORGANISM: Pseudomonas aeruginosa

<400> SEQUENCE: 38

Met Pro Phe Pro Leu Leu His Pro Trp Pro Gln Arg Leu Ala Leu Ala
1               5                   10                  15

Ser Ala Ile Leu Leu Ala Ala Gly Cys Val Thr Ser Glu Gly Leu Glu
            20                  25                  30

Pro Asn Ala Arg Leu Gln Pro Ala Gly Ala Leu Gln Ala Gly Arg Ser
        35                  40                  45

Leu Asp Gly Val Ala Leu Ser Pro Ala Ala Trp Pro Arg Gln Asp Trp
    50                  55                  60

Trp Thr Gly Leu Gly Asp Arg Gln Leu Asp Gln Leu Ile Gly Glu Ala
65                  70                  75                  80

-continued

```
Leu Gln Gly Thr Pro Asp Leu Gln Ile Ala Glu Ala Arg Ala Arg Gln
                85                  90                  95

Ala Ala Ala Thr Ala Gln Ala Gln Asp Ala Ala Arg Gln Pro Thr Leu
            100                 105                 110

Asp Ala Lys Ala Ser Tyr Ser Gly Ile Arg Ala Pro Thr Ser Val Ala
            115                 120                 125

Pro Ala Pro Leu Gly Gly Arg Tyr Ser Ala Ile Lys Tyr Leu Ser Leu
130                 135                 140

Gly Phe Asn Tyr Asp Phe Asp Leu Trp Gly Gly Glu Arg Ala Ala Trp
145                 150                 155                 160

Glu Ala Ala Leu Gly Gln Ala Asn Ala Ala Arg Ile Asp Ser Gln Ala
                165                 170                 175

Ala Arg Ile Gly Leu Ser Ala Ser Ile Ala Arg Ala Tyr Ser Asp Leu
            180                 185                 190

Ala His Ala Phe Thr Val Arg Asp Leu Ala Glu Glu Leu Lys Arg
            195                 200                 205

Ser Gln Arg Met Thr Glu Leu Ser Gln Lys Arg Met Ser Ala Gly Leu
            210                 215                 220

Asp Ser Lys Val Gln Leu Gln Thr Gln Thr Gln Leu Ala Thr Ala
225                 230                 235                 240

Arg Gln Gln Leu Ser Ala Ala Glu Gln Asp Ile Ala Ser Ala Arg Ile
                245                 250                 255

Ala Leu Ala Val Leu Leu Gly Lys Gly Pro Asp Arg Gly Leu Glu Leu
            260                 265                 270

Gln Arg Pro Gln Pro Leu Asn Pro Ala Ser Leu Ser Leu Pro Ser Val
            275                 280                 285

Leu Pro Ala Glu Leu Leu Gly Arg Arg Ala Asp Ile Val Ala Ala Arg
290                 295                 300

Trp Arg Val Glu Ala Ala Arg Arg Asn Ile Asp Ser Ala Lys Thr Glu
305                 310                 315                 320

Phe Tyr Pro Asn Leu Asn Leu Gly Ala Met Ala Gly Leu Ala Ala Leu
                325                 330                 335

His Thr Ser Asp Val Leu Gln Ala Pro Ser Arg Phe Phe Gln Val Ala
            340                 345                 350

Pro Ala Ile Ser Leu Pro Ile Phe Asp Gly Gly Arg Arg Arg Ala Asn
            355                 360                 365

Leu Ala Glu Arg Asp Ala Asp Tyr Asp Leu Ala Val Gly Gln Tyr Asn
370                 375                 380

Lys Thr Leu Val Gln Ala Leu Gly Glu Val Ser Asp Asp Leu Gly Lys
385                 390                 395                 400

Leu Arg Ser Leu Glu Gln Gln Val Ile Asp Gln Arg Gln Ala Arg Asp
                405                 410                 415

Ile Ala Arg Ser Asn Phe Asp Leu Ala Met Arg Arg Tyr Gly Glu Gly
            420                 425                 430

Val Gly Ser Tyr Leu Asp Ala Leu Ser Val Gln Gln Leu Leu Val
            435                 440                 445

Ala Glu Arg Gln Leu Ala Ser Leu Glu Ser Gln Ile Asp Leu Ser
450                 455                 460

Val Gln Leu Val Gln Ala Leu Gly Gly Gly Phe Gln Pro Asp Ser Arg
465                 470                 475                 480

Ser Ala Ala Leu Ala Thr Ala Lys Ala Pro Ala Glu
                485                 490

<210> SEQ ID NO 39
```

```
<211> LENGTH: 506
<212> TYPE: PRT
<213> ORGANISM: Pseudomonas aeruginosa

<400> SEQUENCE: 39

Val Pro Arg Ala Leu Arg Lys Glu Leu Thr Leu Val Gly Ser Phe Val
1               5                   10                  15

Gly Phe Leu Val Val Phe Ser Ala Ile Ser Gly Cys Val Ser Thr Gly
                20                  25                  30

Asp Ile Ala Pro Glu Ala Ala Thr Leu Asp Ala Asn Ala Leu Ala Thr
            35                  40                  45

Asp His Ala Ile Gln Ala Ala Arg Glu Ala Gly Trp Pro Gln Ala
    50                  55                  60

Gln Trp Trp Lys Val Tyr Ala Asp Pro Gln Leu Asp Ala Trp Ile Glu
65                  70                  75                  80

Lys Ala Leu Asp Gly Asn Pro Gly Leu Ala Val Ala His Ala Arg Val
                85                  90                  95

Arg Gln Ala Lys Ser Met Ala Gly Leu Val Glu Ser Ile Glu Ser Pro
                100                 105                 110

Gln Ile Glu Gly Lys Gly Ser Leu Val Arg His Arg Trp Pro Asp Asp
            115                 120                 125

Tyr Phe Tyr Gly Pro Gly Asp Leu Ala Arg Thr Thr Ser Trp Asn Asn
    130                 135                 140

Ser Thr Glu Ile Gly Leu Asn Tyr Lys Leu Asp Leu Trp Gly Arg Asp
145                 150                 155                 160

Arg Ser Asp Ser Glu Arg Ala Val Asp Leu Ala His Met Ala Ala Ala
                165                 170                 175

Glu Ala Arg Gln Ala Gln Leu Glu Leu Glu Gly Asn Ile Val Arg Ala
                180                 185                 190

Tyr Val Gln Leu Ser Leu Gln Tyr Ala Glu Met Asp Ile Ala Lys Ala
            195                 200                 205

Met Leu Gln Gln Gln Arg Asp Ile Leu Ala Leu Ala Gln Arg Arg Leu
    210                 215                 220

Arg Gly Gly Ile Gly Thr His Phe Glu Val Ser Gln Ala Glu Val Pro
225                 230                 235                 240

Leu Pro Glu Thr Glu Arg Arg Ile Glu Val Ile Asp Glu Glu Ile Gln
                245                 250                 255

Leu Thr Arg Asn Leu Leu Ala Ala Leu Ala Gly Lys Gly Pro Gly Glu
                260                 265                 270

Gly Arg Thr Ile Arg Arg Pro Ser Leu Asn Leu Ala Ala Gln Pro Ser
            275                 280                 285

Leu Pro Ser Ala Leu Pro Ala Glu Leu Leu Gly Arg Arg Pro Asp Val
    290                 295                 300

Val Ala Arg Arg Trp Gln Val Ala Ala Leu Ala Lys Gly Val Asp Val
305                 310                 315                 320

Ala Arg Ala Asp Phe Tyr Pro Asn Val Asp Leu Met Ala Ser Val Gly
                325                 330                 335

Phe Ser Ala Val Gly Gly Gly Met Leu Glu Phe Phe Arg Ser Ala Lys
                340                 345                 350

Tyr Thr Tyr Ser Ala Gly Pro Ala Val Thr Leu Pro Ile Phe Asp Gly
            355                 360                 365

Gly Arg Leu Arg Ser Gln Leu Gly Glu Ala Ala Gly Tyr Asp Ala
    370                 375                 380

Ala Val Glu Gln Tyr Asn Gln Thr Leu Val Asp Ala Leu Lys Asn Ile
385                 390                 395                 400
```

-continued

Ser Asp Gln Leu Ile Arg Leu His Ser Val Asp Ile Gln Lys Asp Phe
                405                 410                 415

Ala Ala Gln Ser Val Ala Ser Ala Gln Lys Thr Tyr Asp Ile Ala Thr
            420                 425                 430

Leu Ala Tyr Gln Arg Gly Leu Thr Asp Tyr Leu Asn Val Leu Asn Ala
        435                 440                 445

Gln Thr Arg Leu Phe Gln Gln Leu Val Gln Glu Gln Val Gln Ala
    450                 455                 460

Ala Arg Leu Ala Ala His Ala Ser Leu Leu Thr Ala Leu Gly Gly Gly
465                 470                 475                 480

Val Gly Ala Gly Ala Asp Thr Pro Ala Gln Arg Lys Leu Ala Pro Glu
                485                 490                 495

Asn Val Pro Val Arg Ala Val Ser Ser Arg
                500                 505

<210> SEQ ID NO 40
<211> LENGTH: 482
<212> TYPE: PRT
<213> ORGANISM: Pseudomonas aeruginosa

<400> SEQUENCE: 40

Met Leu Arg Arg Leu Ser Leu Ala Ala Ala Val Ala Ala Ala Thr Gly
1               5                   10                  15

Val Ala Trp Ala Ala Gln Pro Thr Pro Leu Pro Thr Lys Thr Asp Leu
                20                  25                  30

Ile Ser Val Tyr Lys Glu Ala Val Asp Asn Asn Ala Asp Leu Ala Ala
            35                  40                  45

Ala Gln Ala Asp Tyr Leu Ala Arg Lys Glu Val Val Pro Gln Ala Arg
        50                  55                  60

Ala Gly Leu Leu Pro Gln Leu Gly Ala Gly Ala Arg Val Gly Asp Thr
65                  70                  75                  80

Arg Ile Ala Phe Asp Glu Arg Pro Ala Thr Val Lys Arg Asn Ser Gln
                85                  90                  95

Val Val Gln Ala Thr Leu Ser Gln Pro Leu Phe Arg Ala Asp Arg Trp
            100                 105                 110

Phe Gln Trp Gln Ala Ala Lys Glu Thr Ser Asp Gln Ala Arg Leu Glu
        115                 120                 125

Phe Ser Ala Thr Gln Gln Asp Leu Ile Leu Arg Ser Ala Glu Thr Tyr
    130                 135                 140

Phe Thr Val Leu Arg Ala Gln Asp Asn Leu Ala Thr Ser Lys Ala Glu
145                 150                 155                 160

Glu Ala Ala Phe Lys Arg Gln Leu Asp Gln Ala Asn Glu Arg Phe Asp
                165                 170                 175

Val Gly Leu Ser Asp Lys Thr Asp Val Leu Glu Ala Gln Ala Ser Tyr
            180                 185                 190

Asp Thr Ala Arg Ala Asn Arg Leu Ile Ala Glu Gln Arg Val Asp Asp
        195                 200                 205

Ala Phe Gln Ala Leu Val Thr Leu Thr Asn Arg Asp Tyr Ser Ala Ile
    210                 215                 220

Glu Gly Met Arg His Thr Leu Pro Val Pro Pro Ala Pro Asn Asp
225                 230                 235                 240

Ala Lys Ala Trp Val Asp Thr Val Gln Gln Asn Leu Arg Leu Leu
                245                 250                 255

Ala Ser Asn Tyr Ala Val Asn Ala Ala Glu Glu Thr Leu Arg Gln Arg
            260                 265                 270

```
Lys Ala Gly His Leu Pro Thr Leu Asp Ala Val Ala Gln Tyr Gln Lys
            275                 280                 285

Gly Asp Asn Asp Ala Leu Gly Phe Ala Asn Ser Ala Ala Asn Pro Leu
        290                 295                 300

Val His Tyr Gly Lys Tyr Val Asp Glu Arg Ser Ile Gly Leu Glu Leu
305                 310                 315                 320

Asn Ile Pro Ile Tyr Ser Gly Leu Thr Ser Ser Gln Val Arg Glu
                325                 330                 335

Ser Tyr Gln Arg Leu Asn Gln Ser Glu Gln Ser Arg Glu Gly Gln Arg
                340                 345                 350

Arg Gln Val Val Gln Asp Thr Arg Asn Leu His Arg Ala Val Asn Thr
            355                 360                 365

Asp Val Glu Gln Val Gln Ala Arg Arg Gln Ala Ile Ile Ser Asn Gln
        370                 375                 380

Ser Ser Leu Glu Ala Thr Glu Ile Gly Tyr Gln Val Gly Thr Arg Asn
385                 390                 395                 400

Ile Val Asp Val Leu Asn Ala Gln Arg Gln Leu Tyr Ala Ala Val Arg
                405                 410                 415

Asp Tyr Asn Asn Ser Arg Tyr Asp Tyr Ile Leu Asp Thr Leu Arg Leu
                420                 425                 430

Lys Gln Ala Ala Gly Thr Leu Ser Pro Ala Asp Leu Glu Ala Leu Ser
            435                 440                 445

Ala Tyr Leu Lys Gln Asp Tyr Asp Pro Asp Lys Asp Phe Leu Pro Pro
        450                 455                 460

Asp Leu Ala Lys Ala Ala Ala Glu Gln Leu Gln Ser Lys Pro Arg Gln
465                 470                 475                 480

Gln Tyr

<210> SEQ ID NO 41
<211> LENGTH: 471
<212> TYPE: PRT
<213> ORGANISM: Pseudomonas aeruginosa

<400> SEQUENCE: 41

Met Arg Ala Leu Ala Gly Leu Leu Cys Gly Leu Leu Gly Leu Val Pro
1               5                   10                  15

Gly Ala Ala Ala Tyr Glu Pro Asp Val Phe Gly Thr Thr Gly Gln Val
                20                  25                  30

Ala Gly Gln Ala Val Tyr Asp Leu Gly Gly Ser Gly Leu Pro Cys Arg
            35                  40                  45

Gly Gly Pro Pro Thr Glu Leu Ser Leu Glu Glu Ala Ile Glu Arg
    50                  55                  60

Ile Leu Cys His Asp Pro Gln Thr Arg Leu Ala Trp Ala Asn Ala Lys
65                  70                  75                  80

Ala Gln Ala Ala Gln Val Gly Ile Gly Lys Ser Ala Tyr Leu Pro Arg
                85                  90                  95

Leu Asp Gly Arg Leu Asp Ala Ser Arg Gly Tyr Ser Asp Met Asp Tyr
            100                 105                 110

Arg Asp Ala Pro Tyr Leu Ser Gly Asp Gly His Arg His Arg Arg Gly
        115                 120                 125

Ala Ser Leu Gln Leu Ser Trp Val Leu Phe Asp Phe Gly Arg Arg Ser
    130                 135                 140

Ala Ala Leu Arg Asn Ala Gln Gln Leu Leu Ala Ala Asn Ala Ser
145                 150                 155                 160
```

```
Gln Asp Ala Thr Leu Gln Asn Thr Phe Ala Leu Ala Gln Ala Tyr
            165                 170                 175

Tyr Asp Ala Leu Ala Ala Gln Arg Ser Leu Ala Ala Ser Arg Gln Val
        180                 185                 190

Ala Glu Leu Ala Ala Gln Asn Leu Glu Ala Ala Asp Ala Lys Tyr Arg
    195                 200                 205

Ala Gly Ala Ala Ala Leu Ser Asp Arg Leu Gln Ala Gln Thr Ala Leu
210                 215                 220

Ser Gln Ala Ser Leu Ala Gln Val Arg Asp Glu Gly Ala Leu Ser Asn
225                 230                 235                 240

Ala Leu Gly Val Ile Ala Leu Arg Met Gly Leu Ala Pro Asp Thr Pro
                245                 250                 255

Leu Arg Leu Ser Gly Glu Leu Glu Ala Gln Pro Asp Thr Gly Phe Val
            260                 265                 270

Lys Ala Ile Asp Glu Met Leu Ala Glu Ala Arg Arg Glu His Pro Ala
        275                 280                 285

Leu Leu Ala Ala Gln Ala Arg Leu Lys Ala Ala Ala Ser Val Glu
    290                 295                 300

Glu Ser Arg Ala Ala Gly Arg Pro Ser Leu Ala Leu Ser Ala Asn Leu
305                 310                 315                 320

Ala Arg Ser His Ser Asp Gln Ala Met Ala Phe Asn Gly Asp Thr Arg
                325                 330                 335

Glu Arg Asp Arg Ser Ile Gly Leu Gln Leu Asn Ile Pro Leu Phe Glu
            340                 345                 350

Gly Phe Glu Arg Thr Tyr Gln Val Arg Asn Ala Leu Ala Arg Arg Glu
        355                 360                 365

Ala Ser Glu Ala Glu Leu Ala Asp Thr Glu Gln Gln Val Ser Leu Glu
370                 375                 380

Val Trp Asn Asn Tyr Gln Ser Leu Ser Val Glu Thr Arg Ser Leu Ala
385                 390                 395                 400

Arg Thr Arg Glu Leu Val Gln Ser Arg Gln Ser Leu Glu Val Val
                405                 410                 415

Gln Gly Arg Tyr Arg Ser Gly Val Gly Ser Met Ile Glu Leu Leu Asn
            420                 425                 430

Ala Leu Thr Ala Tyr Ala Ser Ala Glu Asp Gln His Ile Arg Ala Leu
        435                 440                 445

Gly Asn Trp Gln Thr Ser Arg Leu Arg Leu Ala Ser Leu Gly Arg
    450                 455                 460

Leu Gly Phe Trp Ser Leu Arg
465                 470

<210> SEQ ID NO 42
<211> LENGTH: 428
<212> TYPE: PRT
<213> ORGANISM: Pseudomonas aeruginosa

<400> SEQUENCE: 42

Met Pro Ile Leu Arg Pro Leu Ala Ser Ala Gly Lys Arg Ala Cys Trp
1               5                   10                  15

Leu Leu Met Gly Leu Cys Leu Gly Leu Pro Ala Leu Ala Asn Glu Ala
            20                  25                  30

Pro Val Ser Phe Asn Gly Thr Ser Ile Ser Leu Glu Gln Ala Leu Glu
        35                  40                  45

Arg Ala Leu Arg Ser Asn Pro Glu Leu Ala Ala Val Gly Arg Glu Thr
    50                  55                  60
```

```
Glu Ile Ala Ser Gly Ala Arg Gln Gln Ala Gly Leu Ile Pro Asn Pro
 65                  70                  75                  80

Asp Leu Ser Trp Ser Val Glu Asp Thr Arg Gln Gly Asn Arg Gln Thr
                 85                  90                  95

Ser Val Ser Ile Ala Gln Pro Leu Glu Leu Gly Gly Lys Arg Gly Ala
            100                 105                 110

Arg Val Glu Val Ala Lys Arg Gly Ser Glu Ile Ala Trp Thr Gln Leu
        115                 120                 125

Glu Val Arg Arg Ala Glu Leu Arg Ala Gln Val Arg Gly Ala Tyr Tyr
130                 135                 140

Ala Ala Leu Thr Ala Gln Glu Arg Val Arg Leu Ala Lys Thr Ser Leu
145                 150                 155                 160

Asp Leu Ala Arg Arg Ala Leu Gln Ala Ala Asp Arg Arg Val Lys Ala
                165                 170                 175

Gly Ser Ile Ser Ser Val Glu Arg Val Arg Ala Gln Val Leu Ala Asp
            180                 185                 190

Asn Ala Gln Leu Asp Leu Ser Gln Ala Glu Leu Glu Gln Gln Arg Thr
        195                 200                 205

Tyr Val Gln Leu Ser Ser Thr Trp Asp Glu Pro Gln Pro Gly Phe Ala
210                 215                 220

Arg Val Gly Gly Ala Leu Asp Ala Val Pro Ala Ser Ile Thr Arg Gly
225                 230                 235                 240

Ala Leu Leu Arg His Leu Asp Glu Ser Pro Thr Leu Arg Leu Ala Ala
                245                 250                 255

Gln Glu Val Ala Arg Gly Glu Ala Gln Val Asp Leu Glu Lys Arg Gln
            260                 265                 270

Arg Ile Pro Asn Leu Thr Val Ser Ile Gly Ser Lys Tyr Asp Gln Thr
        275                 280                 285

Ala Arg Asp Gly Arg Gly Glu Arg Val Asn Leu Ile Gly Leu Ser Met
290                 295                 300

Pro Leu Pro Leu Phe Asp Arg Asn Gln Gly Asn Ile Tyr Ala Ala Gln
305                 310                 315                 320

Ser Arg Ala Asp Gln Ala Arg Asp Leu Gln Arg Ala Thr Leu Leu Arg
                325                 330                 335

Leu Arg Ser Glu Ala Val Gln Ala Tyr Asp Gln Leu Arg Thr Ser Glu
            340                 345                 350

Gln Glu Leu Ala Leu Val Arg Arg Asp Leu Leu Pro Gly Ala Gln Ser
        355                 360                 365

Ala Leu Asp Ser Met Thr Arg Gly Phe Glu Met Gly Lys Phe Asn Phe
370                 375                 380

Leu Asp Val Leu Asp Ala Gln Arg Thr Leu Val Gly Val Arg Ala Gln
385                 390                 395                 400

Tyr Val Arg Ala Leu Asp Ala Ala Gln Ala Arg Val Ser Met Glu
                405                 410                 415

Arg Leu Leu Gly Glu Asp Ile Gly His Leu Gly Gln
            420                 425

<210> SEQ ID NO 43
<211> LENGTH: 493
<212> TYPE: PRT
<213> ORGANISM: Pseudomonas aeruginosa

<400> SEQUENCE: 43

Met Asn Arg Trp Gly Leu Gly Val Leu Trp Leu Val Thr Ala Leu Pro
1               5                   10                  15
```

-continued

Val Ala Ala Ser Val Asn Pro Ala Leu Ser Pro Asp Val Pro Ser Met
            20                  25                  30

Ala Arg Glu Gln Gly Arg Ser Val Leu Leu Ser Glu Gln Val Ile Asp
        35                  40                  45

Leu Ser Leu Ser Asp Ala Val Tyr Leu Gly Leu Arg Asn Asn Arg Gly
    50                  55                  60

Ile Arg Ser Ala Tyr Leu Gln Arg Ile Ala Gln Lys Phe Asp Leu Arg
65                  70                  75                  80

Val Ala Ala Asp Ala Phe Asn Pro Lys Leu Val Arg Gly Asp Tyr
            85                  90                  95

Arg Ala Asn Arg Ala Thr Glu Asp Arg Thr Arg Thr Ser Asn Val Ser
        100                 105                 110

Pro Thr Ala Thr Leu Leu Gly Glu Tyr Gly Thr Arg Phe Ser Leu Ala
    115                 120                 125

Trp Val Lys Gln Phe Arg Thr Ala Asp Glu Ala Gly Arg Tyr Arg Ser
130                 135                 140

Asp Gly Leu Asp Leu Thr Val Val Gln Pro Leu Leu Arg Asp Ala Gly
145                 150                 155                 160

Trp Asp Val Thr Thr Ala Pro Leu Arg Leu Ala Arg Leu Ser Glu Asp
            165                 170                 175

Ala Asn Arg Leu Gln Leu Lys Ala Ser Val Ser Gln Thr Ile Ser Gln
        180                 185                 190

Val Ile Gly Ala Tyr Arg Glu Leu Leu Arg Ala Gln Glu Gln Ala Arg
    195                 200                 205

Ile Ala Arg Glu Ala Leu Ala Arg Thr Gln Leu Leu Glu Val Asn
210                 215                 220

Arg Ala Met Ile Arg Ala Gly Arg Met Ala Glu Phe Glu Ile Val Gln
225                 230                 235                 240

Thr Glu Ala Asp Val Ala Ser Gln Glu Leu Asn Val Glu Glu Ser Thr
            245                 250                 255

Asn Gln Val Asp Ser Ala Arg Leu Ala Leu Leu Gln Leu Leu Ala Leu
        260                 265                 270

Asp Leu Ser Thr Gln Ile Arg Ala Ser Asp Ala Leu Ala Ala Thr Pro
    275                 280                 285

Ile Glu Val Asp Arg Gln Gln Ala Ile Arg Thr Ala Leu Gln Gln
290                 295                 300

Pro Glu Tyr Leu Gln Arg Leu Ile Gly Ser Arg Gln Ala Asp Leu Asn
305                 310                 315                 320

Leu Val Leu Ala Lys Asn Gln Arg Leu Trp Asp Val Ser Leu Val Gly
            325                 330                 335

Gly Ala Ser Gln Ile Arg Asp Arg Tyr Ser Glu Gly Gly Asp Asn
        340                 345                 350

Ser Arg Ser Trp Asp Ser Tyr Ala Gly Val Gln Val Glu Ile Pro Ile
    355                 360                 365

Gly Asp Leu Ser Arg Arg Gln Ala Glu Val Arg Ala Gln Val Asp Val
370                 375                 380

Glu Asn Gln Lys Ile Leu Ile Glu Asp Ala Arg Gln Thr Leu Glu Gln
385                 390                 395                 400

Asn Val Ile Asp Ala Val Arg Asp Leu Gly Thr Arg Trp Arg Gln Tyr
            405                 410                 415

Gln Ile Ala Gln Arg Ala Thr Ala Leu Ser Arg Lys Leu Glu Ile
        420                 425                 430

Glu Arg Glu Lys Leu Arg Val Gly Arg Ser Ser Asn Phe Gln Val Leu
    435                 440                 445

```
Ser Phe Glu Thr Asp Leu Arg Asn Val Glu Asn Thr Gln Leu Asn Ala
    450                 455                 460

Leu Ile Ser Phe Leu Asn Ala Gln Thr Gln Leu Asp Leu Ile Val Gly
465                 470                 475                 480

Met Thr Leu Asp Ser Trp Glu Ile Ser Leu Asn Asp His
                485                 490

<210> SEQ ID NO 44
<211> LENGTH: 425
<212> TYPE: PRT
<213> ORGANISM: Pseudomonas aeruginosa

<400> SEQUENCE: 44

Met Arg Gly Arg Arg Gln Tyr Ala Arg Lys Gly Arg His Gly Lys
1               5                   10                  15

Gly Ala Ile Trp Leu Leu Ser Leu Gly Leu Pro Met Phe Ala Ser Ala
                20                  25                  30

Met Pro Leu Asp Gln Ala Val Arg Ala Gly Leu Ala Ile His Pro Glu
            35                  40                  45

Val Arg Ser Ala Met Ala Glu Ala Asp Arg Ala Gly Thr Glu Val Glu
50                  55                  60

Met Ala Lys Gly Gly Tyr Tyr Pro Ser Val Thr Met Ser Gly Gly Pro
65                  70                  75                  80

Gln Glu Phe Asp Phe Gly Glu Ile Val Tyr Asp Leu Thr Ala Ser Gln
                85                  90                  95

Met Leu Tyr Asp Trp Gly Arg Val Thr Ser Lys Val Asp Ser Ala Ser
            100                 105                 110

Ala Thr Gln Arg Lys Leu Ser Glu Ala Val Leu Val Ala Arg Asp Asp
        115                 120                 125

Ala Ala Leu Asp Ile Val Glu Thr Tyr Leu Asp Val Leu Ala Ser Glu
    130                 135                 140

Arg Arg Val Glu Ala Val Arg Glu His Ile Gln Arg Leu Asp Gly Ile
145                 150                 155                 160

Arg Glu Met Thr Gln Ala Arg Gly Gly Asp Gly Tyr Ala Asp Arg Ser
                165                 170                 175

Glu Leu Asp Arg Ala Asn Leu Glu Leu Ser Arg Ala Gln Glu Gln Leu
            180                 185                 190

Ser Leu Glu Lys Gly Asn Leu Gln Asp Ala Arg Asn Gln Tyr Ala Ile
        195                 200                 205

Leu Val Gly Gln Glu Pro Ala Asp Leu Val Glu Pro Glu Pro Met Ser
    210                 215                 220

Leu Gln Arg Tyr Leu Ala Ala Ser Asp Met Ala Arg Val Ile Arg Glu
225                 230                 235                 240

Ser Pro Leu Gln Arg Lys Ala Leu Glu Asp Ala Asn Val Ala Glu Ala
                245                 250                 255

Glu Val Arg Glu Ala Lys Ala Ser Leu Leu Pro Gln Leu Asn Leu Glu
            260                 265                 270

Ala Ser Ala Leu Arg Arg Glu Ile Gly Gly His Pro Glu Ser Asp Ser
        275                 280                 285

Val Val Ser Leu Arg Phe Arg Met Asp Thr Phe Gln Gly Leu Ser Asn
    290                 295                 300

Phe Arg Arg Pro Thr Ala Ala Gln Gln Arg Leu Glu Ser Ala Lys Trp
305                 310                 315                 320

Ser Ala Asp Ala Met Gln Arg Asp Ile Arg Arg Gln Leu Gln Asn Leu
                325                 330                 335
```

Phe Asp Asn Gly Asp Thr Leu Arg Trp Arg Glu Gln Ser Leu Thr Gln
                340                 345                 350

Gln Val Thr Glu Ser Glu Gln Val Gly Glu Leu Tyr Arg Glu Gln Phe
                355                 360                 365

Glu Val Gly Arg Arg Asp Val Ile Asp Leu Leu Asn Val Gln Arg Glu
370                 375                 380

Arg Phe Glu Ala Glu Arg Gln Leu Ile Asn Leu Arg Ile Glu Arg Lys
385                 390                 395                 400

Arg Ile Glu Tyr Arg Ala Ala Ala Gln Val Gly Leu Leu Gly Pro Leu
                405                 410                 415

Leu Glu Asn Arg Leu Asn His Gly Ser
                420                 425

<210> SEQ ID NO 45
<211> LENGTH: 761
<212> TYPE: PRT
<213> ORGANISM: Bacteriophage phiCTX

<400> SEQUENCE: 45

Met Thr Ser Pro Lys Tyr Gly Gly Leu Leu Thr Asp Ile Gly Ala Ala
1               5                   10                  15

Ala Leu Ile Ala Ala Ser Glu Ala Gly Lys Lys Trp Gln Pro Thr His
                20                  25                  30

Met Leu Ile Gly Asp Ala Gly Ala Pro Gly Glu Thr Ala Asp Pro
                35                  40                  45

Ile Pro Ser Ala Ala Gln Thr Lys Leu Ile Arg Gln Arg Tyr Arg Ala
50                  55                  60

Gln Leu Asn Arg Leu Phe Val Ser Glu Gln Ser Ala Asn Val Leu Val
65                  70                  75                  80

Ala Glu Leu Val Leu Pro Met Ala Ile Gly Gly Phe Trp Ile Arg Glu
                85                  90                  95

Ile Gly Leu Glu Asp Ala Asp Gly Lys Phe Val Ala Val Ala Asn Cys
                100                 105                 110

Pro Pro Ser Phe Lys Ala Ser Val Glu Ser Gly Ser Ala Arg Thr Gln
                115                 120                 125

Thr Ile Arg Val Gln Ile Ile Leu Ser Gly Met Glu His Val Glu Leu
                130                 135                 140

Ile Ile Asp Asp Gly Ile Val Tyr Ala Thr Gln Asp Trp Val Thr Ala
145                 150                 155                 160

Lys Val Ala Ala Asp Phe Lys Gly Arg Lys Val Leu Ala Gly Asn Gly
                165                 170                 175

Leu Val Gly Gly Gly Asp Leu Ser Ala Asp Arg Thr Ile Ala Leu Pro
                180                 185                 190

Ala Ser Gly Val Gly Ala Gly Thr Tyr Arg Ala Val Thr Val Asn Ala
                195                 200                 205

Asn Gly Ile Val Thr Ala Gly Ser Asn Pro Thr Thr Leu Gly Gly Tyr
                210                 215                 220

Gly Ile Thr Asp Ala Leu His Ala Ser Glu Ala Val Thr Thr Pro Thr
225                 230                 235                 240

Ala Asn Lys Leu Leu Arg Leu Asn Ala Ala Gly Leu Leu Pro Ala Ser
                245                 250                 255

Ile Thr Gly Asn Ala Ala Thr Ala Ser Arg Leu Ala Ala Pro Ile Thr
                260                 265                 270

Leu Ser Ala Ser Gly Asp Ala Thr Trp Ser Ala Arg Phe Asp Gly Ala
                275                 280                 285

-continued

Thr Asn Val Asn Gly Val Leu Thr Leu Ala Asn Ser Gly Val Thr Ala
    290                 295                 300

Gly Thr Tyr Ala Lys Val Thr Val Asn Ala Lys Gly Leu Val Thr Gly
305                 310                 315                 320

Ala Thr Gly Leu Val Ala Ser Asp Ile Pro Ala Leu Asp Ala Gly Lys
                325                 330                 335

Ile Thr Ser Gly Ile Leu Pro Ala Ala Arg Gly Gly Thr Gly Asn Gly
            340                 345                 350

Ile Gly Gln Ala Ala Thr Ala Val Lys Leu Val Ala Pro Arg Thr Ile
        355                 360                 365

Tyr Leu Gly Gly Asp Val Ser Gly Ser Thr Thr Phe Asp Gly Ser Ala
    370                 375                 380

Asn Ala Gly Ile Thr Val Thr Leu Ala Asn Gly Val Asn Ala Gly Ser
385                 390                 395                 400

Tyr Pro Lys Val Thr Val Asn Ala Lys Gly Leu Val Thr Gly Gly Gly
                405                 410                 415

Gly Leu Thr Ala Ala Asp Ile Pro Ala Leu Asp Ala Ser Lys Ile Ala
            420                 425                 430

Thr Gly Arg Leu Asp Leu Glu Arg Leu Pro Leu Val Ser Gln Gly Leu
        435                 440                 445

Ala Thr Ala Val His Thr Ser Val Asp Pro Asn Ser Val Val Ile Pro
    450                 455                 460

Leu Val Leu Thr Asn His Ala Asn Gly Pro Val Ala Gly Arg Tyr Tyr
465                 470                 475                 480

Tyr Ile Gln Thr Met Phe Tyr Pro Thr Val Glu Gly Asn Ala Thr Gln
                485                 490                 495

Ile Ala Thr Gly Tyr Ala Gly Val Ala Asp Met Tyr Val Arg Tyr Ala
            500                 505                 510

Tyr Ala Ser Pro Ala Thr Thr Asp Ser Ser Lys Arg Glu Trp Ser Ala
        515                 520                 525

Trp Val Arg Cys Asp Leu Gly Gly Ala Phe Ala His Ala Pro Asp Gly
    530                 535                 540

Glu Leu Gly Gly Tyr Val Asn Leu Asp Ser Met Ile Ala Ser Gly Trp
545                 550                 555                 560

Trp His Gln Pro Phe Thr Ala Asn Ala Lys Asn Gly Ala Asn Tyr Pro
                565                 570                 575

Val Gly Glu Ala Gly Leu Leu Thr Val His Ala Pro Thr Ala Ser Met
            580                 585                 590

Ile Tyr Gln Thr Tyr Arg Gly Tyr Ala Ala Gly Gly Leu Tyr Trp Arg
        595                 600                 605

Cys Arg Tyr Asn Gly Thr Trp Ser Ala Trp Tyr Arg Ala Trp Asp Ser
    610                 615                 620

Gly Asn Phe Asn Pro Ala Asn Tyr Val Ala Lys Ser Glu Tyr Ser Trp
625                 630                 635                 640

Ala Ser Leu Pro Gly Lys Pro Ser Asn Phe Pro Pro Ser Val His Val
                645                 650                 655

His Ser Ala Ala Ser Arg Gly Val Ser Gly Trp Tyr Lys Asn Asn Asp
            660                 665                 670

Thr Gly Val Ile Phe Gln Trp Val Asn Leu Ser Ile Gly Asp His Pro
        675                 680                 685

Gly Gly Val Ile Asp Arg Val Val Thr Phe Pro Ile Ala Phe Pro Asn
    690                 695                 700

Ala Cys Leu His Val Val Pro Thr Val Arg Glu Asn Gly Arg Pro Ala

```
                    705                 710                 715                 720
Ile Pro Ala Ser Thr Val Thr Val Ala Glu Lys Ala Arg Thr Ala Thr
                725                 730                 735

Asn Cys Thr Ile Val Ser Ser Glu Tyr Ile Gly Asn Val Gln Asn Phe
            740                 745                 750

Gly Ile Asn Val Phe Ala Ile Gly Tyr
        755                 760
```

```
<210> SEQ ID NO 46
<211> LENGTH: 21
<212> TYPE: DNA
<213> ORGANISM: Artificial Sequence
<220> FEATURE:
<223> OTHER INFORMATION: AV085 primer

<400> SEQUENCE: 46
gcttcaatgt gcagcgtttg c                                            21

<210> SEQ ID NO 47
<211> LENGTH: 40
<212> TYPE: DNA
<213> ORGANISM: Artificial Sequence
<220> FEATURE:
<223> OTHER INFORMATION: AV088 primer

<400> SEQUENCE: 47
gccacaccgg tagcggaaag gccaccgtat tcggagtat                         40

<210> SEQ ID NO 48
<211> LENGTH: 40
<212> TYPE: DNA
<213> ORGANISM: Artificial Sequence
<220> FEATURE:
<223> OTHER INFORMATION: AV087 primer

<400> SEQUENCE: 48
atactccgaa atacggtggc ctttccgcta ccggtgtggc                        40

<210> SEQ ID NO 49
<211> LENGTH: 31
<212> TYPE: DNA
<213> ORGANISM: Artificial Sequence
<220> FEATURE:
<223> OTHER INFORMATION: AV086 primer

<400> SEQUENCE: 49
tccttgaatt ccgcttgctg ccgaagttct t                                 31

<210> SEQ ID NO 50
<211> LENGTH: 38
<212> TYPE: DNA
<213> ORGANISM: Artificial Sequence
<220> FEATURE:
<223> OTHER INFORMATION: AV110 primer

<400> SEQUENCE: 50
tttattagcg gaagagccga ctgcacggtg caccaatg                          38

<210> SEQ ID NO 51
<211> LENGTH: 38
<212> TYPE: DNA
<213> ORGANISM: Artificial Sequence
<220> FEATURE:
<223> OTHER INFORMATION: AV114 primer

<400> SEQUENCE: 51
```

```
ccctcgaatt catgaatact gtttcctgtg tgaaattg                                    38

<210> SEQ ID NO 52
<211> LENGTH: 29
<212> TYPE: DNA
<213> ORGANISM: Artificial Sequence
<220> FEATURE:
<223> OTHER INFORMATION: AV118 primer

<400> SEQUENCE: 52
cttcctttca tgacgaccaa tactccgaa                                              29

<210> SEQ ID NO 53
<211> LENGTH: 30
<212> TYPE: DNA
<213> ORGANISM: Artificial Sequence
<220> FEATURE:
<223> OTHER INFORMATION: AV116 primer

<400> SEQUENCE: 53
accacgaatt cttcatcgtc caaatgcctc                                             30

<210> SEQ ID NO 54
<211> LENGTH: 31
<212> TYPE: DNA
<213> ORGANISM: Artificial Sequence
<220> FEATURE:
<223> OTHER INFORMATION: AV107 primer

<400> SEQUENCE: 54
caccatctag acaatacgag agcgacaagt c                                           31

<210> SEQ ID NO 55
<211> LENGTH: 34
<212> TYPE: DNA
<213> ORGANISM: Artificial Sequence
<220> FEATURE:
<223> OTHER INFORMATION: AV091 primer

<400> SEQUENCE: 55
tcctcaagct tacgttggtt accgtaacgc cgtg                                        34

<210> SEQ ID NO 56
<211> LENGTH: 30
<212> TYPE: DNA
<213> ORGANISM: Artificial Sequence
<220> FEATURE:
<223> OTHER INFORMATION: AV118 and AV127 primers

<400> SEQUENCE: 56
ttctttaagc ttttccttca cccagtcctg                                             30

<210> SEQ ID NO 57
<211> LENGTH: 29
<212> TYPE: DNA
<213> ORGANISM: Artificial Sequence
<220> FEATURE:
<223> OTHER INFORMATION: AV124 primer

<400> SEQUENCE: 57
cctcctgaat tcttattgcg gcatttccg                                              29

<210> SEQ ID NO 58
<211> LENGTH: 29
<212> TYPE: DNA
<213> ORGANISM: Artificial Sequence
```

```
<220> FEATURE:
<223> OTHER INFORMATION: AV126 primer

<400> SEQUENCE: 58
tccttcgaat tcttacacct gcgcaacgt                                   29

<210> SEQ ID NO 59
<211> LENGTH: 29
<212> TYPE: DNA
<213> ORGANISM: Artificial Sequence
<220> FEATURE:
<223> OTHER INFORMATION: AV124 and AV125 primers

<400> SEQUENCE: 59
cctcctgaat tcttattgcg gcatttccg                                   29

<210> SEQ ID NO 60
<211> LENGTH: 875
<212> TYPE: PRT
<213> ORGANISM: Bacteriophage phiV10

<400> SEQUENCE: 60
```

| | | | | | | | | | | | | | | |
|---|---|---|---|---|---|---|---|---|---|---|---|---|---|---|
| Met | Thr | Val | Ser | Thr | Glu | Val | Asn | His | Asn | Glu | Tyr | Thr | Gly | Asn | Gly |
| 1 | | | | 5 | | | | | 10 | | | | | 15 | |
| Val | Thr | Thr | Ser | Phe | Pro | Tyr | Thr | Phe | Arg | Val | Phe | Lys | Glu | Ser | Asp |
| | | | 20 | | | | | 25 | | | | | 30 | | |
| Leu | Val | Val | Gln | Val | Val | Asp | Leu | Asn | Asp | Asn | Ile | Thr | Val | Leu | Thr |
| | | 35 | | | | | 40 | | | | | 45 | | | |
| Leu | Asp | Thr | Asp | Tyr | Thr | Val | Thr | Gly | Ala | Gly | Gly | Tyr | Glu | Gly | Gly |
| | 50 | | | | | 55 | | | | | 60 | | | | |
| Asn | Val | Ile | Leu | Ala | Thr | Ala | Leu | Ala | Asn | Gly | Tyr | Gln | Ile | Ser | Ile |
| 65 | | | | | 70 | | | | | 75 | | | | | 80 |
| Ser | Arg | Glu | Leu | Ser | Val | Thr | Gln | Glu | Thr | Asp | Leu | Arg | Asn | Gln | Gly |
| | | | | 85 | | | | | 90 | | | | | 95 | |
| Lys | Phe | Phe | Ala | Glu | Val | His | Glu | Asp | Ala | Phe | Asp | Lys | Leu | Thr | Met |
| | | | 100 | | | | | 105 | | | | | 110 | | |
| Leu | Ile | Gln | Gln | Val | Arg | Ser | Trp | Phe | Ser | Leu | Ala | Leu | Arg | Lys | Pro |
| | | 115 | | | | | 120 | | | | | 125 | | | |
| Ser | Phe | Val | Ala | Asn | Tyr | Tyr | Asp | Ala | Met | Asp | Asn | Tyr | Ile | Arg | Asn |
| | 130 | | | | | 135 | | | | | 140 | | | | |
| Leu | Arg | Asp | Pro | Val | Arg | Pro | Gln | Asp | Ala | Ala | Thr | Lys | Lys | Tyr | Val |
| 145 | | | | | 150 | | | | | 155 | | | | | 160 |
| Asp | Gly | Val | Ala | Glu | Thr | Asn | Leu | Ser | Arg | Thr | Leu | Arg | Thr | Pro | Glu |
| | | | | 165 | | | | | 170 | | | | | 175 | |
| Pro | Ile | Pro | Ala | Leu | Pro | Gly | Ile | Glu | Gln | Arg | Lys | Asn | Lys | Ile | Val |
| | | | 180 | | | | | 185 | | | | | 190 | | |
| Ala | Met | Asp | Asp | Thr | Gly | Asn | Pro | Ile | Met | Val | Leu | Pro | Glu | Ser | Gly |
| | | 195 | | | | | 200 | | | | | 205 | | | |
| Ser | Ala | Thr | Asp | Val | Met | Ile | Gln | Leu | Ala | Ala | Asn | Asp | Gly | Phe | Lys |
| | 210 | | | | | 215 | | | | | 220 | | | | |
| Phe | Ile | Gly | Gln | Cys | Pro | Asp | Ile | Leu | Thr | Leu | Arg | Thr | Ile | Glu | Pro |
| 225 | | | | | 230 | | | | | 235 | | | | | 240 |
| Glu | Lys | Asn | Gly | Gln | Arg | Ile | Thr | Leu | Arg | Gln | His | Thr | Ile | Gly | Thr |
| | | | | 245 | | | | | 250 | | | | | 255 | |
| Gly | Leu | Gly | Gly | Gly | Val | Phe | Arg | Ala | Val | Leu | Asp | Gly | Thr | Gly | Tyr |
| | | | 260 | | | | | 265 | | | | | 270 | | |
| Thr | Asp | Asp | Asp | Gly | Val | Val | Ile | Lys | Thr | Ala | Gly | Gly | Ser | Val | Trp |
| | | 275 | | | | | 280 | | | | | 285 | | | |

```
Leu Arg Val Asn Ala Asp Lys Val Asn Pro Phe Met Phe Gly Ala Thr
    290                 295                 300
Gly Val Ala Asp Asp Thr Ala Ala Leu Gln Lys Met Leu Glu Cys Gly
305                 310                 315                 320
Arg Ala Ala Glu Leu Gly Thr Asn Val Trp Lys Ala Ser Asn Leu Glu
                325                 330                 335
Leu Asn Asn Lys Ser Cys Ser Leu Ser Gly Ser Gly Leu His Val Ser
            340                 345                 350
Arg Ile Glu Gln Ile Ser Gly Ala Thr Gly Ala Leu Leu Thr Ile Thr
        355                 360                 365
Gln Asp Cys Ser Leu Ile Tyr Leu Ser Asp Cys Gly Leu Tyr Gly Asp
    370                 375                 380
Gly Ile Thr Ala Gly Thr Ser Gly Val Thr Met Glu Thr Gly Asn Pro
385                 390                 395                 400
Gly Gly Ala Pro Ser Tyr Pro Phe Asn Thr Ala Pro Asp Val Arg Arg
                405                 410                 415
Asp Leu Tyr Ile Ser Asn Val His Ile Thr Gly Phe Asp Glu Leu Gly
            420                 425                 430
Phe Asp Tyr Pro Glu Thr Asn Phe Ser Val Ser Thr His Gly Leu Phe
        435                 440                 445
Ile Arg Asn Ile Lys Lys Thr Gly Ala Lys Ile Gly Thr Thr Asp Phe
    450                 455                 460
Thr Trp Thr Asn Leu Gln Ile Asp Thr Cys Gly Gln Glu Cys Leu Val
465                 470                 475                 480
Leu Asp Gly Ala Gly Asn Cys Arg Ile Ile Gly Ala Lys Leu Ile Trp
                485                 490                 495
Ala Gly Ser Glu Asn Glu Thr Pro Tyr Ser Gly Leu Arg Ile Ser Asn
            500                 505                 510
Ser Gln Asn Val Asn Met Thr Gly Val Glu Leu Gln Asp Cys Ala Tyr
        515                 520                 525
Asp Gly Leu Tyr Ile Lys Asn Ser Thr Val Ala Ile Ser Gly Leu Asn
    530                 535                 540
Thr Asn Arg Asn Ser Ala Ser Ser Asn Leu Ser Tyr His Asn Met Val
545                 550                 555                 560
Phe Glu Asn Ser Ile Val Thr Val Asp Gly Tyr Val Cys Arg Asn Tyr
                565                 570                 575
Ala Ala Thr Ser Leu Tyr Asp Leu Asn Ser Gln Ala Gly Asn Val Arg
            580                 585                 590
Cys Ile Gly Ser Asp Ser Thr Val Leu Ile Asn Gly Ile Tyr Glu Ser
        595                 600                 605
Glu Val Asn Ser Glu Arg Leu Met Gly Asp Asn Leu Ile Gln Pro
    610                 615                 620
Tyr Ser Gly Asp Leu Ile Ile Asn Gly Leu Lys Asn Tyr Tyr Thr Tyr
625                 630                 635                 640
Thr Gly Ser Val Lys Asn Asn Ile Pro Thr Phe Asp Gly Val Val Thr
                645                 650                 655
Thr Ala Thr Tyr Val Ser Ala Pro Ser Ile Leu Gly Gln Gly Asn Met
            660                 665                 670
Leu Lys Leu Thr Gln Ser Asn Lys Asp Lys Leu Leu Phe Ser Asp Lys
        675                 680                 685
Val Ser Arg His Gly Cys Thr Ile Gly Leu Val Leu Ile Pro Ser Phe
    690                 695                 700
Thr Gly Ala Thr Thr Met Thr Ala Phe Thr Leu Gly Ser Gly Tyr Ser
```

```
                    705                 710                 715                 720
Pro Ser Gly Asn Ser Ala Val Met Gln Phe Ile Val Asn Ser Ser Gly
                725                 730                 735

Val Gln Thr Ile Ala Ile Leu Leu Ser Gly Asp Gly Ile Thr Gln Thr
            740                 745                 750

Leu Thr Ser Asp Leu Thr Thr Glu Gln Ala Leu Ala Ser Gly Gly Val
            755                 760                 765

Tyr His Phe Ala Met Gly Phe Ala Pro Gly Arg Leu Trp Trp Ser Ile
            770                 775                 780

Ile Asp Ile Asn Thr Gly Arg Arg Ile Arg Arg Ala Tyr Arg Gln Pro
785                 790                 795                 800

Asp Leu His Ala Ala Phe Asn Ser Ile Phe Asn Ser Gly Thr Ser Ser
                805                 810                 815

Ile Thr Ala Phe Ser Gly Pro Leu Ala Gly Asp Ile Ala Cys Glu Gly
                820                 825                 830

Ala Gly Ser His Val Tyr Val Gly Gly Phe Ser Ser Glu Ser Asp Tyr
            835                 840                 845

Ala Ala Ser Arg Met Tyr Gly Leu Phe Thr Pro Val Asp Leu Asp Lys
            850                 855                 860

Gln Tyr Ser Phe Arg Thr Leu Asn Gly Asn Ile
865                 870                 875

<210> SEQ ID NO 61
<211> LENGTH: 981
<212> TYPE: PRT
<213> ORGANISM: E.coli RS218

<400> SEQUENCE: 61

Met Thr Asp Ile Thr Ala Asn Val Ile Val Ser Met Pro Ser Gln Leu
1               5                   10                  15

Phe Thr Met Ala Arg Ser Phe Lys Ala Val Ala Asn Gly Lys Ile Tyr
            20                  25                  30

Ile Gly Lys Ile Asp Thr Asp Pro Val Asn Thr Glu Asn Gln Ile Gln
        35                  40                  45

Val Tyr Val Glu Asn Glu Asp Gly Ser His Val Pro Val Ser Gln Pro
    50                  55                  60

Ile Ile Ile Asn Ala Ala Gly Tyr Pro Val Tyr Asn Gly Gln Ile Ala
65                  70                  75                  80

Lys Phe Val Thr Val Gln Gly His Ser Met Ala Val Tyr Asp Ala Tyr
                85                  90                  95

Gly Ala Gln Gln Phe Tyr Phe Pro Asn Val Leu Lys Tyr Asp Pro Asp
            100                 105                 110

Gln Leu Arg Gln Leu Glu Asp Thr Asp Gly Ala Asn Lys Tyr Pro
            115                 120                 125

Lys Leu Gln Ile Ala Arg Trp Arg Asp Ser Tyr Asp Val Arg Gly Trp
        130                 135                 140

Gly Ala Ile Gly Asp Gly Val His Asp Thr Ser Ala Leu Ser Glu
145                 150                 155                 160

Leu Leu Ser Val Ala Thr Gly Gly Glu Lys Ile Asp Gly Arg Gly Leu
                165                 170                 175

Thr Phe Lys Val Ser Thr Leu Pro Asp Val Ser Arg Phe Lys Asn Ala
            180                 185                 190

Arg Phe Leu Phe Glu Arg Ile Pro Gly Gln Pro Leu Phe Tyr Val Ser
        195                 200                 205

Glu Asp Phe Ile Gln Gly Glu Leu Phe Lys Ile Thr Asp Thr Pro Trp
```

-continued

```
            210                 215                 220
Tyr Asn Ala Trp Thr Gln Asp Lys Thr Phe Val Tyr Asp Asn Val Ile
225                 230                 235                 240

Tyr Ala Pro Phe Met Ala Gly Asp Arg His Gly Val Asn Asn Leu His
                245                 250                 255

Val Ala Trp Val Arg Ser Gly Asp Asp Gly Lys Thr Trp Thr Thr Pro
                260                 265                 270

Glu Trp Leu Thr Asp Leu His Glu Asn Tyr Pro Thr Val Asn Tyr His
                275                 280                 285

Cys Met Ser Met Gly Val Val Arg Asn Arg Leu Phe Ala Val Ile Glu
                290                 295                 300

Thr Arg Thr Val Ser Gly Asn Lys Leu Gln Val Ala Glu Leu Trp Asp
305                 310                 315                 320

Arg Pro Met Ser Arg Ser Leu Arg Val Tyr Gly Gly Ile Thr Lys Ala
                325                 330                 335

Ala Asn Gln Gln Val Ala Tyr Ile Arg Ile Thr Asp His Gly Leu Phe
                340                 345                 350

Ala Gly Asp Phe Val Asn Phe Ser Asn Ser Gly Val Thr Gly Val Thr
                355                 360                 365

Gly Asn Met Thr Val Thr Val Ile Asp Lys Asn Thr Phe Thr Val
                370                 375                 380

Thr Thr Gln Asn Thr Gln Asp Val Asp Gln Asn Asn Glu Gly Arg Tyr
385                 390                 395                 400

Trp Ser Phe Gly Thr Ser Phe His Ser Ser Pro Trp Arg Lys Thr Ser
                405                 410                 415

Leu Gly Thr Ile Pro Ser Phe Val Asp Gly Ser Thr Pro Val Thr Glu
                420                 425                 430

Ile His Ser Phe Ala Thr Ile Ser Asp Asn Ser Phe Ala Val Gly Tyr
                435                 440                 445

His Asn Gly Asp Ile Gly Pro Arg Glu Leu Gly Ile Leu Tyr Phe Ser
                450                 455                 460

Asp Ala Phe Gly Ser Pro Gly Ser Phe Val Arg Arg Ile Pro Ala
465                 470                 475                 480

Glu Tyr Glu Ala Asn Ala Ser Glu Pro Cys Val Lys Tyr Tyr Asp Gly
                485                 490                 495

Ile Leu Tyr Leu Thr Thr Arg Gly Thr Leu Ser Thr Gln Pro Gly Ser
                500                 505                 510

Ser Leu His Arg Ser Ser Asp Leu Gly Thr Ser Trp Asn Ser Leu Arg
                515                 520                 525

Phe Pro Asn Asn Val His His Ser Asn Leu Pro Phe Ala Lys Val Gly
                530                 535                 540

Asp Glu Leu Ile Ile Phe Gly Ser Glu Arg Ala Phe Gly Glu Trp Glu
545                 550                 555                 560

Gly Gly Glu Pro Asp Asn Arg Tyr Ala Gly Asn Tyr Pro Arg Thr Phe
                565                 570                 575

Met Thr Arg Val Asn Val Asn Glu Trp Ser Leu Asp Asn Val Glu Trp
                580                 585                 590

Val Asn Val Thr Asp Gln Ile Tyr Gln Gly Gly Ile Val Asn Ser Ala
                595                 600                 605

Val Gly Val Gly Ser Val Cys Ile Lys Asp Asn Trp Leu Tyr Tyr Ile
                610                 615                 620

Phe Gly Gly Glu Asp Phe Leu Asn Pro Trp Ser Ile Gly Asp Asn Asn
625                 630                 635                 640
```

```
Arg Lys Tyr Pro Tyr Val His Asp Gly His Pro Ala Asp Leu Tyr Cys
            645                 650                 655

Phe Arg Val Lys Ile Lys Gln Glu Glu Phe Val Ser Arg Asp Phe Val
        660                 665                 670

Tyr Gly Ala Thr Pro Asn Arg Thr Leu Pro Thr Phe Met Ser Thr Ser
    675                 680                 685

Gly Val Arg Thr Val Pro Val Pro Val Asp Phe Thr Asp Asp Val Ala
690                 695                 700

Val Gln Ser Leu Thr Val His Ala Gly Thr Ser Gly Gln Val Arg Ala
705                 710                 715                 720

Glu Val Lys Leu Glu Gly Asn Tyr Ala Ile Ile Ala Lys Lys Val Pro
                725                 730                 735

Ser Asp Asp Val Thr Ala Gln Arg Leu Ile Val Ser Gly Gly Glu Thr
            740                 745                 750

Thr Ser Ser Ala Asp Gly Ala Met Ile Thr Leu His Gly Ser Arg Ser
        755                 760                 765

Ser Thr Pro Arg Arg Ala Val Tyr Asn Ala Leu Glu His Leu Phe Glu
    770                 775                 780

Asn Gly Asp Val Lys Pro Tyr Leu Asp Asn Val Asn Ala Leu Gly Gly
785                 790                 795                 800

Pro Gly Asn Arg Phe Ser Ile Val Tyr Leu Gly Ser Asn Pro Val Val
                805                 810                 815

Thr Ser Asp Gly Thr Leu Lys Thr Glu Pro Val Ser Pro Asp Glu Thr
            820                 825                 830

Leu Leu Asp Ala Trp Gly Asp Val Arg Tyr Ile Ala Tyr Lys Trp Leu
        835                 840                 845

Asn Ala Val Ala Ile Lys Gly Glu Gly Ala Arg Ile His His Gly
    850                 855                 860

Val Ile Ala Gln Gln Leu Arg Asp Val Leu Ile Ser His Gly Leu Met
865                 870                 875                 880

Glu Glu Glu Ser Thr Thr Cys Arg Tyr Ala Phe Leu Cys Tyr Asp Asp
                885                 890                 895

Tyr Pro Ala Val Tyr Asp Asp Val Ile Thr Gly Gln Arg Glu Met Pro
            900                 905                 910

Leu Thr Asp Asn Asp Gly Ser Ile Ile Val Asp Glu Asp Asn Pro
        915                 920                 925

Val Met Val Met Glu Asp Ile Ile Glu Arg Val Glu Ile Thr Pro Ala
930                 935                 940

Gly Ser Arg Trp Gly Val Arg Pro Asp Leu Leu Phe Tyr Ile Glu Ala
945                 950                 955                 960

Ala Trp Gln Arg Arg Glu Ile Glu Arg Ile Lys Ala Arg Leu Asp Leu
                965                 970                 975

Ile Glu Gly Lys His
            980

<210> SEQ ID NO 62
<211> LENGTH: 710
<212> TYPE: PRT
<213> ORGANISM: Bacteriophage HK620

<400> SEQUENCE: 62

Met Thr Asp Ser Ile Asn Ala Asn Val Val Ser Met Pro Ser Gln
1               5                   10                  15

Leu Phe Thr Met Ala Arg Ser Phe Lys Ala Val Ala Asn Gly Lys Ile
                20                  25                  30
```

-continued

```
Tyr Ile Gly Lys Ile Asp Thr Asp Pro Val Asn Pro Glu Asn Arg Ile
             35                  40                  45

Gln Val Tyr Val Glu Asn Glu Asp Gly Ser His Val Pro Val Ser Gln
 50                  55                  60

Pro Ile Ile Ile Asn Ala Ala Gly Tyr Pro Val Tyr Asn Gly Gln Ile
 65                  70                  75                  80

Ala Lys Phe Val Thr Val Gln Gly His Ser Met Ala Val Tyr Asp Ala
                 85                  90                  95

Tyr Gly Ala Gln Gln Phe Tyr Phe Pro Asn Val Leu Lys Tyr Asp Pro
                100                 105                 110

Asp Gln Phe Arg Ala Ile Ile Glu Ser Pro Glu Gly Ala Gly His Val
                115                 120                 125

Gly Tyr Gln Tyr Arg Arg Asn Thr Gly Ser Thr Met Arg Met Val Ser
        130                 135                 140

Asp Val Leu Asp Glu Arg Val Ser Leu Trp Asp Phe His Cys Asp Pro
145                 150                 155                 160

Ser Gly Asn Val Ile Gln Pro Gly Pro Asn Val Asp Ser Arg Gln Tyr
                165                 170                 175

Leu Gln Ala Ala Ile Asp Tyr Val Ser Ser Asn Gly Gly Thr Ile
                180                 185                 190

Thr Ile Pro Ala Gly Tyr Thr Trp Tyr Leu Gly Ser Tyr Gly Val Gly
        195                 200                 205

Gly Ile Ala Gly His Ser Gly Ile Ile Gln Leu Arg Ser Asn Val Asn
210                 215                 220

Leu Asn Ile Glu Gly Arg Ile His Leu Ser Pro Phe Phe Asp Leu Lys
225                 230                 235                 240

Pro Phe Gln Val Phe Val Gly Phe Asp Asn Gly Asp Pro Ala Ser Ser
                245                 250                 255

Gly Asn Leu Glu Asn Cys His Ile Tyr Gly His Gly Val Val Asp Phe
            260                 265                 270

Gly Gly Tyr Glu Phe Gly Ala Ser Ser Gln Leu Arg Asn Gly Val Ala
        275                 280                 285

Phe Gly Arg Ser Tyr Asn Cys Ser Val Thr Gly Ile Thr Phe Gln Asn
290                 295                 300

Gly Asp Val Thr Trp Ala Ile Thr Leu Gly Trp Asn Gly Tyr Gly Ser
305                 310                 315                 320

Asn Cys Tyr Val Arg Lys Cys Arg Phe Ile Asn Leu Val Asn Ser Ser
                325                 330                 335

Val Asn Ala Asp His Ser Thr Val Tyr Val Asn Cys Pro Tyr Ser Gly
                340                 345                 350

Val Glu Ser Cys Tyr Phe Ser Met Ser Ser Ser Phe Ala Arg Asn Ile
            355                 360                 365

Ala Cys Ser Val Glu Leu His Gln His Asp Thr Phe Tyr Arg Gly Ser
    370                 375                 380

Thr Val Asn Gly Tyr Cys Arg Gly Ala Tyr Val Val Met His Ala Ala
385                 390                 395                 400

Glu Ala Ala Gly Ala Gly Ser Tyr Ala Tyr Asn Met Gln Val Glu Asn
                405                 410                 415

Asn Ile Ala Val Ile Tyr Gly Gln Phe Val Ile Leu Gly Ser Asp Val
            420                 425                 430

Thr Ala Thr Val Ser Gly His Leu Asn Asp Val Ile Val Ser Gly Asn
        435                 440                 445

Ile Val Ser Ile Gly Glu Arg Ala Ala Phe Ser Ala Pro Phe Gly Ala
450                 455                 460
```

```
Phe Ile Asp Ile Gly Pro Asp Asn Ser Gly Ala Ser Asn Val Gln Asp
465                 470                 475                 480

Ile Gln Arg Val Leu Val Thr Gly Asn Ser Phe Tyr Ala Pro Ala Asn
                485                 490                 495

Ile Thr Asp Ser Ala Ala Ile Thr Leu Arg Ala Asn Leu Asn Gly Cys
            500                 505                 510

Thr Phe Ile Ala Asn Asn Phe Asp Cys Arg Tyr Met Val Tyr Asn Ala
        515                 520                 525

Pro Gly Thr Thr Ser Pro Val Val Gln Asn Leu Val Trp Asp Lys Ser
    530                 535                 540

Asn Val Ile Gly Gly Thr His Ala Asn Gln Arg Ala Gly Gln Asn Leu
545                 550                 555                 560

Phe Asp Met Gln Phe Ala Ser Val Val Asn Ser Thr Ile Glu Val Gln
                565                 570                 575

Leu Ser Cys Glu Asp Leu Ser Met Phe Ser Cys Ile Leu Phe Pro Ala
            580                 585                 590

Ser Cys Gln Leu Ser Tyr Ser Lys Ile Thr Val Asp Ser Ala Trp Thr
        595                 600                 605

Lys Ser Met Ser Asn Thr Ala Val Phe Glu Gly Asn Gln Gln Ala Gly
    610                 615                 620

Ala Asn Val Tyr Val Ser Tyr Pro Ala Thr Val Asn Leu Thr Ser Tyr
625                 630                 635                 640

Asn Thr Gln Gly Ala Val Pro Phe Phe Ser Thr Asp Thr Asn Tyr Ala
                645                 650                 655

Trp Val Thr Ser Ala Tyr Ser Leu Ser Ile Asn Glu Asn Leu Asp Phe
            660                 665                 670

Ser Pro Pro Ala Thr Tyr Thr Asn Lys Ala Asn Gly Gln Leu Val Gly
        675                 680                 685

Val Gly Tyr Asn Glu Ile Gly Gly Val Arg Ser Val Ser Val Arg Leu
    690                 695                 700

Met Leu Gln Arg Gln Val
705             710

<210> SEQ ID NO 63
<211> LENGTH: 623
<212> TYPE: PRT
<213> ORGANISM: Phage sf6

<400> SEQUENCE: 63

Met Thr Asp Ile Ile Thr Asn Val Val Ile Gly Met Pro Ser Gln Leu
1               5                   10                  15

Phe Thr Met Ala Arg Ser Phe Lys Ala Val Ala Asn Gly Lys Ile Tyr
            20                  25                  30

Ile Gly Lys Ile Asp Thr Asp Pro Val Asn Pro Glu Asn Gln Ile Gln
        35                  40                  45

Val Tyr Val Glu Asn Glu Asp Gly Ser His Val Pro Val Ser Gln Pro
    50                  55                  60

Ile Val Ile Asn Ala Ala Gly Tyr Pro Val Tyr Asn Gly Gln Ile Ala
65                  70                  75                  80

Lys Phe Val Thr Glu Gln Gly His Ser Met Ala Val Tyr Asp Ala Tyr
                85                  90                  95

Gly Ser Gln Gln Phe Tyr Phe Gln Asn Val Leu Lys Tyr Asp Pro Asp
            100                 105                 110

Gln Phe Gly Pro Asp Leu Ile Glu Gln Leu Ala Gln Ser Gly Lys Tyr
        115                 120                 125
```

```
Ser Gln Asp Asn Thr Lys Gly Asp Ala Met Ile Gly Val Lys Gln Pro
    130                 135                 140
Leu Pro Lys Ala Val Leu Arg Thr Gln His Asp Lys Asn Lys Glu Ala
145                 150                 155                 160
Ile Ser Ile Leu Asp Phe Gly Val Ile Asp Gly Val Thr Asp Asn
                165                 170                 175
Tyr Gln Ala Ile Gln Asn Ala Ile Asp Ala Val Ala Ser Leu Pro Ser
            180                 185                 190
Gly Gly Glu Leu Phe Ile Pro Ala Ser Asn Gln Ala Val Gly Tyr Ile
            195                 200                 205
Val Gly Ser Thr Leu Leu Ile Pro Gly Gly Val Asn Ile Arg Gly Val
        210                 215                 220
Gly Lys Ala Ser Gln Leu Arg Ala Lys Ser Gly Leu Thr Gly Ser Val
225                 230                 235                 240
Leu Arg Leu Ser Tyr Asp Ser Asp Thr Ile Gly Arg Tyr Leu Arg Asn
                245                 250                 255
Ile Arg Val Thr Gly Asn Asn Thr Cys Asn Gly Ile Asp Thr Asn Ile
            260                 265                 270
Thr Ala Glu Asp Ser Val Ile Arg Gln Val Tyr Gly Trp Val Phe Asp
        275                 280                 285
Asn Val Met Val Asn Glu Val Glu Thr Ala Tyr Leu Met Gln Gly Leu
290                 295                 300
Trp His Ser Lys Phe Ile Ala Cys Gln Ala Gly Thr Cys Arg Val Gly
305                 310                 315                 320
Leu His Phe Leu Gly Gln Cys Val Ser Val Ser Val Ser Ser Cys His
                325                 330                 335
Phe Ser Arg Gly Asn Tyr Ser Ala Asp Glu Ser Phe Gly Ile Arg Ile
            340                 345                 350
Gln Pro Gln Thr Tyr Ala Trp Ser Ser Glu Ala Val Arg Ser Glu Ala
        355                 360                 365
Ile Ile Leu Asp Ser Glu Thr Met Cys Ile Gly Phe Lys Asn Ala Val
        370                 375                 380
Tyr Val His Asp Cys Leu Asp Leu His Met Glu Gln Leu Asp Leu Asp
385                 390                 395                 400
Tyr Cys Gly Ser Thr Gly Val Val Ile Glu Asn Val Asn Gly Gly Phe
            405                 410                 415
Ser Phe Ser Asn Ser Trp Ile Ala Ala Asp Ala Asp Gly Thr Glu Gln
            420                 425                 430
Phe Thr Gly Ile Tyr Phe Arg Thr Pro Thr Ser Thr Gln Ser His Lys
        435                 440                 445
Ile Val Ser Gly Val His Ile Asn Thr Ala Asn Lys Thr Ala Ala
        450                 455                 460
Asn Asn Gln Ser Ile Ala Ile Glu Gln Ser Ala Ile Phe Val Phe Val
465                 470                 475                 480
Ser Gly Cys Thr Leu Thr Gly Asp Glu Trp Ala Val Asn Ile Val Asp
            485                 490                 495
Ile Asn Glu Cys Val Ser Phe Asp Lys Cys Ile Phe Asn Lys Pro Leu
            500                 505                 510
Arg Tyr Leu Arg Ser Gly Gly Val Ser Val Thr Asp Cys Tyr Leu Ala
        515                 520                 525
Gly Ile Thr Glu Val Gln Lys Pro Glu Gly Arg Tyr Asn Thr Tyr Arg
        530                 535                 540
Gly Cys Ser Gly Val Pro Ser Val Asn Gly Ile Ile Asn Val Pro Val
```

```
             545                 550                 555                 560
Ala Val Gly Ala Thr Ser Gly Ser Ala Ala Ile Pro Asn Pro Gly Asn
                565                 570                 575

Leu Thr Tyr Arg Val Arg Ser Leu Phe Gly Asp Pro Ala Ser Ser Gly
                580                 585                 590

Asp Lys Val Ser Val Ser Gly Val Thr Ile Asn Val Thr Arg Pro Ser
                595                 600                 605

Pro Val Gly Val Ala Leu Pro Ser Met Val Glu Tyr Leu Ala Ile
    610                 615                 620

<210> SEQ ID NO 64
<211> LENGTH: 667
<212> TYPE: PRT
<213> ORGANISM: Phage ST64T

<400> SEQUENCE: 64

Met Thr Asp Ile Thr Ala Asn Val Val Ser Asn Pro Arg Pro Ile
1               5                   10                  15

Phe Thr Glu Ser Arg Ser Phe Lys Ala Val Ala Asn Gly Lys Ile Tyr
                20                  25                  30

Ile Gly Gln Ile Asp Thr Asp Pro Val Asn Pro Ala Asn Gln Ile Pro
            35                  40                  45

Val Tyr Ile Glu Asn Glu Asp Gly Ser His Val Gln Ile Ala Gln Pro
    50                  55                  60

Leu Ile Ile Asn Ala Ala Gly Lys Ile Val Tyr Asn Gly Gln Leu Val
65                  70                  75                  80

Lys Ile Val Thr Val Gln Gly His Ser Met Ala Ile Tyr Asp Ala Asn
                85                  90                  95

Gly Ser Gln Val Asp Tyr Ile Ala Asn Val Leu Lys Tyr Asp Pro Asp
            100                 105                 110

Gln Tyr Ser Ile Glu Ala Asp Lys Lys Phe Lys Tyr Ser Val Lys Leu
        115                 120                 125

Ser Asp Tyr Pro Thr Leu Gln Asp Ala Ala Ser Ala Ala Val Asp Gly
    130                 135                 140

Leu Leu Ile Asp Val Asp Tyr His Phe Tyr Asn Gly Glu Lys Val Asp
145                 150                 155                 160

Phe Gly Gly Lys Val Leu Thr Ile Glu Cys Lys Ala Lys Phe Ile Gly
                165                 170                 175

Asp Gly Asn Leu Ile Phe Thr Lys Leu Gly Lys Gly Ser Arg Ile Ala
            180                 185                 190

Gly Val Phe Met Glu Ser Thr Thr Thr Pro Trp Val Ile Lys Pro Trp
        195                 200                 205

Thr Asp Asp Asn Gln Trp Leu Thr Asp Ala Ala Ala Val Val Ala Thr
    210                 215                 220

Leu Lys Gln Ser Lys Thr Asp Gly Tyr Gln Pro Thr Val Ser Asp Tyr
225                 230                 235                 240

Val Lys Phe Pro Gly Ile Glu Thr Leu Leu Pro Pro Asn Ala Lys Gly
                245                 250                 255

Gln Asn Ile Thr Ser Thr Leu Glu Ile Arg Glu Cys Ile Gly Val Glu
            260                 265                 270

Val His Arg Ala Ser Gly Leu Met Ala Gly Phe Leu Phe Arg Gly Cys
        275                 280                 285

His Phe Cys Lys Met Val Asp Ala Asn Asn Pro Ser Gly Gly Lys Asp
    290                 295                 300

Gly Ile Ile Thr Phe Glu Asn Leu Ser Gly Asp Trp Gly Lys Gly Asn
```

```
                    305                 310                 315                 320
Tyr Val Ile Gly Gly Arg Thr Ser Tyr Gly Ser Val Ser Ser Ala Gln
                    325                 330                 335

Phe Leu Arg Asn Asn Gly Gly Phe Glu Arg Asp Gly Gly Val Ile Gly
                    340                 345                 350

Phe Thr Ser Tyr Arg Ala Gly Glu Ser Gly Val Lys Thr Trp Gln Gly
                    355                 360                 365

Thr Val Gly Ser Thr Thr Ser Arg Asn Tyr Asn Leu Gln Phe Arg Asp
                    370                 375                 380

Ser Val Val Ile Tyr Pro Val Trp Asp Gly Phe Asp Leu Gly Ala Asp
385                 390                 395                 400

Thr Asp Met Asn Pro Glu Leu Asp Arg Pro Gly Asp Tyr Pro Ile Thr
                    405                 410                 415

Gln Tyr Pro Leu His Gln Leu Pro Leu Asn His Leu Ile Asp Asn Leu
                    420                 425                 430

Leu Val Arg Gly Ala Leu Gly Val Gly Phe Gly Met Asp Gly Lys Gly
                    435                 440                 445

Met Tyr Val Ser Asn Ile Thr Val Glu Asp Cys Ala Gly Ser Gly Ala
                    450                 455                 460

Tyr Leu Leu Thr His Glu Ser Val Phe Thr Asn Ile Ala Ile Ile Asp
465                 470                 475                 480

Thr Asn Thr Lys Asp Phe Gln Ala Asn Gln Ile Tyr Ile Ser Gly Ala
                    485                 490                 495

Cys Arg Val Asn Gly Leu Arg Leu Ile Gly Ile Arg Ser Thr Asp Gly
                    500                 505                 510

Gln Gly Leu Thr Ile Asp Ala Pro Asn Ser Thr Val Ser Gly Ile Thr
                    515                 520                 525

Gly Met Val Asp Pro Ser Arg Ile Asn Val Ala Asn Leu Ala Glu Glu
                    530                 535                 540

Gly Leu Gly Asn Ile Arg Ala Asn Ser Phe Gly Tyr Asp Ser Ala Ala
545                 550                 555                 560

Ile Lys Leu Arg Ile His Lys Leu Ser Lys Thr Leu Asp Ser Gly Ala
                    565                 570                 575

Leu Tyr Ser His Ile Asn Val Gly Pro Gly Ser Gly Ser Ala Trp Thr
                    580                 585                 590

Gln Leu Thr Ala Ile Ser Gly Asn Thr Pro Asp Ala Val Ser Leu Lys
                    595                 600                 605

Val Asn His Lys Asp Cys Arg Gly Ala Glu Ile Pro Phe Val Pro Asp
                    610                 615                 620

Ile Ala Ser Asp Asp Phe Ile Lys Asp Ser Ser Cys Phe Leu Pro Tyr
625                 630                 635                 640

Trp Glu Asn Asn Ser Thr Ser Leu Lys Ala Leu Val Lys Lys Pro Asn
                    645                 650                 655

Gly Glu Leu Val Arg Leu Thr Leu Ala Thr Leu
                    660                 665

<210> SEQ ID NO 65
<211> LENGTH: 1070
<212> TYPE: PRT
<213> ORGANISM: Phage epsilon 15

<400> SEQUENCE: 65

Met Thr Val Ser Thr Glu Val Asp His Asn Asp Tyr Thr Gly Asn Gly
1               5                   10                  15

Val Thr Thr Ser Phe Pro Tyr Thr Phe Arg Ile Phe Lys Lys Ser Asp
```

-continued

```
              20                  25                  30
Leu Val Val Gln Val Val Asp Leu Asn Glu Asn Ile Thr Glu Leu Ile
             35                  40                  45
Leu Asp Thr Asp Tyr Thr Val Thr Gly Ala Gly Tyr Thr Cys Gly
 50                  55                  60
Asp Val Val Leu Ser Ser Pro Leu Ala Asn Gly Tyr Gln Ile Ser Ile
 65                  70                  75                  80
Ser Arg Glu Leu Pro Val Thr Gln Glu Thr Asp Leu Arg Asn Gln Gly
             85                  90                  95
Lys Phe Phe Ala Glu Val His Glu Asn Ala Phe Asp Lys Leu Thr Met
            100                 105                 110
Leu Ile Gln Gln Val Arg Ser Trp Leu Ser Leu Ala Leu Arg Lys Pro
            115                 120                 125
Ser Phe Val Ala Asn Tyr Tyr Asp Ala Leu Gly Asn Tyr Ile Arg Asn
            130                 135                 140
Leu Arg Asp Pro Ser Arg Pro Gln Asp Ala Ala Thr Lys Asn Tyr Val
145                 150                 155                 160
Asp Asn Leu Ser Glu Gly Asn Asn Ser Tyr Ala Asp Asn Leu Phe Ser
                165                 170                 175
Arg Thr Leu Arg Val Pro Glu Lys Ile Asn Thr Leu Pro Ser Ser Leu
                180                 185                 190
Asp Arg Ala Asn Lys Ile Pro Ala Phe Asp Ser Asn Gly Asn Ala Ile
                195                 200                 205
Val Ile Ile Pro Gln Ser Gly Ser Ala Ser Asp Val Leu Ile Glu Leu
                210                 215                 220
Ala Lys Pro Ser Gly Ser Gly Leu Val Gly Phe Ser His Ser Asn Asn
225                 230                 235                 240
Tyr Asn Pro Gly Met Val Gly Glu Lys Leu Gln Asn Val Val Tyr Pro
                245                 250                 255
Thr Asp Ala Pro Phe Tyr Ala Pro Thr Asp Gly Thr Ser Asp Ala Thr
                260                 265                 270
Thr Ala Leu Gln Ser Ala Ile Thr His Cys Glu Gly Lys Asn Ala Val
                275                 280                 285
Leu Cys Ile Asn Lys Ser Phe Ser Val Ser Asp Ser Leu Ser Ile Ser
            290                 295                 300
Ser Pro Leu Cys Val Phe Ala Met Asn Glu Gln Cys Gly Ile Val Ser
305                 310                 315                 320
Ser Ala Pro Ala Gly His Ala Val Ile Phe Asn Gly Asp Asn Ile
                325                 330                 335
Cys Trp Asn Gly Gly Phe Ile Arg Gly Leu Asn Gln Pro Ser Ser Ser
            340                 345                 350
Thr Ile Arg Gln Asp Gly Val Leu Leu Asn Gly Asn Asp Cys Val Leu
            355                 360                 365
Asp Asn Val Ser Ile Asn Gly Phe Phe Ala Lys Gly Leu His Thr Ser
            370                 375                 380
Asn Ala Asp Gly Ser Gly Val Gly Ile Arg Asp Tyr Gly Thr Arg Asn
385                 390                 395                 400
Thr Ile Ser Lys Cys Arg Val Glu Tyr Asn Lys Phe Gly Ile Ser Leu
                405                 410                 415
Glu Gly Lys Asp Gly Trp Val Leu Gly Asn Tyr Val Ser Asn His Tyr
                420                 425                 430
Arg Met Ser Ser Glu Ala Lys Pro Trp Asp Asp Thr Ser Asn Tyr Trp
            435                 440                 445
```

-continued

```
Asp Gly Ile Val Gly Gly Glu Trp Leu Gly Val Ala Thr Gly Tyr
450                 455                 460

Leu Ile Asp Gly Asn Glu Phe Glu Asp Asn Gly Gln Ser Gly Ile Tyr
465                 470                 475                 480

Ala Gly Gly Asn Gly Gly Ile Phe Ala Lys Asn Arg Ile Thr Asn Asn
                485                 490                 495

His Ile His Gly Asn Trp Asn Arg Gly Ile Asp Phe Gly Val Val Gln
                500                 505                 510

Arg Leu Ala Asn Ser Asp Val Tyr Glu Asn Ile Ile Thr Asp Asn Ile
                515                 520                 525

Val His Asn Asn Arg Ala Ala Asn Ile Trp Leu Ala Gly Val Arg Asp
530                 535                 540

Ser Ile Ile Asn Asn Asn Ser Trp Phe Thr Asp Asp Tyr Arg Ser
545                 550                 555                 560

Met Phe Ala Gly Asn Phe Asp Ala Cys Val Cys Leu Thr Leu Ala Asp
                565                 570                 575

Gly Gly Glu Lys Ala Ala Pro Thr Gly Asn Gln Val Asn Gly Asn Arg
                580                 585                 590

Cys Lys Thr Leu Glu Ser Asp Asp Gln Ile Ser Gly Phe Thr Leu Asn
                595                 600                 605

Ile Thr Asp Thr Ala Arg Gly Asn Gln Val Arg Asp Asn Val Leu Ser
                610                 615                 620

Pro Ile Gly Glu Ala Tyr Ile Pro Asn Pro Glu Leu Tyr Ala Val Asn
625                 630                 635                 640

Asn Ile Asp Ile Pro Thr Glu Phe Ala Phe Thr Pro Gln Leu Ile Gly
                645                 650                 655

Gly Ser Gly Val Thr Leu Gly Asn Ser Ser Gly Lys Leu Thr Ala Asn
                660                 665                 670

Gly Asn Val Phe Ser Leu Ser Leu Ser Ile Ser Ala Gln Ser Val Ser
                675                 680                 685

Ser Pro Ser Gly Ser Leu Thr Ile Gly Tyr Ile Pro Gly Leu Ser Gly
                690                 695                 700

Thr Ser Val Arg His His Asn Val Arg Thr Glu Phe Tyr Asn Asn Leu
705                 710                 715                 720

Asn Thr Thr Met Gln Arg Ala Gln Pro Tyr Val Asn Ile Gly Asp Ser
                725                 730                 735

Ala Asp Gln Leu Arg Val Tyr Arg Leu Ala Asp Gly Leu Ser Lys Asp
                740                 745                 750

Asp Leu Leu Glu Tyr Phe Met Ser Asn Ser Asp Leu Arg Met Val Gly
                755                 760                 765

Asp Ile Glu Ile Glu Pro Tyr Asn Phe Ser Arg Ser Val Thr Val Val
                770                 775                 780

Gly His Ser Phe Cys Thr Ser Asp Val Met Ser Thr Glu Leu Asn Arg
785                 790                 795                 800

Leu Leu Gly Thr Asp Ile Tyr Asn Phe Ala Arg Gly Ala Ser Asp
                805                 810                 815

Val Glu Val Ala Met Ser Gln Glu Ala Ile Thr Arg Gln Tyr Ala Pro
                820                 825                 830

Val Gly Gly Ser Ile Pro Ala Ser Gly Ser Val Ala Leu Thr Pro Thr
                835                 840                 845

Glu Val Gly Ile Phe Trp Asn Gly Ala Thr Gly Lys Cys Ile Phe Gly
850                 855                 860

Gly Ile Asp Gly Thr Phe Ser Thr Thr Leu Val Asn Ala Gly Thr Gly
865                 870                 875                 880
```

```
Glu Thr Gln Leu Val Phe Thr Arg Asp Ser Ala Gly Ser Ala Val Ser
                885                 890                 895

Val Ser Thr Thr Ala Thr Phe Ala Met Arg Pro Tyr Thr Arg Phe Asn
            900                 905                 910

Thr Asn Thr Ile Pro Ala Gly Arg Lys His Ser Leu His Arg Asp Asp
            915                 920                 925

Ile Tyr Ile Val Trp Gly Gly Arg Asn Ser Thr Asp Tyr Thr Arg Tyr
    930                 935                 940

Val Ser Glu Leu His Thr Met Val Ala Asn Met His Thr Gln Arg Phe
945                 950                 955                 960

Val Ile Cys Pro Glu Phe Pro Tyr Asp Thr Glu Thr Gly Thr Thr
                965                 970                 975

Gly Ala Thr Asn Leu Ala Ala Leu Asn Asn Leu Lys Ala Asp Phe
            980                 985                 990

Pro Asp Asn Tyr Cys Gln Ile Ser Gly Val Asp Leu Leu Gln Asn Phe
            995                 1000                1005

Lys Ser Lys Tyr Asn Pro Ala Tyr Ala Gly Asp Val Thr Asp Ile
        1010                1015                1020

Ala Asn Gly Ile Thr Pro Arg Ser Leu Arg Glu Asp Asn Leu His
        1025                1030                1035

Pro Ser Glu Thr Leu Gln Pro Asn Gly Leu Tyr Ile Gly Ala Lys
        1040                1045                1050

Val Asn Ala Asp Phe Ile Ala Gln Phe Ile Lys Ser Lys Gly Trp
        1055                1060                1065

Gly Gly
        1070

<210> SEQ ID NO 66
<211> LENGTH: 440
<212> TYPE: PRT
<213> ORGANISM: galacturonase

<400> SEQUENCE: 66

Met Arg Gly Leu Phe Leu Leu Ala Leu Gly Ala Ile Pro Ala Leu Val
1               5                   10                  15

Ser Gly Gln Leu Ser Gly Ser Val Gly Pro Leu Thr Ser Ala Ser Thr
            20                  25                  30

Lys Gly Ala Thr Lys Thr Cys Asn Ile Leu Ser Tyr Gly Ala Val Ala
        35                  40                  45

Asp Asn Ser Thr Asp Val Gly Pro Ala Ile Thr Ser Ala Trp Ala Ala
    50                  55                  60

Cys Lys Ser Gly Gly Leu Val Tyr Ile Pro Ser Gly Asn Tyr Ala Leu
65                  70                  75                  80

Asn Thr Trp Val Thr Leu Thr Gly Gly Ser Ala Thr Ala Ile Gln Leu
                85                  90                  95

Asp Gly Ile Ile Tyr Arg Thr Gly Thr Ala Ser Gly Asn Met Ile Ala
            100                 105                 110

Val Thr Asp Thr Asp Phe Glu Leu Phe Ser Ser Ser Lys Gly
            115                 120                 125

Ala Val Gln Gly Phe Gly Tyr Val Tyr His Ala Glu Gly Thr Tyr Gly
        130                 135                 140

Ala Arg Ile Leu Arg Leu Thr Asp Val Thr His Phe Ser Val His Asp
145                 150                 155                 160

Ile Ile Leu Val Asp Ala Pro Ala Phe His Phe Thr Met Asp Thr Cys
                165                 170                 175
```

-continued

```
Ser Asp Gly Glu Val Tyr Asn Met Ala Ile Arg Gly Asn Glu Gly
            180                 185                 190

Gly Leu Asp Gly Ile Asp Val Trp Gly Ser Asn Ile Trp Val His Asp
        195                 200                 205

Val Glu Val Thr Asn Lys Asp Glu Cys Val Thr Val Lys Ser Pro Ala
210                 215                 220

Asn Asn Ile Leu Val Glu Ser Ile Tyr Cys Asn Trp Ser Gly Gly Cys
225                 230                 235                 240

Ala Met Gly Ser Leu Gly Ala Asp Thr Asp Val Thr Asp Ile Val Tyr
                245                 250                 255

Arg Asn Val Tyr Thr Trp Ser Ser Asn Gln Met Tyr Met Ile Lys Ser
                260                 265                 270

Asn Gly Gly Ser Gly Thr Val Ser Asn Val Leu Leu Glu Asn Phe Ile
                275                 280                 285

Gly His Gly Asn Ala Tyr Ser Leu Asp Ile Asp Gly Tyr Trp Ser Ser
        290                 295                 300

Met Thr Ala Val Ala Gly Asp Gly Val Gln Leu Asn Asn Ile Thr Val
305                 310                 315                 320

Lys Asn Trp Lys Gly Thr Glu Ala Asn Gly Ala Thr Arg Pro Pro Ile
                325                 330                 335

Arg Val Val Cys Ser Asp Thr Ala Pro Cys Thr Asp Leu Thr Leu Glu
                340                 345                 350

Asp Ile Ala Ile Trp Thr Glu Ser Gly Ser Ser Glu Leu Tyr Leu Cys
                355                 360                 365

Arg Ser Ala Tyr Gly Ser Gly Tyr Cys Leu Lys Asp Ser Ser Ser His
        370                 375                 380

Thr Ser Tyr Thr Thr Thr Ser Thr Val Thr Ala Ala Pro Ser Gly Tyr
385                 390                 395                 400

Ser Ala Thr Thr Met Ala Ala Asp Leu Ala Thr Ala Phe Gly Leu Thr
                405                 410                 415

Ala Ser Ile Pro Ile Pro Thr Ile Pro Thr Ser Phe Tyr Pro Gly Leu
                420                 425                 430

Thr Pro Tyr Ser Ala Leu Ala Gly
        435                 440

<210> SEQ ID NO 67
<211> LENGTH: 836
<212> TYPE: PRT
<213> ORGANISM: Artificial Sequence
<220> FEATURE:
<223> OTHER INFORMATION: Synthetic construct - R2 - V10 fusion protein

<400> SEQUENCE: 67

Met Ala Thr Asn Thr Pro Lys Tyr Gly Gly Leu Leu Thr Asp Ile Gly
1               5                   10                  15

Ala Ala Ala Leu Ala Thr Ala Ser Ala Ala Gly Lys Lys Trp Gln Pro
                20                  25                  30

Thr His Met Leu Ile Gly Asp Ala Gly Gly Ala Pro Gly Asp Thr Pro
            35                  40                  45

Asp Pro Leu Pro Ser Ala Ala Gln Lys Ser Leu Ile Asn Gln Arg His
        50                  55                  60

Arg Ala Gln Leu Asn Arg Leu Phe Val Ser Asp Lys Asn Ala Asn Thr
65                  70                  75                  80

Leu Val Ala Glu Val Val Leu Pro Val Glu Val Gly Gly Phe Trp Ile
                85                  90                  95
```

-continued

```
Arg Glu Ile Gly Leu Gln Asp Ala Asp Gly Lys Phe Val Ala Val Ser
            100                 105                 110
Asn Cys Pro Pro Ser Tyr Lys Ala Ala Met Glu Ser Gly Ser Ala Arg
        115                 120                 125
Thr Gln Thr Ile Arg Val Asn Ile Ala Leu Ser Gly Leu Glu Asn Val
130                 135                 140
Gln Leu Leu Ile Asp Asn Gly Ile Ile Tyr Ala Thr Gln Asp Trp Val
145                 150                 155                 160
Lys Glu Lys Val Leu Pro Glu Ser Gly Ser Ala Thr Asp Val Met Ile
                165                 170                 175
Gln Leu Ala Ala Asn Asp Gly Phe Lys Phe Ile Gly Gln Cys Pro Asp
            180                 185                 190
Ile Leu Thr Leu Arg Thr Ile Glu Pro Glu Lys Asn Gly Gln Arg Ile
        195                 200                 205
Thr Leu Arg Gln His Thr Ile Gly Thr Gly Leu Gly Gly Val Phe
210                 215                 220
Arg Ala Val Leu Asp Gly Thr Gly Tyr Thr Asp Asp Gly Val Val
225                 230                 235                 240
Ile Lys Thr Ala Gly Gly Ser Val Trp Leu Arg Val Asn Ala Asp Lys
                245                 250                 255
Val Asn Pro Phe Met Phe Gly Ala Thr Gly Val Ala Asp Asp Thr Ala
            260                 265                 270
Ala Leu Gln Lys Met Leu Glu Cys Gly Arg Ala Ala Glu Leu Gly Thr
        275                 280                 285
Asn Val Trp Lys Ala Ser Asn Leu Glu Leu Asn Asn Lys Ser Cys Ser
290                 295                 300
Leu Ser Gly Ser Gly Leu His Val Ser Arg Ile Glu Gln Ile Ser Gly
305                 310                 315                 320
Ala Thr Gly Ala Leu Leu Thr Ile Thr Gln Asp Cys Ser Leu Ile Tyr
                325                 330                 335
Leu Ser Asp Cys Gly Leu Tyr Gly Asp Gly Ile Thr Ala Gly Thr Ser
            340                 345                 350
Gly Val Thr Met Glu Thr Gly Asn Pro Gly Gly Ala Pro Ser Tyr Pro
        355                 360                 365
Phe Asn Thr Ala Pro Asp Val Arg Arg Asp Leu Tyr Ile Ser Asn Val
370                 375                 380
His Ile Thr Gly Phe Asp Glu Leu Gly Phe Asp Tyr Pro Glu Thr Asn
385                 390                 395                 400
Phe Ser Val Ser Thr His Gly Leu Phe Ile Arg Asn Ile Lys Lys Thr
                405                 410                 415
Gly Ala Lys Ile Gly Thr Thr Asp Phe Thr Trp Thr Asn Leu Gln Ile
            420                 425                 430
Asp Thr Cys Gly Gln Glu Cys Leu Val Leu Asp Gly Ala Gly Asn Cys
        435                 440                 445
Arg Ile Ile Gly Ala Lys Leu Ile Trp Ala Gly Ser Glu Asn Glu Thr
450                 455                 460
Pro Tyr Ser Gly Leu Arg Ile Ser Asn Ser Gln Asn Val Asn Met Thr
465                 470                 475                 480
Gly Val Glu Leu Gln Asp Cys Ala Tyr Asp Gly Leu Tyr Ile Lys Asn
                485                 490                 495
Ser Thr Val Ala Ile Ser Gly Leu Asn Thr Asn Arg Asn Ser Ala Ser
            500                 505                 510
Ser Asn Leu Ser Tyr His Asn Met Val Phe Glu Asn Ser Ile Val Thr
        515                 520                 525
```

Val Asp Gly Tyr Val Cys Arg Asn Tyr Ala Ala Thr Ser Leu Tyr Asp
    530                 535                 540

Leu Asn Ser Gln Ala Gly Asn Val Arg Cys Ile Gly Ser Asp Ser Thr
545                 550                 555                 560

Val Leu Ile Asn Gly Ile Tyr Glu Ser Glu Val Asn Ser Glu Arg Leu
                565                 570                 575

Met Gly Asp Asn Asn Leu Ile Gln Pro Tyr Ser Gly Asp Leu Ile Ile
            580                 585                 590

Asn Gly Leu Lys Asn Tyr Tyr Thr Tyr Gly Ser Val Lys Asn Asn
        595                 600                 605

Ile Pro Thr Phe Asp Gly Val Val Thr Thr Ala Thr Tyr Val Ser Ala
    610                 615                 620

Pro Ser Ile Leu Gly Gln Gly Asn Met Leu Lys Leu Thr Gln Ser Asn
625                 630                 635                 640

Lys Asp Lys Leu Leu Phe Ser Asp Lys Val Ser Arg His Gly Cys Thr
                645                 650                 655

Ile Gly Leu Val Leu Ile Pro Ser Phe Thr Gly Ala Thr Thr Met Thr
            660                 665                 670

Ala Phe Thr Leu Gly Ser Gly Tyr Ser Pro Ser Gly Asn Ser Ala Val
        675                 680                 685

Met Gln Phe Ile Val Asn Ser Ser Gly Val Gln Thr Ile Ala Ile Leu
    690                 695                 700

Leu Ser Gly Asp Gly Ile Thr Gln Thr Leu Thr Ser Asp Leu Thr Thr
705                 710                 715                 720

Glu Gln Ala Leu Ala Ser Gly Val Tyr His Phe Ala Met Gly Phe
                725                 730                 735

Ala Pro Gly Arg Leu Trp Trp Ser Ile Ile Asp Ile Asn Thr Gly Arg
            740                 745                 750

Arg Ile Arg Arg Ala Tyr Arg Gln Pro Asp Leu His Ala Ala Phe Asn
        755                 760                 765

Ser Ile Phe Asn Ser Gly Thr Ser Ser Ile Thr Ala Phe Ser Gly Pro
    770                 775                 780

Leu Ala Gly Asp Ile Ala Cys Glu Gly Ala Gly Ser His Val Tyr Val
785                 790                 795                 800

Gly Gly Phe Ser Ser Glu Ser Asp Tyr Ala Ala Ser Arg Met Tyr Gly
                805                 810                 815

Leu Phe Thr Pro Val Asp Leu Asp Lys Gln Tyr Ser Phe Arg Thr Leu
            820                 825                 830

Asn Gly Asn Ile
        835

<210> SEQ ID NO 68
<211> LENGTH: 823
<212> TYPE: PRT
<213> ORGANISM: Artificial Sequence
<220> FEATURE:
<223> OTHER INFORMATION: Synthetic construct - R2 - V10 fusion protein

<400> SEQUENCE: 68

Met Ala Thr Asn Thr Pro Lys Tyr Gly Gly Leu Leu Thr Asp Ile Gly
1               5                   10                  15

Ala Ala Ala Leu Ala Thr Ala Ser Ala Ala Gly Lys Lys Trp Gln Pro
            20                  25                  30

Thr His Met Leu Ile Gly Asp Ala Gly Gly Ala Pro Gly Asp Thr Pro
        35                  40                  45

```
Asp Pro Leu Pro Ser Ala Ala Gln Lys Ser Leu Ile Asn Gln Arg His
    50                  55                  60

Arg Ala Gln Leu Asn Arg Leu Phe Val Ser Asp Lys Asn Ala Asn Thr
65                  70                  75                  80

Leu Val Ala Glu Val Val Leu Pro Val Glu Val Gly Gly Phe Trp Ile
                85                  90                  95

Arg Glu Ile Gly Leu Gln Asp Ala Asp Gly Lys Phe Val Ala Val Ser
            100                 105                 110

Asn Cys Pro Pro Ser Tyr Lys Ala Ala Met Glu Ser Gly Ser Ala Arg
            115                 120                 125

Thr Gln Thr Ile Arg Val Asn Ile Ala Leu Ser Gly Leu Glu Asn Val
    130                 135                 140

Gln Leu Leu Ile Asp Asn Gly Ile Ile Tyr Ala Thr Gln Asp Trp Val
145                 150                 155                 160

Lys Glu Lys Val Leu Ala Ala Asn Asp Gly Phe Lys Phe Ile Gly Gln
                165                 170                 175

Cys Pro Asp Ile Leu Thr Leu Arg Thr Ile Glu Pro Glu Lys Asn Gly
            180                 185                 190

Gln Arg Ile Thr Leu Arg Gln His Thr Ile Gly Thr Gly Leu Gly Gly
            195                 200                 205

Gly Val Phe Arg Ala Val Leu Asp Gly Thr Gly Tyr Thr Asp Asp Asp
    210                 215                 220

Gly Val Val Ile Lys Thr Ala Gly Gly Ser Val Trp Leu Arg Val Asn
225                 230                 235                 240

Ala Asp Lys Val Asn Pro Phe Met Phe Gly Ala Thr Gly Val Ala Asp
                245                 250                 255

Asp Thr Ala Ala Leu Gln Lys Met Leu Glu Cys Gly Arg Ala Ala Glu
            260                 265                 270

Leu Gly Thr Asn Val Trp Lys Ala Ser Asn Leu Glu Leu Asn Asn Lys
            275                 280                 285

Ser Cys Ser Leu Ser Gly Ser Gly Leu His Val Ser Arg Ile Glu Gln
    290                 295                 300

Ile Ser Gly Ala Thr Gly Ala Leu Leu Thr Ile Thr Gln Asp Cys Ser
305                 310                 315                 320

Leu Ile Tyr Leu Ser Asp Cys Gly Leu Tyr Gly Asp Gly Ile Thr Ala
                325                 330                 335

Gly Thr Ser Gly Val Thr Met Glu Thr Gly Asn Pro Gly Gly Ala Pro
            340                 345                 350

Ser Tyr Pro Phe Asn Thr Ala Pro Asp Val Arg Arg Asp Leu Tyr Ile
            355                 360                 365

Ser Asn Val His Ile Thr Gly Phe Asp Glu Leu Gly Phe Asp Tyr Pro
    370                 375                 380

Glu Thr Asn Phe Ser Val Ser Thr His Gly Leu Phe Ile Arg Asn Ile
385                 390                 395                 400

Lys Lys Thr Gly Ala Lys Ile Gly Thr Thr Asp Phe Thr Trp Thr Asn
                405                 410                 415

Leu Gln Ile Asp Thr Cys Gly Gln Glu Cys Leu Val Leu Asp Gly Ala
            420                 425                 430

Gly Asn Cys Arg Ile Ile Gly Ala Lys Leu Ile Trp Ala Gly Ser Glu
            435                 440                 445

Asn Glu Thr Pro Tyr Ser Gly Leu Arg Ile Ser Asn Ser Gln Asn Val
    450                 455                 460

Asn Met Thr Gly Val Glu Leu Gln Asp Cys Ala Tyr Asp Gly Leu Tyr
465                 470                 475                 480
```

Ile Lys Asn Ser Thr Val Ala Ile Ser Gly Leu Asn Thr Asn Arg Asn
            485                 490                 495

Ser Ala Ser Ser Asn Leu Ser Tyr His Asn Met Val Phe Glu Asn Ser
            500                 505                 510

Ile Val Thr Val Asp Gly Tyr Val Cys Arg Asn Tyr Ala Ala Thr Ser
            515                 520                 525

Leu Tyr Asp Leu Asn Ser Gln Ala Gly Asn Val Arg Cys Ile Gly Ser
            530                 535                 540

Asp Ser Thr Val Leu Ile Asn Gly Ile Tyr Glu Ser Glu Val Asn Ser
545                 550                 555                 560

Glu Arg Leu Met Gly Asp Asn Leu Ile Gln Pro Tyr Ser Gly Asp
            565                 570                 575

Leu Ile Ile Asn Gly Leu Lys Asn Tyr Tyr Thr Tyr Thr Gly Ser Val
            580                 585                 590

Lys Asn Asn Ile Pro Thr Phe Asp Gly Val Val Thr Ala Thr Tyr
            595                 600                 605

Val Ser Ala Pro Ser Ile Leu Gly Gln Gly Asn Met Leu Lys Leu Thr
            610                 615                 620

Gln Ser Asn Lys Asp Lys Leu Leu Phe Ser Asp Lys Val Ser Arg His
625                 630                 635                 640

Gly Cys Thr Ile Gly Leu Val Leu Ile Pro Ser Phe Thr Gly Ala Thr
            645                 650                 655

Thr Met Thr Ala Phe Thr Leu Gly Ser Gly Tyr Ser Pro Ser Gly Asn
            660                 665                 670

Ser Ala Val Met Gln Phe Ile Val Asn Ser Ser Gly Val Gln Thr Ile
            675                 680                 685

Ala Ile Leu Leu Ser Gly Asp Gly Ile Thr Gln Thr Leu Thr Ser Asp
            690                 695                 700

Leu Thr Thr Glu Gln Ala Leu Ala Ser Gly Val Tyr His Phe Ala
705                 710                 715                 720

Met Gly Phe Ala Pro Gly Arg Leu Trp Trp Ser Ile Ile Asp Ile Asn
            725                 730                 735

Thr Gly Arg Arg Ile Arg Arg Ala Tyr Arg Gln Pro Asp Leu His Ala
            740                 745                 750

Ala Phe Asn Ser Ile Phe Asn Ser Gly Thr Ser Ser Ile Thr Ala Phe
            755                 760                 765

Ser Gly Pro Leu Ala Gly Asp Ile Ala Cys Glu Gly Ala Gly Ser His
            770                 775                 780

Val Tyr Val Gly Gly Phe Ser Ser Glu Ser Asp Tyr Ala Ala Ser Arg
785                 790                 795                 800

Met Tyr Gly Leu Phe Thr Pro Val Asp Leu Asp Lys Gln Tyr Ser Phe
            805                 810                 815

Arg Thr Leu Asn Gly Asn Ile
            820

<210> SEQ ID NO 69
<211> LENGTH: 826
<212> TYPE: PRT
<213> ORGANISM: Artificial Sequence
<220> FEATURE:
<223> OTHER INFORMATION: Synthetic construct - R2 - V10 fusion protein

<400> SEQUENCE: 69

Met Ala Thr Asn Thr Pro Lys Tyr Gly Gly Leu Leu Thr Asp Ile Gly
1               5                   10                  15

-continued

```
Ala Ala Ala Leu Ala Thr Ala Ser Ala Ala Gly Lys Lys Trp Gln Pro
             20              25              30

Thr His Met Leu Ile Gly Asp Ala Gly Gly Ala Pro Gly Asp Thr Pro
         35              40              45

Asp Pro Leu Pro Ser Ala Ala Gln Lys Ser Leu Ile Asn Gln Arg His
 50              55              60

Arg Ala Gln Leu Asn Arg Leu Phe Val Ser Asp Lys Asn Ala Asn Thr
 65              70              75              80

Leu Val Ala Glu Val Val Leu Pro Val Glu Val Gly Gly Phe Trp Ile
             85              90              95

Arg Glu Ile Gly Leu Gln Asp Ala Asp Gly Lys Phe Val Ala Val Ser
             100             105             110

Asn Cys Pro Pro Ser Tyr Lys Ala Ala Met Glu Ser Gly Ser Ala Arg
             115             120             125

Thr Gln Thr Ile Arg Val Asn Ile Ala Leu Ser Gly Leu Glu Asn Val
 130             135             140

Gln Leu Leu Ile Asp Asn Gly Ile Ile Tyr Ala Thr Gln Asp Trp Val
145             150             155             160

Lys Thr Asp Val Met Ile Gln Leu Ala Ala Asn Asp Gly Phe Lys Phe
             165             170             175

Ile Gly Gln Cys Pro Asp Ile Leu Thr Leu Arg Thr Ile Glu Pro Glu
             180             185             190

Lys Asn Gly Gln Arg Ile Thr Leu Arg Gln His Thr Ile Gly Thr Gly
             195             200             205

Leu Gly Gly Gly Val Phe Arg Ala Val Leu Asp Gly Thr Gly Tyr Thr
             210             215             220

Asp Asp Asp Gly Val Val Ile Lys Thr Ala Gly Gly Ser Val Trp Leu
225             230             235             240

Arg Val Asn Ala Asp Lys Val Asn Pro Phe Met Phe Gly Ala Thr Gly
             245             250             255

Val Ala Asp Asp Thr Ala Ala Leu Gln Lys Met Leu Glu Cys Gly Arg
             260             265             270

Ala Ala Glu Leu Gly Thr Asn Val Trp Lys Ala Ser Asn Leu Glu Leu
             275             280             285

Asn Asn Lys Ser Cys Ser Leu Ser Gly Ser Gly Leu His Val Ser Arg
             290             295             300

Ile Glu Gln Ile Ser Gly Ala Thr Gly Ala Leu Leu Thr Ile Thr Gln
305             310             315             320

Asp Cys Ser Leu Ile Tyr Leu Ser Asp Cys Gly Leu Tyr Gly Asp Gly
             325             330             335

Ile Thr Ala Gly Thr Ser Gly Val Thr Met Glu Thr Gly Asn Pro Gly
             340             345             350

Gly Ala Pro Ser Tyr Pro Phe Asn Thr Ala Pro Asp Val Arg Arg Asp
             355             360             365

Leu Tyr Ile Ser Asn Val His Ile Thr Gly Phe Asp Glu Leu Gly Phe
             370             375             380

Asp Tyr Pro Glu Thr Asn Phe Ser Val Ser Thr His Gly Leu Phe Ile
385             390             395             400

Arg Asn Ile Lys Lys Thr Gly Ala Lys Ile Gly Thr Thr Asp Phe Thr
             405             410             415

Trp Thr Asn Leu Gln Ile Asp Thr Cys Gly Gln Glu Cys Leu Val Leu
             420             425             430

Asp Gly Ala Gly Asn Cys Arg Ile Ile Gly Ala Lys Leu Ile Trp Ala
             435             440             445
```

Gly Ser Glu Asn Glu Thr Pro Tyr Ser Gly Leu Arg Ile Ser Asn Ser
            450                 455                 460

Gln Asn Val Asn Met Thr Gly Val Glu Leu Gln Asp Cys Ala Tyr Asp
465                 470                 475                 480

Gly Leu Tyr Ile Lys Asn Ser Thr Val Ala Ile Ser Gly Leu Asn Thr
                485                 490                 495

Asn Arg Asn Ser Ala Ser Ser Asn Leu Ser Tyr His Asn Met Val Phe
            500                 505                 510

Glu Asn Ser Ile Val Thr Val Asp Gly Tyr Val Cys Arg Asn Tyr Ala
            515                 520                 525

Ala Thr Ser Leu Tyr Asp Leu Asn Ser Gln Ala Gly Asn Val Arg Cys
            530                 535                 540

Ile Gly Ser Asp Ser Thr Val Leu Ile Asn Gly Ile Tyr Glu Ser Glu
545                 550                 555                 560

Val Asn Ser Glu Arg Leu Met Gly Asp Asn Asn Leu Ile Gln Pro Tyr
                565                 570                 575

Ser Gly Asp Leu Ile Ile Asn Gly Leu Lys Asn Tyr Tyr Thr Tyr Thr
            580                 585                 590

Gly Ser Val Lys Asn Asn Ile Pro Thr Phe Asp Gly Val Thr Thr
            595                 600                 605

Ala Thr Tyr Val Ser Ala Pro Ser Ile Leu Gly Gln Gly Asn Met Leu
610                 615                 620

Lys Leu Thr Gln Ser Asn Lys Asp Lys Leu Leu Phe Ser Asp Lys Val
625                 630                 635                 640

Ser Arg His Gly Cys Thr Ile Gly Leu Val Leu Ile Pro Ser Phe Thr
                645                 650                 655

Gly Ala Thr Thr Met Thr Ala Phe Thr Leu Gly Ser Gly Tyr Ser Pro
            660                 665                 670

Ser Gly Asn Ser Ala Val Met Gln Phe Ile Val Asn Ser Ser Gly Val
            675                 680                 685

Gln Thr Ile Ala Ile Leu Leu Ser Gly Asp Gly Ile Thr Gln Thr Leu
690                 695                 700

Thr Ser Asp Leu Thr Thr Glu Gln Ala Leu Ala Ser Gly Gly Val Tyr
705                 710                 715                 720

His Phe Ala Met Gly Phe Ala Pro Gly Arg Leu Trp Trp Ser Ile Ile
                725                 730                 735

Asp Ile Asn Thr Gly Arg Arg Ile Arg Arg Ala Tyr Arg Gln Pro Asp
            740                 745                 750

Leu His Ala Ala Phe Asn Ser Ile Phe Asn Ser Gly Thr Ser Ser Ile
            755                 760                 765

Thr Ala Phe Ser Gly Pro Leu Ala Gly Asp Ile Ala Cys Glu Gly Ala
            770                 775                 780

Gly Ser His Val Tyr Val Gly Gly Phe Ser Ser Glu Ser Asp Tyr Ala
785                 790                 795                 800

Ala Ser Arg Met Tyr Gly Leu Phe Thr Pro Val Asp Leu Asp Lys Gln
            805                 810                 815

Tyr Ser Phe Arg Thr Leu Asn Gly Asn Ile
            820                 825

<210> SEQ ID NO 70
<211> LENGTH: 667
<212> TYPE: PRT
<213> ORGANISM: Bacteriophage p22

<400> SEQUENCE: 70

```
Met Thr Asp Ile Thr Ala Asn Val Val Ser Asn Pro Arg Pro Ile
1               5                   10                  15

Phe Thr Glu Ser Arg Ser Phe Lys Ala Val Ala Asn Gly Lys Ile Tyr
            20                  25                  30

Ile Gly Gln Ile Asp Thr Asp Pro Val Asn Pro Ala Asn Gln Ile Pro
            35                  40                  45

Val Tyr Ile Glu Asn Glu Asp Gly Ser His Val Gln Ile Thr Gln Pro
    50                  55                  60

Leu Ile Ile Asn Ala Ala Gly Lys Ile Val Tyr Asn Gly Gln Leu Val
65                  70                  75                  80

Lys Ile Val Thr Val Gln Gly His Ser Met Ala Ile Tyr Asp Ala Asn
                85                  90                  95

Gly Ser Gln Val Asp Tyr Ile Ala Asn Val Leu Lys Tyr Asp Pro Asp
                100                 105                 110

Gln Tyr Ser Ile Glu Ala Asp Lys Lys Phe Lys Tyr Ser Val Lys Leu
            115                 120                 125

Ser Asp Tyr Pro Thr Leu Gln Asp Ala Ala Ser Ala Ala Val Asp Gly
            130                 135                 140

Leu Leu Ile Asp Arg Asp Tyr Asn Phe Tyr Gly Glu Thr Val Asp
145                 150                 155                 160

Phe Gly Gly Lys Val Leu Thr Ile Glu Cys Lys Ala Lys Phe Ile Gly
                165                 170                 175

Asp Gly Asn Leu Ile Phe Thr Lys Leu Gly Lys Gly Ser Arg Ile Ala
            180                 185                 190

Gly Val Phe Met Glu Ser Thr Thr Thr Pro Trp Val Ile Lys Pro Trp
        195                 200                 205

Thr Asp Asp Asn Gln Trp Leu Thr Asp Ala Ala Ala Val Val Ala Thr
        210                 215                 220

Leu Lys Gln Ser Lys Thr Asp Gly Tyr Gln Pro Thr Val Ser Asp Tyr
225                 230                 235                 240

Val Lys Phe Pro Gly Ile Glu Thr Leu Leu Pro Pro Asn Ala Lys Gly
                245                 250                 255

Gln Asn Ile Thr Ser Thr Leu Glu Ile Arg Glu Cys Ile Gly Val Glu
            260                 265                 270

Val His Arg Ala Ser Gly Leu Met Ala Gly Phe Leu Phe Arg Gly Cys
        275                 280                 285

His Phe Cys Lys Met Val Asp Ala Asn Asn Pro Ser Gly Gly Lys Asp
        290                 295                 300

Gly Ile Ile Thr Phe Glu Asn Leu Ser Gly Asp Trp Gly Lys Gly Asn
305                 310                 315                 320

Tyr Val Ile Gly Gly Arg Thr Ser Tyr Gly Ser Val Ser Ser Ala Gln
                325                 330                 335

Phe Leu Arg Asn Asn Gly Gly Phe Glu Arg Asp Gly Gly Val Ile Gly
            340                 345                 350

Phe Thr Ser Tyr Arg Ala Gly Glu Ser Gly Val Lys Thr Trp Gln Gly
            355                 360                 365

Thr Val Gly Ser Thr Thr Ser Arg Asn Tyr Asn Leu Gln Phe Arg Asp
        370                 375                 380

Ser Val Val Ile Tyr Pro Val Trp Asp Gly Phe Asp Leu Gly Ala Asp
385                 390                 395                 400

Thr Asp Met Asn Pro Glu Leu Asp Arg Pro Gly Asp Tyr Pro Ile Thr
                405                 410                 415

Gln Tyr Pro Leu His Gln Leu Pro Leu Asn His Leu Ile Asp Asn Leu
```

```
                420            425             430
Leu Val Arg Gly Ala Leu Gly Val Gly Phe Gly Met Asp Gly Lys Gly
            435                 440                 445
Met Tyr Val Ser Asn Ile Thr Val Glu Asp Cys Ala Gly Ser Gly Ala
            450                 455                 460
Tyr Leu Leu Thr His Glu Ser Val Phe Thr Asn Ile Ala Ile Ile Asp
465                 470                 475                 480
Thr Asn Thr Lys Asp Phe Gln Ala Asn Gln Ile Tyr Ile Ser Gly Ala
            485                 490                 495
Cys Arg Val Asn Gly Leu Arg Leu Ile Gly Ile Arg Ser Thr Asp Gly
            500                 505                 510
Gln Gly Leu Thr Ile Asp Ala Pro Asn Ser Thr Val Ser Gly Ile Thr
            515                 520                 525
Gly Met Val Asp Pro Ser Arg Ile Asn Val Ala Asn Leu Ala Glu Glu
            530                 535                 540
Gly Leu Gly Asn Ile Arg Ala Asn Ser Phe Gly Tyr Asp Ser Ala Ala
545                 550                 555                 560
Ile Lys Leu Arg Ile His Lys Leu Ser Lys Thr Leu Asp Ser Gly Ala
            565                 570                 575
Leu Tyr Ser His Ile Asn Gly Gly Ala Gly Ser Gly Ser Ala Tyr Thr
            580                 585                 590
Gln Leu Thr Ala Ile Ser Gly Ser Thr Pro Asp Ala Val Ser Leu Lys
            595                 600                 605
Val Asn His Lys Asp Cys Arg Gly Ala Glu Ile Pro Phe Val Pro Asp
            610                 615                 620
Ile Ala Ser Asp Asp Phe Ile Lys Asp Ser Ser Cys Phe Leu Pro Tyr
625                 630                 635                 640
Trp Glu Asn Asn Ser Thr Ser Leu Lys Ala Leu Val Lys Lys Pro Asn
            645                 650                 655
Gly Glu Leu Val Arg Leu Thr Leu Ala Thr Leu
            660                 665

<210> SEQ ID NO 71
<211> LENGTH: 2798
<212> TYPE: DNA
<213> ORGANISM: Artificial Sequence
<220> FEATURE:
<223> OTHER INFORMATION: Synthetic construct - PS17 phage DNA- pUC19
      vector DNA overlapping ORFs

<400> SEQUENCE: 71
atgagcacca atcaatacgg gggcttcctc accgacaagg gggccgccaa gcaggtcgag      60
gctgcatccg gcggcttgcg acggaacatc acccacatgc tgatcggtga cgcgggcggt     120
gcgcccggcc agacgccgga cccggtaccc agccccttgc aaaccaagct cgttcggcag     180
cgctatcggg tcaagttgaa ccgcctggta gccgctgaca cagtcccag cgtgttgatc      240
gccgaggcga tcttgccgca ggacgtgggc ggttggtgga tgcgtgagct gggactggag     300
gactccgatg cgacatgat cgctgttgcc aactgcgcgc cgagttacaa gccgctggtg      360
aacgaggggt cgggacggac gcaaacggtg cgcctgcata tcgcgttcag tcatgcggaa     420
acggtcgatc tgctgatcga cccgaacgtg gtcaccgcga cggtggcgga tctgcaaaat     480
gcgctgctgg aagtgcgcgc gaccaacgac gcgaccggac agatgacgcg aggcacagac     540
ggaaagctgg ccctgccgct ctcgctgagc ctgacaggac ttgccgccgg cacctatcgc     600
agcctcacgg tcgacgcgaa ggggcgcgct accagcggca gcaaccctac cacccctgggc    660
```

```
gggtacggca ttaccgacgc gctggccaag agcgatgctg tcgacgtgcc cgcgccgaat    720
aagctgctgc ggctcaacgc tgccagccag ttgccggcat cgattaccgg caacgcggcg    780
actgccacca agcttgccgt tccgcgcatg ctgtcgttta caggggacgc cacgggggc    840
gcatcgttcg acgggagtgc caacgcggct gtagcgctga ccctggcgaa ttcgggggtt    900
actgctggta cctatgccaa ggtcacggtg aacggcaagg gtttggtcac cggcggggcg    960
cagctcactg cggcagatat cccggcgctg gatgctggca agttgtttc gggtgtcctg    1020
cccatagctc gtggcggcac cggcaacgcc atcggccagg ctgcaactgc ggtcaaactg    1080
gcatcccctc gcacactggc aatcgctggg gatgccaccg gcagcgctgc attcgacggc    1140
agcgcaaacg ccagcatttc ggttacgctg gccaataccg gtgtcgccgt cggcacctac    1200
acgaaggtca gagtgaacgc taaaggactt gtcaccagtg ccgcatcgtt gacggctgac    1260
gatgttcctt ggctggacgc gtcaaaagtg acgtcgggca tgttcgccga tgcccgcctg    1320
ccctggtacg cacaagggct atgcaccagc gcacccaaca cgacggaccc gaacaccacg    1380
aacatcccgc tcatcctcac gaatcacgag aacggtccga ttccggggac ttttttctat    1440
atccagacga tgatgtacaa ccagcgcaac ggcaatgccg cccagattgc agtgcgctac    1500
gcggcgaatg ccgaaatgta tgtgcgctac atgtacgacg tcgggaacaa gcgcggggtc    1560
tggtcggcct ggaaacgctg cgatgtgggc ggctcatttg ctaaagaggc ggatggcgaa    1620
ctgggggtg gggtcaacct agacaccatg attgcctctg ggtggtggca tcaaccgttc    1680
agcgcgaacg ccaagaacgg cacgaactat cccgtgggag aggccggttt gctgaccgtc    1740
cacgcaccca cttccacgat gatttatcag acttaccgtg gctacgccgc cggcggtctg    1800
tactggcgct gccgctacaa cggcacctgg tcagcatggt atcgcgcatg ggactccggc    1860
aacttcaacc ctgccaacta cgtggccagg tcggaatact cctgggcgtc cttaccaggg    1920
aagcccgcaa cattccctcc ttccgggcac aaccatgacg ccacccaaat tacatcgggc    1980
attttgccgc tggcccgtgg cggccttggc gccaacaacg ccgtaacggc acgaagcaac    2040
atcggcgcgg ggactatcgc gaccgcatcg ctgggaagca gcggctggtg gcgggataac    2100
gatacggggt acatccggca gtggggccgg gtgactgtgc ctggtgatgg ctccgcggcg    2160
atcaccttcc ccatcgcgtt ccccagtgtc tgcttgggtg gattcgctgg ccaaactgcg    2220
aatttccacc caggaaccga cgcgagcaca tcgttctata accagtcgac gacaggtgca    2280
actttggaaa acgggtatca attccaggcg gttttgcttt gggaggcatt cggtcgatga    2340
gcgctagcga ctatgttttc tcgccgtccg cgcgggtgtt ctatcccgtg gcgttgcggg    2400
aggtgtacga gaccggggag ggctggccgg ccgatgcggt gcctgtcagc aatgaacgct    2460
atctgcacct gcttgccggg caggaggccg ggatgcggat cgctgctaac gcctccggcc    2520
agccggttct tgtcgatccg ccacccctca ccgaggcgga gcggcggacg aaggctcggg    2580
cctggcgtga cgctcagctt gcacagaccg atggcatggt ggctcggcat cgtgacgagc    2640
gcgacctggg gaatgacacc actctccaac ctgagcagtt cgtagaggtt atgaactatc    2700
gcgcggccct gcgcaattgg ccggacgacc cggcattccc cgaccccgcc tccaggccgg    2760
agccgcctgc ctggctggcc gaagaaggca ccaactaa                            2798
```

<210> SEQ ID NO 72
<211> LENGTH: 21
<212> TYPE: DNA
<213> ORGANISM: Artificial Sequence
<220> FEATURE:
<223> OTHER INFORMATION: AV168 primer

```
<400> SEQUENCE: 72
tcacggtaac gaatgtggac g                                              21

<210> SEQ ID NO 73
<211> LENGTH: 21
<212> TYPE: DNA
<213> ORGANISM: Artificial Sequence
<220> FEATURE:
<223> OTHER INFORMATION: AV167 primer

<400> SEQUENCE: 73
tttcagccag ttggtcgaca c                                              21

<210> SEQ ID NO 74
<211> LENGTH: 45
<212> TYPE: DNA
<213> ORGANISM: Artificial Sequence
<220> FEATURE:
<223> OTHER INFORMATION: AV140 primer

<400> SEQUENCE: 74
cctgacggat ggccttttct attatcactg cccgctttcc agtcg                    45

<210> SEQ ID NO 75
<211> LENGTH: 48
<212> TYPE: DNA
<213> ORGANISM: Artificial Sequence
<220> FEATURE:
<223> OTHER INFORMATION: AV141 primer

<400> SEQUENCE: 75
tttctttgct cttccgctag aaggccatcc tgacggatgg ccttttct                 48

<210> SEQ ID NO 76
<211> LENGTH: 36
<212> TYPE: DNA
<213> ORGANISM: Artificial Sequence
<220> FEATURE:
<223> OTHER INFORMATION: AV027 primer

<400> SEQUENCE: 76
tttctgctct tcaagccgac accatcgaat ggtgca                              36

<210> SEQ ID NO 77
<211> LENGTH: 44
<212> TYPE: DNA
<213> ORGANISM: Artificial Sequence
<220> FEATURE:
<223> OTHER INFORMATION: AV169 primer

<400> SEQUENCE: 77
tttattagcg gaagagccac gcgtgactgc acggtgcacc aatg                     44

<210> SEQ ID NO 78
<211> LENGTH: 38
<212> TYPE: DNA
<213> ORGANISM: Artificial Sequence
<220> FEATURE:
<223> OTHER INFORMATION: AV114 primer

<400> SEQUENCE: 78
ccctcgaatt catgaatact gtttcctgtg tgaaattg                            38

<210> SEQ ID NO 79
<211> LENGTH: 35
<212> TYPE: DNA
```

```
<213> ORGANISM: Artificial Sequence
<220> FEATURE:
<223> OTHER INFORMATION: AV238 primer

<400> SEQUENCE: 79
aacccacgaa gacctcatga gcaccaatca atacg                              35

<210> SEQ ID NO 80
<211> LENGTH: 24
<212> TYPE: DNA
<213> ORGANISM: Artificial Sequence
<220> FEATURE:
<223> OTHER INFORMATION: AV047 primer

<400> SEQUENCE: 80
cgccagggtt ttcccagtca cgac                                          24

<210> SEQ ID NO 81
<211> LENGTH: 22
<212> TYPE: DNA
<213> ORGANISM: Artificial Sequence
<220> FEATURE:
<223> OTHER INFORMATION: PRF13-F primer

<400> SEQUENCE: 81
tatcgagaac tgctgctgcg gg                                            22

<210> SEQ ID NO 82
<211> LENGTH: 31
<212> TYPE: DNA
<213> ORGANISM: Artificial Sequence
<220> FEATURE:
<223> OTHER INFORMATION: AV086 primer

<400> SEQUENCE: 82
tccttgaatt ccgcttgctg ccgaagttct t                                  31

<210> SEQ ID NO 83
<211> LENGTH: 29
<212> TYPE: DNA
<213> ORGANISM: Artificial Sequence
<220> FEATURE:
<223> OTHER INFORMATION: AV118 primer

<400> SEQUENCE: 83
cttcctttca tgacgaccaa tactccgaa                                     29

<210> SEQ ID NO 84
<211> LENGTH: 40
<212> TYPE: DNA
<213> ORGANISM: Artificial Sequence
<220> FEATURE:
<223> OTHER INFORMATION: AV287 primer

<400> SEQUENCE: 84
tcggtaatgc cgtacccgcc cagggtggtc ggattgctgc                         40

<210> SEQ ID NO 85
<211> LENGTH: 40
<212> TYPE: DNA
<213> ORGANISM: Artificial Sequence
<220> FEATURE:
<223> OTHER INFORMATION: AV286 primer

<400> SEQUENCE: 85
gcagcaatcc gaccaccctg ggcgggtacg gcattaccga                         40
```

```
<210> SEQ ID NO 86
<211> LENGTH: 34
<212> TYPE: DNA
<213> ORGANISM: Artificial Sequence
<220> FEATURE:
<223> OTHER INFORMATION: AV293 primer

<400> SEQUENCE: 86
aaaccaagag ctcttagttg gtgccttctt cggc                                34

<210> SEQ ID NO 87
<211> LENGTH: 21
<212> TYPE: DNA
<213> ORGANISM: Artificial Sequence
<220> FEATURE:
<223> OTHER INFORMATION: PRF13-F primer

<400> SEQUENCE: 87
gcaccgttac ccgatccgcg a                                              21

<210> SEQ ID NO 88
<211> LENGTH: 23
<212> TYPE: DNA
<213> ORGANISM: Artificial Sequence
<220> FEATURE:
<223> OTHER INFORMATION: av333 primer

<400> SEQUENCE: 88
tcgagacgat ttaccaagag ctg                                            23

<210> SEQ ID NO 89
<211> LENGTH: 23
<212> TYPE: DNA
<213> ORGANISM: Artificial Sequence
<220> FEATURE:
<223> OTHER INFORMATION: av334 primer

<400> SEQUENCE: 89
ttccacgacc agtccggaaa atg                                            23

<210> SEQ ID NO 90
<211> LENGTH: 36
<212> TYPE: DNA
<213> ORGANISM: Artificial Sequence
<220> FEATURE:
<223> OTHER INFORMATION: av337 primer

<400> SEQUENCE: 90
tttatttgcg gccgcgacga aagggcctcg tgatac                              36

<210> SEQ ID NO 91
<211> LENGTH: 38
<212> TYPE: DNA
<213> ORGANISM: Artificial Sequence
<220> FEATURE:
<223> OTHER INFORMATION: av338 primer

<400> SEQUENCE: 91
tttatttgcg gccgcaaata ccgcatcagg cgctcttc                            38

<210> SEQ ID NO 92
<211> LENGTH: 42
<212> TYPE: DNA
<213> ORGANISM: Artificial Sequence
<220> FEATURE:
<223> OTHER INFORMATION: av339 primer
```

<400> SEQUENCE: 92
ggccgcttat taacaagctt cacacacgct agcccaccac gc                              42

<210> SEQ ID NO 93
<211> LENGTH: 42
<212> TYPE: DNA
<213> ORGANISM: Artificial Sequence
<220> FEATURE:
<223> OTHER INFORMATION: av340 primer

<400> SEQUENCE: 93
ggccgcgtgg tgggctagcg tgtgtgaagc ttgttaataa gc                              42

<210> SEQ ID NO 94
<211> LENGTH: 35
<212> TYPE: DNA
<213> ORGANISM: Artificial Sequence
<220> FEATURE:
<223> OTHER INFORMATION: av404 primer

<400> SEQUENCE: 94 cccccccta attaacttga gtcaggatgg acatg                                      35

<210> SEQ ID NO 95
<211> LENGTH: 21
<212> TYPE: DNA
<213> ORGANISM: Artificial Sequence
<220> FEATURE:
<223> OTHER INFORMATION: av407 primer

<400> SEQUENCE: 95
aaggcattcg agaccgtcaa g                                                    21

<210> SEQ ID NO 96
<211> LENGTH: 36
<212> TYPE: DNA
<213> ORGANISM: Artificial Sequence
<220> FEATURE:
<223> OTHER INFORMATION: av461 primer

<400> SEQUENCE: 96
tttccttgaa ttcgctcggc aatctacaga ccgatg                                    36

<210> SEQ ID NO 97
<211> LENGTH: 41
<212> TYPE: DNA
<213> ORGANISM: Artificial Sequence
<220> FEATURE:
<223> OTHER INFORMATION: AV529 primer

<400> SEQUENCE: 97
tttccctgaa ttcattactt gcccacgcag aaggcgcttt c                              41

<210> SEQ ID NO 98
<211> LENGTH: 50
<212> TYPE: DNA
<213> ORGANISM: Artificial Sequence
<220> FEATURE:
<223> OTHER INFORMATION: AV530 primer

<400> SEQUENCE: 98
agctgcggcc gcgaattcac gcgtaagctt actagtgcta gcttaattaa                     50

<210> SEQ ID NO 99
<211> LENGTH: 50
<212> TYPE: DNA

```
<213> ORGANISM: Artificial Sequence
<220> FEATURE:
<223> OTHER INFORMATION: AV531 primer

<400> SEQUENCE: 99
aattttaatt aagctagcac tagtaagctt acgcgtgaat tcgcggccgc          50
```